(12) United States Patent
Yu et al.

(10) Patent No.: US 10,703,761 B2
(45) Date of Patent: Jul. 7, 2020

(54) BILE ACID RECEPTOR MODULATORS AND METHODS OF USE THEREOF

(71) Applicant: City of Hope, Duarte, CA (US)

(72) Inventors: Donna Yu, Arcadia, CA (US); Barry Forman, Irvine, CA (US)

(73) Assignee: City of Hope, Duarte, CA (US)

(*) Notice: Subject to any disclaimer, the term of this patent is extended or adjusted under 35 U.S.C. 154(b) by 0 days.

(21) Appl. No.: 15/787,407

(22) Filed: Oct. 18, 2017

(65) Prior Publication Data

US 2018/0105533 A1  Apr. 19, 2018

Related U.S. Application Data

(60) Provisional application No. 62/409,641, filed on Oct. 18, 2016.

(51) Int. Cl.
| | | |
|---|---|---|
| *C07D 455/03* | (2006.01) | |
| *C07D 491/056* | (2006.01) | |
| *A61P 35/00* | (2006.01) | |
| *A61P 3/00* | (2006.01) | |

(52) U.S. Cl.
CPC ............ *C07D 491/056* (2013.01); *A61P 3/00* (2018.01); *A61P 35/00* (2018.01); *C07D 455/03* (2013.01)

(58) Field of Classification Search
CPC .................................................. C07D 455/03
See application file for complete search history.

(56) References Cited

U.S. PATENT DOCUMENTS

| | | | | |
|---|---|---|---|---|
| 7,650,848 B2* | 1/2010 | Brennan | ................ | B08B 17/06 114/222 |
| 8,410,083 B2* | 4/2013 | Pellicciari | ................ | C07J 9/005 514/182 |
| 9,393,221 B2* | 7/2016 | Wu | ................... | A61K 31/137 |
| 10,301,303 B2* | 5/2019 | Liu | ................... | A61K 31/4375 |
| 2008/0221161 A1* | 9/2008 | Pinkerton | ............... | A61K 31/47 514/314 |
| 2011/0092582 A1* | 4/2011 | Jacquot | ............... | C07C 49/737 514/450 |

FOREIGN PATENT DOCUMENTS

| | | | | |
|---|---|---|---|---|
| CN | 102702190 A | * | 10/2012 | |
| CN | 105693805 A | * | 6/2016 | |
| WO | WO-2014/100025 A1 | | 6/2014 | |
| WO | WO-2016015634 A1 | * | 2/2016 | .......... A61K 31/4375 |
| WO | WO-2016046680 A2 | * | 3/2016 | ........... C07J 41/0055 |

OTHER PUBLICATIONS

Chemotherapy of Neoplastic Diseases in, Goodman & Gilman's: The Pharmacological Basis of Therapeutics 853-908 (L.L. Brunton et al., eds., 11th ed., 2008).*
Oxford Dictionary of Chemistry 169 (John Daintith ed., 6th ed., 2008) (Year: 2008).*
L. Zhang et al., 17 Molecules, 11294-11302 (2012) (Year: 2012).*
Y. Wang et al., 19 Bioorganic & Medicinal Chemistry Letters, 6004-6008 (2009) (Year: 2009).*
P. Yang et al., 18 Bioorganic & Medicinal Chemistry Letters, 4657-4677 (2008) (Year: 2008).*
C. Faustino et al, 13 Expert Opinion on Drug Delivery, 1133-1148 (2016) (Year: 2016).*
O. Bortolini et al. 17 Chirality, 121-130 (2005) (Year: 2005).*
D. W. Russell, Journal of Applied Lipid Research (2009) (Year: 2009).*
S. Kundu et al., IUBMB Life, 514-523 (2015) (Year: 2015).*
M.D. Krasowski et al., 19 Molecular Endocrinology, 1720-1730 (2005) (Year: 2005).*
C. Wang et al., 16 Crystal Growth and Design, 933-939 (2015) (Year: 2015).*
W. Tan et al., 6, International Journal of Nanomedicine, 1773-1777 (2011) (Year: 2011).*
J. Dostál et al., 687 Journal of Molecular Structure, 135-142 (2004) (Year: 2004).*
B. K. Sarma et al., 44 Folia Microbiol., 164-166 (1999) (Year: 1999).*
G. Zollner et al., 39 Journal of Hepatology. 480-488 (2003) (Year: 2003).*
I.P. Singh et al., Expert Opinion on Therapeutic Patents, 215-231 (2012) (Year: 2012).*
I.V. Nechepurenko et al., 18 Chemistry for Sustainable Development, 1-23 (2010) (Year: 2010).*
CAS Abstract of CN 105693805 (Jun. 22, 2016) (Year: 2016).*
English-Language Machine Translation of Y. Gao et al., CN 105693805 A (Jun. 22, 2016) (Year: 2016).*
CAS Abstract of CN 102702190 (2012) (Year: 2012).*
English-Language Machine Translation of Y. Ji et al., CN 102702190 A (2012) (Year: 2012).*
Q. Li et al., 9 Letters in Drug Design & Discovery, 573-580 (2012) (Year: 2012).*
Barrera, J.G. et al. (Jun. 2011). "GLP-1 and energy balance: an integrated model of short-term and long-term control," *Nat Rev Endocrinol* 7(9):507-516.
Berge, S.M. et al. (Jan. 1977). "Pharmaceutical salts," *J Pharm Sci* 66(1):1-19. Brusq, J.M. et al. (Jun. 2006, e-published Feb. 28, 2006). "Inhibition of lipid synthesis through activation of AMP kinase: an additional mechanism for the hypolipidemic effects of berberine," *J Lipid Res* 47(6):1281-1288.
Flegal, K.M. et al. (Jan. 20, 2010, e-published Jan. 13, 2010). "Prevalence and trends in obesity among US adults, 1999-2008," *JAMA* 303(3):235-241.
Forman, B.M. et al. (Jun. 2, 1995). "Identification of a nuclear receptor that is activated by farnesol metabolites," *Cell* 81(5):687-693.
Horuk, R. et al. (May 1994). "Molecular properties of the chemokine receptor family," *Trends Pharmacol Sci* 15(5):159-165.
Kalantzi, L. et al. (Jan. 2006, e-published Dec. 1, 2006). "Characterization of the human upper gastrointestinal contents under conditions simulating bioavailability/bioequivalence studies," *Pharm Res* 23(1):165-176.

(Continued)

*Primary Examiner* — Alexander R Pagano
(74) *Attorney, Agent, or Firm* — Mintz Levin Cohn Ferris Glovsky and Popeo, P.C.; Kenneth E. Jenkins; Joohee Lee

(57) ABSTRACT

Disclosed herein, inter alia, compounds and methods of use thereof for the modulation of bile acid receptor activity.

11 Claims, 15 Drawing Sheets

(56) References Cited

OTHER PUBLICATIONS

Kawamata, Y. et al. (Mar. 14, 2003, e-published Jan. 10, 2003). "A G protein-coupled receptor responsive to bile acids," *J Biol Chem* 278(11):9435-9440.

Ko, B.S. et al. (Aug. 2005). "Insulin sensitizing and insulinotropic action of berberine from Cortidis rhizoma," *Biol Pharm Bull* 28(8):1431-1437.

Li, T. et al. (Jun. 2011, e-published Mar. 31, 2011). "The G protein-coupled bile acid receptor, TGR5, stimulates gallbladder filling," *Mol Endocrinol* 25(6):1066-1071.

Lipinski, C.A. et al. (Mar. 1, 2001). "Experimental and computational approaches to estimate solubility and permeability in drug discovery and development settings," *Adv Drug Deliv Rev* 46(1-3):3-26.

Lu, S.S. et al. (Feb. 2009, e-published Nov. 7, 2008). "Berberine promotes glucagon-like peptide-1 (7-36) amide secretion in streptozotocin-induced diabetic rats," *J Endocrinol* 200(2):159-165.

Maruyama, T. et al. (Nov. 15, 2002). "Identification of membrane-type receptor for bile acids (M-BAR)," *Biochem Biophys Res Comm* 298(5):714-719.

Megyesi, M. et al. (Oct. 2007). "Effect of ion pairing on the fluorescence of berberine, a natural isoquinoline alkaloid," *Chemical Physics Letters* 447(4-6):247-251.

Mercer, S.L. (Apr. 20, 2011). "ACS chemical neuroscience molecule spotlight on Qnexa," *ACS Chem Neurosci* 2(4):183-184.

Naruto, S. et al. (1976). "A Novel Amination of Isoquinolinium Salts via Nucleophilic Substitution Reaction," *Tetrahedron Lett* 17:1597-1600.

Pentikainen, P.J. et al. (Sep. 1979). "Pharmacokinetics of metformin after intravenous and oral administration to man," *Eur J Clin Pharmacol* 16(3):195-202.

Thomas, C. et al. (Aug. 2008). "Targeting bile-acid signalling for metabolic diseases," *Nat Rev Drug Discov* 7(8):678-693.

Yu, D.D. et al. (Apr. 1, 2015). "Stereoselective synthesis, biological evaluation, and modeling of novel bile acid-derived G-protein coupled bile acid receptor 1 (GP-BAR1, TGR5) agonists," *Bioorg Med Chem* 23(7):1613-1628.

Wild, S. et al. (May 2004). "Global prevalence of diabetes: estimates for the year 2000 and projections for 2030," *Diabetes Care* 27(5):1047-1053.

Yu, Y. et al. (Apr. 1, 2010, e-published Nov. 27, 2009). "Modulation of glucagon-like peptide-1 release by berberine: in vivo and in vitro studies," *Biochem Pharmacol* 79(7):1000-1006.

Yu, D.D. et al. (Jun. 2014, e-published Apr. 16, 2014). "Identification of trisubstituted-pyrazol carboxamide analogs as novel and potent antagonists of farnesoid X receptor," *Bioorg Med Chem* 22(11):2919-2938.

Zhang, Y. et al. (Jul. 2008, e-published Apr. 8, 2008). "Treatment of type 2 diabetes and dyslipidemia with the natural plant alkaloid berberine," *J Clin Endocrinol Meta* 93(7):2559-2565.

Zhong, M. et al. (2010). "TGR5 as a therapeutic target for treating obesity," *Curr Top Med Chem* 10(4):386-396.

\* cited by examiner

Berberine chloride

DY433

BILE ACID RECEPTOR MODULATORS AND METHODS OF USE THEREOF

CROSS-REFERENCES TO RELATED APPLICATIONS

This application claims the benefit of U.S. Provisional Patent Application No. 62/409,641, filed Oct. 18, 2016, which is incorporated herein in its entirety and for all purposes.

BACKGROUND

Diabetes is a burgeoning, worldwide health problem affecting almost twenty-six million people in the United States, with obesity-associated type II diabetes (T2D) accounting for ninety-five percent of all diabetes cases. To date, two bile acids (BAs) receptors have been identified: the nuclear farnesoid X receptor (FXR) and the Takeda G-protein-coupled Receptor 5 (TGR5). TGR5 is a cell surface receptor and expressed in monocytes, gall bladder, brown adipose tissue, muscle, liver, and intestine. Its activation by BAs triggers an increase in energy expenditure and attenuates diet-induced obesity. TGR5 activation by BAs, may regulate glucose homeostasis and insulin sensitivity.

Endogenous BAs are the physiological ligands of TGR5 but are, however, very weak TGR5 ligands in the context of both potency and specificity. BAs not only activate TGR5, but also trigger activation of the nuclear receptor FXR. Thus, the identification of selective and potent modulators for TGR5 with enhanced efficacy is of crucial and significant value. Provided herein are solutions to these and other problems in the art.

BRIEF SUMMARY OF THE INVENTION

In a first aspect, there is provided is a compound having the formula:

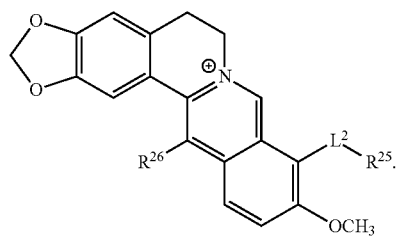

(I)

$L^2$ is a bond, —C(O)—, —C(O)O—, —O—, —S—, —NR$^{2L}$—, —C(O)NR$^{2L}$—, —NR$^{2L}$C(O)—, —S(O)$_2$—, —S(O)NR$^{2L}$—, —NR$^{2L}$C(O)NH—, —NHC(O)NR$^{2L}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^{25}$ is —OCH$_3$, substituted or unsubstituted cycloalkyl, substituted or unsubstituted heterocycloalkyl, substituted or unsubstituted aryl or substituted or unsubstituted heteroaryl. $R^{26}$ is hydrogen, halogen, —CX$^{26}{}_3$, —CHX$^{26}{}_2$, —CH$_2$X$^{26}$, —OCX$^{26}{}_3$, —OCH$_2$X$^{26}$, —OCHX$^{26}{}_2$, —CN, —SO$_{n26}$R$^{26C}$, —SO$_{v26}$NR$^{26A}$R$^{26B}$, —NHC(O)NR$^{26A}$R$^{26B}$, —N(O)$_{m26}$, —NR$^{26A}$R$^{26B}$, —C(O)R$^{26C}$, —C(O)—OR$^{26C}$, —C(O)NR$^{26A}$R$^{26B}$, —OR$^{26C}$, —NR$^{26A}$SO$_2$R$^{26C}$, —NR$^{26A}$C(O)R$^{26C}$, —NR$^{26A}$C(O)OR$^{26C}$, —NR$^{26A}$OR$^{26C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{2L}$, $R^{26A}$, $R^{26B}$ and $R^{26C}$ are independently hydrogen, —CX$^{26A}{}_3$, —CN, —COOH, —CONH$_2$, —CHX$^{26A}{}_2$, —CH$_2$X$^{26A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $X^{26}$ and $X^{26A}$ are independently halogen. n26 is an integer from 0 to 4; and m26 and v26 are independently 1 or 2.

In another aspect, there is provided a composition including a bile acid receptor modulator and compound of the formula:

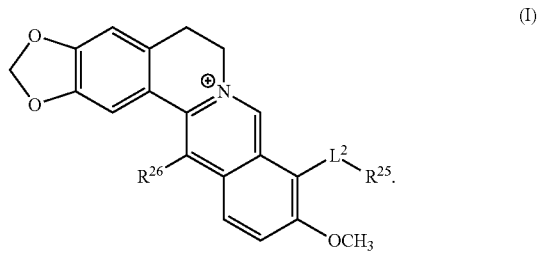

(I)

$L^2$ is a bond, —C(O)—, —C(O)O—, —O—, —S—, —NR$^{2L}$—, —C(O)NR$^{2L}$—, —NR$^{2L}$C(O)—, —S(O)$_2$—, —S(O)NR$^{2L}$—, —NR$^{2L}$C(O)NH—, —NHC(O)NR$^{2L}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^{25}$ is —OCH$_3$, substituted or unsubstituted cycloalkyl, substituted or unsubstituted heterocycloalkyl, substituted or unsubstituted aryl or substituted or unsubstituted heteroaryl. $R^{26}$ is hydrogen, halogen, —CX$^{26}{}_3$, —CHX$^{26}{}_2$, —CH$_2$X$^{26}$, —OCX$^{26}{}_3$, —OCH$_2$X$^{26}$, —OCHX$^{26}{}_2$, —CN, —SO$_{n26}$R$^{26C}$, —SO$_{v26}$NR$^{26A}$R$^{26B}$, —NHC(O)NR$^{26A}$R$^{26B}$, —N(O)$_{m26}$, —NR$^{26A}$R$^{26B}$, —C(O)R$^{26C}$, —C(O)—OR$^{26C}$, —C(O)NR$^{26A}$R$^{26B}$, —OR$^{26C}$, —NR$^{26A}$SO$_2$R$^{26C}$, —NR$^{26A}$C(O)R$^{26C}$, —NR$^{26A}$C(O)OR$^{26C}$, —NR$^{26A}$OR$^{26C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{2L}$, $R^{26A}$, $R^{26B}$ and $R^{26C}$ are independently hydrogen, —CX$^{26A}{}_3$, —CN, —COOH, —CONH$_2$, —CHX$^{26A}{}_2$, —CH$_2$X$^{26A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $X^{26}$ and $X^{26A}$ are independently halogen. n26 is an integer from 0 to 4; and m26 and v26 are independently 1 or 2.

In other aspect, provided is a salt composition having the formula:

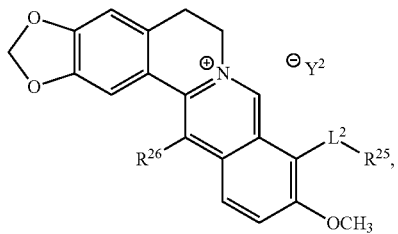

(II)

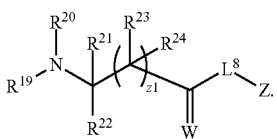

wherein the compound of Formula (I) and the bile acid receptor modulator Y² are ionically bound together to form a salt composition.

In one aspect, provided is a compound having the formula:

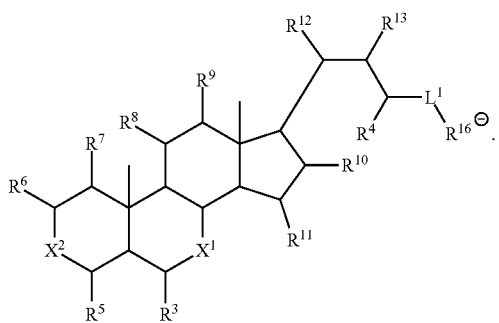

(III)

$L^1$ is a bond, —C(O)—, —C(O)O—, —C(O)NH—, or —CH$_2$—. $X^1$ is —C(O)— or —C(R$^1$)(R$^2$)—. $X^2$ is —C(O)— or —C(R$^{14}$)(R$^{15}$)—. $R^1$ is hydrogen, unsubstituted alkyl, or —OR$^{1A}$. $R^2$ is hydrogen, unsubstituted alkyl, or —OR$^{2A}$. $R^3$ is hydrogen, unsubstituted alkyl, or —OR$^{3A}$. $R^4$ is hydrogen or unsubstituted alkyl. $R^5$ is hydrogen, unsubstituted alkyl, or —OR$^{5A}$. $R^6$ is hydrogen, unsubstituted alkyl, or —OR$^{6A}$. $R^7$ is hydrogen, unsubstituted alkyl, or —OR$^{7A}$. $R^8$ is hydrogen, unsubstituted alkyl, or —OR$^{8A}$. $R^9$ is hydrogen, unsubstituted alkyl, or —OR$^{9A}$. $R^{10}$ is hydrogen, unsubstituted alkyl, or —OR$^{10A}$. $R^{11}$ is hydrogen, unsubstituted alkyl, or —OR$^{11A}$. $R^{12}$ is hydrogen, unsubstituted alkyl, or —OR$^{12A}$. $R^{13}$ is hydrogen, unsubstituted alkyl, or —OR$^{13A}$. $R^{14}$ is hydrogen, unsubstituted alkyl, or —OR$^{14A}$. $R^{15}$ is hydrogen, unsubstituted alkyl, or —OR$^{15A}$. $R^{16}$ is —COO⁻, —S(O)$_3$⁻, —SO$_4$⁻ or —NHS(O)$_3$⁻. $R^{1A}$, $R^{2A}$, $R^{3A}$, $R^{5A}$, $R^{6A}$, $R^{7A}$, $R^{8A}$, $R^{9A}$, $R^{10A}$, $R^{11A}$, $R^{12A}$, $R^{13A}$, $R^{14A}$, and $R^{15A}$ are independently hydrogen, unsubstituted alkyl, or an alcohol protecting group.

In one aspect, provided is a compound having the formula:

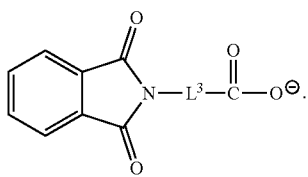

(IV)

$L^3$ is substituted or unsubstituted alkylene.

In one aspect, provided is a compound having the formula:

(V)

W is ═O or ═S. Z is hydrogen, —OR$^{27A}$, —CX$^{27}_3$, —CHX$^{27}_2$, —CH$_2$X$^{27}$, —OCX$^{27}_3$, —OCH$_2$X$^{27}$, —OCHX$^{27}_2$, —CN, —SO$_{n27}$R$^{27D}$, —SO$_{v27}$NR$^{27A}$R$^{27B}$, —NHC(O)NR$^{27A}$R$^{27B}$, —N(O)$_{m27}$, —NR$^{27A}$R$^{27B}$, —C(O) R$^{27C}$, —C(O)—OR$^{27C}$, —C(O)NR$^{27A}$R$^{27B}$, —OR$^{27C}$, —NR$^{27A}$SO$_2$R$^{27C}$, —NR$^{27A}$C(O)R$^{27C}$, —NR$^{27A}$C(O) OR$^{27C}$, —NR$^{27A}$OR$^{27C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, —O⁻, —C(O)O⁻, —CH$_2$C(O) O⁻, —SO$_3$⁻, —SO$_4$⁻, —NHS(O)$_3$⁻, —NR$^{27A}$SO$_3$⁻, —NR$^{27A}$C(O)O⁻, —NR$^{27A}$O⁻; or negatively charged carbohydrate, peptide, nucleic acid or amino acid. $L^8$ is a bond, —C(O)—, —C(O)O—, —O—, —S—, —NR$^{8L}$—, —C(O) NR$^{8L}$—, —NR$^{8L}$C(O)—, —S(O)$_2$—, —O—S(O)$_2$NR$^{8L}$—, —NR$^{8L}$C(O)NH—, —NHC(O)NR$^{8L}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^{19}$ and $R^{20}$ are independently, hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $R^{19}$ and $R^{20}$ substituents bonded to the same nitrogen atom may optionally be joined to form a substituted or unsubstituted heterocycloalkyl or substituted or unsubstituted heteroaryl. $R^{21}$ is hydrogen, halogen, —CX$^{21}_3$, —CHX$^{21}_2$, —CH$_2$X$^{21}$, —CN, —SO$_{n21}$R$^{21D}$, —SO$_{v21}$NR$^{21A}$R$^{21B}$, —NHC(O)NR$^{21A}$R$^{21B}$, —N(O)$_{m21}$, —NR$^{21A}$R$^{21B}$, —C(O) R$^{21C}$, —C(O)—OR$^{21C}$, —C(O)NR$^{21A}$R$^{21B}$, —OR$^{21D}$, —NR$^{21A}$SO$_2$R$^{21D}$, —NR$^{21A}$C(O)R$^{21C}$, —NR$^{21A}$C(O) OR$^{21C}$, —NR$^{21A}$OR$^{21C}$, —OCX$^{21}_3$, —OCHX$^{21}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{21A}$ and $R^{21B}$ substituents bonded to the same nitrogen atom may optionally be joined to form a substituted or unsubstituted heterocycloalkyl or substituted or unsubstituted heteroaryl. $R^{22}$ is hydrogen, halogen, —CX$^{22}_3$, —CHX$^{22}_2$, —CH$_2$X$^{22}$, —CN, —SO$_{n22}$R$^{22D}$, —SO$_{v22}$NR$^{22A}$R$^{22B}$, —NHC(O)NR$^{22A}$R$^{22B}$, —N(O)$_{m22}$, —NR$^{22A}$R$^{22B}$, —C(O) R$^{22C}$, —C(O)—OR$^{22C}$, —C(O) NR$^{22A}$R$^{22B}$, —OR$^{22D}$, —NR$^{22A}$SO$_2$R$^{22D}$, —NR$^{22A}$C(O) R$^{22C}$, —NR$^{22A}$C(O)OR$^{22C}$, —NR$^{22A}$OR$^{22C}$, —OCX$^{22}_3$, —OCHX$^{22}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{22A}$ and $R^{22B}$ substituents bonded to the same nitrogen atom may optionally be joined to form a substituted or unsubstituted heterocycloalkyl or substituted or unsubstituted heteroaryl. $R^{23}$ is hydrogen, halogen, —$CX^{23}_3$, —$CHX^{23}_2$, —$CH_2X^{23}$, —CN, —$SO_{n23}R^{23D}$, —$SO_{v23}NR^{23A}R^{23B}$, —$NHC(O)NR^{23A}R^{23B}$, —$N(O)_{m23}$, —$NR^{23A}R^{23B}$, —$C(O)R^{23C}$, —$C(O)$—$OR^{23C}$, —$C(O)NR^{23A}R^{23B}$, —$OR^{23D}$, —$NR^{23A}SO_2R^{23D}$, —$NR^{23A}C(O)R^{23C}$, —$NR^{23A}C(O)OR^{23C}$, —$NR^{23A}OR^{23C}$, —$OCX^{23}_3$, —$OCHX^{23}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{23A}$ and $R^{23B}$ substituents bonded to the same nitrogen atom may optionally be joined to form a substituted or unsubstituted heterocycloalkyl or substituted or unsubstituted heteroaryl. $R^{24}$ is hydrogen, halogen, —$CX^{24}_3$, —$CHX^{24}_2$, —$CH_2X^{24}$, —CN, —$SO_{n24}R^{24D}$, —$SO_{v24}NR^{24A}R^{24B}$, —$NHC(O)NR^{24A}R^{24B}$, —$N(O)_{m24}$, —$NR^{24A}R^{24B}$, —$C(O)R^{24C}$, —$C(O)$—$OR^{24C}$, —$C(O)NR^{24A}R^{24B}$, —$OR^{24D}$, —$NR^{24A}SO_2R^{24D}$, —$NR^{24A}C(O)R^{24C}$, —$NR^{24A}C(O)OR^{24C}$, —$NR^{24A}OR^{24C}$, —$OCX^{24}_3$, —$OCHX^{24}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{24A}$ and $R^{24B}$ substituents bonded to the same nitrogen atom may optionally be joined to form a substituted or unsubstituted heterocycloalkyl or substituted or unsubstituted heteroaryl. $R^{8L}$, $R^{21A}$, $R^{21B}$, $R^{21C}$, $R^{21D}$, $R^{22A}$, $R^{22B}$, $R^{22C}$, $R^{22D}$, $R^{23A}$, $R^{23B}$, $R^{23C}$, $R^{23D}$, $R^{24A}$, $R^{24B}$, $R^{24C}$, $R^{24D}$, $R^{27A}$, $R^{27B}$, $R^{27C}$ and $R^{27D}$ are independently hydrogen, —$CF_3$, —$CCl_3$, —$CBr_3$, —$CI_3$, —CN, —COOH, —$CONH_2$, —$CHF_2$, —$CHCl_2$, —$CHBr_2$, —$CHI_2$, —$CH_2F_2$, —$CH_2Cl$, —$CH_2Br$, —$CH_2I$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $X^{21}$, $X^{22}$, $X^{23}$, $X^{24}$ and $X^{27}$ are independently halogen. z1 is an integer from 0 to 12. n21, n22, n23, n24 and n27 are independently an integer from 0 to 4. m21, m22, m23, m24; m27, v21, v22, v23, v24 and v27 are independently 1 or 2.

In another aspect, there is provided a compound having the formula:

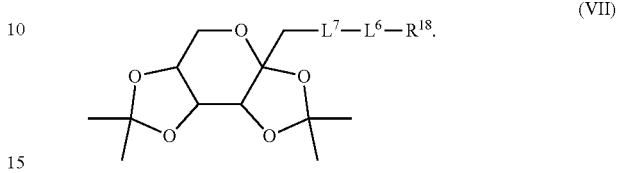

(VI)

$L^4$ is a bond, —$NR^{4L}$—, —$NR^{4L}C(O)$—, —$NR^{4L}C(O)$—$S(O)_2$—O—, —$NR^{4L}C(O)$—$S(O)_2$—O—$CH_2$—, —$NR^{4L}$—$S(O)_2$—O—$CH_2$—, —$S(O)_2$—, —O— —$NR^{4L}C(O)NH$—, —$NHC(O)NR^{4L}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $L^5$ is substituted or unsubstituted alkylene. $R^{17}$ is —OH, substituted or unsubstituted cycloalkyl, substituted or unsubstituted heterocycloalkyl, substituted or unsubstituted aryl or substituted or unsubstituted heteroaryl. $R^{4L}$ is hydrogen, —$CX^{4L}_3$, —CN, —COOH, —$CONH_2$, —$CHX^{4L}_2$, —$CH_2X^{4L}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $X^{4L}$ is halogen.

In another aspect, there is provided a compound of the formula:

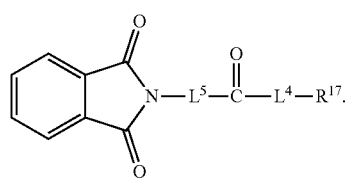

(VII)

$L^6$ is a substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $L^7$ is a bond, —C(O)—, —C(O)O—, —O—, —S—, —$NR^{7L}$—, —$C(O)NR^{7L}$—, —$NR^{7L}C(O)$—, —$S(O)_2$—, —O—$S(O)_2NR^{7L}$—, —O—$S(O)_2NR^{7L}C(O)$—, —$NR^{7L}C(O)NH$—, —$NHC(O)NR^{7L}$. $R^{18}$ is —$NH_2$ or

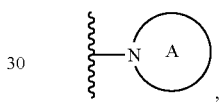

wherein ring A is a substituted or unsubstituted heteroaryl or substituted or unsubstituted heterocycloalkyl. $R^{7L}$ is hydrogen, —$CX^{7L}_3$, —CN, —COOH, —$CONH_2$, —$CHX^{7L}_2$, —$CH_2X^{7L}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $X^{7L}$ is halogen.

In another aspect, there is provided a method of activating TGR5 in a cell. The method includes contacting TGR5 with a compound or a composition disclosed herein.

In another aspect, there is provided a method of inhibiting FXR in a cell. The method includes contacting FXR with a compound or a composition disclosed herein.

In another aspect, there is provided a method of treating or preventing a TGR5-mediated disease or disorder. The method includes administering to a subject in need thereof a therapeutically effective amount of a compound or a composition disclosed herein.

In another aspect, there is provided a method of treating or preventing an FXR-mediated disease or disorder. The method includes administering to a subject in need thereof a therapeutically effective amount of a compound or a composition disclosed herein.

BRIEF DESCRIPTION OF THE DRAWINGS

FIG. 1(A-C)

FIG. 2: The natural compound berberine is a ligand for the G protein-coupled receptor TGR5.

DETAILED DESCRIPTION OF THE INVENTION

Definitions

Figures 1A, 1B, 1C:
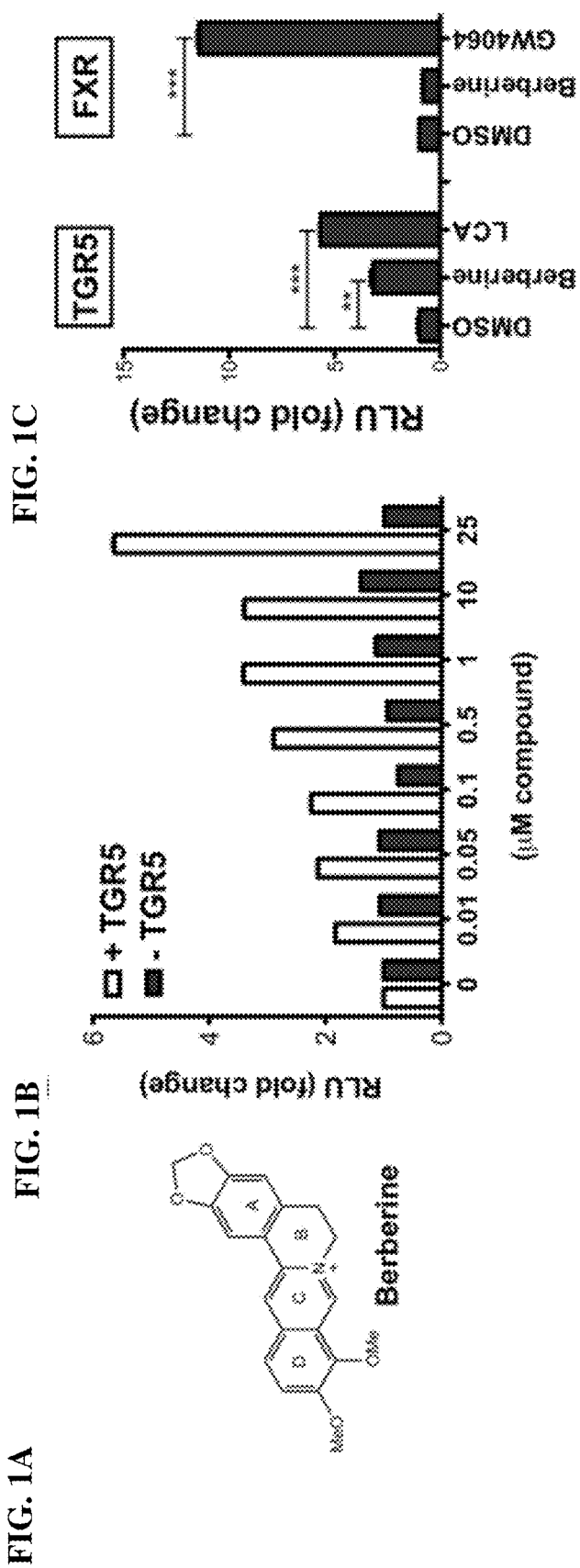
FIG. 1(A) Chemical structure of berberine.
FIG. 1(B) HEK293 cells lacking or stably-overexpressing TGR5 were treated with increasing doses of berberine for 16 h. TGR5-reporting activity was evaluated by luciferase assay (n=8).
FIG. 1(C) The ability of berberine to activate TGR5 and FXR was evaluated in comparison to the synthetic FXR agonist GW4064. Ligands were used at a concentration of 10 mM (n=4). Statistical analysis was performed using paired t-test. p<0.05, *p<0.001.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., C$_1$-C$_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., N, S, Si, or P) may be placed at any interior position of the heteroalkyl group or at the position at which the alkyl group is attached to the remainder of the molecule. Heteroalkyl is an uncyclized chain. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH-$_2$-CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(C$_1$-C$_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocyclic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "⤳" denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkylene moiety (also referred to herein as an alkylene linker). In embodiments, the alkylarylene group has the formula:

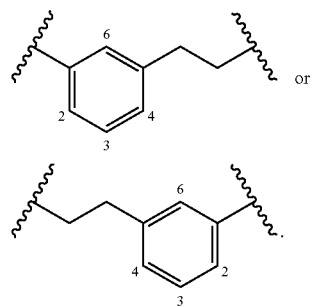

An alkylarylene moiety may be substituted (e.g. with a substituent group) on the alkylene moiety or the arylene linker (e.g. at carbons 2, 3, 4, or 6) with halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$CH$_3$— SO$_3$H, —OSO$_3$H, —SO$_2$NH$_2$, —NHNH$_2$, —ONH$_2$, —NHC(O)NHNH$_2$, substituted or unsubstituted C$_1$-C$_8$ alkyl or substituted or unsubstituted 2 to 5 membered heteroalkyl). In embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"R'"R"", —CN, —NO$_2$, —NR'SO$_2$R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO₂R', —CONR'R", —OC(O)NR'R", —NR"C(O)R', —NR', —C(O)NR"R'", —NR"C(O)₂R', —NR—C(NR'R"R'")=NR"", —NR—C(NR'R")=NR'", —S(O)R', —S(O)₂R', —S(O)₂NR'R", —NRSO₂R', —NR'NR"R'", —ONR'R", —NR'C(O)NR"NR'"R"", —CN, —NO₂, —R', —N₃, —CH(Ph)₂, fluoro(C₁-C₄)alkoxy, and fluoro(C₁-C₄)alkyl, —NR'SO₂R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH₂)$_r$—B—, wherein A and B are independently —CRR'—, —O—, —NR—, —S—, —S(O)—, —S(O)₂—, —S(O)₂NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R'")$_d$—, where s and d are independently integers of from 0 to 3, and X' is —O—, —NR'—, —S—, —S(O)—, —S(O)₂—, or —S(O)₂NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), boron (B) and silicon (Si).

A "substituent group," as used herein, means a group selected from the following moieties:

(A) oxo,
halogen, —CCl₃, —CBr₃, —CF₃, —CI₃, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, unsubstituted alkyl (e.g., C₁-C₈ alkyl, C₁-C₆ alkyl, or C₁-C₄ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C₃-C₈ cycloalkyl, C₃-C₆ cycloalkyl, or C₅-C₆ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C₆-C₁₀ aryl, C₁₀ aryl, or phenyl), or unsubstituted heteroaryl (e.g., 5 to 10 membered heteroaryl, 5 to 9 membered heteroaryl, or 5 to 6 membered heteroaryl), and (B) alkyl, heteroalkyl, cycloalkyl, heterocycloalkyl, aryl, heteroaryl, substituted with at least one substituent selected from:
(i) oxo,
halogen, —CCl₃, —CBr₃, —CF₃, —CI₃, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, unsubstituted alkyl (e.g., C₁-C₈ alkyl, C₁-C₆ alkyl, or C₁-C₄ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C₃-C₈ cycloalkyl, C₃-C₆ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl, heteroalkyl, cycloalkyl, heterocycloalkyl, aryl, heteroaryl, substituted with at least one substituent selected from:

(a) oxo,
halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl, heteroalkyl, cycloalkyl, heterocycloalkyl, aryl, heteroaryl, substituted with at least one substituent selected from: oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted C$_1$-C$_{20}$ alkylene, each substituted or unsubstituted heteroalkylene is a substituted or unsubstituted 2 to 20 membered heteroalkylene, each substituted or unsubstituted cycloalkylene is a substituted or unsubstituted C$_3$-C$_8$ cycloalkylene, each substituted or unsubstituted heterocycloalkylene is a substituted or unsubstituted 3 to 8 membered heterocycloalkylene, each substituted or unsubstituted arylene is a substituted or unsubstituted C$_6$-C$_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted C$_1$-C$_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

Certain compounds of the present disclosure possess asymmetric carbon atoms (optical or chiral centers) or double bonds; the enantiomers, racemates, diastereomers, tautomers, geometric isomers, stereoisomeric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

A "detectable agent" or "detectable moiety" is an agent or moiety of an agent, respectively, which is detectable by appropriate means such as spectroscopic, photochemical, biochemical, immunochemical, chemical, magnetic resonance imaging, or other physical means. For example, useful detectable agents include $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y, $^{90}$Y, $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154\text{-}158}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra, $^{225}$Ac, Cr, V, Mn, Fe, Co, Ni, Cu, La, Ce, Pr, Nd, Pm, Sm, Eu, Gd, Tb, Dy, Ho, Er, Tm, Yb, Lu, $^{32}$P, fluorophore (e.g. fluorescent dyes), electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monochrystalline iron oxide nanoparticles, monochrystalline iron oxide, nanoparticle contrast agents, liposomes or other delivery vehicles containing Gadolinium chelate ("Gd-chelate") molecules, Gadolinium, radioisotopes, radionuclides (e.g. carbon-11, nitrogen-13, oxygen-15, fluorine-18, rubidium-82), fluorodeoxyglucose (e.g. fluorine-18 labeled), any gamma ray emitting radionuclides, positron-emitting radionuclide, radiolabeled glucose, radiolabeled water, radiolabeled ammonia, biocolloids, microbubbles (e.g. including microbubble shells including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agents (e.g. iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide. A detectable moiety is a monovalent detectable agent or a detectable agent capable of forming a bond with another composition.

Radioactive substances (e.g., radioisotopes) that may be used as imaging and/or labeling agents in accordance with the embodiments of the disclosure include, but are not limited to, $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y, $^{90}$Y, $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154\text{-}158}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra and $^{225}$Ac. Paramagnetic ions that may be used as additional imaging agents in accordance with the embodiments of the disclosure include, but are not limited to, ions of transition and lanthanide metals (e.g. metals having atomic numbers of 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb and Lu.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "leaving group" is used in accordance with its ordinary meaning in chemistry and refers to a moiety (e.g., atom, functional group, molecule) that separates from the molecule following a chemical reaction (e.g., bond formation, reductive elimination, condensation, cross-coupling reaction) involving an atom or chemical moiety to which the leaving group is attached, also referred to herein as the "leaving group reactive moiety", and a complementary reactive moiety (i.e. a chemical moiety that reacts with the leaving group reactive moiety) to form a new bond between the remnants of the leaving groups reactive moiety and the complementary reactive moiety. Thus, the leaving group reactive moiety and the complementary reactive moiety form a complementary reactive group pair. Non limiting examples of leaving groups include hydrogen, hydroxide, organotin moieties (e.g., organotin heteroalkyl), halogen (e.g., Br), perfluoroalkylsulfonates (e.g. triflate), tosylates, mesylates, water, alcohols, nitrate, phosphate, thioether, amines, ammonia, fluoride, carboxylate, phenoxides, boronic acid, boronate esters, and alkoxides. In embodiments, two molecules with leaving groups are allowed to contact, and upon a reaction and/or bond formation (e.g., acyloin condensation, aldol condensation, Claisen condensation, Stille reaction) the leaving groups separates from the respective molecule. In embodiments, a leaving group is a bioconjugate reactive moiety. In embodiments, at least two leaving groups (e.g., $R^1$ and $R^{13}$) are allowed to contact such that the leaving groups are sufficiently proximal to react, interact or physically touch. In embodiments, the leaving groups is designed to facilitate the reaction.

The term "protecting group" is used in accordance with its ordinary meaning in organic chemistry and refers to a moiety covalently bound to a heteroatom, heterocycloalkyl, or heteroaryl to prevent reactivity of the heteroatom, heterocycloalkyl, or heteroaryl during one or more chemical reactions performed prior to removal of the protecting group. Typically a protecting group is bound to a heteroatom (e.g., O) during a part of a multipart synthesis wherein it is not desired to have the heteroatom react (e.g., a chemical reduction) with the reagent. Following protection the protecting group may be removed (e.g., by modulating the pH). In embodiments the protecting group is an alcohol protecting group. Non-limiting examples of alcohol protecting groups include acetyl, benzoyl, benzyl, methoxymethyl ether (MOM), tetrahydropyranyl (THP), and silyl ether (e.g., trimethylsilyl (TMS)). In embodiments the protecting group is an amine protecting group. Non-limiting examples of amine protecting groups include carbobenzyloxy (Cbz), tert-butyloxycarbonyl (BOC), 9-Fluorenylmethyloxycarbonyl (FMOC), acetyl, benzoyl, benzyl, carbamate, p-methoxybenzyl ether (PMB), and tosyl (Ts).

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present disclosure contain both basic and acidic functionalities that allow the compounds to be converted into either base or acid addition salts.

Thus, the compounds of the present disclosure may exist as salts, such as with pharmaceutically acceptable acids. The present disclosure includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents. In embodiments, compounds of the present disclosure contain both basic and acidic functionalities that allow the compounds to be converted into either base or acid addition salts. The neutral forms of the compounds may be regenerated by contacting the salt with a base or acid and isolating the parent compound in a conventional manner. The parent form of the compounds differs from the various salt forms in certain physical properties, such as solubility in polar solvents, but, unless specifically indicated, the salts disclosed herein are equivalent to the parent form of the compound for the purposes of the present disclosure.

In addition to salt forms, the present disclosure provides compounds which are in a prodrug form. Prodrugs of the compounds described herein are those compounds that readily undergo chemical changes under physiological conditions to provide the compounds of the present disclosure. Prodrugs of the compounds described herein may be converted in vivo after administration. Additionally, prodrugs can be converted to the compounds of the present disclosure by chemical or biochemical methods in an ex vivo environment, such as, for example, when contacted with a suitable enzyme or chemical reagent.

Thus, the compounds of the present disclosure may exist as salts, such as with pharmaceutically acceptable acids. The present disclosure includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present disclosure provides compounds, which are in a prodrug form. Prodrugs of the compounds described herein are those compounds that readily undergo chemical changes under physiological conditions to provide the compounds of the present disclosure. Prodrugs of the compounds described herein may be converted in vivo after administration. Additionally, prodrugs can be converted to the compounds of the present disclosure by chemical or biochemical methods in an ex vivo environment, such as, for example, when contacted with a suitable enzyme or chemical reagent.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

"Pharmaceutically acceptable excipient" and "pharmaceutically acceptable carrier" refer to a substance that aids the administration of an active agent to and absorption by a subject and can be included in the compositions of the present disclosure without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure. One of skill in the art will recognize that other pharmaceutical excipients are useful in the present disclosure.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

A "TGR5 activator" refers to a compound (e.g., compounds described herein) that promotes, activates, or increases the activity of TGR5 when compared to a control, such as absence of the compound or a compound with known inactivity.

An "FXR inhibitor" refers to a compound (e.g. compounds described herein) that reduces the activity of FXR when compared to a control, such as absence of the compound or a compound with known inactivity.

The terms "polypeptide," "peptide" and "protein" are used interchangeably herein to refer to a polymer of amino acid residues, wherein the polymer may in embodiments be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single protein.

As may be used herein, the terms "nucleic acid," "nucleic acid molecule," "nucleic acid oligomer," "oligonucleotide," "nucleic acid sequence," "nucleic acid fragment" and "polynucleotide" are used interchangeably and are intended to include, but are not limited to, a polymeric form of nucleotides covalently linked together that may have various lengths, either deoxyribonucleotides or ribonucleotides, or analogs, derivatives or modifications thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the disclosure may comprise natural nucleic acid sequences and variants thereof, artificial nucleic acid sequences, or a combination of such sequences.

As may be used herein, the term "derivative" or "derivatives" refers to compounds set forth in one or more derivatized forms of the compounds, which include but not limited to salts, metabolites, prodrugs, isomers, crystals, polymorphs, analogues, solvates, hydrates of the compounds.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway (e.g., MAP kinase pathway).

As defined herein, the term "activation", "activate", "activating" and the like in reference to a protein refers to conversion of a protein into a biologically active derivative from an initial inactive or deactivated state. The terms reference activation, or activating, sensitizing, or up-regulating signal transduction or enzymatic activity or the amount of a protein decreased in a disease.

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In embodiments inhibition means negatively affecting (e.g. decreasing) the concentration or levels of the protein relative to the concentration or level of the protein in the absence of the inhibitor. In embodiments inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g. an inhibitor binds to a protein that activates the target protein, thereby preventing target protein activation). A "FXR inhibitor" is a compound that negatively affects (e.g. decreases) the activity or function of FXR relative to the activity or function of FXR in the absence of the inhibitor.

The terms "inhibitor," "repressor" or "antagonist" or "downregulator" interchangeably refer to a substance capable of detectably decreasing the expression or activity of a given gene or protein. The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist.

As defined herein, the term "activation", "activate," "activating" and the like in reference to a protein-activator interaction means positively affecting (e.g., increasing) the activity or function of the protein relative to the activity or function of the protein in the absence of the activator. In embodiments activation means positively affecting (e.g., increasing) the concentration or levels of the protein relative to the concentration or level of the protein in the absence of the activator. In embodiments activation refers to reduction of a disease or symptoms of disease. In embodiments, activation refers to an increase in the activity of a particular protein target. Thus, activation includes, at least in part, partially or totally stimulation, increasing, promoting, or enhancing activation, or activating, sensitizing, or up-regulating signal transduction or enzymatic activity or the amount of a protein. In embodiments, activation refers to an increase in activity of a target protein resulting from a direct interaction (e.g. an activator binds to the target protein). In embodiments, activation refers to an increase in activity of a target protein from an indirect interaction (e.g., an activator binds to a protein that activates the target protein, thereby promoting target protein activation).

The terms "activator," "promoter" or "agonist" or "upregulator" interchangeably refer to a substance capable of detectably increasing the expression or activity of a given gene or protein. The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist. An agonist prevents, reduces, inhibits, or neutralizes the activity of an antagonist, and an agonist can also prevent, reduce, inhibit, or neutralize constitutive activity of a target, e.g., a target receptor, even where there is no identified antagonist. In embodiments, activators are molecules that increase, stimulate, enhance, promote activation, activate, sensitize, or up-regulate, e.g., a gene, protein, ligand, receptor, or cell. An activator may also be defined as a molecule that promotes, enhances, increases or activates a constitutive activity. An "agonist" is a molecule that opposes the action(s) of an antagonist.

The terms "Takeda G-protein-coupled Receptor 5" and "TGR5" refer to a protein (including homologs, isoforms, and functional fragments thereof) and is a G protein-coupled receptor (GPCR), activation of which promotes secretion of glucagon-like peptide-1 (GLP-1) and modulates insulin secretion. The term includes any recombinant or naturally-occurring form of TGR5 variants thereof that maintain TGR5 activity (e.g. within at least 1%, 5%, 10%, 20%, 30%, 40%, 50%, 60%, 70%, 80%, 90%, 95%, or 100% activity compared to wildtype TGR5). The term includes any mutant form of TGR5 variants (e.g., frameshift mutations) thereof that maintain TGR5 activity (e.g., within at least 1%, 5%, 10%, 20%, 30%, 40%, 50%, 60%, 70%, 80%, 90%, 95%, or 100% activity compared to wildtype TGR5). In embodiments, the TGR5 protein encoded by the TGR5 gene has the amino acid sequence set forth in or corresponding to Entrez 1233, UniProt P51679, or RefSeq (protein) NP_005499.1. In embodiments, the TGR5 gene has the nucleic acid sequence set forth in RefSeq (mRNA) NM_005508. In embodiments, the amino acid sequence or nucleic acid sequence is the sequence known at the time of filing of the present application. In embodiments, the sequence corresponds to GI:5031627. In embodiments, the sequence corresponds to NP_005499.1. In embodiments, the sequence corresponds to NM_005508.4. In embodiments, the sequence corresponds to GI:48762930. In embodiments, the TGR5 is a human TGR5. The genomic sequence of TGR5 is present on chromosome 3 (NC_000003.12), and the TGR5 gene is conserved in a number of species, including chimpanzee, Rhesus monkey, dog, cow, mouse, rat, chicken, and zebrafish. The TGR5 polypeptide comprises 360 amino acid residues (NP_005499.1), and, like other chemokine receptors, TGR5 is a G protein-coupled receptor found on the surface of leukocytes (see Horuk (1994) Trends Pharm. Sci. 15:159-165).

The terms "Farnesoid X Receptor" and "FXR" refer to a protein (including homologs, isoforms, and functional fragments thereof) and is a member of the bile acid nuclear hormone receptor superfamily, is a ligand-dependent transcription factor that regulates gene networks involved in regulating lipid and cholesterol homeostasis. The term includes any recombinant or naturally-occurring form of FXR variants thereof that maintain FXR activity (e.g. within at least 30%, 40%, 50%, 60%, 70%, 80%, 90%, 95%, or 100% activity compared to wildtype FXR). The term includes any mutant form of FXR variants (e.g., frameshift mutations) thereof that maintain FXR activity (e.g., within at least 30%, 40%, 50%, 60%, 70%, 80%, 90%, 95%, or 100% activity compared to wildtype FXR). In embodiments, the FXR protein encoded by the FXR gene has the amino acid sequence set forth in or corresponding to Entrez 9971, UniProt NR1H4, or RefSeq (protein) NP_001193906. In embodiments, the FXR gene has the nucleic acid sequence set forth in RefSeq (mRNA), NM_001206977, NM_001206978, NM_001206979, NM_001206992, NM_001206993, NM_005123, NM_001163504, NM_001163700, or NM_009108. In embodiments, the amino acid sequence or nucleic acid sequence is the sequence known at the time of filing of the present application. In embodiments, the sequence corresponds to NP_001193906, NP_001193907, NP_001193908, NP_001193921, NP_001193922, NP_005114, NP_001193906.1, NP_001193908.1, NP_001156976, NP_001157172, or NP_033134. In embodiments, the FXR is a human FXR. The genomic sequence of human FXR is present on chromosome 12 (NC_000012.12), and the FXR gene is conserved in a number of species, including chimpanzee, Rhesus monkey, dog, cow, mouse, rat, chicken, and zebrafish. The FXR polypeptide comprises 476 amino acid residues (NP_001193906), and, like other chemokine receptors, FXR is a G protein-coupled receptor found on the surface of leukocytes (see Horuk (1994) Trends Pharm. Sci. 15:159-165).

The term "bile acid receptor" refer to a receptor that binds to a bile acid. In embodiments, the bile acid receptor is a nuclear receptor, also referred to herein as a bile acid nuclear receptor. Bile acid nuclear receptors typically respond to bile acids by activating transcriptional networks and/or signaling cascades. In embodiments, the bile acid receptor is a farnesoid X receptor or a TGR5 receptor.

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The terms "disease" or "condition" refer to a state of being or health status of a patient or subject capable of being treated with the compounds or methods provided herein. The disease may be a cancer. The disease may be an autoimmune disease. The disease may be an inflammatory disease. The disease may be an infectious disease. In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including MDS, AML, ALL, ATLL and CML), or multiple myeloma.

As used herein, the term "inflammatory disease" refers to a disease or condition characterized by aberrant inflammation (e.g. an increased level of inflammation compared to a control such as a healthy person not suffering from a disease). Examples of inflammatory diseases include autoimmune diseases, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, ischemia reperfusion injury, stroke, sarcoidosis, transplant rejection, interstitial cystitis, atherosclerosis, scleroderma, and atopic dermatitis. Such conditions are frequently inextricably intertwined with other diseases, disorders and conditions. A non-limiting list of inflammatory-related diseases, disorders and conditions which may, for example, be caused by inflammatory cytokines, include, arthritis, kidney failure, lupus, asthma, psoriasis, colitis, pancreatitis, allergies, fibrosis, surgical complications (e.g., where inflammatory cytokines prevent healing), anemia, and fibromyalgia. Other diseases and disorders, which may be associated with chronic inflammation include Alzheimer's disease, congestive heart failure, stroke, aortic valve stenosis, arteriosclerosis, osteoporosis, Parkinson's disease, infections, inflammatory bowel disease (IBD), allergic contact dermatitis and other eczemas, systemic sclerosis, transplantation and multiple sclerosis. Some of the aforementioned diseases, disorders and conditions for which a compound of the present disclosure may be particularly efficacious (due to, for example, limitations of current therapies) are described in more detail hereafter.

As used herein, the term "cancer" refers to all types of cancer, neoplasm or malignant tumors found in mammals (e.g. humans), including leukemia, carcinomas and sarcomas. Exemplary cancers that may be treated with a compound or method provided herein include brain cancer, glioma, glioblastoma, neuroblastoma, prostate cancer, colorectal cancer, pancreatic cancer, cervical cancer, gastric cancer, ovarian cancer, lung cancer, and cancer of the head. Exemplary cancers that may be treated with a compound or method provided herein include cancer of the thyroid, endocrine system, brain, breast, cervix, colon, head & neck, liver, kidney, lung, non-small cell lung, melanoma, mesothelioma, ovary, sarcoma, stomach, uterus, Medulloblastoma, colorectal cancer, pancreatic cancer. Additional examples include, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abernethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma *mucosum*, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

As used herein, the term "autoimmune disease" refers to a disease or condition in which a subject's immune system has an aberrant immune response against a substance that does not normally elicit an immune response in a healthy subject. Examples of autoimmune diseases that may be treated with a compound, pharmaceutical composition, or method described herein include Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal or neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic esophagitis, Eosinophilic fasciitis, Erythema nodosum, Experimental allergic encephalomyelitis, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Type 1 diabetes, Ulcerative colitis, Undifferentiated connective tissue disease (UCTD), Uveitis, Vasculitis, Vesiculobullous dermatosis, Vitiligo, or Wegener's granulomatosis (i.e., Granulomatosis with Polyangiitis (GPA).

As used herein, the term "inflammatory disease" refers to a disease or condition characterized by aberrant inflammation (e.g. an increased level of inflammation compared to a control such as a healthy person not suffering from a disease). Examples of inflammatory diseases include traumatic brain injury, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, asthma, allergic asthma, acne vulgaris, celiac disease, chronic prostatitis, inflammatory bowel disease, pelvic inflammatory disease, reperfusion injury, sarcoidosis, transplant rejection, interstitial cystitis, atherosclerosis, and atopic dermatitis.

The terms "treating" or "treatment" refer to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In embodiments, treating is preventing. In embodiments, treating does not include preventing.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms, fully or partially remove the disease's underlying cause, shorten a disease's duration, or do a combination of these things.

"Treating" and "treatment" as used herein include prophylactic treatment. Treatment methods include administering to a subject a therapeutically effective amount of a compound described herein. The administering step may consist of a single administration or may include a series of administrations. The length of the treatment period depends on a variety of factors, such as the severity of the condition, the age of the patient, the concentration of the compound, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient.

The term "prevent" refers to a decrease in the occurrence of disease symptoms in a patient. As indicated above, the prevention may be complete (no detectable symptoms) or partial, such that fewer symptoms are observed than would likely occur absent treatment. In embodiments, prevent refers to slowing the progression of the disease, disorder or condition or inhibiting progression thereof to a harmful or otherwise undesired state.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

The term "diabetes" as used herein refers to onset and inducement of diabetes mellitus in any manner and includes type 1, type 2, gestational, steroid-induced, HIV treatment induced and autoimmune diabetes. Diabetes is recognized as a complex, chronic disease in which 60% to 70% of all case fatalities among diabetic patients are a result of cardiovascular complications. Diabetes is not only considered a coronary heart disease risk equivalent but is also identified as an independent predictor of adverse events, including recurrent myocardial infarction, congestive heart failure, and death following a cardiovascular incident. The adoption of tighter glucose control and aggressive treatment for cardiovascular risk factors would be expected to reduce the risk of coronary heart disease complications and improve overall survival among diabetic patients. Yet, diabetic patients are two to three times more likely to experience an acute myocardial infarction than non-diabetic patients, and diabetic patients live eight to thirteen years less than non-diabetic patients.

As used herein, the term "liver disease" refers to any symptoms related to liver dysfunction including physical signs and symptoms related to digestive problems, blood sugar disorders, immune disorders, and abnormal fat absorption and metabolism. Liver disease as used herein refers to all types of liver dysfunction including hepatitis, alcoholic liver disease, fatty liver disease, non-alcoholic fatty liver disease, inflammatory liver disease, cirrhosis, hereditary diseases, and cancers associated with the liver.

An "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom (s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins). The therapeutically effective amount can be ascertained by measuring relevant physiological effects, and it can be adjusted in connection with the dosing regimen and diagnostic analysis of the subject's condition, and the like. By way of example, measurement of the serum level of a TGR5 agonist and/or FXR antagonist (or, e.g., a metabolite thereof) at a particular time post-administration may be indicative of whether a therapeutically effective amount has been administered.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan. Adjusting the dose to achieve maximal therapeutic window efficacy or toxicity in humans based on the methods described above and other methods is well within the capabilities of the ordinarily skilled artisan.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Dosages may be varied depending upon the requirements of the patient and the compound being employed. The dose administered to a patient, in the context of the present disclosure should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages, which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal) compatible with the preparation. Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. In embodiments, administration includes contact (e.g., in vitro or ex vivo) of a compound to the cell, as well as contact of a compound to a fluid, where the fluid is in contact with the cell.

"Co-administer" means that a composition described herein is administered at the same time, just prior to, or just after the administration of one or more additional therapies. The compounds of the disclosure can be administered alone or can be coadministered to the patient. Co-administration is meant to include simultaneous or sequential administration of the compounds individually or in combination (more than one compound). The compositions of the present disclosure can be delivered transdermally, by a topical route, or formulated as applicator sticks, solutions, suspensions, emulsions, gels, creams, ointments, pastes, jellies, paints, powders, and aerosols.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., spodoptera) and human cells. Cells may be useful when they are naturally nonadherent or have been treated not to adhere to surfaces, for example by trypsinization.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

The term "modulator" refers to a composition that increases or decreases the level of a target molecule or the function of a target molecule or the physical state of the target of the molecule relative to the absence of the modulator. In some embodiments, an TGR5 and/or FXR associated disease modulator is a compound that reduces the severity of one or more symptoms of a disease associated with TGR5 and/or FXR (e.g. cancer, inflammatory disease, or autoimmune disease). A TGR5 and/or FXR modulator is a compound that increases or decreases the activity or function or level of activity or level of function of TGR5 and/or FXR.

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

The term "bile acid receptor modulator" is a modulator of a bile acid receptor.

In some embodiments, a TGR5 and/or FXR associated disease modulator is a compound that reduces the severity of one or more symptoms of a disease associated with a TGR5 and/or FXR (e.g. diabetes, obesity, cancer, etc.). A TGR5 and/or FXR modulator is a compound that increases or decreases the activity or function or level of activity or level of function of TGR5 and/or FXR. A modulator may act alone, or it may use a cofactor, e.g., a protein, metal ion, or small molecule. Examples of modulators include small molecule compounds and other bioorganic molecules. Numerous libraries of small molecule compounds (e.g., combinatorial libraries) are commercially available and can serve as a starting point for identifying a modulator. The skilled artisan is able to develop one or more assays (e.g., biochemical or cell-based assays) in which such compound libraries can be screened in order to identify one or more compounds having the desired properties; thereafter, the skilled medicinal chemist is able to optimize such one or more compounds by, for example, synthesizing and evaluating analogs and derivatives thereof. Synthetic and/or molecular modeling studies can also be utilized in the identification of an activator The term "associated" or "associated with" in the context of a substance or substance activity or function associated with a disease (e.g. a protein associated disease, a cancer associated with TGR5 and/or FXR activity, TGR5 and/or FXR associated cancer, TGR5 and/or FXR associated disease (e.g., cancer, inflammatory disease, or autoimmune disease)) means that the disease (e.g. cancer, inflammatory disease, or autoimmune disease) is caused by (in whole or in part), or a symptom of the disease is caused by (in whole or in part) the substance or substance activity or function. For example, a cancer associated with TGR5 and/or FXR activity or function may be a cancer that results (entirely or partially) from aberrant TGR5 and/or FXR function (e.g. enzyme activity, protein-protein interaction, signaling pathway) or a cancer wherein a particular symptom of the disease is caused (entirely or partially) by aberrant TGR5 and/or FXR activity or function. As used herein, what is described as being associated with a disease, if a causative agent, could be a target for treatment of the disease. For example, a cancer associated with TGR5 and/or FXR activity or function or a TGR5 and/or FXR associated disease (e.g., cancer, inflammatory disease, or autoimmune disease), may be treated with a TGR5 and/or FXR modulator or TGR5 and/or FXR inhibitor, in the instance where increased TGR5 and/or FXR activity or function (e.g. signaling pathway activity) causes the disease (e.g., cancer, inflammatory disease, or autoimmune disease). For example, an inflammatory disease associated with TGR5 and/or FXR activity or function or an TGR5 and/or FXR associated inflammatory disease, may be treated with an TGR5 and/or FXR modulator or TGR5 and/or FXR inhibitor, in the instance where increased TGR5 and/or FXR activity or function (e.g. signaling pathway activity) causes the disease.

The term "aberrant" as used herein refers to different from normal. When used to describe enzymatic activity or protein function, aberrant refers to activity or function that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

The term "signaling pathway" as used herein refers to a series of interactions between cellular and optionally extracellular components (e.g., proteins, nucleic acids, small molecules, ions, lipids) that conveys a change in one component to one or more other components, which in turn may convey a change to additional components, which is optionally propagated to other signaling pathway components. For example, binding of TGR5 and/or FXR with a compound as described herein may reduce the level of a product of the TGR5 and/or FXR catalyzed reaction or the level of a downstream derivative of the product or binding may reduce the interactions between the TGR5 and/or FXR or a reaction product and downstream effectors or signaling pathway components (e.g., MAP kinase pathway), resulting in changes in cell growth, proliferation, or survival.

As used herein, the terms "TGR5 activator," "TGR5 agonist," "Takeda G-protein-coupled Receptor 5" and "Takeda G-protein-coupled Receptor 5 agonist" and all other related art-accepted terms, many of which are set forth below, refer to a compound capable of activating, either directly or indirectly, the TGR5 receptor in an in vitro assay, an in vivo model, and/or other means indicative of therapeutic efficacy. The terms also refer to a compound that exhibits at least some therapeutic benefit in a human subject.

As used herein, the terms "FXR inhibitor," "FXR antagonist," "Farnesoid X receptor inhibitor" and "Farnesoid X receptor antagonist" and all other related art-accepted terms, many of which are set forth below, refer to a compound capable of inhibiting, either directly or indirectly, the FXR receptor in an in vitro assay, an in vivo model, and/or other means indicative of therapeutic efficacy. The terms also refer to a compound that exhibits at least some therapeutic benefit in a human subject.

The phrase "in a sufficient amount to effect a change" means that there is a detectable difference between a level of an indicator measured before (e.g., a baseline level) and after administration of a particular therapy. Indicators include any objective parameter (e.g., serum concentration) or subjective parameter (e.g., a subject's feeling of well-being).

The "activity" of a molecule may describe or refer to the binding of the molecule to a ligand or to a receptor; to catalytic activity; to the ability to stimulate gene expression or cell signaling, differentiation, or maturation; to antigenic activity; to the modulation of activities of other molecules; and the like. The term "proliferative activity" encompasses an activity that promotes, that is necessary for, or that is specifically associated with, for example, normal cell division, as well as cancer, tumors, dysplasia, cell transformation, metastasis, and angiogenesis.

"Substantially pure" indicates that a component makes up greater than about 50% of the total content of the composition, and typically greater than about 60% of the total polypeptide content. More typically, "substantially pure" refers to compositions in which at least 75%, at least 85%, at least 90% or more of the total composition is the component of interest. In some cases, the polypeptide will make up greater than about 90%, or greater than about 95% of the total content of the composition (percentage in a weight per weight basis).

The terms "specifically binds" and "selectively binds," when referring to a ligand/receptor, antibody/antigen, or other binding pair, indicates a binding reaction which is determinative of the presence of the protein in a heterogeneous population of proteins and other biologics. Thus, under designated conditions, a specified ligand binds to a particular receptor and does not bind in a significant amount to other proteins present in the sample.

As used herein, the terms "variants" and "homologs" are used interchangeably to refer to amino acid or nucleic acid sequences that are similar to reference amino acid or nucleic acid sequences, respectively. The term encompasses naturally-occurring variants and non-naturally-occurring variants. Naturally-occurring variants include homologs (polypeptides and nucleic acids that differ in amino acid or nucleotide sequence, respectively, from one species to another), and allelic variants (polypeptides and nucleic acids that differ in amino acid or nucleotide sequence, respectively, from one individual to another within a species). Thus, variants and homologs encompass naturally occurring amino acid and nucleic acid sequences encoded thereby and their isoforms, as well as splice variants of a protein or gene. The terms also encompass nucleic acid sequences that vary in one or more bases from a naturally-occurring nucleic acid sequence but still translate into an amino acid sequence that corresponds to the naturally-occurring protein due to degeneracy of the genetic code. Non-naturally-occurring variants and homologs include polypeptides and nucleic acids that comprise a change in amino acid or nucleotide sequence, respectively, where the change in sequence is artificially introduced (e.g., muteins); for example, the change is generated in the laboratory by human intervention ("hand of man"). Therefore, non-naturally occurring variants and homologs may also refer to those that differ from the naturally-occurring sequences by one or more conservative substitutions and/or tags and/or conjugates.

Compounds and Compositions

In a first aspect, there is provided a compound having the formula:

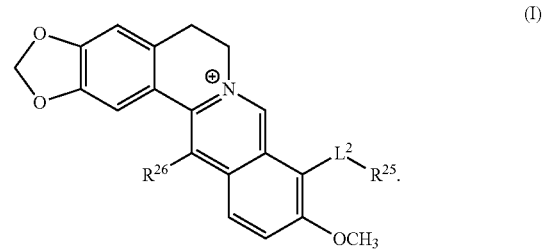

(I)

$L^2$ is a bond, —C(O)—, —C(O)O—, —O—, —S—, —$NR^{2L}$—, —C(O)$NR^{2L}$—, —$NR^{2L}$C(O)—, —S(O)$_2$—, —S(O)$NR^{2L}$—, —$NR^{2L}$C(O)NH—, —NHC(O)$NR^{2L}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^{25}$ is —$OCH_3$, substituted or unsubstituted cycloalkyl, substituted or unsubstituted heterocycloalkyl, substituted or unsubstituted aryl or substituted or unsubstituted heteroaryl. $R^{26}$ is hydrogen, halogen, —$CX^{26}_3$, —$CHX^{26}_2$, —$CH_2X^{26}$, —$OCX^{26}_3$, —$OCH_2X^{26}$, —$OCHX^{26}_2$, —CN, —$SO_{n26}R^{26C}$, —$SO_{v26}NR^{26A}R^{26B}$, —NHC(O)$NR^{26A}R^{26B}$, —N(O)$_{m26}$, —$NR^{26A}R^{26B}$, —C(O)$R^{26C}$, —C(O)—$OR^{26C}$, —C(O)$NR^{26A}R^{26B}$, —$OR^{26C}$, —$NR^{26A}SO_2R^{26C}$, —$NR^{26A}C(O)R^{26C}$, —$NR^{26A}C(O)OR^{26C}$, —$NR^{26A}OR^{26C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{2L}$, $R^{26A}$, $R^{26B}$, and $R^{26C}$ are independently hydrogen, —$CX^{26A}_3$, —CN, —COOH, —$CONH_2$, —$CHX^{26A}_2$, —$CH_2X^{26A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $X^{26}$ and $X^{26A}$ are independently halogen. n26 is an integer from 0 to 4. m26 and v26 are independently 1 or 2. $R^{26A}$ and $R^{26B}$ substituents bonded to the same nitrogen atom may optionally be joined to form a substituted or unsubstituted heterocycloalkyl or substituted or unsubstituted heteroaryl.

In embodiments, n26 is 0. In embodiments, n26 is 1. In embodiments, n26 is 2. In embodiments, n26 is 3. In embodiments, n26 is 4.

In embodiments, m26 is 1. In embodiments, m26 is 2. In embodiments, v26 is 1. In embodiments, v26 is 2.

In embodiments, $X^{26}$ is F. In embodiments, $X^{26}$ is Cl. In embodiments, $X^{26}$ is Br. In embodiments, $X^{26}$ is I.

In embodiments, $X^{26A}$ is F. In embodiments, $X^{26A}$ is Cl. In embodiments, $X^{26A}$ is Br. In embodiments, $X^{26A}$ is I.

In embodiments, $L^2$ is a bond, —C(O)—, —C(O)O—, —O—, —S—, —$NR^{2L}$—, —C(O)$NR^{2L}$—, —$NR^{2L}$C(O)—, —S(O)$_2$—, —S(O)$NR^{2L}$—, —$NR^{2L}$C(O)NH—, —NHC(O)$NR^{2L}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

In embodiments, $L^2$ is a bond, —C(O)—, —C(O)O—, —O—, —S—, —$NR^{2L}$—, —C(O)$NR^{2L}$—, —$NR^{2L}$C(O)—, —S(O)$_2$—, —S(O)$NR^{2L}$—, —$NR^{2L}$C(O)NH—, —NHC(O)$NR^{2L}$—, substituted or unsubstituted alkylene (e.g., $C_1$-$C_8$ alkylene, $C_1$-$C_6$ alkylene, or $C_1$-$C_4$ alkylene), substituted or unsubstituted heteroalkylene (e.g., 2 to 8 membered heteroalkylene, 2 to 6 membered heteroalkylene, or 2 to 4 membered heteroalkylene), substituted or unsubstituted cycloalkylene (e.g., $C_3$-$C_8$ cycloalkylene, $C_3$-$C_6$ cycloalkylene, or $C_5$-$C_6$ cycloalkylene), substituted or unsubstituted heterocycloalkylene (e.g., 3 to 8 membered heterocycloalkylene, 3 to 6 membered heterocycloalkylene, or 5 to 6 membered heterocycloalkylene), substituted or unsubstituted arylene (e.g., $C_6$-$C_{10}$ arylene, $C_{10}$ arylene, or phenylene), or substituted or unsubstituted heteroarylene (e.g., 5 to 10 membered heteroarylene, 5 to 9 membered heteroarylene, or 5 to 6 membered heteroarylene).

In embodiments, $L^2$ is a bond, —C(O)—, —C(O)O—, —O—, —S—, —$NR^{2L}$—, —C(O)$NR^{2L}$—, —$NR^{2L}$C(O)—, —S(O)$_2$—, —S(O)$NR^{2L}$—, —$NR^{2L}$C(O)NH—, —NHC(O)$NR^{2L}$—, $R^{28}$-substituted or unsubstituted alkylene (e.g., $C_1$-$C_8$ alkylene, $C_1$-$C_6$ alkylene, or $C_1$-$C_4$ alkylene), $R^{28}$-substituted or unsubstituted heteroalkylene (e.g., 2 to 8 membered heteroalkylene, 2 to 6 membered heteroalkylene, or 2 to 4 membered heteroalkylene), $R^{28}$-substituted or unsubstituted cycloalkylene (e.g., $C_3$-$C_8$ cycloalkylene, $C_3$-$C_6$ cycloalkylene, or $C_5$-$C_6$ cycloalkylene), $R^{28}$-substituted or unsubstituted heterocycloalkylene (e.g., 3 to 8 membered heterocycloalkylene, 3 to 6 membered heterocycloalkylene, or 5 to 6 membered heterocycloalkylene), $R^{28}$-substituted or unsubstituted arylene (e.g., $C_6$-$C_{10}$ arylene, $C_{10}$ arylene, or phenylene), or $R^{28}$-substituted or unsubstituted heteroarylene (e.g., 5 to 10 membered heteroarylene, 5 to 9 membered heteroarylene, or 5 to 6 membered heteroarylene). In embodiments, $L^2$ is a bond.

In embodiments, $L^2$ is $R^{28}$-substituted or unsubstituted alkylene (e.g., $C_1$-$C_8$ alkylene, $C_1$-$C_6$ alkylene, or $C_1$-$C_4$ alkylene). In embodiments, $L^2$ is $R^{28}$-substituted alkylene (e.g., $C_1$-$C_8$ alkylene, $C_1$-$C_6$ alkylene, or $C_1$-$C_4$ alkylene). In embodiments, $L^2$ is an unsubstituted alkylene (e.g., $C_1$-$C_8$ alkylene, $C_1$-$C_6$ alkylene, or $C_1$-$C_4$ alkylene).

In embodiments, $L^2$ is $R^{28}$-substituted or unsubstituted heteroalkylene (e.g., 2 to 8 membered heteroalkylene, 2 to 6 membered heteroalkylene, or 2 to 4 membered heteroalkylene). In embodiments, $L^2$ is $R^{28}$-substituted heteroalkylene (e.g., 2 to 8 membered heteroalkylene, 2 to 6 membered heteroalkylene, or 2 to 4 membered heteroalkylene). In embodiments, $L^2$ is an unsubstituted heteroalkylene (e.g., 2 to 8 membered heteroalkylene, 2 to 6 membered heteroalkylene, or 2 to 4 membered heteroalkylene).

In embodiments, $L^2$ is $R^{28}$-substituted or unsubstituted cycloalkylene (e.g., $C_3$-$C_8$ cycloalkylene, $C_3$-$C_6$ cycloalkylene, or $C_5$-$C_6$ cycloalkylene). In embodiments, $L^2$ is $R^{28}$-substituted cycloalkylene (e.g., $C_3$-$C_8$ cycloalkylene, $C_3$-$C_6$ cycloalkylene, or $C_5$-$C_6$ cycloalkylene). In embodiments, $L^2$ is an unsubstituted cycloalkylene (e.g., $C_3$-$C_8$ cycloalkylene, $C_3$-$C_6$ cycloalkylene, or $C_5$-$C_6$ cycloalkylene).

In embodiments, $L^2$ is $R^{28}$-substituted or unsubstituted heterocycloalkylene (e.g., 3 to 8 membered heterocycloalkylene, 3 to 6 membered heterocycloalkylene, or 5 to 6 membered heterocycloalkylene). In embodiments, $L^2$ is $R^{28}$-substituted heterocycloalkylene (e.g., 3 to 8 membered heterocycloalkylene, 3 to 6 membered heterocycloalkylene, or 5 to 6 membered heterocycloalkylene). In embodiments, $L^2$ is an unsubstituted heterocycloalkylene (e.g., 3 to 8 membered heterocycloalkylene, 3 to 6 membered heterocycloalkylene, or 5 to 6 membered heterocycloalkylene).

In embodiments, $L^2$ is $R^{28}$-substituted or unsubstituted arylene (e.g., $C_6$-$C_{10}$ arylene, $C_{10}$ arylene, or phenylene). In embodiments, $L^2$ is $R^{28}$-substituted arylene (e.g., $C_6$-$C_{10}$ arylene, $C_{10}$ arylene, or phenylene). In embodiments, $L^2$ is an unsubstituted arylene (e.g., $C_6$-$C_{10}$ arylene, $C_{10}$ arylene, or phenylene).

In embodiments, $L^2$ is $R^{28}$-substituted or unsubstituted heteroarylene (e.g., 5 to 10 membered heteroarylene, 5 to 9 membered heteroarylene, or 5 to 6 membered heteroarylene). In embodiments, $L^2$ is $R^{28}$-substituted heteroarylene (e.g., 5 to 10 membered heteroarylene, 5 to 9 membered heteroarylene, or 5 to 6 membered heteroarylene). In embodiments, $L^2$ is an unsubstituted heteroarylene (e.g., 5 to 10 membered heteroarylene, 5 to 9 membered heteroarylene, or 5 to 6 membered heteroarylene).

In embodiments, $R^{25}$ is substituted or unsubstituted cycloalkyl, substituted or unsubstituted heterocycloalkyl, substituted or unsubstituted aryl or substituted or unsubstituted heteroaryl;

In embodiments, $R^{25}$ is $R^{30}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{25}$ is $R^{30}$-substituted cycloalkyl (e.g., $C_3$-$C_8$ cycloalkyl, $C_3$-$C_6$ cycloalkyl, or $C_5$-$C_6$ cycloalkyl). In embodiments, $R^{25}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{25}$ is $R^{30}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{25}$ is $R^{30}$-substituted heterocycloalkyl (e.g., 3 to 8 membered heterocycloalkyl, 3 to 6 membered heterocycloalkyl, or 5 to 6 membered heterocycloalkyl). In embodiments, $R^{25}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{25}$ is $R^{30}$-substituted or unsubstituted aryl (e.g., $C_6$-$C_{10}$ aryl, $C_{10}$ aryl, or phenyl). In embodiments, $R^{25}$ is $R^{30}$-substituted aryl (e.g., $C_6$-$C_{10}$ aryl, $C_{10}$ aryl, or phenyl). In embodiments, $R^{25}$ is an unsubstituted aryl (e.g., $C_6$-$C_{10}$ aryl, $C_{10}$ aryl, or phenyl).

In embodiments, $R^{25}$ is $R^{30}$-substituted or unsubstituted heteroaryl (e.g., 5 to 10 membered heteroaryl, 5 to 9 membered heteroaryl, or 5 to 6 membered heteroaryl). In embodiments, $R^{25}$ is $R^{30}$-substituted heteroaryl (e.g., 5 to 10 membered heteroaryl, 5 to 9 membered heteroaryl, or 5 to 6 membered heteroaryl). In embodiments, $R^{25}$ is an unsubstituted heteroaryl (e.g., 5 to 10 membered heteroaryl, 5 to 9 membered heteroaryl, or 5 to 6 membered heteroaryl).

In embodiments, $R^{26}$ is hydrogen, halogen, $-CX^{26}_3$, $-CHX^{26}_2$, $-CH_2X^{26}$, $-OCX^{26}_3$, $-OCH_2X^{26}$, $-OCHX^{26}_2$, $-CN$, $-SO_{n26}R^{26C}$, $-SO_{v26}NR^{26A}R^{26B}$, $-NHC(O)NR^{26A}R^{26B}$, $-N(O)_{m26}$, $-NR^{26A}R^{26B}$, $-C(O)R^{26C}$, $-C(O)-OR^{26C}$, $-C(O)NR^{26A}R^{26B}$, $-OR^{26C}$, $-NR^{26A}SO_2R^{26C}$, $-NR^{26A}C(O)R^{26C}$, $-NR^{26A}C(O)OR^{26C}$, $-NR^{26A}OR^{26C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{26}$ is halogen, $-CX^{26}_3$, $-CHX^{26}_2$, $-CH_2X^{26}$, $-OCX^{26}_3$, $-OCH_2X^{26}$, $-OCHX^{26}_2$, $-CN$, $-SO_{n26}R^{26C}$, $-SO_{v26}NR^{26A}R^{26B}$, $-NHC(O)NR^{26A}R^{26B}$, $-N(O)_{m26}$, $-NR^{26A}R^{26B}$, $-C(O)R^{26C}$, $-C(O)-OR^{26C}$, $-C(O)NR^{26A}R^{26B}$, $-OR^{26C}$, $-NR^{26A}SO_2R^{26C}$, $-NR^{26A}C(O)R^{26C}$, $-NR^{26A}C(O)OR^{26C}$, $-NR^{26A}OR^{26C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{26}$ is hydrogen. In embodiments, $R^{26}$ is halogen. In embodiments, $R^{26}$ is $-CX^{26}_3$, $-CHX^{26}_2$, $-CH_2X^{26}$, $-OCX^{26}_3$, $-OCH_2X^{26}$, $-OCHX^{26}_2$, $-CN$, $-SO_{n26}R^{26C}$, $-SO_{v26}NR^{26A}R^{26B}$, $-NHC(O)NR^{26A}R^{26B}$, $-N(O)_{m26}$, $-NR^{26A}R^{26B}$, $-C(O)R^{26C}$, $-C(O)-OR^{26C}$, $-C(O)NR^{26A}R^{26B}$, $-OR^{26C}$, $-NR^{26A}SO_2R^{26C}$, $-NR^{26A}C(O)R^{26C}$, $-NR^{26A}C(O)OR^{26C}$, or $-NR^{26A}OR^{26C}$.

In embodiments, $R^{26}$ is $R^{33}$-substituted or unsubstituted alkyl (e.g., $C_1$-$C_8$ alkyl, $C_1$-$C_6$ alkyl, or $C_1$-$C_4$ alkyl). In embodiments, $R^{26}$ is $R^{33}$-substituted alkyl (e.g., $C_1$-$C_8$ alkyl, $C_1$-$C_6$ alkyl, or $C_1$-$C_4$ alkyl). In embodiments, $R^{26}$ is an unsubstituted alkyl (e.g., $C_1$-$C_8$ alkyl, $C_1$-$C_6$ alkyl, or $C_1$-$C_4$ alkyl).

In embodiments, $R^{26}$ is $R^{33}$-substituted or unsubstituted heteroalkyl (e.g., 2 to 8 membered heteroalkyl, 2 to 6 membered heteroalkyl, or 2 to 4 membered heteroalkyl). In embodiments, $R^{26}$ is $R^{33}$-substituted heteroalkyl (e.g., 2 to 8 membered heteroalkyl, 2 to 6 membered heteroalkyl, or 2 to 4 membered heteroalkyl). In embodiments, $R^{26}$ is an unsubstituted heteroalkyl (e.g., 2 to 8 membered heteroalkyl, 2 to 6 membered heteroalkyl, or 2 to 4 membered heteroalkyl).

In embodiments, $R^{26}$ is $R^{33}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{26}$ is $R^{33}$-substituted cycloalkyl (e.g., $C_3$-$C_8$ cycloalkyl, $C_3$-$C_6$ cycloalkyl, or $C_5$-$C_6$ cycloalkyl). In embodiments, $R^{26}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{26}$ is $R^{33}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{26}$ is $R^{33}$-substituted heterocycloalkyl (e.g., 3 to 8 membered heterocycloalkyl, 3 to 6 membered heterocycloalkyl, or 5 to 6 membered heterocycloalkyl). In embodiments, $R^{26}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{26}$ is $R^{33}$-substituted or unsubstituted aryl (e.g., $C_6$-$C_{10}$ aryl, $C_{10}$ aryl, or phenyl). In embodiments, $R^{26}$ is $R^{33}$-substituted aryl (e.g., $C_6$-$C_{10}$ aryl, $C_{10}$ aryl, or phenyl). In embodiments, $R^{26}$ is an unsubstituted aryl (e.g., $C_6$-$C_{10}$ aryl, $C_{10}$ aryl, or phenyl).

In embodiments, $R^{26}$ is $R^{33}$-substituted or unsubstituted heteroaryl (e.g., 5 to 10 membered heteroaryl, 5 to 9 membered heteroaryl, or 5 to 6 membered heteroaryl). In embodiments, $R^{26}$ is $R^{33}$-substituted heteroaryl (e.g., 5 to 10 membered heteroaryl, 5 to 9 membered heteroaryl, or 5 to 6 membered heteroaryl). In embodiments, $R^{26}$ is an unsubstituted heteroaryl (e.g., 5 to 10 membered heteroaryl, 5 to 9 membered heteroaryl, or 5 to 6 membered heteroaryl).

In embodiments, $R^{2L}$ is hydrogen, $-CX^{26A}_3$, $-CN$, $-COOH$, $-CONH_2$, $-CHX^{26A}_2$, $-CH_2X^{26A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

In embodiments, $R^{2L}$ is $R^{28L}$-substituted or unsubstituted alkyl (e.g., $C_1$-$C_8$ alkyl, $C_1$-$C_6$ alkyl, or $C_1$-$C_4$ alkyl). In embodiments, $R^{2L}$ is $R^{28L}$-substituted alkyl (e.g., $C_1$-$C_8$ alkyl, $C_1$-$C_6$ alkyl, or $C_1$-$C_4$ alkyl). In embodiments, $R^{2L}$ is an unsubstituted alkyl (e.g., $C_1$-$C_8$ alkyl, $C_1$-$C_6$ alkyl, or $C_1$-$C_4$ alkyl).

In embodiments, $R^{2L}$ is $R^{28L}$-substituted or unsubstituted heteroalkyl (e.g., 2 to 8 membered heteroalkyl, 2 to 6 membered heteroalkyl, or 2 to 4 membered heteroalkyl). In embodiments, $R^{2L}$ is $R^{28L}$-substituted heteroalkyl (e.g., 2 to 8 membered heteroalkyl, 2 to 6 membered heteroalkyl, or 2 to 4 membered heteroalkyl). In embodiments, $R^{2L}$ is an unsubstituted heteroalkyl (e.g., 2 to 8 membered heteroalkyl, 2 to 6 membered heteroalkyl, or 2 to 4 membered heteroalkyl).

In embodiments, $R^{2L}$ is $R^{28L}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{2L}$ is $R^{28L}$-substituted cycloalkyl (e.g., $C_3$-$C_8$ cycloalkyl, $C_3$-$C_6$ cycloalkyl, or $C_5$-$C_6$ cycloalkyl). In embodiments, $R^{2L}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{2L}$ is $R^{28L}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{2L}$ is $R^{28L}$-substituted heterocycloalkyl (e.g., 3 to 8 membered heterocycloalkyl, 3 to 6 membered heterocycloalkyl, or 5 to 6 membered heterocycloalkyl). In embodiments, $R^{2L}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{2L}$ is $R^{28L}$-substituted or unsubstituted aryl (e.g., $C_6$-$C_{10}$ aryl, $C_{10}$ aryl, or phenyl). In embodiments, $R^{2L}$ is $R^{28L}$-substituted aryl (e.g., $C_6$-$C_{10}$ aryl, $C_{10}$ aryl, or phenyl). In embodiments, $R^{2L}$ is an unsubstituted aryl (e.g., $C_6$-$C_{10}$ aryl, $C_{10}$ aryl, or phenyl).

In embodiments, $R^{2L}$ is $R^{28L}$-substituted or unsubstituted heteroaryl (e.g., 5 to 10 membered heteroaryl, 5 to 9 membered heteroaryl, or 5 to 6 membered heteroaryl). In embodiments, $R^{2L}$ is $R^{28L}$-substituted heteroaryl (e.g., 5 to 10 membered heteroaryl, 5 to 9 membered heteroaryl, or 5 to 6 membered heteroaryl). In embodiments, $R^{2L}$ is an unsubstituted heteroaryl (e.g., 5 to 10 membered heteroaryl, 5 to 9 membered heteroaryl, or 5 to 6 membered heteroaryl).

In embodiments, $R^{26A}$ is hydrogen, $-CX^{26A}_3$, $-CN$, $-COOH$, $-CONH_2$, $-CHX^{26A}_2$, $-CH_2X^{26A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

In embodiments, $R^{26A}$ is hydrogen, halogen, $-CF_3$, $-CCl_3$, $-CBr_3$, $-CI_3$, $-COOH$, $-CONH_2$, $R^{33A}$-substituted or unsubstituted alkyl (e.g., $C_1$-$C_8$ alkyl, $C_1$-$C_6$ alkyl, or $C_1$-$C_4$ alkyl), $R^{33A}$-substituted or unsubstituted heteroalkyl (e.g., 2 to 8 membered heteroalkyl, 2 to 6 membered heteroalkyl, or 2 to 4 membered heteroalkyl), $R^{33A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{33A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{33A}$-substituted or unsubstituted aryl (e.g., $C_6$-$C_{10}$ aryl, $C_{10}$ aryl, or phenyl), or $R^{33A}$-substituted or unsubstituted heteroaryl (e.g., 5 to 10 membered heteroaryl, 5 to 9 membered heteroaryl, or 5 to 6 membered heteroaryl).

In embodiments, $R^{26B}$ is hydrogen, halogen, —$CF_3$, —$CCl_3$, —$CBr_3$, —$CI_3$, —COOH, —$CONH_2$, $R^{33B}$-substituted or unsubstituted alkyl (e.g., $C_1$-$C_8$ alkyl, $C_1$-$C_6$ alkyl, or $C_1$-$C_4$ alkyl), $R^{33B}$-substituted or unsubstituted heteroalkyl (e.g., 2 to 8 membered heteroalkyl, 2 to 6 membered heteroalkyl, or 2 to 4 membered heteroalkyl), $R^{33B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{33B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{33B}$-substituted or unsubstituted aryl (e.g., $C_6$-$C_{10}$ aryl, $C_{10}$ aryl, or phenyl), or $R^{33B}$-substituted or unsubstituted heteroaryl (e.g., 5 to 10 membered heteroaryl, 5 to 9 membered heteroaryl, or 5 to 6 membered heteroaryl). In embodiments, $R^{26A}$ and $R^{26B}$ substituents bonded to the same nitrogen atom may optionally be joined to form a $R^{33B}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{33B}$-substituted or unsubstituted heteroaryl (e.g., 5 to 10 membered heteroaryl, 5 to 9 membered heteroaryl, or 5 to 6 membered heteroaryl).

In embodiments, $R^{26C}$ is hydrogen, halogen, —$CF_3$, —$CCl_3$, —$CBr_3$, —$CI_3$, —COOH, —$CONH_2$, $R^{33C}$-substituted or unsubstituted alkyl (e.g., $C_1$-$C_8$ alkyl, $C_1$-$C_6$ alkyl, or $C_1$-$C_4$ alkyl), $R^{33C}$-substituted or unsubstituted heteroalkyl (e.g., 2 to 8 membered heteroalkyl, 2 to 6 membered heteroalkyl, or 2 to 4 membered heteroalkyl), $R^{33C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{33C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{33C}$-substituted or unsubstituted aryl (e.g., $C_6$-$C_{10}$ aryl, $C_{10}$ aryl, or phenyl), or $R^{33C}$-substituted or unsubstituted heteroaryl (e.g., 5 to 10 membered heteroaryl, 5 to 9 membered heteroaryl, or 5 to 6 membered heteroaryl). In embodiments, $R^{26A}$ and $R^{26B}$ substituents bonded to the same nitrogen atom may optionally be joined to form a $R^{33C}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{33C}$-substituted or unsubstituted heteroaryl (e.g., 5 to 10 membered heteroaryl, 5 to 9 membered heteroaryl, or 5 to 6 membered heteroaryl).

$R^{28}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{29}$-substituted or unsubstituted alkyl (e.g., $C_1$-$C_8$ alkyl, $C_1$-$C_6$ alkyl, or $C_1$-$C_4$ alkyl), $R^{29}$-substituted or unsubstituted heteroalkyl (e.g., 2 to 8 membered heteroalkyl, 2 to 6 membered heteroalkyl, or 2 to 4 membered heteroalkyl), $R^{29}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{29}$-substituted or unsubstituted heterocycloalkyl (e.g., 3 to 8 membered heterocycloalkyl, 3 to 6 membered heterocycloalkyl, or 5 to 6 membered heterocycloalkyl), $R^{29}$-substituted or unsubstituted aryl (e.g., $C_6$-$C_{10}$ aryl, $C_{10}$ aryl, or phenyl), or $R^{29}$-substituted or unsubstituted heteroaryl (e.g., 5 to 10 membered heteroaryl, 5 to 9 membered heteroaryl, or 5 to 6 membered heteroaryl).

In embodiments, $R^{28}$ is $R^{29}$-substituted or unsubstituted alkyl (e.g., $C_1$-$C_8$ alkyl, $C_1$-$C_6$ alkyl, or $C_1$-$C_4$ alkyl). In embodiments, $R^{28}$ is $R^{29}$-substituted alkyl (e.g., $C_1$-$C_8$ alkyl, $C_1$-$C_6$ alkyl, or $C_1$-$C_4$ alkyl). In embodiments, $R^{28}$ is an unsubstituted alkyl (e.g., $C_1$-$C_8$ alkyl, $C_1$-$C_6$ alkyl, or $C_1$-$C_4$ alkyl).

In embodiments, $R^{28}$ is $R^{29}$-substituted or unsubstituted heteroalkyl (e.g., 2 to 8 membered heteroalkyl, 2 to 6 membered heteroalkyl, or 2 to 4 membered heteroalkyl). In embodiments, $R^{28}$ is $R^{29}$-substituted heteroalkyl (e.g., 2 to 8 membered heteroalkyl, 2 to 6 membered heteroalkyl, or 2 to 4 membered heteroalkyl). In embodiments, $R^{28}$ is an unsubstituted heteroalkyl (e.g., 2 to 8 membered heteroalkyl, 2 to 6 membered heteroalkyl, or 2 to 4 membered heteroalkyl).

In embodiments, $R^{28}$ is $R^{29}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{28}$ is $R^{29}$-substituted cycloalkyl (e.g., $C_3$-$C_8$ cycloalkyl, $C_3$-$C_6$ cycloalkyl, or $C_5$-$C_6$ cycloalkyl). In embodiments, $R^{28}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{28}$ is $R^{29}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{28}$ is $R^{29}$-substituted heterocycloalkyl (e.g., 3 to 8 membered heterocycloalkyl, 3 to 6 membered heterocycloalkyl, or 5 to 6 membered heterocycloalkyl). In embodiments, $R^{28}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{28}$ is $R^{29}$-substituted or unsubstituted aryl (e.g., $C_6$-$C_{10}$ aryl, $C_{10}$ aryl, or phenyl). In embodiments, $R^{28}$ is $R^{29}$-substituted aryl (e.g., $C_6$-$C_{10}$ aryl, $C_{10}$ aryl, or phenyl). In embodiments, $R^{28}$ is an unsubstituted aryl (e.g., $C_6$-$C_{10}$ aryl, $C_{10}$ aryl, or phenyl).

In embodiments, $R^{28}$ is $R^{29}$-substituted or unsubstituted heteroaryl (e.g., 5 to 10 membered heteroaryl, 5 to 9 membered heteroaryl, or 5 to 6 membered heteroaryl). In embodiments, $R^{28}$ is $R^{29}$-substituted heteroaryl (e.g., 5 to 10 membered heteroaryl, 5 to 9 membered heteroaryl, or 5 to 6 membered heteroaryl). In embodiments, $R^{28}$ is an unsubstituted heteroaryl (e.g., 5 to 10 membered heteroaryl, 5 to 9 membered heteroaryl, or 5 to 6 membered heteroaryl).

$R^{28L}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{29L}$-substituted or unsubstituted alkyl (e.g., $C_1$-$C_8$ alkyl, $C_1$-$C_6$ alkyl, or $C_1$-$C_4$ alkyl), $R^{29L}$-substituted or unsubstituted heteroalkyl (e.g., 2 to 8 membered heteroalkyl, 2 to 6 membered heteroalkyl, or 2 to 4 membered heteroalkyl), $R^{29L}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{29L}$-substituted or unsubstituted heterocycloalkyl (e.g., 3 to 8 membered heterocycloalkyl, 3 to 6 membered heterocycloalkyl, or 5 to 6 membered heterocycloalkyl), $R^{29L}$-substituted or unsubstituted aryl (e.g., $C_6$-$C_{10}$ aryl, $C_{10}$ aryl, or phenyl), or $R^{29L}$-substituted or unsubstituted heteroaryl (e.g., 5 to 10 membered heteroaryl, 5 to 9 membered heteroaryl, or 5 to 6 membered heteroaryl).

In embodiments, $R^{28L}$ is $R^{29L}$-substituted or unsubstituted alkyl (e.g., $C_1$-$C_8$ alkyl, $C_1$-$C_6$ alkyl, or $C_1$-$C_4$ alkyl). In embodiments, $R^{28L}$ is $R^{29L}$-substituted alkyl (e.g., $C_1$-$C_8$ alkyl, $C_1$-$C_6$ alkyl, or $C_1$-$C_4$ alkyl). In embodiments, $R^{28L}$ is an unsubstituted alkyl (e.g., $C_1$-$C_8$ alkyl, $C_1$-$C_6$ alkyl, or $C_1$-$C_4$ alkyl).

In embodiments, $R^{28L}$ is $R^{29L}$-substituted or unsubstituted heteroalkyl (e.g., 2 to 8 membered heteroalkyl, 2 to 6 membered heteroalkyl, or 2 to 4 membered heteroalkyl). In embodiments, $R^{28L}$ is $R^{29L}$-substituted heteroalkyl (e.g., 2 to 8 membered heteroalkyl, 2 to 6 membered heteroalkyl, or 2 to 4 membered heteroalkyl). In embodiments, $R^{28L}$ is an unsubstituted heteroalkyl (e.g., 2 to 8 membered heteroalkyl, 2 to 6 membered heteroalkyl, or 2 to 4 membered heteroalkyl).

In embodiments, $R^{28L}$ is $R^{29L}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{28L}$ is $R^{29L}$-substituted cycloalkyl (e.g., $C_3$-$C_8$ cycloalkyl, $C_3$-$C_6$ cycloalkyl, or $C_5$-$C_6$ cycloalkyl). In embodiments, $R^{28L}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{28L}$ is $R^{29L}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{28L}$ is $R^{29L}$-substituted heterocycloalkyl (e.g., 3 to 8 membered heterocycloalkyl, 3 to 6 membered heterocycloalkyl, or 5 to 6 membered heterocycloalkyl). In embodiments, $R^{28L}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{28L}$ is $R^{29L}$-substituted or unsubstituted aryl (e.g., $C_6$-$C_{10}$ aryl, $C_{10}$ aryl, or phenyl). In embodiments, $R^{28L}$ is $R^{29L}$-substituted aryl (e.g., $C_6$-$C_{10}$ aryl, $C_{10}$ aryl, or phenyl). In embodiments, $R^{28L}$ is an unsubstituted aryl (e.g., $C_6$-$C_{10}$ aryl, $C_{10}$ aryl, or phenyl).

In embodiments, $R^{28L}$ is $R^{29L}$-substituted or unsubstituted heteroaryl (e.g., 5 to 10 membered heteroaryl, 5 to 9 membered heteroaryl, or 5 to 6 membered heteroaryl). In embodiments, $R^{28L}$ is $R^{29L}$-substituted heteroaryl (e.g., 5 to 10 membered heteroaryl, 5 to 9 membered heteroaryl, or 5 to 6 membered heteroaryl). In embodiments, $R^{28L}$ is an unsubstituted heteroaryl (e.g., 5 to 10 membered heteroaryl, 5 to 9 membered heteroaryl, or 5 to 6 membered heteroaryl).

$R^{30}$ is independently oxo, halogen, $-CCl_3$, $-CBr_3$, $-CF_3$, $-CI_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $R^{31}$-substituted or unsubstituted alkyl (e.g., $C_1$-$C_8$ alkyl, $C_1$-$C_6$ alkyl, or $C_1$-$C_4$ alkyl), $R^{31}$-substituted or unsubstituted heteroalkyl (e.g., 2 to 8 membered heteroalkyl, 2 to 6 membered heteroalkyl, or 2 to 4 membered heteroalkyl), $R^{31}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{31}$-substituted or unsubstituted heterocycloalkyl (e.g., 3 to 8 membered heterocycloalkyl, 3 to 6 membered heterocycloalkyl, or 5 to 6 membered heterocycloalkyl), $R^{31}$-substituted or unsubstituted aryl (e.g., $C_6$-$C_{10}$ aryl, $C_{10}$ aryl, or phenyl), or $R^{31}$-substituted or unsubstituted heteroaryl (e.g., 5 to 10 membered heteroaryl, 5 to 9 membered heteroaryl, or 5 to 6 membered heteroaryl).

In embodiments, $R^{30}$ is $R^{31}$-substituted or unsubstituted alkyl (e.g., $C_1$-$C_8$ alkyl, $C_1$-$C_6$ alkyl, or $C_1$-$C_4$ alkyl). In embodiments, $R^{30}$ is $R^{31}$-substituted alkyl (e.g., $C_1$-$C_8$ alkyl, $C_1$-$C_6$ alkyl, or $C_1$-$C_4$ alkyl). In embodiments, $R^{30}$ is an unsubstituted alkyl (e.g., $C_1$-$C_8$ alkyl, $C_1$-$C_6$ alkyl, or $C_1$-$C_4$ alkyl).

In embodiments, $R^{30}$ is $R^{31}$-substituted or unsubstituted heteroalkyl (e.g., 2 to 8 membered heteroalkyl, 2 to 6 membered heteroalkyl, or 2 to 4 membered heteroalkyl). In embodiments, $R^{30}$ is $R^{31}$-substituted heteroalkyl (e.g., 2 to 8 membered heteroalkyl, 2 to 6 membered heteroalkyl, or 2 to 4 membered heteroalkyl). In embodiments, $R^{30}$ is an unsubstituted heteroalkyl (e.g., 2 to 8 membered heteroalkyl, 2 to 6 membered heteroalkyl, or 2 to 4 membered heteroalkyl).

In embodiments, $R^{30}$ is $R^{31}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{30}$ is $R^{31}$-substituted cycloalkyl (e.g., $C_3$-$C_8$ cycloalkyl, $C_3$-$C_6$ cycloalkyl, or $C_5$-$C_6$ cycloalkyl). In embodiments, $R^{30}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{30}$ is $R^{31}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{30}$ is $R^{31}$-substituted heterocycloalkyl (e.g., 3 to 8 membered heterocycloalkyl, 3 to 6 membered heterocycloalkyl, or 5 to 6 membered heterocycloalkyl). In embodiments, $R^{30}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{30}$ is $R^{31}$-substituted or unsubstituted aryl (e.g., $C_6$-$C_{10}$ aryl, $C_{10}$ aryl, or phenyl). In embodiments, $R^{30}$ is $R^{31}$-substituted aryl (e.g., $C_6$-$C_{10}$ aryl, $C_{10}$ aryl, or phenyl). In embodiments, $R^{30}$ is an unsubstituted aryl (e.g., $C_6$-$C_{10}$ aryl, $C_{10}$ aryl, or phenyl).

In embodiments, $R^{30}$ is $R^{31}$-substituted or unsubstituted heteroaryl (e.g., 5 to 10 membered heteroaryl, 5 to 9 membered heteroaryl, or 5 to 6 membered heteroaryl). In embodiments, $R^{30}$ is $R^{31}$-substituted heteroaryl (e.g., 5 to 10 membered heteroaryl, 5 to 9 membered heteroaryl, or 5 to 6 membered heteroaryl). In embodiments, $R^{30}$ is an unsubstituted heteroaryl (e.g., 5 to 10 membered heteroaryl, 5 to 9 membered heteroaryl, or 5 to 6 membered heteroaryl).

$R^{31}$ is independently oxo, halogen, $-CCl_3$, $-CBr_3$, $-CF_3$, $-CI_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $R^{32}$-substituted or unsubstituted alkyl (e.g., $C_1$-$C_8$ alkyl, $C_1$-$C_6$ alkyl, or $C_1$-$C_4$ alkyl), $R^{32}$-substituted or unsubstituted heteroalkyl (e.g., 2 to 8 membered heteroalkyl, 2 to 6 membered heteroalkyl, or 2 to 4 membered heteroalkyl), $R^{32}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{32}$-substituted or unsubstituted heterocycloalkyl (e.g., 3 to 8 membered heterocycloalkyl, 3 to 6 membered heterocycloalkyl, or 5 to 6 membered heterocycloalkyl), $R^{32}$-substituted or unsubstituted aryl (e.g., $C_6$-$C_{10}$ aryl, $C_{10}$ aryl, or phenyl), or $R^{32}$-substituted or unsubstituted heteroaryl (e.g., 5 to 10 membered heteroaryl, 5 to 9 membered heteroaryl, or 5 to 6 membered heteroaryl).

In embodiments, $R^{31}$ is $R^{32}$-substituted or unsubstituted alkyl (e.g., $C_1$-$C_8$ alkyl, $C_1$-$C_6$ alkyl, or $C_1$-$C_4$ alkyl). In embodiments, $R^{31}$ is $R^{32}$-substituted alkyl (e.g., $C_1$-$C_8$ alkyl, $C_1$-$C_6$ alkyl, or $C_1$-$C_4$ alkyl). In embodiments, $R^{31}$ is an unsubstituted alkyl (e.g., $C_1$-$C_8$ alkyl, $C_1$-$C_6$ alkyl, or $C_1$-$C_4$ alkyl).

In embodiments, $R^{31}$ is $R^{32}$-substituted or unsubstituted heteroalkyl (e.g., 2 to 8 membered heteroalkyl, 2 to 6 membered heteroalkyl, or 2 to 4 membered heteroalkyl). In embodiments, $R^{31}$ is $R^{32}$-substituted heteroalkyl (e.g., 2 to 8 membered heteroalkyl, 2 to 6 membered heteroalkyl, or 2 to 4 membered heteroalkyl). In embodiments, $R^{31}$ is an unsubstituted heteroalkyl (e.g., 2 to 8 membered heteroalkyl, 2 to 6 membered heteroalkyl, or 2 to 4 membered heteroalkyl).

In embodiments, $R^{31}$ is $R^{32}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{31}$ is $R^{32}$-substituted cycloalkyl (e.g., $C_3$-$C_8$ cycloalkyl, $C_3$-$C_6$ cycloalkyl, or $C_5$-$C_6$ cycloalkyl). In embodiments, $R^{31}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{31}$ is $R^{32}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{31}$ is $R^{32}$-substituted heterocycloalkyl (e.g., 3 to 8 membered heterocycloalkyl, 3 to 6 membered heterocycloalkyl, or 5 to 6 membered heterocycloalkyl). In embodiments, $R^{31}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{31}$ is $R^{32}$-substituted or unsubstituted aryl (e.g., $C_6$-$C_{10}$ aryl, $C_{10}$ aryl, or phenyl). In embodiments, $R^{31}$ is $R^{32}$-substituted aryl (e.g., $C_6$-$C_{10}$ aryl, $C_{10}$ aryl, or phenyl). In embodiments, $R^{31}$ is an unsubstituted aryl (e.g., $C_6$-$C_{10}$ aryl, $C_{10}$ aryl, or phenyl).

In embodiments, $R^{31}$ is $R^{32}$-substituted or unsubstituted heteroaryl (e.g., 5 to 10 membered heteroaryl, 5 to 9 membered heteroaryl, or 5 to 6 membered heteroaryl). In embodiments, $R^{31}$ is $R^{32}$-substituted heteroaryl (e.g., 5 to 10 membered heteroaryl, 5 to 9 membered heteroaryl, or 5 to 6 membered heteroaryl). In embodiments, $R^{31}$ is an unsubstituted heteroaryl (e.g., 5 to 10 membered heteroaryl, 5 to 9 membered heteroaryl, or 5 to 6 membered heteroaryl).

$R^{33}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{34}$-substituted or unsubstituted alkyl (e.g., $C_1$-$C_8$ alkyl, $C_1$-$C_6$ alkyl, or $C_1$-$C_4$ alkyl), $R^{34}$-substituted or unsubstituted heteroalkyl (e.g., 2 to 8 membered heteroalkyl, 2 to 6 membered heteroalkyl, or 2 to 4 membered heteroalkyl), $R^{34}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{34}$-substituted or unsubstituted heterocycloalkyl (e.g., 3 to 8 membered heterocycloalkyl, 3 to 6 membered heterocycloalkyl, or 5 to 6 membered heterocycloalkyl), $R^{34}$-substituted or unsubstituted aryl (e.g., $C_6$-$C_{10}$ aryl, $C_{10}$ aryl, or phenyl), or $R^{34}$-substituted or unsubstituted heteroaryl (e.g., 5 to 10 membered heteroaryl, 5 to 9 membered heteroaryl, or 5 to 6 membered heteroaryl).

In embodiments, $R^{33}$ is $R^{34}$-substituted or unsubstituted alkyl (e.g., $C_1$-$C_8$ alkyl, $C_1$-$C_6$ alkyl, or $C_1$-$C_4$ alkyl). In embodiments, $R^{33}$ is $R^{34}$-substituted alkyl (e.g., $C_1$-$C_8$ alkyl, $C_1$-$C_6$ alkyl, or $C_1$-$C_4$ alkyl). In embodiments, $R^{33}$ is an unsubstituted alkyl (e.g., $C_1$-$C_8$ alkyl, $C_1$-$C_6$ alkyl, or $C_1$-$C_4$ alkyl).

In embodiments, $R^{33}$ is $R^{34}$-substituted or unsubstituted heteroalkyl (e.g., 2 to 8 membered heteroalkyl, 2 to 6 membered heteroalkyl, or 2 to 4 membered heteroalkyl). In embodiments, $R^{33}$ is $R^{34}$-substituted heteroalkyl (e.g., 2 to 8 membered heteroalkyl, 2 to 6 membered heteroalkyl, or 2 to 4 membered heteroalkyl). In embodiments, $R^{33}$ is an unsubstituted heteroalkyl (e.g., 2 to 8 membered heteroalkyl, 2 to 6 membered heteroalkyl, or 2 to 4 membered heteroalkyl).

In embodiments, $R^{33}$ is $R^{34}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{33}$ is $R^{34}$-substituted cycloalkyl (e.g., $C_3$-$C_8$ cycloalkyl, $C_3$-$C_6$ cycloalkyl, or $C_5$-$C_6$ cycloalkyl). In embodiments, $R^{33}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{33}$ is $R^{34}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{33}$ is $R^{34}$-substituted heterocycloalkyl (e.g., 3 to 8 membered heterocycloalkyl, 3 to 6 membered heterocycloalkyl, or 5 to 6 membered heterocycloalkyl). In embodiments, $R^{33}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{33}$ is $R^{34}$-substituted or unsubstituted aryl (e.g., $C_6$-$C_{10}$ aryl, $C_{10}$ aryl, or phenyl). In embodiments, $R^{33}$ is $R^{34}$-substituted aryl (e.g., $C_6$-$C_{10}$ aryl, $C_{10}$ aryl, or phenyl). In embodiments, $R^{33}$ is an unsubstituted aryl (e.g., $C_6$-$C_{10}$ aryl, $C_{10}$ aryl, or phenyl).

In embodiments, $R^{33}$ is $R^{34}$-substituted or unsubstituted heteroaryl (e.g., 5 to 10 membered heteroaryl, 5 to 9 membered heteroaryl, or 5 to 6 membered heteroaryl). In embodiments, $R^{33}$ is $R^{34}$-substituted heteroaryl (e.g., 5 to 10 membered heteroaryl, 5 to 9 membered heteroaryl, or 5 to 6 membered heteroaryl). In embodiments, $R^{33}$ is an unsubstituted heteroaryl (e.g., 5 to 10 membered heteroaryl, 5 to 9 membered heteroaryl, or 5 to 6 membered heteroaryl).

$R^{34}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{35}$-substituted or unsubstituted alkyl (e.g., $C_1$-$C_8$ alkyl, $C_1$-$C_6$ alkyl, or $C_1$-$C_4$ alkyl), $R^{35}$-substituted or unsubstituted heteroalkyl (e.g., 2 to 8 membered heteroalkyl, 2 to 6 membered heteroalkyl, or 2 to 4 membered heteroalkyl), $R^{35}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{35}$-substituted or unsubstituted heterocycloalkyl (e.g., 3 to 8 membered heterocycloalkyl, 3 to 6 membered heterocycloalkyl, or 5 to 6 membered heterocycloalkyl), $R^{35}$-substituted or unsubstituted aryl (e.g., $C_6$-$C_{10}$ aryl, $C_{10}$ aryl, or phenyl), or $R^{35}$-substituted or unsubstituted heteroaryl (e.g., 5 to 10 membered heteroaryl, 5 to 9 membered heteroaryl, or 5 to 6 membered heteroaryl).

In embodiments, $R^{34}$ is $R^{35}$-substituted or unsubstituted alkyl (e.g., $C_1$-$C_8$ alkyl, $C_1$-$C_6$ alkyl, or $C_1$-$C_4$ alkyl). In embodiments, $R^{34}$ is $R^{35}$-substituted alkyl (e.g., $C_1$-$C_8$ alkyl, $C_1$-$C_6$ alkyl, or $C_1$-$C_4$ alkyl). In embodiments, $R^{34}$ is an unsubstituted alkyl (e.g., $C_1$-$C_8$ alkyl, $C_1$-$C_6$ alkyl, or $C_1$-$C_4$ alkyl).

In embodiments, $R^{34}$ is $R^{35}$-substituted or unsubstituted heteroalkyl (e.g., 2 to 8 membered heteroalkyl, 2 to 6 membered heteroalkyl, or 2 to 4 membered heteroalkyl). In embodiments, $R^{34}$ is $R^{35}$-substituted heteroalkyl (e.g., 2 to 8 membered heteroalkyl, 2 to 6 membered heteroalkyl, or 2 to 4 membered heteroalkyl). In embodiments, $R^{34}$ is an unsubstituted heteroalkyl (e.g., 2 to 8 membered heteroalkyl, 2 to 6 membered heteroalkyl, or 2 to 4 membered heteroalkyl).

In embodiments, $R^{34}$ is $R^{35}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{34}$ is $R^{35}$-substituted cycloalkyl (e.g., $C_3$-$C_8$ cycloalkyl, $C_3$-$C_6$ cycloalkyl, or $C_5$-$C_6$ cycloalkyl). In embodiments, $R^{34}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{34}$ is $R^{35}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{34}$ is $R^{35}$-substituted heterocycloalkyl (e.g., 3 to 8 membered heterocycloalkyl, 3 to 6 membered heterocycloalkyl, or 5 to 6 membered heterocycloalkyl). In embodiments, $R^{34}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{34}$ is $R^{35}$-substituted or unsubstituted aryl (e.g., $C_6$-$C_{10}$ aryl, $C_{10}$ aryl, or phenyl). In embodiments, $R^{34}$ is $R^{35}$-substituted aryl (e.g., $C_6$-$C_{10}$ aryl, $C_{10}$ aryl, or phenyl). In embodiments, $R^{34}$ is an unsubstituted aryl (e.g., $C_6$-$C_{10}$ aryl, $C_{10}$ aryl, or phenyl).

In embodiments, $R^{34}$ is $R^{35}$-substituted or unsubstituted heteroaryl (e.g., 5 to 10 membered heteroaryl, 5 to 9 membered heteroaryl, or 5 to 6 membered heteroaryl). In embodiments, $R^{34}$ is $R^{35}$-substituted heteroaryl (e.g., 5 to 10 membered heteroaryl, 5 to 9 membered heteroaryl, or 5 to 6 membered heteroaryl). In embodiments, $R^{34}$ is an unsubstituted heteroaryl (e.g., 5 to 10 membered heteroaryl, 5 to 9 membered heteroaryl, or 5 to 6 membered heteroaryl).

$R^{29}$, $R^{29L}$, $R^{32}$, $R^{33A}$, $R^{33B}$, $R^{33C}$, $R^{33D}$, $R^{35}$, $R^{37}$, and $R^{39}$ are independently hydrogen, oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, the compound of Formula (I) is ionically bound to $Y^1$, wherein $Y^1$ is an anionic counterion selected from the groups consisting of a halogen anion, an inorganic anion, an organic anion or an anionic bile acid receptor modulator. In embodiments, the halogen anion is $F^-$, $Cl^-$, $Br^-$ or $I^-$.

In embodiments, the inorganic anion is selected from the group consisting of carbonate, bicarbonate, chlorate, chromate, cyanide, dichromate, dihydrogen phosphate, hydrogen carbonate, hydrogen bicarbonate, hydrogen phosphate, hydrogen sulfate, hydrogen bisulfate, hydroxide, nitrate, nitride, nitrite, oxide, permanganate, peroxide, phosphate, sulfate, sulfide, sulfite and thiocyanate.

In embodiments, the organic anion is selected from the group consisting of a bile acid, a bile acid derivative, a carboxylate, phosphate, mesylate, tosylate and triflate.

In embodiments, the anionic bile acid receptor modulator is an anionic farnesoid X receptor (FXR) modulator or an anionic Takeda G-protein-coupled Receptor 5 (TGR5) modulator.

In embodiments, the anionic bile acid receptor modulator is an anionic TGR5 agonist. In embodiments, the anionic TGR5 agonist is a berberine derivative, a berberine salt, a bile acid derivative or a bile acid salt.

In embodiments, the anionic bile acid receptor modulator is an anionic FXR antagonist. In embodiments, the anionic FXR antagonist is a berberine derivative, a berberine salt, a bile acid derivative, a bile acid salt or a γ-aminobutyric acid (GABA) derivative.

In another aspect, there is provided a composition including a bile acid receptor modulator and compound of the formula:

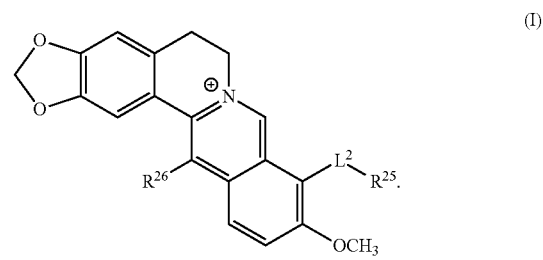

(I)

$L^2$ is a bond, —C(O)—, —C(O)O—, —O—, —S—, —$NR^{2L}$—, —$C(O)NR^{2L}$—, —$NR^{2L}C(O)$—, —$S(O)_2$—, —$S(O)NR^{2L}$—, —$NR^{2L}C(O)NH$—, —$NHC(O)NR^{2L}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^{25}$ is —$OCH_3$, substituted or unsubstituted cycloalkyl, substituted or unsubstituted heterocycloalkyl, substituted or unsubstituted aryl or substituted or unsubstituted heteroaryl. $R^{26}$ is hydrogen, halogen, —$CX^{26}_3$, —$CHX^{26}_2$, —$CH_2X^{26}$, —$OCX^{26}_3$, —$OCH_2X^{26}$, —$OCHX^{26}_2$, —CN, —$SO_{n26}R^{26C}$, —$SO_{v26}NR^{26A}R^{26B}$, —$NHC(O)NR^{26A}R^{26B}$, —$N(O)_{m26}$, —$NR^{26A}R^{26B}$, —$C(O)R^{26C}$, —C(O)—$OR^{26C}$, —$C(O)NR^{26A}R^{26B}$, —$OR^{26C}$, —$NR^{26A}SO_2R^{26C}$, —$NR^{26A}C(O)R^{26C}$, —$NR^{26A}C(O)OR^{26C}$, —$NR^{26A}OR^{26C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{2L}$, $R^{26A}$, $R^{26B}$ and $R^{26C}$ are independently hydrogen, —$CX^{26A}_3$, —CN, —COOH, —$CONH_2$, —$CHX^{26A}_2$, —$CH_2X^{26A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $X^{26}$ and $X^{26A}$ are independently halogen. n26 is an integer from 0 to 4. m26 and v26 are independently 1 or 2. In embodiments, the bile acid receptor modulator is a farnesoid X receptor (FXR) modulator. In embodiments, the bile acid receptor modulator is a Takeda G-protein-coupled Receptor 5 (TGR5) modulator.

In embodiments, n26, m26, v26, $X^{26}$, $X^{26A}$, $L^2$, $R^{25}$, $R^{26}$, $R^{2L}$, $R^{26A}$, $R^{26B}$, and $R^{26C}$ are as described herein, including embodiments.

In embodiments, $L^2$ is substituted heteroalkylene. In embodiments, $L^2$ is —NH—$(CH_2)_3$—NH—$S(O)_2$—O—$CH_2$—, —NH—$(CH_2)_6$NH—$S(O)_2$—O—$CH_2$—, —NH—$S(O)_2$—O—$CH_2$—, —NH—$(CH_2)_3$—C(O)—NH—$S(O)_2$—O—$CH_2$—, —NH($CH_2$)— or —NH$(CH_2)_2$—. In embodiments, $L^2$ is substituted 2 to 15 membered heteroalkylene. In embodiments, $L^2$ is substituted 2 to 12 membered heteroalkylene. In embodiments, $L^2$ is substituted 2 to 10 membered heteroalkylene. In embodiments, $L^2$ is substituted 2 to 8 membered heteroalkylene. In embodiments, $L^2$ is substituted 3 to 15 membered heteroalkylene. In embodiments, $L^2$ is unsubstituted 2 to 15 membered heteroalkylene. In embodiments, $L^2$ is unsubstituted 2 to 12 membered heteroalkylene. In embodiments, $L^2$ is unsubstituted 2 to 10 membered heteroalkylene. In embodiments, $L^2$ is unsubstituted 2 to 8 membered heteroalkylene. In embodiments, $L^2$ is unsubstituted 3 to 15 membered heteroalkylene.

In embodiments, $R^{25}$ is substituted heterocycloalkyl. In embodiments, $R^{25}$ is substituted 6 to 12 membered heterocycloalkyl. In embodiments, $R^{25}$ is

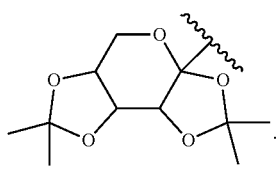

In embodiments, $R^{25}$ is

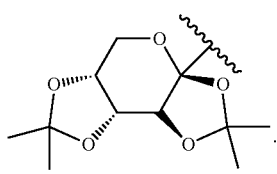

In embodiments, $R^{25}$ is

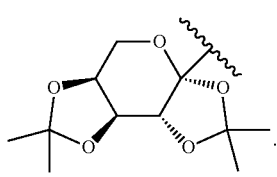

In embodiments, $R^{25}$ is substituted aryl. In embodiments, $R^{25}$ is substituted phenyl. In embodiments, $R^{25}$ is

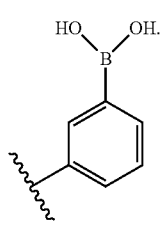 [SMILES: *c1cccc(B(O)O)c1]

In embodiments, $R^{25}$ is

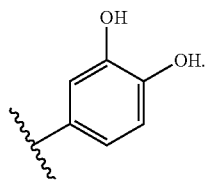 [SMILES: *c1ccc(O)c(O)c1]

In embodiments, the compound of formula (I) is

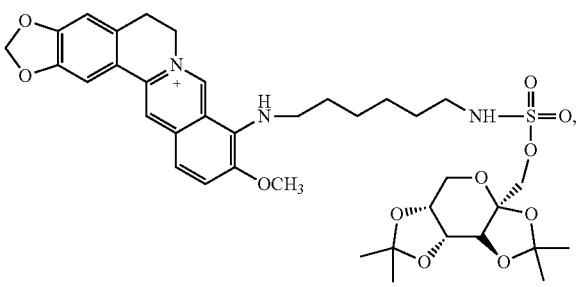

DY429

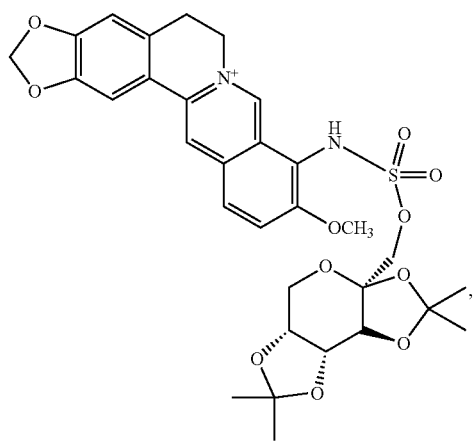

DY319

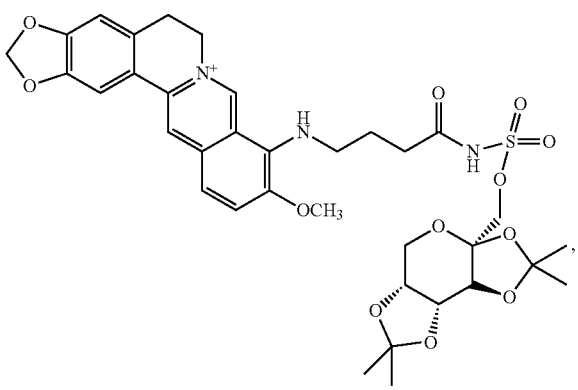

DY324

-continued

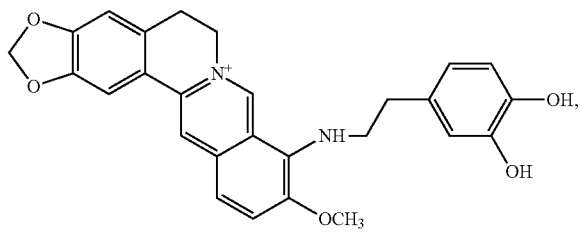
DY322

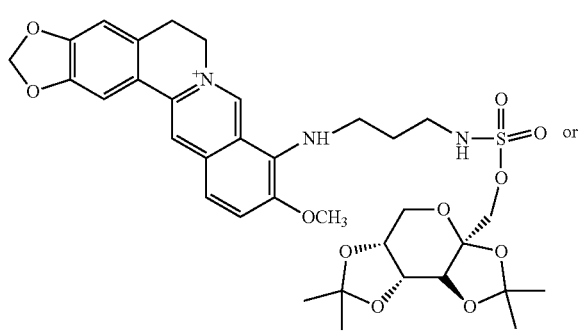
DY328

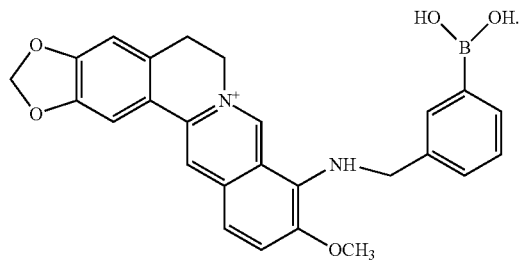
DY323

In embodiments, the compound of Formula (I) and the bile acid modulator are ionically bound together to form a salt composition having the formula:

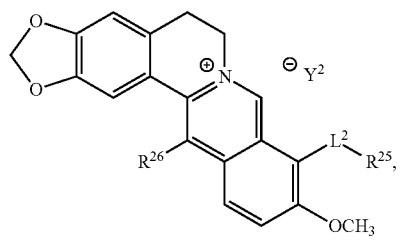
(II)

wherein $Y^2$ is an anionic bile acid receptor modulator.

In embodiments, $Y^2$ has the formula:

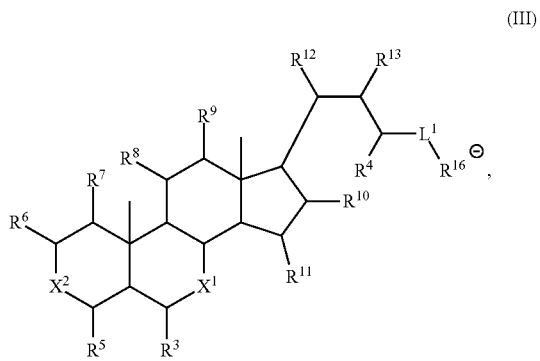
(III)

wherein: $L^1$ is a bond, —C(O)—, —C(O)O—, —C(O)NH—, or —CH$_2$—; $X^1$ is —C(O)— or —C(R$^1$)(R$^2$)—; $X^2$ is —C(O)— or —C(R$^{14}$)(R$^{15}$)—; $R^1$ is hydrogen, unsubstituted alkyl, or —OR$^{1A}$; $R^2$ is hydrogen, unsubstituted alkyl, or —OR$^{2A}$; $R^3$ is hydrogen, unsubstituted alkyl, or —OR$^{3A}$; $R^4$ is hydrogen or unsubstituted alkyl; $R^5$ is hydrogen, unsubstituted alkyl, or —OR$^{5A}$; $R^6$ is hydrogen, unsubstituted alkyl, or —OR$^{6A}$; $R^7$ is hydrogen, unsubstituted alkyl, or —OR$^{7A}$; $R^8$ is hydrogen, unsubstituted alkyl, or —OR$^{8A}$; $R^9$ is hydrogen, unsubstituted alkyl, or —OR$^{9A}$; $R^{10}$ is hydrogen, unsubstituted alkyl, or —OR$^{10A}$; $R^{11}$ is hydrogen, unsubstituted alkyl, or —OR$^{11A}$; $R^{12}$ is hydrogen, unsubstituted alkyl, or —OR$^{12A}$; $R^{13}$ is hydrogen, unsubstituted alkyl, or —OR$^{13A}$; $R^{14}$ is hydrogen, unsubstituted alkyl, or —OR$^{14A}$; $R^{15}$ is hydrogen, unsubstituted alkyl, or —OR$^{15A}$; $R^{16}$ is —COO$^-$, —S(O)$_3^-$, —SO$_4^-$ or —NH—S(O)$_3^-$; and $R^{1A}$, $R^{2A}$, $R^{3A}$, $R^{5A}$, $R^{6A}$, $R^{7A}$, $R^{8A}$, $R^{9A}$, $R^{10A}$, $R^{11A}$, $R^{12A}$, $R^{13A}$, $R^{14A}$, and $R^{15A}$ are independently hydrogen, unsubstituted alkyl, or an alcohol protecting group.

In embodiments, the compound has a structure of:

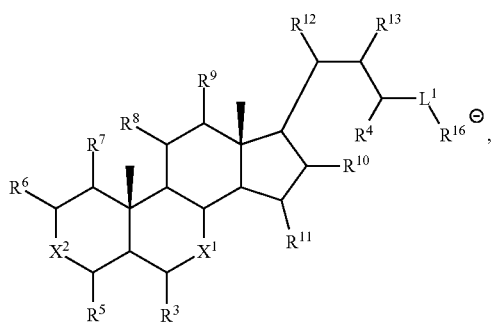

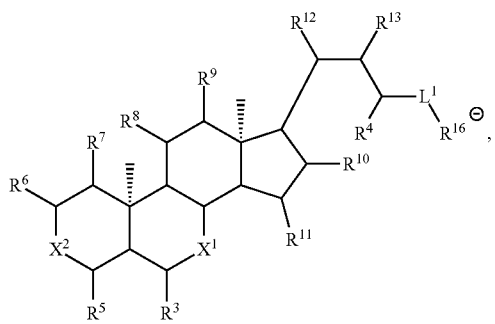

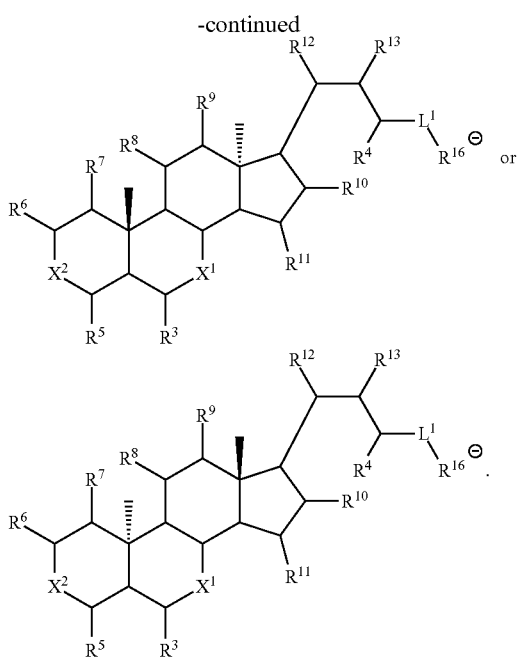

In embodiments, R¹ is hydrogen. In embodiments, R¹ is unsubstituted $C_1$-$C_3$ alkyl. In embodiments, R¹ is unsubstituted methyl or ethyl. In embodiments, R¹ is —OH, or —OCH₃. In embodiments, R² is hydrogen. In embodiments, R² is unsubstituted $C_1$-$C_3$ alkyl. In embodiments, R² is unsubstituted methyl or ethyl. In embodiments, R² is —OH, or —OCH₃. In embodiments, R³ is hydrogen. In embodiments, R¹⁴ is hydrogen. In embodiments, R¹⁴ is unsubstituted $C_1$-$C_3$ alkyl. In embodiments, R¹⁴ is unsubstituted methyl or ethyl. In embodiments, R¹⁴ is —OH, or —OCH₃. In embodiments, R¹⁵ is hydrogen. In embodiments, R¹⁵ is unsubstituted $C_1$-$C_3$ alkyl. In embodiments, R¹⁵ is unsubstituted methyl or ethyl. In embodiments, R¹⁵ is —OH, or —OCH₃.

In embodiments, X¹ is —CH₂—. In embodiments, X² is —CH₂—.

In embodiments, R³ is unsubstituted $C_1$-$C_3$ alkyl. In embodiments, R³ is unsubstituted methyl or ethyl. In embodiments, R³ is —OH, or —OCH₃. In embodiments, R⁵ is hydrogen. In embodiments, R⁵ is unsubstituted $C_1$-$C_3$ alkyl. In embodiments, R⁵ is unsubstituted methyl or ethyl. In embodiments, R⁵ is —OH, or —OCH₃. In embodiments, R⁶ is hydrogen. In embodiments, R⁶ is unsubstituted $C_1$-$C_3$ alkyl. In embodiments, R⁶ is unsubstituted methyl or ethyl. In embodiments, R⁶ is —OH, or —OCH₃. In embodiments, R⁷ is hydrogen. In embodiments, R⁷ is unsubstituted $C_1$-$C_3$ alkyl. In embodiments, R⁷ is unsubstituted methyl or ethyl. In embodiments, R⁷ is —OH, or —OCH₃. In embodiments, R⁸ is hydrogen. In embodiments, R⁸ is unsubstituted $C_1$-$C_3$ alkyl. In embodiments, R⁸ is unsubstituted methyl or ethyl. In embodiments, R⁸ is —OH, or —OCH₃. In embodiments, R⁹ is hydrogen. In embodiments, R⁹ is unsubstituted $C_1$-$C_3$ alkyl. In embodiments, R⁹ is unsubstituted methyl or ethyl. In embodiments, R⁹ is —OH, or —OCH₃. In embodiments, R¹⁰ is hydrogen. In embodiments, R¹⁰ is unsubstituted $C_1$-$C_3$ alkyl. In embodiments, R¹⁰ is unsubstituted methyl or ethyl. In embodiments, R¹⁰ is —OH, or —OCH₃.

In embodiments, R⁴ is hydrogen. In embodiments, R⁴ is unsubstituted $C_1$-$C_3$ alkyl. In embodiments, R⁴ is unsubstituted methyl or ethyl.

In embodiments, L¹ is a bond. In embodiments, L¹ is —C(O)—. In embodiments, L¹ is —C(O)O—. In embodiments, L¹ is —C(O)NH—. In embodiments, L¹ is —CH₂—.

In embodiments, R¹⁶ is —COO⁻. In embodiments, R¹⁶ is —S(O)₃⁻, —SO₄⁻ or —NH—S(O)₃⁻. In embodiments, R¹⁶ is —NHCH₂CH₂—S(O)₃⁻.

In embodiments, the compound of formula (III) is

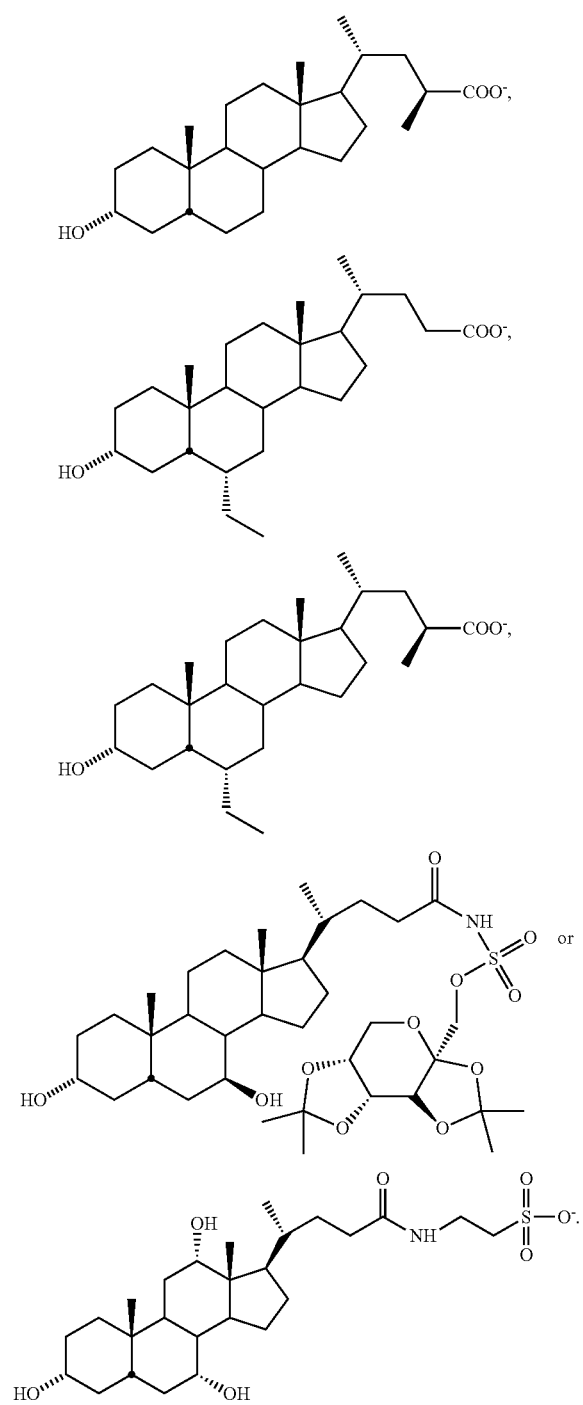

In embodiments, $Y^2$ is

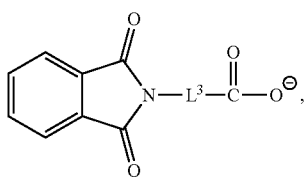

(IV)

wherein $L^3$ is substituted or unsubstituted alkylene.

In embodiments, $L^3$ is $R^{36}$-substituted or unsubstituted alkylene (e.g., $C_1$-$C_{12}$ alkylene, $C_1$-$C_8$ alkylene, $C_1$-$C_6$ alkylene, or $C_1$-$C_4$ alkylene). In embodiments, $L^3$ is $R^{36}$-substituted alkylene (e.g., $C_1$-$C_{12}$ alkylene, $C_1$-$C_8$ alkylene, $C_1$-$C_6$ alkylene, or $C_1$-$C_4$ alkylene). In embodiments, $L^3$ is an unsubstituted alkylene (e.g., $C_1$-$C_{12}$ alkylene, $C_1$-$C_8$ alkylene, $C_1$-$C_6$ alkylene, or $C_1$-$C_4$ alkylene).

$R^{36}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{37}$-substituted or unsubstituted alkyl (e.g., $C_1$-$C_8$ alkyl, $C_1$-$C_6$ alkyl, or $C_1$-$C_4$ alkyl), $R^{37}$-substituted or unsubstituted heteroalkyl (e.g., 2 to 8 membered heteroalkyl, 2 to 6 membered heteroalkyl, or 2 to 4 membered heteroalkyl), $R^{37}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{37}$-substituted or unsubstituted heterocycloalkyl (e.g., 3 to 8 membered heterocycloalkyl, 3 to 6 membered heterocycloalkyl, or 5 to 6 membered heterocycloalkyl), $R^{37}$-substituted or unsubstituted aryl (e.g., $C_6$-$C_{10}$ aryl, $C_{10}$ aryl, or phenyl), or $R^{37}$-substituted or unsubstituted heteroaryl (e.g., 5 to 10 membered heteroaryl, 5 to 9 membered heteroaryl, or 5 to 6 membered heteroaryl).

In embodiments, $R^{36}$ is $R^{37}$-substituted or unsubstituted alkyl (e.g., $C_1$-$C_8$ alkyl, $C_1$-$C_6$ alkyl, or $C_1$-$C_4$ alkyl). In embodiments, $R^{36}$ is $R^{37}$-substituted alkyl (e.g., $C_1$-$C_8$ alkyl, $C_1$-$C_6$ alkyl, or $C_1$-$C_4$ alkyl). In embodiments, $R^{36}$ is an unsubstituted alkyl (e.g., $C_1$-$C_8$ alkyl, $C_1$-$C_6$ alkyl, or $C_1$-$C_4$ alkyl).

In embodiments, $R^{36}$ is $R^{37}$-substituted or unsubstituted heteroalkyl (e.g., 2 to 8 membered heteroalkyl, 2 to 6 membered heteroalkyl, or 2 to 4 membered heteroalkyl). In embodiments, $R^{36}$ is $R^{37}$-substituted heteroalkyl (e.g., 2 to 8 membered heteroalkyl, 2 to 6 membered heteroalkyl, or 2 to 4 membered heteroalkyl). In embodiments, $R^{36}$ is an unsubstituted heteroalkyl (e.g., 2 to 8 membered heteroalkyl, 2 to 6 membered heteroalkyl, or 2 to 4 membered heteroalkyl).

In embodiments, $R^{36}$ is $R^{37}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{36}$ is $R^{37}$-substituted cycloalkyl (e.g., $C_3$-$C_8$ cycloalkyl, $C_3$-$C_6$ cycloalkyl, or $C_5$-$C_6$ cycloalkyl). In embodiments, $R^{36}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{36}$ is $R^{37}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{36}$ is $R^{37}$-substituted heterocycloalkyl (e.g., 3 to 8 membered heterocycloalkyl, 3 to 6 membered heterocycloalkyl, or 5 to 6 membered heterocycloalkyl). In embodiments, $R^{36}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{36}$ is $R^{37}$-substituted or unsubstituted aryl (e.g., $C_6$-$C_{10}$ aryl, $C_{10}$ aryl, or phenyl). In embodiments, $R^{36}$ is $R^{37}$-substituted aryl (e.g., $C_6$-$C_{10}$ aryl, $C_{10}$ aryl, or phenyl). In embodiments, $R^{36}$ is an unsubstituted aryl (e.g., $C_6$-$C_{10}$ aryl, $C_{10}$ aryl, or phenyl).

In embodiments, $R^{36}$ is $R^{37}$-substituted or unsubstituted heteroaryl (e.g., 5 to 10 membered heteroaryl, 5 to 9 membered heteroaryl, or 5 to 6 membered heteroaryl). In embodiments, $R^{36}$ is $R^{37}$-substituted heteroaryl (e.g., 5 to 10 membered heteroaryl, 5 to 9 membered heteroaryl, or 5 to 6 membered heteroaryl). In embodiments, $R^{36}$ is an unsubstituted heteroaryl (e.g., 5 to 10 membered heteroaryl, 5 to 9 membered heteroaryl, or 5 to 6 membered heteroaryl).

$R^{37}$ is hydrogen, oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$—$OCHF_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $L^3$ is unsubstituted $C_1$-$C_{12}$ alkylene. In embodiments, $L^3$ is unsubstituted $C_3$-$C_{12}$ alkylene. In embodiments, $L^3$ is unsubstituted linear $C_3$-$C_{12}$ alkylene.

In embodiments, the compound of formula (IV) is

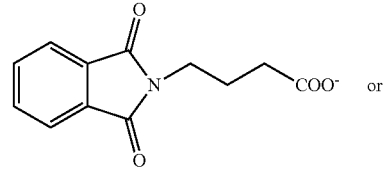

DY419 or

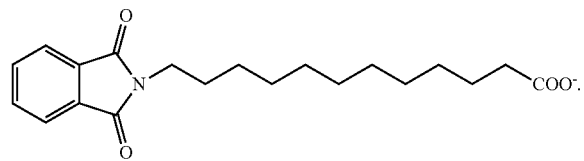

DY420

In embodiments, $Y^2$ is γ-aminobutyric acid or biologically active derivative thereof.

In embodiments, $Y^2$ is

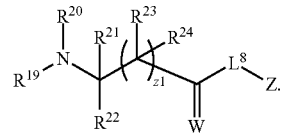

(V)

W is =O or =S; Z is hydrogen, —OR$^{27A}$, —CX$^{27}_3$, —CHX$^{27}_2$, —CH$_2$X$^{27}$, —OCX$^{27}_3$, —OCH$_2$X$^{27}$, —OCHX$^{27}_2$, —CN, —SO$_{n27}$R$^{27D}$, —SO$_{v27}$NR$^{27A}$R$^{27B}$, —NHC(O)NR$^{27A}$R$^{27B}$, —N(O)$_{m27}$, —NR$^{27A}$R$^{27B}$, —C(O) R$^{27C}$, —C(O)—OR$^{27C}$, —C(O)NR$^{27A}$R$^{27B}$, —OR$^{27C}$, —NR$^{27A}$SO$_2$R$^{27C}$, —NR$^{27A}$C(O)R$^{27C}$, —NR$^{27A}$C(O) OR$^{27C}$, —NR$^{27A}$OR$^{27C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, —O$^-$, —C(O)O$^-$, —CH$_2$C(O) O$^-$, —SO$_3^-$, —SO$_4^-$, —NHS(O)$_3^-$, —NR$^{27A}$SO$_3^-$, —NR$^{27A}$C(O)O$^-$, —NR$^{27A}$O$^-$; or negatively charged carbohydrate, peptide, nucleic acid or amino acid; L$^8$ is a bond, —C(O)—, —C(O)O—, —O—, —S—, —NR$^{8L}$—, —C(O) NR$^{8L}$—, —NR$^{8L}$C(O)—, —S(O)$_2$—, —O—S(O)$_2$NR$^{8L}$—, —NR$^{8L}$C(O)NH—, —NHC(O)NR$^{8L}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; R$^{19}$ and R$^{20}$ are independently, hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. R$^{19}$ and R$^{20}$ substituents bonded to the same nitrogen atom may optionally be joined to form a substituted or unsubstituted heterocycloalkyl or substituted or unsubstituted heteroaryl. R$^{21}$ is hydrogen, halogen, —CX$^{21}_3$, —CHX$^{21}_2$, —CH$_2$X$^{21}$, —CN, —SO$_{n21}$R$^{21D}$, —SO$_{v21}$NR$^{21A}$R$^{21B}$, —NHC(O)NR$^{21A}$R$^{21B}$, —N(O)$_{m21}$, —NR$^{21A}$R$^{21B}$, —C(O) R$^{21C}$, —C(O)—OR$^{21C}$, —C(O)NR$^{21A}$R$^{21B}$, —OR$^{21D}$, —NR$^{21A}$SO$_2$R$^{21D}$, —NR$^{21A}$C(O)R$^{21C}$, —NR$^{21A}$C(O) OR$^{21C}$, —NR$^{21A}$OR$^{21C}$, —OCX$^{21}_3$, —OCHX$^{21}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{21A}$ and R$^{21B}$ substituents bonded to the same nitrogen atom may optionally be joined to form a substituted or unsubstituted heterocycloalkyl or substituted or unsubstituted heteroaryl; R$^{22}$ is hydrogen, halogen, —CX$^{22}_3$, —CHX$^{22}_2$, —CH$_2$X$^{22}$, —CN, —SO$_{n22}$R$^{22D}$, —SO$_{v22}$NR$^{22A}$R$^{22B}$, —NHC(O)NR$^{22A}$R$^{22B}$, —N(O)$_{m22}$, —NR$^{22A}$R$^{22B}$, —C(O)R$^{22C}$, —C(O)—OR$^{22C}$, —C(O) NR$^{22A}$R$^{22B}$, —OR$^{22D}$, —NR$^{22A}$SO$_2$R$^{22D}$—NR$^{22A}$C(O) R$^{22C}$, —NR$^{22A}$C(O)OR$^{22C}$, —NR$^{22A}$OR$^{22C}$, —OCX$^{22}_3$, —OCHX$^{22}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{22A}$ and R$^{22B}$ substituents bonded to the same nitrogen atom may optionally be joined to form a substituted or unsubstituted heterocycloalkyl or substituted or unsubstituted heteroaryl; R$^{23}$ is hydrogen, halogen, —CX$^{23}_3$, —CHX$^{23}_2$, —CH$_2$X$^{23}$, —CN, —SO$_{n23}$R$^{23D}$, —SO$_{v23}$NR$^{23A}$R$^{23B}$, —NHC(O)NR$^{23A}$R$^{23B}$, —N(O)$_{m23}$, —NR$^{23A}$R$^{23B}$, —C(O)R$^{23C}$, —C(O)—OR$^{23C}$, —C(O) NR$^{23A}$R$^{23B}$, —OR$^{23D}$, —NR$^{23A}$SO$_2$R$^{23D}$, —NR$^{23A}$C(O) R$^{23C}$, —NR$^{23A}$C(O)OR$^{23C}$, —NR$^{23A}$OR$^{23C}$, —OCX$^{23}_3$, —OCHX$^{23}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{23A}$ and R$^{23B}$ substituents bonded to the same nitrogen atom may optionally be joined to form a substituted or unsubstituted heterocycloalkyl or substituted or unsubstituted heteroaryl; R$^{24}$ is hydrogen, halogen, —CX$^{24}_3$, —CHX$^{24}_2$, —CH$_2$X$^{24}$, —CN, —SO$_{n24}$R$^{24D}$, —SO$_{24}$NR$^{24A}$R$^{24B}$, —NHC(O)NR$^{24A}$R$^{24B}$, —N(O)$_{m24}$, —NR$^{24A}$R$^{24B}$, —C(O) R$^{24C}$, —C(O)—OR$^{24C}$, —C(O) NR$^{24A}$R$^{24B}$, —OR$^{24D}$, —NR$^{24A}$SO$_2$R$^{24D}$, —NR$^{24A}$C(O) R$^{24C}$, —NR$^{24A}$C(O)OR$^{24C}$, —NR$^{24A}$OR$^{24C}$, —OCX$^{24}_3$, —OCHX$^{24}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{24A}$ and R$^{24B}$ substituents bonded to the same nitrogen atom may optionally be joined to form a substituted or unsubstituted heterocycloalkyl or substituted or unsubstituted heteroaryl; R$^{8L}$, R$^{21A}$, R$^{21B}$, R$^{21C}$, R$^{21D}$, R$^{22A}$, R$^{22B}$, R$^{22C}$, R$^{22D}$, R$^{23A}$, R$^{23B}$, R$^{23C}$, R$^{23D}$, R$^{24A}$, R$^{24B}$, R$^{24C}$, R$^{24D}$, R$^{27A}$, R$^{27B}$, R$^{27C}$ and R$^{27D}$ are independently hydrogen, —CF$_3$, —CCl$_3$, —CBr$_3$, —CI$_3$, —CN, —COOH, —CONH$_2$, —CHF$_2$, —CHCl$_2$, —CHBr$_2$, —CHI$_2$, —CH$_2$F$_2$, —CH$_2$Cl, —CH$_2$Br, —CH$_2$I, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; X$^{21}$, X$^{22}$, X$^{23}$, X$^{24}$ and X$^{27}$ are independently halogen; z1 is an integer from 0 to 12; n21, n22, n23, n24 and n27 are independently an integer from 0 to 4; and m21, m22, m23, m24; m27, v21, v22, v23, v24 and v27 are independently 1 or 2.

In embodiments, L$^8$ is a bond, —C(O)—, —C(O)O—, —O—, —S—, —NR$^{8L}$—, —C(O)NR$^{8L}$, —NR$^{8L}$C(O)—, —S(O)$_2$—, —O—S(O)$_2$NR$^{8L}$—, —NR$^{8L}$C(O)NH—, —NHC(O)NR$^{8L}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, L$^8$ is a bond, —C(O)—, —C(O)O—, —O—, —S—, —NR$^{8L}$—, —C(O)NR$^{8L}$—, —NR$^{8L}$C (O)—, —S(O)$_2$—, —S(O)NR$^{8L}$—, —NR$^{8L}$C(O)NH—, —NHC(O)NR$^{8L}$—, substituted or unsubstituted alkylene (e.g., C$_1$-C$_8$ alkylene, C$_1$-C$_6$ alkylene, or C$_1$-C$_4$ alkylene), substituted or unsubstituted heteroalkylene (e.g., 2 to 8 membered heteroalkylene, 2 to 6 membered heteroalkylene, or 2 to 4 membered heteroalkylene), substituted or unsubstituted cycloalkylene (e.g., C$_3$-C$_8$ cycloalkylene, C$_3$-C$_6$ cycloalkylene, or C$_5$-C$_6$ cycloalkylene), substituted or unsubstituted heterocycloalkylene (e.g., 3 to 8 membered heterocycloalkylene, 3 to 6 membered heterocycloalkylene, or 5 to 6 membered heterocycloalkylene), substituted or unsubstituted arylene (e.g., C$_6$-C$_{10}$ arylene, C$_{10}$ arylene, or phenylene), or substituted or unsubstituted heteroarylene (e.g., 5 to 10 membered heteroarylene, 5 to 9 membered heteroarylene, or 5 to 6 membered heteroarylene).

In embodiments, L$^8$ is a bond, —C(O)—, —C(O)O—, —O—, —S—, —NR$^{8L}$—, —C(O)NR$^{8L}$—, —NR$^{8L}$C (O)—, —S(O)$_2$—, —S(O)NR$^{8L}$—, —NR$^{8L}$C(O)NH—, —NHC(O)NR$^{8L}$—, R$^{38}$-substituted or unsubstituted alkylene (e.g., C$_1$-C$_8$ alkylene, C$_1$-C$_6$ alkylene, or C$_1$-C$_4$ alkylene), R$^{38}$-substituted or unsubstituted heteroalkylene (e.g., 2 to 8 membered heteroalkylene, 2 to 6 membered heteroalkylene, or 2 to 4 membered heteroalkylene), R$^{38}$-substituted or unsubstituted cycloalkylene (e.g., C$_3$-C$_8$ cycloalkylene, C$_3$-C$_6$ cycloalkylene, or C$_5$-C$_6$ cycloalkylene), R$^{38}$-substituted or unsubstituted heterocycloalkylene (e.g., 3 to 8 membered heterocycloalkylene, 3 to 6 membered heterocycloalkylene, or 5 to 6 membered heterocycloalkylene), $R^{38}$-substituted or unsubstituted arylene (e.g., $C_6$-$C_{10}$ arylene, $C_{10}$ arylene, or phenylene), or $R^{38}$-substituted or unsubstituted heteroarylene (e.g., 5 to 10 membered heteroarylene, 5 to 9 membered heteroarylene, or 5 to 6 membered heteroarylene). In embodiments, $L^8$ is a bond.

In embodiments, $L^8$ is $R^{38}$-substituted or unsubstituted alkylene (e.g., $C_1$-$C_8$ alkylene, $C_1$-$C_6$ alkylene, or $C_1$-$C_4$ alkylene). In embodiments, $L^8$ is $R^{38}$-substituted alkylene (e.g., $C_1$-$C_8$ alkylene, $C_1$-$C_6$ alkylene, or $C_1$-$C_4$ alkylene). In embodiments, $L^8$ is an unsubstituted alkylene (e.g., $C_1$-$C_8$ alkylene, $C_1$-$C_6$ alkylene, or $C_1$-$C_4$ alkylene).

In embodiments, $L^8$ is $R^{38}$-substituted or unsubstituted heteroalkylene (e.g., 2 to 8 membered heteroalkylene, 2 to 6 membered heteroalkylene, or 2 to 4 membered heteroalkylene). In embodiments, $L^8$ is $R^{38}$-substituted heteroalkylene (e.g., 2 to 8 membered heteroalkylene, 2 to 6 membered heteroalkylene, or 2 to 4 membered heteroalkylene). In embodiments, $L^8$ is an unsubstituted heteroalkylene (e.g., 2 to 8 membered heteroalkylene, 2 to 6 membered heteroalkylene, or 2 to 4 membered heteroalkylene).

In embodiments, $L^8$ is $R^{38}$-substituted or unsubstituted cycloalkylene (e.g., $C_3$-$C_8$ cycloalkylene, $C_3$-$C_6$ cycloalkylene, or $C_5$-$C_6$ cycloalkylene). In embodiments, $L^8$ is $R^{38}$-substituted cycloalkylene (e.g., $C_3$-$C_8$ cycloalkylene, $C_3$-$C_6$ cycloalkylene, or $C_5$-$C_6$ cycloalkylene). In embodiments, $L^8$ is an unsubstituted cycloalkylene (e.g., $C_3$-$C_8$ cycloalkylene, $C_3$-$C_6$ cycloalkylene, or $C_5$-$C_6$ cycloalkylene).

In embodiments, $L^8$ is $R^{38}$-substituted or unsubstituted heterocycloalkylene (e.g., 3 to 8 membered heterocycloalkylene, 3 to 6 membered heterocycloalkylene, or 5 to 6 membered heterocycloalkylene). In embodiments, $L^8$ is $R^{38}$-substituted heterocycloalkylene (e.g., 3 to 8 membered heterocycloalkylene, 3 to 6 membered heterocycloalkylene, or 5 to 6 membered heterocycloalkylene). In embodiments, $L^8$ is an unsubstituted heterocycloalkylene (e.g., 3 to 8 membered heterocycloalkylene, 3 to 6 membered heterocycloalkylene, or 5 to 6 membered heterocycloalkylene).

In embodiments, $L^8$ is $R^{38}$-substituted or unsubstituted arylene (e.g., $C_6$-$C_{10}$ arylene, $C_{10}$ arylene, or phenylene). In embodiments, $L^8$ is $R^{38}$-substituted arylene (e.g., $C_6$-$C_{10}$ arylene, $C_{10}$ arylene, or phenylene). In embodiments, $L^8$ is an unsubstituted arylene (e.g., $C_6$-$C_{10}$ arylene, $C_{10}$ arylene, or phenylene).

In embodiments, $L^8$ is $R^{38}$-substituted or unsubstituted heteroarylene (e.g., 5 to 10 membered heteroarylene, 5 to 9 membered heteroarylene, or 5 to 6 membered heteroarylene). In embodiments, $L^8$ is $R^{38}$-substituted heteroarylene (e.g., 5 to 10 membered heteroarylene, 5 to 9 membered heteroarylene, or 5 to 6 membered heteroarylene). In embodiments, $L^8$ is an unsubstituted heteroarylene (e.g., 5 to 10 membered heteroarylene, 5 to 9 membered heteroarylene, or 5 to 6 membered heteroarylene).

$R^{38}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{39}$-substituted or unsubstituted alkyl (e.g., $C_1$-$C_8$ alkyl, $C_1$-$C_6$ alkyl, or $C_1$-$C_4$ alkyl), $R^{39}$-substituted or unsubstituted heteroalkyl (e.g., 2 to 8 membered heteroalkyl, 2 to 6 membered heteroalkyl, or 2 to 4 membered heteroalkyl), $R^{39}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{39}$-substituted or unsubstituted heterocycloalkyl (e.g., 3 to 8 membered heterocycloalkyl, 3 to 6 membered heterocycloalkyl, or 5 to 6 membered heterocycloalkyl), $R^{39}$-substituted or unsubstituted aryl (e.g., $C_6$-$C_{10}$ aryl, $C_{10}$ aryl, or phenyl), or $R^{39}$-substituted or unsubstituted heteroaryl (e.g., 5 to 10 membered heteroaryl, 5 to 9 membered heteroaryl, or 5 to 6 membered heteroaryl).

In embodiments, $R^{38}$ is $R^{39}$-substituted or unsubstituted alkyl (e.g., $C_1$-$C_8$ alkyl, $C_1$-$C_6$ alkyl, or $C_1$-$C_4$ alkyl). In embodiments, $R^{38}$ is $R^{39}$-substituted alkyl (e.g., $C_1$-$C_8$ alkyl, $C_1$-$C_6$ alkyl, or $C_1$-$C_4$ alkyl). In embodiments, $R^{38}$ is an unsubstituted alkyl (e.g., $C_1$-$C_8$ alkyl, $C_1$-$C_6$ alkyl, or $C_1$-$C_4$ alkyl).

In embodiments, $R^{38}$ is $R^{39}$-substituted or unsubstituted heteroalkyl (e.g., 2 to 8 membered heteroalkyl, 2 to 6 membered heteroalkyl, or 2 to 4 membered heteroalkyl). In embodiments, $R^{38}$ is $R^{39}$-substituted heteroalkyl (e.g., 2 to 8 membered heteroalkyl, 2 to 6 membered heteroalkyl, or 2 to 4 membered heteroalkyl). In embodiments, $R^{38}$ is an unsubstituted heteroalkyl (e.g., 2 to 8 membered heteroalkyl, 2 to 6 membered heteroalkyl, or 2 to 4 membered heteroalkyl).

In embodiments, $R^{38}$ is $R^{39}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{38}$ is $R^{39}$-substituted cycloalkyl (e.g., $C_3$-$C_8$ cycloalkyl, $C_3$-$C_6$ cycloalkyl, or $C_5$-$C_6$ cycloalkyl). In embodiments, $R^{38}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{38}$ is $R^{39}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{38}$ is $R^{39}$-substituted heterocycloalkyl (e.g., 3 to 8 membered heterocycloalkyl, 3 to 6 membered heterocycloalkyl, or 5 to 6 membered heterocycloalkyl). In embodiments, $R^{38}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{38}$ is $R^{39}$-substituted or unsubstituted aryl (e.g., $C_6$-$C_{10}$ aryl, $C_{10}$ aryl, or phenyl). In embodiments, $R^{38}$ is $R^{39}$-substituted aryl (e.g., $C_6$-$C_{10}$ aryl, $C_{10}$ aryl, or phenyl). In embodiments, $R^{38}$ is an unsubstituted aryl (e.g., $C_6$-$C_{10}$ aryl, $C_{10}$ aryl, or phenyl).

In embodiments, $R^{38}$ is $R^{39}$-substituted or unsubstituted heteroaryl (e.g., 5 to 10 membered heteroaryl, 5 to 9 membered heteroaryl, or 5 to 6 membered heteroaryl). In embodiments, $R^{38}$ is $R^{39}$-substituted heteroaryl (e.g., 5 to 10 membered heteroaryl, 5 to 9 membered heteroaryl, or 5 to 6 membered heteroaryl). In embodiments, $R^{38}$ is an unsubstituted heteroaryl (e.g., 5 to 10 membered heteroaryl, 5 to 9 membered heteroaryl, or 5 to 6 membered heteroaryl).

$R^{39}$ is oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, n21 is 0. In embodiments, n21 is 1. In embodiments, n21 is 2. In embodiments, n21 is 3. In embodiments, n21 is 4. In embodiments, n22 is 0. In embodiments, n22 is 1. In embodiments, n22 is 2. In embodiments, n22 is 3. In embodiments, n22 is 4. In embodiments, n23 is 0. In embodiments, n23 is 1. In embodiments, n23 is 2. In embodiments, n23 is 3. In embodiments, n23 is 4. In embodiments, n24 is 0. In embodiments, n24 is 1. In embodiments, n24 is 2. In embodiments, n24 is 3. In embodiments, n24 is 4. In embodiments, n27 is 0. In embodiments, n27 is 1. In embodiments, n27 is 2. In embodiments, n27 is 3. In embodiments, n27 is 4.

In embodiments, m21 is 1. In embodiments, m21 is 2. In embodiments, v21 is 1. In embodiments, v21 is 2. In embodiments, m22 is 1. In embodiments, m22 is 2. In embodiments, v22 is 1. In embodiments, v22 is 2. In embodiments, m23 is 1. In embodiments, m23 is 2. In embodiments, v23 is 1. In embodiments, v23 is 2. In embodiments, m24 is 1. In embodiments, m24 is 2. In embodiments, v24 is 1. In embodiments, v24 is 2. In embodiments, m27 is 1. In embodiments, m27 is 2. In embodiments, v27 is 1. In embodiments, v27 is 2.

In embodiments, z1 is 0. In embodiments, z1 is 1. In embodiments, z1 is 2. In embodiments, z1 is 3. In embodiments, z1 is 4. In embodiments, z1 is 5. In embodiments, z1 is 6. In embodiments, z1 is 7. In embodiments, z1 is 8. In embodiments, z1 is 9. In embodiments, z1 is 10. In embodiments, z1 is 11. In embodiments, z1 is 12.

In embodiments, $X^{21}$ is F. In embodiments, $X^{21}$ is Cl. In embodiments, $X^{21}$ is Br. In embodiments, $X^{21}$ is I. In embodiments, $X^{22}$ is F. In embodiments, $X^{22}$ is Cl. In embodiments, $X^{22}$ is Br. In embodiments, $X^{22}$ is I. In embodiments, $X^{23}$ is F. In embodiments, $X^{23}$ is Cl. In embodiments, $X^{23}$ is Br. In embodiments, $X^{23}$ is I. In embodiments, $X^{24}$ is F. In embodiments, $X^{24}$ is Cl. In embodiments, $X^{24}$ is Br. In embodiments, $X^{24}$ is I. In embodiments, $X^{27}$ is F. In embodiments, $X^{27}$ is Cl. In embodiments, $X^{27}$ is Br. In embodiments, $X^{27}$ is I.

In embodiments, Z is hydrogen, $-OR^{27A}$, $-CX^{27}_3$, $-CHX^{27}_2$, $-CH_2X^{27}$, $-OCX^{27}_3$, $-OCH_2X^{27}$, $-OCHX^{27}_2$, $-CN$, $-SO_{n27}R^{27D}$, $-SO_{v27}NR^{27A}R^{27B}$, $-NHC(O)NR^{27A}R^{27B}$, $-N(O)_{m27}$, $-NR^{27A}R^{27B}$, $-C(O)R^{27C}$, $-C(O)-OR^{27C}$, $-C(O)NR^{27A}R^{27B}$, $-OR^{27C}$, $-NR^{27A}SO_2R^{27C}$, $-NR^{27A}C(O)R^{27C}$, $-NR^{27A}C(O)OR^{27C}$, $-NR^{27A}OR^{27C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl.

In embodiments, Z is hydrogen, $-OR^{27A}$, $-CX^{27}_3$, $-CHX^{27}_2$, $-CH_2X^{27}$, $-OCX^{27}_3$, $-OCH_2X^{27}$, $-OCHX^{27}_2$, $-CN$, $-SO_{n27}R^{27D}$, $-SO_{v27}NR^{27A}R^{27B}$, $-NHC(O)NR^{27A}R^{27B}$, $-N(O)_{m27}$, $-NR^{27A}R^{27B}$, $-C(O)R^{27C}$, $-C(O)-OR^{27C}$, $-C(O)NR^{27A}R^{27B}$, $-OR^{27C}$, $-NR^{27A}SO_2R^{27C}$, $-NR^{27A}C(O)R^{27C}$, $-NR^{27A}C(O)OR^{27C}$, $-NR^{27A}OR^{27C}$, $R^{27}$-substituted or unsubstituted alkyl, $R^{27}$-substituted or unsubstituted heteroalkyl, $R^{27}$-substituted or unsubstituted cycloalkyl, $R^{27}$-substituted or unsubstituted heterocycloalkyl, $R^{27}$-substituted or unsubstituted aryl, $R^{27}$-substituted or unsubstituted heteroaryl.

In embodiments, Z is a biologically active compound. In embodiments, Z is a negatively charged carbohydrate, peptide, nucleic acid or amino acid.

In embodiments, Z is, $-O^-$, $-C(O)O^-$, $-CH_2C(O)O^-$, $-SO_3^-$, $-SO_4^-$, $-NHS(O)_3^-$, $-NR^{27A}SO_3^-$, $-NR^{27A}C(O)O^-$, $-NR^{27A}O^-$; substituted alkyl, substituted cycloalkyl, or substituted aryl, each of which is substituted with at least one negatively charged substituent; or substituted or unsubstituted heteroalkyl, substituted or unsubstituted heterocycloalkyl, substituted or unsubstituted heteroaryl, each of which is negatively charged.

In embodiments, Z is $-O^-$. In embodiments, Z is $-C(O)O-$. In embodiments, Z is $-SO_3^-$ or $-SO_4^-$. In embodiments, Z is $-NHS(O)_3^-$. In embodiments, Z is $-NR^{27A}SO_3^-$, $-NR^{27A}C(O)O^-$ or $-NR^{27A}O^-$.

In embodiments, Z is $R^{27}$-substituted (e.g., with at least one negatively charged substituent) or unsubstituted alkyl (e.g., $C_1$-$C_8$ alkyl, $C_1$-$C_6$ alkyl, or $C_1$-$C_4$ alkyl). In embodiments, Z is $R^{27}$-substituted (e.g., with at least one negatively charged substituent) alkyl (e.g., $C_1$-$C_8$ alkyl, $C_1$-$C_6$ alkyl, or $C_1$-$C_4$ alkyl). In embodiments, Z is an unsubstituted alkyl (e.g., $C_1$-$C_8$ alkyl, $C_1$-$C_6$ alkyl, or $C_1$-$C_4$ alkyl).

In embodiments, Z is $R^{27}$-substituted (e.g., with at least one negatively charged substituent) or unsubstituted cycloalkyl (e.g., $C_3$-$C_8$ cycloalkyl, $C_3$-$C_6$ cycloalkyl, or $C_5$-$C_6$ cycloalkyl). In embodiments, Z is $R^{27}$-substituted (e.g., with at least one negatively charged substituent) cycloalkyl (e.g., $C_3$-$C_8$ cycloalkyl, $C_3$-$C_6$ cycloalkyl, or $C_5$-$C_6$ cycloalkyl). In embodiments, Z is an unsubstituted cycloalkyl (e.g., $C_3$-$C_8$ cycloalkyl, $C_3$-$C_6$ cycloalkyl, or $C_5$-$C_6$ cycloalkyl).

In embodiments, Z is $R^{27}$-substituted (e.g., with at least one negatively charged substituent) or unsubstituted aryl (e.g., $C_6$-$C_{10}$ aryl, $C_{10}$ aryl, or phenyl). In embodiments, Z is $R^{27}$-substituted (e.g., with at least one negatively charged substituent) aryl (e.g., $C_6$-$C_{10}$ aryl, $C_{10}$ aryl, or phenyl). In embodiments, Z is an unsubstituted aryl (e.g., $C_6$-$C_{10}$ aryl, $C_{10}$ aryl, or phenyl).

In embodiments, Z is $R^{27}$-substituted or unsubstituted heteroalkyl (e.g., 2 to 8 membered heteroalkyl, 2 to 6 membered heteroalkyl, or 2 to 4 membered heteroalkyl), (e.g., each of which is negatively charged). In embodiments, Z is $R^{27}$-substituted heteroalkyl (e.g., 2 to 8 membered heteroalkyl, 2 to 6 membered heteroalkyl, or 2 to 4 membered heteroalkyl), (e.g., each of which is negatively charged). In embodiments, Z is an unsubstituted heteroalkyl (e.g., 2 to 8 membered heteroalkyl, 2 to 6 membered heteroalkyl, or 2 to 4 membered heteroalkyl), (e.g., each of which is negatively charged).

In embodiments, Z is $R^{27}$-substituted or unsubstituted heterocycloalkyl (e.g., 3 to 8 membered heterocycloalkyl, 3 to 6 membered heterocycloalkyl, or 5 to 6 membered heterocycloalkyl), (e.g., each of which is negatively charged). In embodiments, Z is $R^{27}$-substituted heterocycloalkyl (e.g., 3 to 8 membered heterocycloalkyl, 3 to 6 membered heterocycloalkyl, or 5 to 6 membered heterocycloalkyl), (e.g., each of which is negatively charged). In embodiments, Z is an unsubstituted heterocycloalkyl (e.g., 3 to 8 membered heterocycloalkyl, 3 to 6 membered heterocycloalkyl, or 5 to 6 membered heterocycloalkyl), (e.g., each of which is negatively charged).

In embodiments, Z is $R^{27}$-substituted or unsubstituted heteroaryl (e.g., 5 to 10 membered heteroaryl, 5 to 9 membered heteroaryl, or 5 to 6 membered heteroaryl), (e.g., each of which is negatively charged). In embodiments, Z is $R^{27}$-substituted heteroaryl (e.g., 5 to 10 membered heteroaryl, 5 to 9 membered heteroaryl, or 5 to 6 membered heteroaryl), (e.g., each of which is negatively charged). In embodiments, Z is an unsubstituted heteroaryl (e.g., 5 to 10 membered heteroaryl, 5 to 9 membered heteroaryl, or 5 to 6 membered heteroaryl), (e.g., each of which is negatively charged).

In embodiments, $R^{19}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

In embodiments, $R^{19}$ is $R^{43}$-substituted or unsubstituted alkyl (e.g., $C_1$-$C_8$ alkyl, $C_1$-$C_6$ alkyl, or $C_1$-$C_4$ alkyl). In embodiments, $R^{19}$ is $R^{43}$-substituted alkyl (e.g., $C_1$-$C_8$ alkyl, $C_1$-$C_6$ alkyl, or $C_1$-$C_4$ alkyl). In embodiments, $R^{19}$ is an unsubstituted alkyl (e.g., $C_1$-$C_8$ alkyl, $C_1$-$C_6$ alkyl, or $C_1$-$C_4$ alkyl).

In embodiments, $R^{19}$ is $R^{43}$-substituted or unsubstituted heteroalkyl (e.g., 2 to 8 membered heteroalkyl, 2 to 6 membered heteroalkyl, or 2 to 4 membered heteroalkyl). In embodiments, $R^{19}$ is $R^{43}$-substituted heteroalkyl (e.g., 2 to 8 membered heteroalkyl, 2 to 6 membered heteroalkyl, or 2 to 4 membered heteroalkyl). In embodiments, $R^{19}$ is an unsubstituted heteroalkyl (e.g., 2 to 8 membered heteroalkyl, 2 to 6 membered heteroalkyl, or 2 to 4 membered heteroalkyl).

In embodiments, $R^{19}$ is $R^{43}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{19}$ is $R^{43}$-substituted cycloalkyl (e.g., $C_3$-$C_8$ cycloalkyl, $C_3$-$C_6$ cycloalkyl, or $C_5$-$C_6$ cycloalkyl). In embodiments, $R^{19}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{19}$ is $R^{43}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{19}$ is $R^{43}$-substituted heterocycloalkyl (e.g., 3 to 8 membered heterocycloalkyl, 3 to 6 membered heterocycloalkyl, or 5 to 6 membered heterocycloalkyl). In embodiments, $R^{19}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{19}$ is $R^{43}$-substituted or unsubstituted aryl (e.g., $C_6$-$C_{10}$ aryl, $C_{10}$ aryl, or phenyl). In embodiments, $R^{19}$ is $R^{43}$-substituted aryl (e.g., $C_6$-$C_{10}$ aryl, $C_{10}$ aryl, or phenyl). In embodiments, $R^{19}$ is an unsubstituted aryl (e.g., $C_6$-$C_{10}$ aryl, $C_{10}$ aryl, or phenyl).

In embodiments, $R^{19}$ is $R^{43}$-substituted or unsubstituted heteroaryl (e.g., 5 to 10 membered heteroaryl, 5 to 9 membered heteroaryl, or 5 to 6 membered heteroaryl). In embodiments, $R^{19}$ is $R^{43}$-substituted heteroaryl (e.g., 5 to 10 membered heteroaryl, 5 to 9 membered heteroaryl, or 5 to 6 membered heteroaryl). In embodiments, $R^{19}$ is an unsubstituted heteroaryl (e.g., 5 to 10 membered heteroaryl, 5 to 9 membered heteroaryl, or 5 to 6 membered heteroaryl).

$R^{19}$ and $R^{20}$ substituents bonded to the same nitrogen atom may optionally be joined to form a $R^{43}$-substituted or unsubstituted heterocycloalkyl or $R^{43}$-substituted or unsubstituted heteroaryl.

In embodiments, $R^{20}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

In embodiments, $R^{20}$ is $R^{45}$-substituted or unsubstituted alkyl (e.g., $C_1$-$C_8$ alkyl, $C_1$-$C_6$ alkyl, or $C_1$-$C_4$ alkyl). In embodiments, $R^{20}$ is $R^{45}$-substituted alkyl (e.g., $C_1$-$C_8$ alkyl, $C_1$-$C_6$ alkyl, or $C_1$-$C_4$ alkyl). In embodiments, $R^{20}$ is an unsubstituted alkyl (e.g., $C_1$-$C_8$ alkyl, $C_1$-$C_6$ alkyl, or $C_1$-$C_4$ alkyl).

In embodiments, $R^{20}$ is $R^{45}$-substituted or unsubstituted heteroalkyl (e.g., 2 to 8 membered heteroalkyl, 2 to 6 membered heteroalkyl, or 2 to 4 membered heteroalkyl). In embodiments, $R^{20}$ is $R^{45}$-substituted heteroalkyl (e.g., 2 to 8 membered heteroalkyl, 2 to 6 membered heteroalkyl, or 2 to 4 membered heteroalkyl). In embodiments, $R^{20}$ is an unsubstituted heteroalkyl (e.g., 2 to 8 membered heteroalkyl, 2 to 6 membered heteroalkyl, or 2 to 4 membered heteroalkyl).

In embodiments, $R^{20}$ is $R^{45}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{20}$ is $R^{45}$-substituted cycloalkyl (e.g., $C_3$-$C_8$ cycloalkyl, $C_3$-$C_6$ cycloalkyl, or $C_5$-$C_6$ cycloalkyl). In embodiments, $R^{20}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{20}$ is $R^{45}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{20}$ is $R^{45}$-substituted heterocycloalkyl (e.g., 3 to 8 membered heterocycloalkyl, 3 to 6 membered heterocycloalkyl, or 5 to 6 membered heterocycloalkyl). In embodiments, $R^{20}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{20}$ is $R^{45}$-substituted or unsubstituted aryl (e.g., $C_6$-$C_{10}$ aryl, $C_{10}$ aryl, or phenyl). In embodiments, $R^{20}$ is $R^{45}$-substituted aryl (e.g., $C_6$-$C_{10}$ aryl, $C_{10}$ aryl, or phenyl). In embodiments, $R^{20}$ is an unsubstituted aryl (e.g., $C_6$-$C_{10}$ aryl, $C_{10}$ aryl, or phenyl).

In embodiments, $R^{20}$ is $R^{45}$-substituted or unsubstituted heteroaryl (e.g., 5 to 10 membered heteroaryl, 5 to 9 membered heteroaryl, or 5 to 6 membered heteroaryl). In embodiments, $R^{20}$ is $R^{45}$-substituted heteroaryl (e.g., 5 to 10 membered heteroaryl, 5 to 9 membered heteroaryl, or 5 to 6 membered heteroaryl). In embodiments, $R^{20}$ is an unsubstituted heteroaryl (e.g., 5 to 10 membered heteroaryl, 5 to 9 membered heteroaryl, or 5 to 6 membered heteroaryl).

$R^{19}$ and $R^{20}$ substituents bonded to the same nitrogen atom may optionally be joined to form a $R^{45}$-substituted or unsubstituted heterocycloalkyl or $R^{45}$-substituted or unsubstituted heteroaryl.

In embodiments, $R^{21}$ is hydrogen, halogen, $-CX^{21}_3$, $-CHX^{21}_2$, $-CH_2X^{21}$, $-CN$, $-SO_{n21}R^{21D}$, $-SO_{v21}NR^{21A}R^{21B}$, $-NHC(O)NR^{21A}R^{21B}$, $-N(O)_{m21}$, $-NR^{21A}R^{21B}$, $-C(O)R^{21C}$, $-C(O)-OR^{21C}$, $-C(O)NR^{21A}R^{21B}$, $-OR^{21D}$, $-NR^{21A}SO_2R^{21D}$, $-NR^{21A}C(O)R^{21C}$, $-NR^{21A}C(O)OR^{21C}$, $-NR^{21A}OR^{21C}$, $-OCX^{21}_3$, $-OCHX^{21}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{21A}$ and $R^{21B}$ substituents bonded to the same nitrogen atom may optionally be joined to form a substituted or unsubstituted heterocycloalkyl or substituted or unsubstituted heteroaryl.

In embodiments, $R^{21}$ is $R^{47}$-substituted or unsubstituted alkyl (e.g., $C_1$-$C_8$ alkyl, $C_1$-$C_6$ alkyl, or $C_1$-$C_4$ alkyl). In embodiments, $R^{21}$ is $R^{47}$-substituted alkyl (e.g., $C_1$-$C_8$ alkyl, $C_1$-$C_6$ alkyl, or $C_1$-$C_4$ alkyl). In embodiments, $R^{21}$ is an unsubstituted alkyl (e.g., $C_1$-$C_8$ alkyl, $C_1$-$C_6$ alkyl, or $C_1$-$C_4$ alkyl).

In embodiments, $R^{21}$ is $R^{47}$-substituted or unsubstituted heteroalkyl (e.g., 2 to 8 membered heteroalkyl, 2 to 6 membered heteroalkyl, or 2 to 4 membered heteroalkyl). In embodiments, $R^{21}$ is $R^{47}$-substituted heteroalkyl (e.g., 2 to 8 membered heteroalkyl, 2 to 6 membered heteroalkyl, or 2 to 4 membered heteroalkyl). In embodiments, $R^{21}$ is an unsubstituted heteroalkyl (e.g., 2 to 8 membered heteroalkyl, 2 to 6 membered heteroalkyl, or 2 to 4 membered heteroalkyl).

In embodiments, $R^{21}$ is $R^{47}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{21}$ is $R^{47}$-substituted cycloalkyl (e.g., $C_3$-$C_8$ cycloalkyl, $C_3$-$C_6$ cycloalkyl, or $C_5$-$C_6$ cycloalkyl). In embodiments, $R^{21}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{21}$ is $R^{47}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{21}$ is $R^{47}$-substituted heterocycloalkyl (e.g., 3 to 8 membered heterocycloalkyl, 3 to 6 membered heterocycloalkyl, or 5 to 6 membered heterocycloalkyl). In embodiments, $R^{21}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{21}$ is $R^{47}$-substituted or unsubstituted aryl (e.g., $C_6$-$C_{10}$ aryl, $C_{10}$ aryl, or phenyl). In embodiments, $R^{21}$ is $R^{47}$-substituted aryl (e.g., $C_6$-$C_{10}$ aryl, $C_{10}$ aryl, or phenyl). In embodiments, $R^{21}$ is an unsubstituted aryl (e.g., $C_6$-$C_{10}$ aryl, $C_{10}$ aryl, or phenyl).

In embodiments, $R^{21}$ is $R^{47}$-substituted or unsubstituted heteroaryl (e.g., 5 to 10 membered heteroaryl, 5 to 9 membered heteroaryl, or 5 to 6 membered heteroaryl). In embodiments, $R^{21}$ is $R^{47}$-substituted heteroaryl (e.g., 5 to 10 membered heteroaryl, 5 to 9 membered heteroaryl, or 5 to 6 membered heteroaryl). In embodiments, $R^{21}$ is an unsubstituted heteroaryl (e.g., 5 to 10 membered heteroaryl, 5 to 9 membered heteroaryl, or 5 to 6 membered heteroaryl).

In embodiments, $R^{22}$ is hydrogen, halogen, $-CX^{22}_3$, $-CHX^{22}_2$, $-CH_2X^{22}$, $-CN$, $-SO_{n22}R^{22D}$, $-SO_{v22}NR^{22A}R^{22B}$, $-NHC(O)NR^{22A}R^{22B}$, $-N(O)_{m22}$, $-NR^{22A}R^{22B}$, $-C(O)R^{22C}$, $-C(O)-OR^{22C}$, $-C(O)NR^{22A}R^{22B}$, $-OR^{22D}$, $-NR^{22A}SO_2R^{22D}$, $-NR^{22A}C(O)R^{22C}$, $-NR^{22A}C(O)OR^{22C}$, $-NR^{22A}OR^{22C}$, $-OCX^{22}_3$, $-OCHX^{22}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{22A}$ and $R^{22B}$ substituents bonded to the same nitrogen atom may optionally be joined to form a substituted or unsubstituted heterocycloalkyl or substituted or unsubstituted heteroaryl.

In embodiments, $R^{22}$ is $R^{50}$-substituted or unsubstituted alkyl (e.g., $C_1$-$C_8$ alkyl, $C_1$-$C_6$ alkyl, or $C_1$-$C_4$ alkyl). In embodiments, $R^{22}$ is $R^{50}$-substituted alkyl (e.g., $C_1$-$C_8$ alkyl, $C_1$-$C_6$ alkyl, or $C_1$-$C_4$ alkyl). In embodiments, $R^{22}$ is an unsubstituted alkyl (e.g., $C_1$-$C_8$ alkyl, $C_1$-$C_6$ alkyl, or $C_1$-$C_4$ alkyl).

In embodiments, $R^{22}$ is $R^{50}$-substituted or unsubstituted heteroalkyl (e.g., 2 to 8 membered heteroalkyl, 2 to 6 membered heteroalkyl, or 2 to 4 membered heteroalkyl). In embodiments, $R^{22}$ is $R^{50}$-substituted heteroalkyl (e.g., 2 to 8 membered heteroalkyl, 2 to 6 membered heteroalkyl, or 2 to 4 membered heteroalkyl). In embodiments, $R^{22}$ is an unsubstituted heteroalkyl (e.g., 2 to 8 membered heteroalkyl, 2 to 6 membered heteroalkyl, or 2 to 4 membered heteroalkyl).

In embodiments, $R^{22}$ is $R^{50}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{22}$ is $R^{50}$-substituted cycloalkyl (e.g., $C_3$-$C_8$ cycloalkyl, $C_3$-$C_6$ cycloalkyl, or $C_5$-$C_6$ cycloalkyl). In embodiments, $R^{22}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{22}$ is $R^{50}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{22}$ is $R^{50}$-substituted heterocycloalkyl (e.g., 3 to 8 membered heterocycloalkyl, 3 to 6 membered heterocycloalkyl, or 5 to 6 membered heterocycloalkyl). In embodiments, $R^{22}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{22}$ is $R^{50}$-substituted or unsubstituted aryl (e.g., $C_6$-$C_{10}$ aryl, $C_{10}$ aryl, or phenyl). In embodiments, $R^{22}$ is $R^{50}$-substituted aryl (e.g., $C_6$-$C_{10}$ aryl, $C_{10}$ aryl, or phenyl). In embodiments, $R^{22}$ is an unsubstituted aryl (e.g., $C_6$-$C_{10}$ aryl, $C_{10}$ aryl, or phenyl).

In embodiments, $R^{22}$ is $R^{50}$-substituted or unsubstituted heteroaryl (e.g., 5 to 10 membered heteroaryl, 5 to 9 membered heteroaryl, or 5 to 6 membered heteroaryl). In embodiments, $R^{22}$ is $R^{50}$-substituted heteroaryl (e.g., 5 to 10 membered heteroaryl, 5 to 9 membered heteroaryl, or 5 to 6 membered heteroaryl). In embodiments, $R^{22}$ is an unsubstituted heteroaryl (e.g., 5 to 10 membered heteroaryl, 5 to 9 membered heteroaryl, or 5 to 6 membered heteroaryl).

In embodiments, $R^{23}$ is hydrogen, halogen, $-CX^{23}_3$, $-CHX^{23}_2$, $-CH_2X^{23}$, $-CN$, $-SO_{n23}R^{23D}$, $-SO_{v23}NR^{23A}R^{23B}$, $-NHC(O)NR^{23A}R^{23B}$, $-N(O)_{m23}$, $-NR^{23A}R^{23B}$, $-C(O)R^{23C}$, $-C(O)-OR^{23C}$, $-C(O)NR^{23A}R^{23B}$, $-OR^{23D}$, $-NR^{23A}SO_2R^{23D}$, $-NR^{23A}C(O)R^{23C}$, $-NR^{23A}C(O)OR^{23C}$, $-NR^{23A}OR^{23C}$, $-OCX^{23}_3$, $-OCHX^{23}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{23A}$ and $R^{23B}$ substituents bonded to the same nitrogen atom may optionally be joined to form a substituted or unsubstituted heterocycloalkyl or substituted or unsubstituted heteroaryl.

In embodiments, $R^{23}$ is $R^{53}$-substituted or unsubstituted alkyl (e.g., $C_1$-$C_8$ alkyl, $C_1$-$C_6$ alkyl, or $C_1$-$C_4$ alkyl). In embodiments, $R^{23}$ is $R^{53}$-substituted alkyl (e.g., $C_1$-$C_8$ alkyl, $C_1$-$C_6$ alkyl, or $C_1$-$C_4$ alkyl). In embodiments, $R^{23}$ is an unsubstituted alkyl (e.g., $C_1$-$C_8$ alkyl, $C_1$-$C_6$ alkyl, or $C_1$-$C_4$ alkyl).

In embodiments, $R^{23}$ is $R^{53}$-substituted or unsubstituted heteroalkyl (e.g., 2 to 8 membered heteroalkyl, 2 to 6 membered heteroalkyl, or 2 to 4 membered heteroalkyl). In embodiments, $R^{23}$ is $R^{53}$-substituted heteroalkyl (e.g., 2 to 8 membered heteroalkyl, 2 to 6 membered heteroalkyl, or 2 to 4 membered heteroalkyl). In embodiments, $R^{23}$ is an unsubstituted heteroalkyl (e.g., 2 to 8 membered heteroalkyl, 2 to 6 membered heteroalkyl, or 2 to 4 membered heteroalkyl).

In embodiments, $R^{23}$ is $R^{53}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{23}$ is $R^{53}$-substituted cycloalkyl (e.g., $C_3$-$C_8$ cycloalkyl, $C_3$-$C_6$ cycloalkyl, or $C_5$-$C_6$ cycloalkyl). In embodiments, $R^{23}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{23}$ is $R^{53}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{23}$ is $R^{53}$-substituted heterocycloalkyl (e.g., 3 to 8 membered heterocycloalkyl, 3 to 6 membered heterocycloalkyl, or 5 to 6 membered heterocycloalkyl). In embodiments, $R^{23}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{23}$ is $R^{53}$-substituted or unsubstituted aryl (e.g., $C_6$-$C_{10}$ aryl, $C_{10}$ aryl, or phenyl). In embodiments, $R^{23}$ is $R^{53}$-substituted aryl (e.g., $C_6$-$C_{10}$ aryl, $C_{10}$ aryl, or phenyl). In embodiments, $R^{23}$ is an unsubstituted aryl (e.g., $C_6$-$C_{10}$ aryl, $C_{10}$ aryl, or phenyl).

In embodiments, $R^{23}$ is $R^{53}$-substituted or unsubstituted heteroaryl (e.g., 5 to 10 membered heteroaryl, 5 to 9 membered heteroaryl, or 5 to 6 membered heteroaryl). In embodiments, $R^{23}$ is $R^{53}$-substituted heteroaryl (e.g., 5 to 10 membered heteroaryl, 5 to 9 membered heteroaryl, or 5 to 6 membered heteroaryl). In embodiments, $R^{23}$ is an unsubstituted heteroaryl (e.g., 5 to 10 membered heteroaryl, 5 to 9 membered heteroaryl, or 5 to 6 membered heteroaryl).

In embodiments, $R^{24}$ is hydrogen, halogen, $-CX^{24}_3$, $-CHX^{24}_2$, $-CH_2X^{24}$, $-CN$, $-SO_{n24}R^{24D}$, $-SO_{24}NR^{24A}R^{24B}$, $-NHC(O)NR^{24A}R^{24B}$, $-N(O)_{m24}$, $-NR^{24A}R^{24B}$, $-C(O)$ $R^{24C}$, $-C(O)-OR^{24C}$, $-C(O)NR^{24A}R^{24B}$, $-OR^{24D}$, $-NR^{24A}SO_2R^{24D}$, $-NR^{24A}C(O)R^{24C}$, $-NR^{24A}C(O)OR^{24C}$, $-NR^{24A}OR^{24C}$, $-OCX^{24}_3$, $-OCHX^{24}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{24A}$ and $R^{24B}$ substituents bonded to the same nitrogen atom may optionally be joined to form a substituted or unsubstituted heterocycloalkyl or substituted or unsubstituted heteroaryl.

In embodiments, $R^{24}$ is $R^{56}$-substituted or unsubstituted alkyl (e.g., $C_1$-$C_8$ alkyl, $C_1$-$C_6$ alkyl, or $C_1$-$C_4$ alkyl). In embodiments, $R^{24}$ is $R^{56}$-substituted alkyl (e.g., $C_1$-$C_8$ alkyl, $C_1$-$C_6$ alkyl, or $C_1$-$C_4$ alkyl). In embodiments, $R^{24}$ is an unsubstituted alkyl (e.g., $C_1$-$C_8$ alkyl, $C_1$-$C_6$ alkyl, or $C_1$-$C_4$ alkyl).

In embodiments, $R^{24}$ is $R^{56}$-substituted or unsubstituted heteroalkyl (e.g., 2 to 8 membered heteroalkyl, 2 to 6 membered heteroalkyl, or 2 to 4 membered heteroalkyl). In embodiments, $R^{24}$ is $R^{56}$-substituted heteroalkyl (e.g., 2 to 8 membered heteroalkyl, 2 to 6 membered heteroalkyl, or 2 to 4 membered heteroalkyl). In embodiments, $R^{24}$ is an unsubstituted heteroalkyl (e.g., 2 to 8 membered heteroalkyl, 2 to 6 membered heteroalkyl, or 2 to 4 membered heteroalkyl).

In embodiments, $R^{24}$ is $R^{56}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{24}$ is $R^{56}$-substituted cycloalkyl (e.g., $C_3$-$C_8$ cycloalkyl, $C_3$-$C_6$ cycloalkyl, or $C_5$-$C_6$ cycloalkyl). In embodiments, $R^{24}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{24}$ is $R^{56}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{24}$ is $R^{56}$-substituted heterocycloalkyl (e.g., 3 to 8 membered heterocycloalkyl, 3 to 6 membered heterocycloalkyl, or 5 to 6 membered heterocycloalkyl). In embodiments, $R^{24}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{24}$ is $R^{56}$-substituted or unsubstituted aryl (e.g., $C_6$-$C_{10}$ aryl, $C_{10}$ aryl, or phenyl). In embodiments, $R^{24}$ is $R^{56}$-substituted aryl (e.g., $C_6$-$C_{10}$ aryl, $C_{10}$ aryl, or phenyl). In embodiments, $R^{24}$ is an unsubstituted aryl (e.g., $C_6$-$C_{10}$ aryl, $C_{10}$ aryl, or phenyl).

In embodiments, $R^{24}$ is $R^{56}$-substituted or unsubstituted heteroaryl (e.g., 5 to 10 membered heteroaryl, 5 to 9 membered heteroaryl, or 5 to 6 membered heteroaryl). In embodiments, $R^{24}$ is $R^{56}$-substituted heteroaryl (e.g., 5 to 10 membered heteroaryl, 5 to 9 membered heteroaryl, or 5 to 6 membered heteroaryl). In embodiments, $R^{24}$ is an unsubstituted heteroaryl (e.g., 5 to 10 membered heteroaryl, 5 to 9 membered heteroaryl, or 5 to 6 membered heteroaryl).

In embodiments, $R^{8L}$ is hydrogen, $-CF_3$, $-CCl_3$, $-CBr_3-$, $-CI_3$, $-CN$, $-COOH$, $-CONH_2$, $-CHF_2$, $-CHCl_2$, $-CHBr_2-$, $-CHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

In embodiments, $R^{8L}$ is $R^{38L}$-substituted or unsubstituted alkyl (e.g., $C_1$-$C_8$ alkyl, $C_1$-$C_6$ alkyl, or $C_1$-$C_4$ alkyl). In embodiments, $R^{8L}$ is $R^{38L}$-substituted alkyl (e.g., $C_1$-$C_8$ alkyl, $C_1$-$C_6$ alkyl, or $C_1$-$C_4$ alkyl). In embodiments, $R^{8L}$ is an unsubstituted alkyl (e.g., $C_1$-$C_8$ alkyl, $C_1$-$C_6$ alkyl, or $C_1$-$C_4$ alkyl).

In embodiments, $R^{8L}$ is $R^{38L}$-substituted or unsubstituted heteroalkyl (e.g., 2 to 8 membered heteroalkyl, 2 to 6 membered heteroalkyl, or 2 to 4 membered heteroalkyl). In embodiments, $R^{8L}$ is $R^{38L}$-substituted heteroalkyl (e.g., 2 to 8 membered heteroalkyl, 2 to 6 membered heteroalkyl, or 2 to 4 membered heteroalkyl). In embodiments, $R^{8L}$ is an unsubstituted heteroalkyl (e.g., 2 to 8 membered heteroalkyl, 2 to 6 membered heteroalkyl, or 2 to 4 membered heteroalkyl).

In embodiments, $R^{8L}$ is $R^{38L}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{8L}$ is $R^{38L}$-substituted cycloalkyl (e.g., $C_3$-$C_8$ cycloalkyl, $C_3$-$C_6$ cycloalkyl, or $C_5$-$C_6$ cycloalkyl). In embodiments, $R^{8L}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{8L}$ is $R^{38L}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{8L}$ is $R^{38L}$-substituted heterocycloalkyl (e.g., 3 to 8 membered heterocycloalkyl, 3 to 6 membered heterocycloalkyl, or 5 to 6 membered heterocycloalkyl). In embodiments, $R^{8L}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{8L}$ is $R^{38L}$-substituted or unsubstituted aryl (e.g., $C_6$-$C_{10}$ aryl, $C_{10}$ aryl, or phenyl). In embodiments, $R^{8L}$ is $R^{38L}$-substituted aryl (e.g., $C_6$-$C_{10}$ aryl, $C_{10}$ aryl, or phenyl). In embodiments, $R^{8L}$ is an unsubstituted aryl (e.g., $C_6$-$C_{10}$ aryl, $C_{10}$ aryl, or phenyl).

In embodiments, $R^{8L}$ is $R^{38L}$-substituted or unsubstituted heteroaryl (e.g., 5 to 10 membered heteroaryl, 5 to 9 membered heteroaryl, or 5 to 6 membered heteroaryl). In embodiments, $R^{8L}$ is $R^{38L}$-substituted heteroaryl (e.g., 5 to 10 membered heteroaryl, 5 to 9 membered heteroaryl, or 5 to 6 membered heteroaryl). In embodiments, $R^{8L}$ is an unsubstituted heteroaryl (e.g., 5 to 10 membered heteroaryl, 5 to 9 membered heteroaryl, or 5 to 6 membered heteroaryl).

In embodiments, $R^{27A}$ is hydrogen, $-CF_3$, $-CCl_3$, $-CBr_3-$, $-CI_3$, $-CN$, $-COOH$, $-CONH_2$, $-CHF_2$, $-CHCl_2$, $-CHBr_2-$, $-CHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{27A}$ is $R^{40A}$-substituted or unsubstituted alkyl (e.g., $C_1$-$C_8$ alkyl, $C_1$-$C_6$ alkyl, or $C_1$-$C_4$ alkyl), $R^{40A}$-substituted or unsubstituted heteroalkyl (e.g., 2 to 8 membered heteroalkyl, 2 to 6 membered heteroalkyl, or 2 to 4 membered heteroalkyl), $R^{40A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{40A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{40A}$-substituted or unsubstituted aryl (e.g., $C_6$-$C_{10}$ aryl, $C_{10}$ aryl, or phenyl), or $R^{40A}$-substituted or unsubstituted heteroaryl (e.g., 5 to 10 membered heteroaryl, 5 to 9 membered heteroaryl, or 5 to 6 membered heteroaryl).

In embodiments, $R^{27B}$ is hydrogen, —$CF_3$, —$CCl_3$, —$CBr_3$—, —$CI_3$, —CN, —COOH, —$CONH_2$, —$CHF_2$, —$CHCl_2$, —$CHBr_2$—, —$CHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{27B}$ is $R^{40B}$-substituted or unsubstituted alkyl (e.g., $C_1$-$C_8$ alkyl, $C_1$-$C_6$ alkyl, or $C_1$-$C_4$ alkyl), $R^{40B}$-substituted or unsubstituted heteroalkyl (e.g., 2 to 8 membered heteroalkyl, 2 to 6 membered heteroalkyl, or 2 to 4 membered heteroalkyl), $R^{40B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{40B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{40B}$-substituted or unsubstituted aryl (e.g., $C_6$-$C_{10}$ aryl, $C_{10}$ aryl, or phenyl), or $R^{40B}$-substituted or unsubstituted heteroaryl (e.g., 5 to 10 membered heteroaryl, 5 to 9 membered heteroaryl, or 5 to 6 membered heteroaryl). In embodiments, $R^{27A}$ and $R^{27B}$ substituents bonded to the same nitrogen atom may optionally be joined to form a $R^{40B}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{40B}$-substituted or unsubstituted heteroaryl (e.g., 5 to 10 membered heteroaryl, 5 to 9 membered heteroaryl, or 5 to 6 membered heteroaryl).

In embodiments, $R^{27C}$ is hydrogen, —$CF_3$, —$CCl_3$, —$CBr_3$—, —$CI_3$, —CN, —COOH, —$CONH_2$, —$CHF_2$, —$CHCl_2$, —$CHBr_2$—, —$CHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{27C}$ is $R^{40C}$-substituted or unsubstituted alkyl (e.g., $C_1$-$C_8$ alkyl, $C_1$-$C_6$ alkyl, or $C_1$-$C_4$ alkyl), $R^{40C}$-substituted or unsubstituted heteroalkyl (e.g., 2 to 8 membered heteroalkyl, 2 to 6 membered heteroalkyl, or 2 to 4 membered heteroalkyl), $R^{40C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{40C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{40C}$-substituted or unsubstituted aryl (e.g., $C_6$-$C_{10}$ aryl, $C_{10}$ aryl, or phenyl), or $R^{40C}$-substituted or unsubstituted heteroaryl (e.g., 5 to 10 membered heteroaryl, 5 to 9 membered heteroaryl, or 5 to 6 membered heteroaryl). In embodiments, $R^{27A}$ and $R^{27B}$ substituents bonded to the same nitrogen atom may optionally be joined to form a $R^{40A}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{40C}$-substituted or unsubstituted heteroaryl (e.g., 5 to 10 membered heteroaryl, 5 to 9 membered heteroaryl, or 5 to 6 membered heteroaryl).

In embodiments, $R^{27D}$ is hydrogen, —$CF_3$, —$CCl_3$, —$CBr_3$—, —$CI_3$, —CN, —COOH, —$CONH_2$, —$CHF_2$, —$CHCl_2$, —$CHBr_2$—, —$CHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{27D}$ is $R^{40D}$-substituted or unsubstituted alkyl (e.g., $C_1$-$C_8$ alkyl, $C_1$-$C_6$ alkyl, or $C_1$-$C_4$ alkyl), $R^{40D}$-substituted or unsubstituted heteroalkyl (e.g., 2 to 8 membered heteroalkyl, 2 to 6 membered heteroalkyl, or 2 to 4 membered heteroalkyl), $R^{40D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{40D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{40D}$-substituted or unsubstituted aryl (e.g., $C_6$-$C_{10}$ aryl, $C_{10}$ aryl, or phenyl), or $R^{40D}$-substituted or unsubstituted heteroaryl (e.g., 5 to 10 membered heteroaryl, 5 to 9 membered heteroaryl, or 5 to 6 membered heteroaryl).

In embodiments, $R^{21A}$ is hydrogen, hydrogen, —$CF_3$, —$CCl_3$, —$CBr_3$—, —$CI_3$, —CN, —COOH, —$CONH_2$, —$CHF_2$, —$CHCl_2$, —$CHBr_2$—, —$CHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{21A}$ is hydrogen, —$CF_3$, —$CCl_3$, —$CBr_3$—, —$CI_3$, —CN, —COOH, —$CONH_2$, —$CHF_2$, —$CHCl_2$, —$CHBr_2$—, —$CHI_2$, $R^{47A}$-substituted or unsubstituted alkyl (e.g., $C_1$-$C_8$ alkyl, $C_1$-$C_6$ alkyl, or $C_1$-$C_4$ alkyl), $R^{47A}$-substituted or unsubstituted heteroalkyl (e.g., 2 to 8 membered heteroalkyl, 2 to 6 membered heteroalkyl, or 2 to 4 membered heteroalkyl), $R^{47A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{47A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{47A}$-substituted or unsubstituted aryl (e.g., $C_6$-$C_{10}$ aryl, $C_{10}$ aryl, or phenyl), or $R^{47A}$-substituted or unsubstituted heteroaryl (e.g., 5 to 10 membered heteroaryl, 5 to 9 membered heteroaryl, or 5 to 6 membered heteroaryl). In embodiments, $R^{21A}$ and $R^{21B}$ substituents bonded to the same nitrogen atom may optionally be joined to form a $R^{47A}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{47A}$-substituted or unsubstituted heteroaryl (e.g., 5 to 10 membered heteroaryl, 5 to 9 membered heteroaryl, or 5 to 6 membered heteroaryl).

In embodiments, $R^{21B}$ is hydrogen, hydrogen, —$CF_3$, —$CCl_3$, —$CBr_3$—, —$CI_3$, —CN, —COOH, —$CONH_2$, —$CHF_2$, —$CHCl_2$, —$CHBr_2$—, —$CHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{2B}$ is hydrogen, —$CF_3$, —$CCl_3$, —$CBr_3$—, —$CI_3$, —CN, —COOH, —$CONH_2$, —$CHF_2$, —$CHCl_2$, —$CHBr_2$—, —$CHI_2$, $R^{47B}$-substituted or unsubstituted alkyl (e.g., $C_1$-$C_8$ alkyl, $C_1$-$C_6$ alkyl, or $C_1$-$C_4$ alkyl), $R^{47B}$-substituted or unsubstituted heteroalkyl (e.g., 2 to 8 membered heteroalkyl, 2 to 6 membered heteroalkyl, or 2 to 4 membered heteroalkyl), $R^{47B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{47B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{47B}$-substituted or unsubstituted aryl (e.g., $C_6$-$C_{10}$ aryl, $C_{10}$ aryl, or phenyl), or $R^{47B}$-substituted or unsubstituted heteroaryl (e.g., 5 to 10 membered heteroaryl, 5 to 9 membered heteroaryl, or 5 to 6 membered heteroaryl). In embodiments, $R^{21A}$ and $R^{21B}$ substituents bonded to the same nitrogen atom may optionally be joined to form a $R^{47B}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{47B}$-substituted or unsubstituted heteroaryl (e.g., 5 to 10 membered heteroaryl, 5 to 9 membered heteroaryl, or 5 to 6 membered heteroaryl).

In embodiments, $R^{21C}$ is hydrogen, hydrogen, —CF$_3$, —CCl$_3$, —CBr$_3$—, —CI$_3$, —CN, —COOH, —CONH$_2$, —CHF$_2$, —CHCl$_2$, —CHBr$_2$—, —CHI$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{21C}$ is hydrogen, —CF$_3$, —CCl$_3$, —CBr$_3$—, —CI$_3$, —CN, —COOH, —CONH$_2$, —CHF$_2$, —CHCl$_2$, —CHBr$_2$—, —CHI$_2$, $R^{47C}$-substituted or unsubstituted alkyl (e.g., $C_1$-$C_8$ alkyl, $C_1$-$C_6$ alkyl, or $C_1$-$C_4$ alkyl), $R^{47C}$-substituted or unsubstituted heteroalkyl (e.g., 2 to 8 membered heteroalkyl, 2 to 6 membered heteroalkyl, or 2 to 4 membered heteroalkyl), $R^{47C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{47C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{47C}$-substituted or unsubstituted aryl (e.g., $C_6$-$C_{10}$ aryl, $C_{10}$ aryl, or phenyl), or $R^{47C}$-substituted or unsubstituted heteroaryl (e.g., 5 to 10 membered heteroaryl, 5 to 9 membered heteroaryl, or 5 to 6 membered heteroaryl).

In embodiments, $R^{21D}$ is hydrogen, hydrogen, —CF$_3$, —CCl$_3$, —CBr$_3$—, —CI$_3$, —CN, —COOH, —CONH$_2$, —CHF$_2$, —CHCl$_2$, —CHBr$_2$—, —CHI$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{21D}$ is hydrogen, —CF$_3$, —CCl$_3$, —CBr$_3$—, —C13, —CN, —COOH, —CONH$_2$, —CHF$_2$, —CHCl$_2$, —CHBr$_2$—, —CHI$_2$, $R^{47D}$-substituted or unsubstituted alkyl (e.g., $C_1$-$C_8$ alkyl, $C_1$-$C_6$ alkyl, or $C_1$-$C_4$ alkyl), $R^{47D}$-substituted or unsubstituted heteroalkyl (e.g., 2 to 8 membered heteroalkyl, 2 to 6 membered heteroalkyl, or 2 to 4 membered heteroalkyl), $R^{47D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{47D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{47D}$-substituted or unsubstituted aryl (e.g., $C_6$-$C_{10}$ aryl, $C_{10}$ aryl, or phenyl), or $R^{47D}$-substituted or unsubstituted heteroaryl (e.g., 5 to 10 membered heteroaryl, 5 to 9 membered heteroaryl, or 5 to 6 membered heteroaryl).

In embodiments, $R^{22A}$ is hydrogen, —CF$_3$, —CCl$_3$, —CBr$_3$—, —CI$_3$, —CN, —COOH, —CONH$_2$, —CHF$_2$, —CHCl$_2$, —CHBr$_2$—, —CHI$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{22A}$ is hydrogen, —CF$_3$, —CCl$_3$, —CBr$_3$—, —CI$_3$, —CN, —COOH, —CONH$_2$, —CHF$_2$, —CHCl$_2$, —CHBr$_2$—, —CHI$_2$, $R^{50A}$-substituted or unsubstituted alkyl (e.g., $C_1$-$C_8$ alkyl, $C_1$-$C_6$ alkyl, or $C_1$-$C_4$ alkyl), $R^{50A}$-substituted or unsubstituted heteroalkyl (e.g., 2 to 8 membered heteroalkyl, 2 to 6 membered heteroalkyl, or 2 to 4 membered heteroalkyl), $R^{50A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{50A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{50A}$-substituted or unsubstituted aryl (e.g., $C_6$-$C_{10}$ aryl, $C_{10}$ aryl, or phenyl), or $R^{50A}$-substituted or unsubstituted heteroaryl (e.g., 5 to 10 membered heteroaryl, 5 to 9 membered heteroaryl, or 5 to 6 membered heteroaryl).

In embodiments, $R^{22A}$ and $R^{22B}$ substituents bonded to the same nitrogen atom may optionally be joined to form a $R^{50A}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{50A}$-substituted or unsubstituted heteroaryl (e.g., 5 to 10 membered heteroaryl, 5 to 9 membered heteroaryl, or 5 to 6 membered heteroaryl).

In embodiments, $R^{22B}$ is hydrogen, hydrogen, —CF$_3$, —CCl$_3$, —CBr$_3$—, —CI$_3$, —CN, —COOH, —CONH$_2$, —CHF$_2$, —CHCl$_2$, —CHBr$_2$—, —CHI$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{22B}$ is hydrogen, —CF$_3$, —CCl$_3$, —CBr$_3$—, —CI$_3$, —CN, —COOH, —CONH$_2$, —CHF$_2$, —CHCl$_2$, —CHBr$_2$—, —CHI$_2$, $R^{50B}$-substituted or unsubstituted alkyl (e.g., $C_1$-$C_8$ alkyl, $C_1$-$C_6$ alkyl, or $C_1$-$C_4$ alkyl), $R^{50B}$-substituted or unsubstituted heteroalkyl (e.g., 2 to 8 membered heteroalkyl, 2 to 6 membered heteroalkyl, or 2 to 4 membered heteroalkyl), $R^{50B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{50B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{50B}$-substituted or unsubstituted aryl (e.g., $C_6$-$C_{10}$ aryl, $C_{10}$ aryl, or phenyl), or $R^{50B}$-substituted or unsubstituted heteroaryl (e.g., 5 to 10 membered heteroaryl, 5 to 9 membered heteroaryl, or 5 to 6 membered heteroaryl).

In embodiments, $R^{22A}$ and $R^{22B}$ substituents bonded to the same nitrogen atom may optionally be joined to form a $R^{50B}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{50B}$-substituted or unsubstituted heteroaryl (e.g., 5 to 10 membered heteroaryl, 5 to 9 membered heteroaryl, or 5 to 6 membered heteroaryl).

In embodiments, $R^{22C}$ is hydrogen, hydrogen, —CF$_3$, —CCl$_3$, —CBr$_3$—, —CI$_3$, —CN, —COOH, —CONH$_2$, —CHF$_2$, —CHCl$_2$, —CHBr$_2$—, —CHI$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{22C}$ is hydrogen, —CF$_3$, —CCl$_3$, —CBr$_3$—, —CI$_3$, —CN, —COOH, —CONH$_2$, —CHF$_2$, —CHCl$_2$, —CHBr$_2$—, —CHI$_2$, $R^{50C}$-substituted or unsubstituted alkyl (e.g., $C_1$-$C_8$ alkyl, $C_1$-$C_6$ alkyl, or $C_1$-$C_4$ alkyl), $R^{50C}$-substituted or unsubstituted heteroalkyl (e.g., 2 to 8 membered heteroalkyl, 2 to 6 membered heteroalkyl, or 2 to 4 membered heteroalkyl), $R^{50C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{50C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{50C}$-substituted or unsubstituted aryl (e.g., $C_6$-$C_{10}$ aryl, $C_{10}$ aryl, or phenyl), or $R^{50C}$-substituted or unsubstituted heteroaryl (e.g., 5 to 10 membered heteroaryl, 5 to 9 membered heteroaryl, or 5 to 6 membered heteroaryl).

In embodiments, $R^{22D}$ is hydrogen, hydrogen, —$CF_3$, —$CCl_3$, —$CBr_3$—, —$CI_3$, —CN, —COOH, —$CONH_2$, —$CHF_2$, —$CHCl_2$, —$CHBr_2$—, —$CHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{22D}$ is hydrogen, —$CF_3$, —$CCl_3$, —$CBr_3$—, —$CI_3$, —CN, —COOH, —$CONH_2$, —$CHF_2$, —$CHCl_2$, —$CHBr_2$—, —$CHI_2$, $R^{50D}$-substituted or unsubstituted alkyl (e.g., $C_1$-$C_8$ alkyl, $C_1$-$C_6$ alkyl, or $C_1$-$C_4$ alkyl), $R^{50D}$-substituted or unsubstituted heteroalkyl (e.g., 2 to 8 membered heteroalkyl, 2 to 6 membered heteroalkyl, or 2 to 4 membered heteroalkyl), $R^{50D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{50D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{50D}$-substituted or unsubstituted aryl (e.g., $C_6$-$C_{10}$ aryl, $C_{10}$ aryl, or phenyl), or $R^{50D}$-substituted or unsubstituted heteroaryl (e.g., 5 to 10 membered heteroaryl, 5 to 9 membered heteroaryl, or 5 to 6 membered heteroaryl).

In embodiments, $R^{23A}$ is hydrogen, —$CF_3$, —$CCl_3$, —$CBr_3$—, —$CI_3$, —CN, —COOH, —$CONH_2$, —$CHF_2$, —$CHCl_2$, —$CHBr_2$—, —$CHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{23A}$ is hydrogen, —$CF_3$, —$CCl_3$, —$CBr_3$—, —$CI_3$, —CN, —COOH, —$CONH_2$, —$CHF_2$, —$CHCl_2$, —$CHBr_2$—, —$CHI_2$, $R^{53A}$-substituted or unsubstituted alkyl (e.g., $C_1$-$C_8$ alkyl, $C_1$-$C_6$ alkyl, or $C_1$-$C_4$ alkyl), $R^{53A}$-substituted or unsubstituted heteroalkyl (e.g., 2 to 8 membered heteroalkyl, 2 to 6 membered heteroalkyl, or 2 to 4 membered heteroalkyl), $R^{53A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{53A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{53A}$-substituted or unsubstituted aryl (e.g., $C_6$-$C_{10}$ aryl, $C_{10}$ aryl, or phenyl), or $R^{53A}$-substituted or unsubstituted heteroaryl (e.g., 5 to 10 membered heteroaryl, 5 to 9 membered heteroaryl, or 5 to 6 membered heteroaryl). In embodiments, $R^{23A}$ and $R^{23B}$ substituents bonded to the same nitrogen atom may optionally be joined to form a $R^{53A}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{53A}$-substituted or unsubstituted heteroaryl (e.g., 5 to 10 membered heteroaryl, 5 to 9 membered heteroaryl, or 5 to 6 membered heteroaryl).

In embodiments, $R^{23B}$ is hydrogen, hydrogen, —$CF_3$, —$CCl_3$, —$CBr_3$—, —$CI_3$, —CN, —COOH, —$CONH_2$, —$CHF_2$, —$CHCl_2$, —$CHBr_2$—, —$CHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{23B}$ is hydrogen, —$CF_3$, —$CCl_3$, —$CBr_3$—, —$CI_3$, —CN, —COOH, —$CONH_2$, —$CHF_2$, —$CHCl_2$, —$CHBr_2$—, —$CHI_2$, $R^{53B}$-substituted or unsubstituted alkyl (e.g., $C_1$-$C_8$ alkyl, $C_1$-$C_6$ alkyl, or $C_1$-$C_4$ alkyl), $R^{53B}$-substituted or unsubstituted heteroalkyl (e.g., 2 to 8 membered heteroalkyl, 2 to 6 membered heteroalkyl, or 2 to 4 membered heteroalkyl), $R^{53B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{53B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{53B}$-substituted or unsubstituted aryl (e.g., $C_6$-$C_{10}$ aryl, $C_{10}$ aryl, or phenyl), or $R^{53B}$-substituted or unsubstituted heteroaryl (e.g., 5 to 10 membered heteroaryl, 5 to 9 membered heteroaryl, or 5 to 6 membered heteroaryl). In embodiments, $R^{23A}$ and $R^{23B}$ substituents bonded to the same nitrogen atom may optionally be joined to form a $R^{53B}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{53B}$-substituted or unsubstituted heteroaryl (e.g., 5 to 10 membered heteroaryl, 5 to 9 membered heteroaryl, or 5 to 6 membered heteroaryl).

In embodiments, $R^{23C}$ is hydrogen, hydrogen, —$CF_3$, —$CCl_3$, —$CBr_3$—, —$CI_3$, —CN, —COOH, —$CONH_2$, —$CHF_2$, —$CHCl_2$, —$CHBr_2$—, —$CHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{23C}$ is hydrogen, —$CF_3$, —$CCl_3$, —$CBr_3$—, —$CI_3$, —CN, —COOH, —$CONH_2$, —$CHF_2$, —$CHCl_2$, —$CHBr_2$—, —$CHI_2$, $R^{53C}$-substituted or unsubstituted alkyl (e.g., $C_1$-$C_8$ alkyl, $C_1$-$C_6$ alkyl, or $C_1$-$C_4$ alkyl), $R^{53C}$-substituted or unsubstituted heteroalkyl (e.g., 2 to 8 membered heteroalkyl, 2 to 6 membered heteroalkyl, or 2 to 4 membered heteroalkyl), $R^{53C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{53C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{53C}$-substituted or unsubstituted aryl (e.g., $C_6$-$C_{10}$ aryl, $C_{10}$ aryl, or phenyl), or $R^{53C}$-substituted or unsubstituted heteroaryl (e.g., 5 to 10 membered heteroaryl, 5 to 9 membered heteroaryl, or 5 to 6 membered heteroaryl).

In embodiments, $R^{23D}$ is hydrogen, hydrogen, —$CF_3$, —$CCl_3$, —$CBr_3$—, —$CI_3$, —CN, —COOH, —$CONH_2$, —$CHF_2$, —$CHCl_2$, —$CHBr_2$—, —$CHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{23D}$ is hydrogen, —$CF_3$, —$CCl_3$, —$CBr_3$—, —$CI_3$, —CN, —COOH, —$CONH_2$, —$CHF_2$, —$CHCl_2$, —$CHBr_2$—, —$CHI_2$, $R^{53D}$-substituted or unsubstituted alkyl (e.g., $C_1$-$C_8$ alkyl, $C_1$-$C_6$ alkyl, or $C_1$-$C_4$ alkyl), $R^{53D}$-substituted or unsubstituted heteroalkyl (e.g., 2 to 8 membered heteroalkyl, 2 to 6 membered heteroalkyl, or 2 to 4 membered heteroalkyl), $R^{53D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{53D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{53D}$-substituted or unsubstituted aryl (e.g., $C_6$-$C_{10}$ aryl, $C_{10}$ aryl, or phenyl), or $R^{53D}$-substituted or unsubstituted heteroaryl (e.g., 5 to 10 membered heteroaryl, 5 to 9 membered heteroaryl, or 5 to 6 membered heteroaryl).

In embodiments, $R^{24A}$ is hydrogen, —$CF_3$, —$CCl_3$, —$CBr_3$—, —$CI_3$, —CN, —COOH, —$CONH_2$, —$CHF_2$, —$CHCl_2$, —$CHBr_2$—, —$CHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{24A}$ is hydrogen, —$CF_3$, —$CCl_3$, —$CBr_3$—, —$CI_3$, —CN, —COOH, —$CONH_2$, —$CHF_2$, —$CHCl_2$, —$CHBr_2$—, —$CHI_2$, $R^{56A}$-substituted or unsubstituted alkyl (e.g., $C_1$-$C_8$ alkyl, $C_1$-$C_6$ alkyl, or $C_1$-$C_4$ alkyl), $R^{56A}$-substituted or unsubstituted heteroalkyl (e.g., 2 to 8 membered heteroalkyl, 2 to 6 membered heteroalkyl, or 2 to 4 membered heteroalkyl), $R^{56A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{56A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{56A}$-substituted or unsubstituted aryl (e.g., $C_6$-$C_{10}$ aryl, $C_{10}$ aryl, or phenyl), or $R^{56A}$-substituted or unsubstituted heteroaryl (e.g., 5 to 10 membered heteroaryl, 5 to 9 membered heteroaryl, or 5 to 6 membered heteroaryl). In embodiments, $R^{24A}$ and $R^{24B}$ substituents bonded to the same nitrogen atom may optionally be joined to form a $R^{56A}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{56A}$-substituted or unsubstituted heteroaryl (e.g., 5 to 10 membered heteroaryl, 5 to 9 membered heteroaryl, or 5 to 6 membered heteroaryl).

In embodiments, $R^{24B}$ is hydrogen, hydrogen, —$CF_3$, —$CCl_3$, —$CBr_3$—, —C13, —CN, —COOH, —$CONH_2$, —$CHF_2$, —$CHCl_2$, —$CHBr_2$—, —$CHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{24B}$ is hydrogen, —$CF_3$, —$CCl_3$, —$CBr_3$—, —$CI_3$, —CN, —COOH, —$CONH_2$, —$CHF_2$, —$CHCl_2$, —$CHBr_2$—, —$CHI_2$, $R^{56B}$-substituted or unsubstituted alkyl (e.g., $C_1$-$C_8$ alkyl, $C_1$-$C_6$ alkyl, or $C_1$-$C_4$ alkyl), $R^{56B}$-substituted or unsubstituted heteroalkyl (e.g., 2 to 8 membered heteroalkyl, 2 to 6 membered heteroalkyl, or 2 to 4 membered heteroalkyl), $R^{56B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{56B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{56B}$-substituted or unsubstituted aryl (e.g., $C_6$-$C_{10}$ aryl, $C_{10}$ aryl, or phenyl), or $R^{56B}$-substituted or unsubstituted heteroaryl (e.g., 5 to 10 membered heteroaryl, 5 to 9 membered heteroaryl, or 5 to 6 membered heteroaryl). In embodiments, $R^{24A}$ and $R^{24B}$ substituents bonded to the same nitrogen atom may optionally be joined to form a $R^{56B}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{56B}$-substituted or unsubstituted heteroaryl (e.g., 5 to 10 membered heteroaryl, 5 to 9 membered heteroaryl, or 5 to 6 membered heteroaryl).

In embodiments, $R^{24C}$ is hydrogen, hydrogen, —$CF_3$, —$CCl_3$, —$CBr_3$—, —$CI_3$, —CN, —COOH, —$CONH_2$, —$CHF_2$, —$CHCl_2$, —$CHBr_2$—, —$CHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{24C}$ is hydrogen, —$CF_3$, —$CCl_3$, —$CBr_3$—, —$CI_3$, —CN, —COOH, —$CONH_2$, —$CHF_2$, —$CHCl_2$, —$CHBr_2$—, —$CHI_2$, $R^{56C}$-substituted or unsubstituted alkyl (e.g., $C_1$-$C_8$ alkyl, $C_1$-$C_6$ alkyl, or $C_1$-$C_4$ alkyl), $R^{56C}$-substituted or unsubstituted heteroalkyl (e.g., 2 to 8 membered heteroalkyl, 2 to 6 membered heteroalkyl, or 2 to 4 membered heteroalkyl), $R^{56C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{56C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{56C}$-substituted or unsubstituted aryl (e.g., $C_6$-$C_{10}$ aryl, $C_{10}$ aryl, or phenyl), or $R^{56C}$-substituted or unsubstituted heteroaryl (e.g., 5 to 10 membered heteroaryl, 5 to 9 membered heteroaryl, or 5 to 6 membered heteroaryl).

In embodiments, $R^{24D}$ is hydrogen, hydrogen, —$CF_3$, —$CCl_3$, —$CBr_3$—, —$CI_3$, —CN, —COOH, —$CONH_2$, —$CHF_2$, —$CHCl_2$, —$CHBr_2$—, —$CHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{24D}$ is hydrogen, —$CF_3$, —$CCl_3$, —$CBr_3$—, —$CI_3$, —CN, —COOH, —$CONH_2$, —$CHF_2$, —$CHCl_2$, —$CHBr_2$—, —$CHI_2$, $R^{56D}$-substituted or unsubstituted alkyl (e.g., $C_1$-$C_8$ alkyl, $C_1$-$C_6$ alkyl, or $C_1$-$C_4$ alkyl), $R^{56D}$-substituted or unsubstituted heteroalkyl (e.g., 2 to 8 membered heteroalkyl, 2 to 6 membered heteroalkyl, or 2 to 4 membered heteroalkyl), $R^{56D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{56D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{56D}$-substituted or unsubstituted aryl (e.g., $C_6$-$C_{10}$ aryl, $C_{10}$ aryl, or phenyl), or $R^{56D}$-substituted or unsubstituted heteroaryl (e.g., 5 to 10 membered heteroaryl, 5 to 9 membered heteroaryl, or 5 to 6 membered heteroaryl).

$R^{27}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{40}$-substituted or unsubstituted alkyl (e.g., $C_1$-$C_8$ alkyl, $C_1$-$C_6$ alkyl, or $C_1$-$C_4$ alkyl), $R^{40}$-substituted or unsubstituted heteroalkyl (e.g., 2 to 8 membered heteroalkyl, 2 to 6 membered heteroalkyl, or 2 to 4 membered heteroalkyl), $R^{40}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{40}$-substituted or unsubstituted heterocycloalkyl (e.g., 3 to 8 membered heterocycloalkyl, 3 to 6 membered heterocycloalkyl, or 5 to 6 membered heterocycloalkyl), $R^{40}$-substituted or unsubstituted aryl (e.g., $C_6$-$C_{10}$ aryl, $C_{10}$ aryl, or phenyl), or $R^{40}$-substituted or unsubstituted heteroaryl (e.g., 5 to 10 membered heteroaryl, 5 to 9 membered heteroaryl, or 5 to 6 membered heteroaryl).

In embodiments, $R^{27}$ is $R^{40}$-substituted or unsubstituted alkyl (e.g., $C_1$-$C_8$ alkyl, $C_1$-$C_6$ alkyl, or $C_1$-$C_4$ alkyl). In embodiments, $R^{27}$ is $R^{40}$-substituted alkyl (e.g., $C_1$-$C_8$ alkyl, $C_1$-$C_6$ alkyl, or $C_1$-$C_4$ alkyl). In embodiments, $R^{27}$ is an unsubstituted alkyl (e.g., $C_1$-$C_8$ alkyl, $C_1$-$C_6$ alkyl, or $C_1$-$C_4$ alkyl).

In embodiments, $R^{27}$ is $R^{40}$-substituted or unsubstituted heteroalkyl (e.g., 2 to 8 membered heteroalkyl, 2 to 6 membered heteroalkyl, or 2 to 4 membered heteroalkyl). In embodiments, $R^{27}$ is $R^{40}$-substituted heteroalkyl (e.g., 2 to 8 membered heteroalkyl, 2 to 6 membered heteroalkyl, or 2 to 4 membered heteroalkyl). In embodiments, $R^{27}$ is an unsubstituted heteroalkyl (e.g., 2 to 8 membered heteroalkyl, 2 to 6 membered heteroalkyl, or 2 to 4 membered heteroalkyl).

In embodiments, $R^{27}$ is $R^{40}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{27}$ is $R^{40}$-substituted cycloalkyl (e.g., $C_3$-$C_8$ cycloalkyl, $C_3$-$C_6$ cycloalkyl, or $C_5$-$C_6$ cycloalkyl). In embodiments, $R^{27}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{27}$ is $R^{40}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{27}$ is $R^{40}$-substituted heterocycloalkyl (e.g., 3 to 8 membered heterocycloalkyl, 3 to 6 membered heterocycloalkyl, or 5 to 6 membered heterocycloalkyl). In embodiments, $R^{27}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{27}$ is $R^{40}$-substituted or unsubstituted aryl (e.g., $C_6$-$C_{10}$ aryl, $C_{10}$ aryl, or phenyl). In embodiments, $R^{27}$ is $R^{40}$-substituted aryl (e.g., $C_6$-$C_{10}$ aryl, $C_{10}$ aryl, or phenyl). In embodiments, $R^{27}$ is an unsubstituted aryl (e.g., $C_6$-$C_{10}$ aryl, $C_{10}$ aryl, or phenyl).

In embodiments, $R^{27}$ is $R^{40}$-substituted or unsubstituted heteroaryl (e.g., 5 to 10 membered heteroaryl, 5 to 9 membered heteroaryl, or 5 to 6 membered heteroaryl). In embodiments, $R^{27}$ is $R^{40}$-substituted heteroaryl (e.g., 5 to 10 membered heteroaryl, 5 to 9 membered heteroaryl, or 5 to 6 membered heteroaryl). In embodiments, $R^{27}$ is an unsubstituted heteroaryl (e.g., 5 to 10 membered heteroaryl, 5 to 9 membered heteroaryl, or 5 to 6 membered heteroaryl).

$R^{40}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{41}$-substituted or unsubstituted alkyl (e.g., $C_1$-$C_8$ alkyl, $C_1$-$C_6$ alkyl, or $C_1$-$C_4$ alkyl), $R^{41}$-substituted or unsubstituted heteroalkyl (e.g., 2 to 8 membered heteroalkyl, 2 to 6 membered heteroalkyl, or 2 to 4 membered heteroalkyl), $R^{41}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{41}$-substituted or unsubstituted heterocycloalkyl (e.g., 3 to 8 membered heterocycloalkyl, 3 to 6 membered heterocycloalkyl, or 5 to 6 membered heterocycloalkyl), $R^{41}$-substituted or unsubstituted aryl (e.g., $C_6$-$C_{10}$ aryl, $C_{10}$ aryl, or phenyl), or $R^{41}$-substituted or unsubstituted heteroaryl (e.g., 5 to 10 membered heteroaryl, 5 to 9 membered heteroaryl, or 5 to 6 membered heteroaryl).

In embodiments, $R^{40}$ is $R^{41}$-substituted or unsubstituted alkyl (e.g., $C_1$-$C_8$ alkyl, $C_1$-$C_6$ alkyl, or $C_1$-$C_4$ alkyl). In embodiments, $R^{40}$ is $R^{41}$-substituted alkyl (e.g., $C_1$-$C_8$ alkyl, $C_1$-$C_6$ alkyl, or $C_1$-$C_4$ alkyl). In embodiments, $R^{40}$ is an unsubstituted alkyl (e.g., $C_1$-$C_8$ alkyl, $C_1$-$C_6$ alkyl, or $C_1$-$C_4$ alkyl).

In embodiments, $R^{40}$ is $R^{41}$-substituted or unsubstituted heteroalkyl (e.g., 2 to 8 membered heteroalkyl, 2 to 6 membered heteroalkyl, or 2 to 4 membered heteroalkyl). In embodiments, $R^{40}$ is $R^{41}$-substituted heteroalkyl (e.g., 2 to 8 membered heteroalkyl, 2 to 6 membered heteroalkyl, or 2 to 4 membered heteroalkyl). In embodiments, $R^{40}$ is an unsubstituted heteroalkyl (e.g., 2 to 8 membered heteroalkyl, 2 to 6 membered heteroalkyl, or 2 to 4 membered heteroalkyl).

In embodiments, $R^{40}$ is $R^{41}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{40}$ is $R^{41}$-substituted cycloalkyl (e.g., $C_3$-$C_8$ cycloalkyl, $C_3$-$C_6$ cycloalkyl, or $C_5$-$C_6$ cycloalkyl). In embodiments, $R^{40}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{40}$ is $R^{41}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{40}$ is $R^{41}$-substituted heterocycloalkyl (e.g., 3 to 8 membered heterocycloalkyl, 3 to 6 membered heterocycloalkyl, or 5 to 6 membered heterocycloalkyl). In embodiments, $R^{40}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{40}$ is $R^{41}$-substituted or unsubstituted aryl (e.g., $C_6$-$C_{10}$ aryl, $C_{10}$ aryl, or phenyl). In embodiments, $R^{40}$ is $R^{41}$-substituted aryl (e.g., $C_6$-$C_{10}$ aryl, $C_{10}$ aryl, or phenyl). In embodiments, $R^{40}$ is an unsubstituted aryl (e.g., $C_6$-$C_{10}$ aryl, $C_{10}$ aryl, or phenyl).

In embodiments, $R^{40}$ is $R^{41}$-substituted or unsubstituted heteroaryl (e.g., 5 to 10 membered heteroaryl, 5 to 9 membered heteroaryl, or 5 to 6 membered heteroaryl). In embodiments, $R^{40}$ is $R^{41}$-substituted heteroaryl (e.g., 5 to 10 membered heteroaryl, 5 to 9 membered heteroaryl, or 5 to 6 membered heteroaryl). In embodiments, $R^{40}$ is an unsubstituted heteroaryl (e.g., 5 to 10 membered heteroaryl, 5 to 9 membered heteroaryl, or 5 to 6 membered heteroaryl).

$R^{43}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{44}$-substituted or unsubstituted alkyl (e.g., $C_1$-$C_8$ alkyl, $C_1$-$C_6$ alkyl, or $C_1$-$C_4$ alkyl), $R^{44}$-substituted or unsubstituted heteroalkyl (e.g., 2 to 8 membered heteroalkyl, 2 to 6 membered heteroalkyl, or 2 to 4 membered heteroalkyl), $R^{44}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{44}$-substituted or unsubstituted heterocycloalkyl (e.g., 3 to 8 membered heterocycloalkyl, 3 to 6 membered heterocycloalkyl, or 5 to 6 membered heterocycloalkyl), $R^{44}$-substituted or unsubstituted aryl (e.g., $C_6$-$C_{10}$ aryl, $C_{10}$ aryl, or phenyl), or $R^{44}$-substituted or unsubstituted heteroaryl (e.g., 5 to 10 membered heteroaryl, 5 to 9 membered heteroaryl, or 5 to 6 membered heteroaryl).

In embodiments, $R^{43}$ is $R^{44}$-substituted or unsubstituted alkyl (e.g., $C_1$-$C_8$ alkyl, $C_1$-$C_6$ alkyl, or $C_1$-$C_4$ alkyl). In embodiments, $R^{43}$ is $R^{44}$-substituted alkyl (e.g., $C_1$-$C_8$ alkyl, $C_1$-$C_6$ alkyl, or $C_1$-$C_4$ alkyl). In embodiments, $R^{43}$ is an unsubstituted alkyl (e.g., $C_1$-$C_8$ alkyl, $C_1$-$C_6$ alkyl, or $C_1$-$C_4$ alkyl).

In embodiments, $R^{43}$ is $R^{44}$-substituted or unsubstituted heteroalkyl (e.g., 2 to 8 membered heteroalkyl, 2 to 6 membered heteroalkyl, or 2 to 4 membered heteroalkyl). In embodiments, $R^{43}$ is $R^{44}$-substituted heteroalkyl (e.g., 2 to 8 membered heteroalkyl, 2 to 6 membered heteroalkyl, or 2 to 4 membered heteroalkyl). In embodiments, $R^{43}$ is an unsubstituted heteroalkyl (e.g., 2 to 8 membered heteroalkyl, 2 to 6 membered heteroalkyl, or 2 to 4 membered heteroalkyl).

In embodiments, $R^{43}$ is $R^{44}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{43}$ is $R^{44}$-substituted cycloalkyl (e.g., $C_3$-$C_8$ cycloalkyl, $C_3$-$C_6$ cycloalkyl, or $C_5$-$C_6$ cycloalkyl). In embodiments, $R^{43}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{43}$ is $R^{44}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{43}$ is $R^{44}$-substituted heterocycloalkyl (e.g., 3 to 8 membered heterocycloalkyl, 3 to 6 membered heterocycloalkyl, or 5 to 6 membered heterocycloalkyl). In embodiments, $R^{43}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{43}$ is $R^{44}$-substituted or unsubstituted aryl (e.g., $C_6$-$C_{10}$ aryl, $C_{10}$ aryl, or phenyl). In embodiments, $R^{43}$ is $R^{44}$-substituted aryl (e.g., $C_6$-$C_{10}$ aryl, $C_{10}$ aryl, or phenyl). In embodiments, $R^{43}$ is an unsubstituted aryl (e.g., $C_6$-$C_{10}$ aryl, $C_{10}$ aryl, or phenyl).

In embodiments, $R^{43}$ is $R^{44}$-substituted or unsubstituted heteroaryl (e.g., 5 to 10 membered heteroaryl, 5 to 9 membered heteroaryl, or 5 to 6 membered heteroaryl). In embodiments, $R^{43}$ is $R^{44}$-substituted heteroaryl (e.g., 5 to 10 membered heteroaryl, 5 to 9 membered heteroaryl, or 5 to 6 membered heteroaryl). In embodiments, $R^{43}$ is an unsubstituted heteroaryl (e.g., 5 to 10 membered heteroaryl, 5 to 9 membered heteroaryl, or 5 to 6 membered heteroaryl).

$R^{45}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{46}$-substituted or unsubstituted alkyl (e.g., $C_1$-$C_8$ alkyl, $C_1$-$C_6$ alkyl, or $C_1$-$C_4$ alkyl), $R^{46}$-substituted or unsubstituted heteroalkyl (e.g., 2 to 8 membered heteroalkyl, 2 to 6 membered heteroalkyl, or 2 to 4 membered heteroalkyl), $R^{46}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{46}$-substituted or unsubstituted heterocycloalkyl (e.g., 3 to 8 membered heterocycloalkyl, 3 to 6 membered heterocycloalkyl, or 5 to 6 membered heterocycloalkyl), $R^{46}$-substituted or unsubstituted aryl (e.g., $C_6$-$C_{10}$ aryl, $C_{10}$ aryl, or phenyl), or $R^{46}$-substituted or unsubstituted heteroaryl (e.g., 5 to 10 membered heteroaryl, 5 to 9 membered heteroaryl, or 5 to 6 membered heteroaryl).

In embodiments, $R^{45}$ is $R^{46}$-substituted or unsubstituted alkyl (e.g., $C_1$-$C_8$ alkyl, $C_1$-$C_6$ alkyl, or $C_1$-$C_4$ alkyl). In embodiments, $R^{45}$ is $R^{46}$-substituted alkyl (e.g., $C_1$-$C_8$ alkyl, $C_1$-$C_6$ alkyl, or $C_1$-$C_4$ alkyl). In embodiments, $R^{45}$ is an unsubstituted alkyl (e.g., $C_1$-$C_8$ alkyl, $C_1$-$C_6$ alkyl, or $C_1$-$C_4$ alkyl).

In embodiments, $R^{45}$ is $R^{46}$-substituted or unsubstituted heteroalkyl (e.g., 2 to 8 membered heteroalkyl, 2 to 6 membered heteroalkyl, or 2 to 4 membered heteroalkyl). In embodiments, $R^{45}$ is $R^{46}$-substituted heteroalkyl (e.g., 2 to 8 membered heteroalkyl, 2 to 6 membered heteroalkyl, or 2 to 4 membered heteroalkyl). In embodiments, $R^{45}$ is an unsubstituted heteroalkyl (e.g., 2 to 8 membered heteroalkyl, 2 to 6 membered heteroalkyl, or 2 to 4 membered heteroalkyl).

In embodiments, $R^{45}$ is $R^{46}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{45}$ is $R^{46}$-substituted cycloalkyl (e.g., $C_3$-$C_8$ cycloalkyl, $C_3$-$C_6$ cycloalkyl, or $C_5$-$C_6$ cycloalkyl). In embodiments, $R^{45}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{45}$ is $R^{46}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{45}$ is $R^{46}$-substituted heterocycloalkyl (e.g., 3 to 8 membered heterocycloalkyl, 3 to 6 membered heterocycloalkyl, or 5 to 6 membered heterocycloalkyl). In embodiments, $R^{45}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{45}$ is $R^{46}$-substituted or unsubstituted aryl (e.g., $C_6$-$C_{10}$ aryl, $C_{10}$ aryl, or phenyl). In embodiments, $R^{45}$ is $R^{46}$-substituted aryl (e.g., $C_6$-$C_{10}$ aryl, $C_{10}$ aryl, or phenyl). In embodiments, $R^{45}$ is an unsubstituted aryl (e.g., $C_6$-$C_{10}$ aryl, $C_{10}$ aryl, or phenyl).

In embodiments, $R^{45}$ is $R^{46}$-substituted or unsubstituted heteroaryl (e.g., 5 to 10 membered heteroaryl, 5 to 9 membered heteroaryl, or 5 to 6 membered heteroaryl). In embodiments, $R^{45}$ is $R^{46}$-substituted heteroaryl (e.g., 5 to 10 membered heteroaryl, 5 to 9 membered heteroaryl, or 5 to 6 membered heteroaryl). In embodiments, $R^{45}$ is an unsubstituted heteroaryl (e.g., 5 to 10 membered heteroaryl, 5 to 9 membered heteroaryl, or 5 to 6 membered heteroaryl).

$R^{47}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{48}$-substituted or unsubstituted alkyl (e.g., $C_1$-$C_8$ alkyl, $C_1$-$C_6$ alkyl, or $C_1$-$C_4$ alkyl), $R^{48}$-substituted or unsubstituted heteroalkyl (e.g., 2 to 8 membered heteroalkyl, 2 to 6 membered heteroalkyl, or 2 to 4 membered heteroalkyl), $R^{48}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{48}$-substituted or unsubstituted heterocycloalkyl (e.g., 3 to 8 membered heterocycloalkyl, 3 to 6 membered heterocycloalkyl, or 5 to 6 membered heterocycloalkyl), $R^{48}$-substituted or unsubstituted aryl (e.g., $C_6$-$C_{10}$ aryl, $C_{10}$ aryl, or phenyl), or $R^{48}$-substituted or unsubstituted heteroaryl (e.g., 5 to 10 membered heteroaryl, 5 to 9 membered heteroaryl, or 5 to 6 membered heteroaryl).

In embodiments, $R^{47}$ is $R^{48}$-substituted or unsubstituted alkyl (e.g., $C_1$-$C_8$ alkyl, $C_1$-$C_6$ alkyl, or $C_1$-$C_4$ alkyl). In embodiments, $R^{47}$ is $R^{48}$-substituted alkyl (e.g., $C_1$-$C_8$ alkyl, $C_1$-$C_6$ alkyl, or $C_1$-$C_4$ alkyl). In embodiments, $R^{47}$ is an unsubstituted alkyl (e.g., $C_1$-$C_8$ alkyl, $C_1$-$C_6$ alkyl, or $C_1$-$C_4$ alkyl).

In embodiments, $R^{47}$ is $R^{48}$-substituted or unsubstituted heteroalkyl (e.g., 2 to 8 membered heteroalkyl, 2 to 6 membered heteroalkyl, or 2 to 4 membered heteroalkyl). In embodiments, $R^{47}$ is $R^{48}$-substituted heteroalkyl (e.g., 2 to 8 membered heteroalkyl, 2 to 6 membered heteroalkyl, or 2 to 4 membered heteroalkyl). In embodiments, $R^{47}$ is an unsubstituted heteroalkyl (e.g., 2 to 8 membered heteroalkyl, 2 to 6 membered heteroalkyl, or 2 to 4 membered heteroalkyl).

In embodiments, $R^{47}$ is $R^{48}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{47}$ is $R^{48}$-substituted cycloalkyl (e.g., $C_3$-$C_8$ cycloalkyl, $C_3$-$C_6$ cycloalkyl, or $C_5$-$C_6$ cycloalkyl). In embodiments, $R^{47}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{47}$ is $R^{48}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{47}$ is $R^{48}$-substituted heterocycloalkyl (e.g., 3 to 8 membered heterocycloalkyl, 3 to 6 membered heterocycloalkyl, or 5 to 6 membered heterocycloalkyl). In embodiments, $R^{47}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{47}$ is $R^{48}$-substituted or unsubstituted aryl (e.g., $C_6$-$C_{10}$ aryl, $C_{10}$ aryl, or phenyl). In embodiments, $R^{47}$ is $R^{48}$-substituted aryl (e.g., $C_6$-$C_{10}$ aryl, $C_{10}$ aryl, or phenyl). In embodiments, $R^{47}$ is an unsubstituted aryl (e.g., $C_6$-$C_{10}$ aryl, $C_{10}$ aryl, or phenyl).

In embodiments, $R^{47}$ is $R^{48}$-substituted or unsubstituted heteroaryl (e.g., 5 to 10 membered heteroaryl, 5 to 9 membered heteroaryl, or 5 to 6 membered heteroaryl). In embodiments, $R^{47}$ is $R^{48}$-substituted heteroaryl (e.g., 5 to 10 membered heteroaryl, 5 to 9 membered heteroaryl, or 5 to 6 membered heteroaryl). In embodiments, $R^{47}$ is an unsubstituted heteroaryl (e.g., 5 to 10 membered heteroaryl, 5 to 9 membered heteroaryl, or 5 to 6 membered heteroaryl).

$R^{48}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{49}$-substituted or unsubstituted alkyl (e.g., $C_1$-$C_8$ alkyl, $C_1$-$C_6$ alkyl, or $C_1$-$C_4$ alkyl), $R^{49}$-substituted or unsubstituted heteroalkyl (e.g., 2 to 8 membered heteroalkyl, 2 to 6 membered heteroalkyl, or 2 to 4 membered heteroalkyl), $R^{49}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{49}$-substituted or unsubstituted heterocycloalkyl (e.g., 3 to 8 membered heterocycloalkyl, 3 to 6 membered heterocycloalkyl, or 5 to 6 membered heterocycloalkyl), $R^{49}$-substituted or unsubstituted aryl (e.g., $C_6$-$C_{10}$ aryl, $C_{10}$ aryl, or phenyl), or $R^{49}$-substituted or unsubstituted heteroaryl (e.g., 5 to 10 membered heteroaryl, 5 to 9 membered heteroaryl, or 5 to 6 membered heteroaryl).

In embodiments, $R^{48}$ is $R^{49}$-substituted or unsubstituted alkyl (e.g., $C_1$-$C_8$ alkyl, $C_1$-$C_6$ alkyl, or $C_1$-$C_4$ alkyl). In embodiments, $R^{48}$ is $R^{49}$-substituted alkyl (e.g., $C_1$-$C_8$ alkyl, $C_1$-$C_6$ alkyl, or $C_1$-$C_4$ alkyl). In embodiments, $R^{48}$ is an unsubstituted alkyl (e.g., $C_1$-$C_8$ alkyl, $C_1$-$C_6$ alkyl, or $C_1$-$C_4$ alkyl).

In embodiments, $R^{48}$ is $R^{49}$-substituted or unsubstituted heteroalkyl (e.g., 2 to 8 membered heteroalkyl, 2 to 6 membered heteroalkyl, or 2 to 4 membered heteroalkyl). In embodiments, $R^{48}$ is $R^{49}$-substituted heteroalkyl (e.g., 2 to 8 membered heteroalkyl, 2 to 6 membered heteroalkyl, or 2 to 4 membered heteroalkyl). In embodiments, $R^{48}$ is an unsubstituted heteroalkyl (e.g., 2 to 8 membered heteroalkyl, 2 to 6 membered heteroalkyl, or 2 to 4 membered heteroalkyl).

In embodiments, $R^{48}$ is $R^{49}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{48}$ is $R^{49}$-substituted cycloalkyl (e.g., $C_3$-$C_8$ cycloalkyl, $C_3$-$C_6$ cycloalkyl, or $C_5$-$C_6$ cycloalkyl). In embodiments, $R^{48}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{48}$ is $R^{49}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{48}$ is $R^{49}$-substituted heterocycloalkyl (e.g., 3 to 8 membered heterocycloalkyl, 3 to 6 membered heterocycloalkyl, or 5 to 6 membered heterocycloalkyl). In embodiments, $R^{48}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{48}$ is $R^{49}$-substituted or unsubstituted aryl (e.g., $C_6$-$C_{10}$ aryl, $C_{10}$ aryl, or phenyl). In embodiments, $R^{48}$ is $R^{49}$-substituted aryl (e.g., $C_6$-$C_{10}$ aryl, $C_{10}$ aryl, or phenyl). In embodiments, $R^{48}$ is an unsubstituted aryl (e.g., $C_6$-$C_{10}$ aryl, $C_{10}$ aryl, or phenyl).

In embodiments, $R^{48}$ is $R^{49}$-substituted or unsubstituted heteroaryl (e.g., 5 to 10 membered heteroaryl, 5 to 9 membered heteroaryl, or 5 to 6 membered heteroaryl). In embodiments, $R^{48}$ is $R^{49}$-substituted heteroaryl (e.g., 5 to 10 membered heteroaryl, 5 to 9 membered heteroaryl, or 5 to 6 membered heteroaryl). In embodiments, $R^{48}$ is an unsubstituted heteroaryl (e.g., 5 to 10 membered heteroaryl, 5 to 9 membered heteroaryl, or 5 to 6 membered heteroaryl).

$R^{50}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{51}$-substituted or unsubstituted alkyl (e.g., $C_1$-$C_8$ alkyl, $C_1$-$C_6$ alkyl, or $C_1$-$C_4$ alkyl), $R^{51}$-substituted or unsubstituted heteroalkyl (e.g., 2 to 8 membered heteroalkyl, 2 to 6 membered heteroalkyl, or 2 to 4 membered heteroalkyl), $R^{51}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{51}$-substituted or unsubstituted heterocycloalkyl (e.g., 3 to 8 membered heterocycloalkyl, 3 to 6 membered heterocycloalkyl, or 5 to 6 membered heterocycloalkyl), $R^{51}$-substituted or unsubstituted aryl (e.g., $C_6$-$C_{10}$ aryl, $C_{10}$ aryl, or phenyl), or $R^{51}$-substituted or unsubstituted heteroaryl (e.g., 5 to 10 membered heteroaryl, 5 to 9 membered heteroaryl, or 5 to 6 membered heteroaryl).

In embodiments, $R^{50}$ is $R^{51}$-substituted or unsubstituted alkyl (e.g., $C_1$-$C_8$ alkyl, $C_1$-$C_6$ alkyl, or $C_1$-$C_4$ alkyl). In embodiments, $R^{50}$ is $R^{51}$-substituted alkyl (e.g., $C_1$-$C_8$ alkyl, $C_1$-$C_6$ alkyl, or $C_1$-$C_4$ alkyl). In embodiments, $R^{50}$ is an unsubstituted alkyl (e.g., $C_1$-$C_8$ alkyl, $C_1$-$C_6$ alkyl, or $C_1$-$C_4$ alkyl).

In embodiments, $R^{50}$ is $R^{51}$-substituted or unsubstituted heteroalkyl (e.g., 2 to 8 membered heteroalkyl, 2 to 6 membered heteroalkyl, or 2 to 4 membered heteroalkyl). In embodiments, $R^{50}$ is $R^{51}$-substituted heteroalkyl (e.g., 2 to 8 membered heteroalkyl, 2 to 6 membered heteroalkyl, or 2 to 4 membered heteroalkyl). In embodiments, $R^{50}$ is an unsubstituted heteroalkyl (e.g., 2 to 8 membered heteroalkyl, 2 to 6 membered heteroalkyl, or 2 to 4 membered heteroalkyl).

In embodiments, $R^{50}$ is $R^{51}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{50}$ is $R^{51}$-substituted cycloalkyl (e.g., $C_3$-$C_8$ cycloalkyl, $C_3$-$C_6$ cycloalkyl, or $C_5$-$C_6$ cycloalkyl). In embodiments, $R^{50}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{50}$ is $R^{51}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{50}$ is $R^{51}$-substituted heterocycloalkyl (e.g., 3 to 8 membered heterocycloalkyl, 3 to 6 membered heterocycloalkyl, or 5 to 6 membered heterocycloalkyl). In embodiments, $R^{50}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{50}$ is $R^{51}$-substituted or unsubstituted aryl (e.g., $C_6$-$C_{10}$ aryl, $C_{10}$ aryl, or phenyl). In embodiments, $R^{50}$ is $R^{51}$-substituted aryl (e.g., $C_6$-$C_{10}$ aryl, $C_{10}$ aryl, or phenyl). In embodiments, $R^{50}$ is an unsubstituted aryl (e.g., $C_6$-$C_{10}$ aryl, $C_{10}$ aryl, or phenyl).

In embodiments, $R^{50}$ is $R^{51}$-substituted or unsubstituted heteroaryl (e.g., 5 to 10 membered heteroaryl, 5 to 9 membered heteroaryl, or 5 to 6 membered heteroaryl). In embodiments, $R^{50}$ is $R^{51}$-substituted heteroaryl (e.g., 5 to 10 membered heteroaryl, 5 to 9 membered heteroaryl, or 5 to 6 membered heteroaryl). In embodiments, $R^{50}$ is an unsubstituted heteroaryl (e.g., 5 to 10 membered heteroaryl, 5 to 9 membered heteroaryl, or 5 to 6 membered heteroaryl).

$R^{51}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{52}$-substituted or unsubstituted alkyl (e.g., $C_1$-$C_8$ alkyl, $C_1$-$C_6$ alkyl, or $C_1$-$C_4$ alkyl), $R^{52}$-substituted or unsubstituted heteroalkyl (e.g., 2 to 8 membered heteroalkyl, 2 to 6 membered heteroalkyl, or 2 to 4 membered heteroalkyl), $R^{52}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{52}$-substituted or unsubstituted heterocycloalkyl (e.g., 3 to 8 membered heterocycloalkyl, 3 to 6 membered heterocycloalkyl, or 5 to 6 membered heterocycloalkyl), $R^{52}$-substituted or unsubstituted aryl (e.g., $C_6$-$C_{10}$ aryl, $C_{10}$ aryl, or phenyl), or $R^{52}$-substituted or unsubstituted heteroaryl (e.g., 5 to 10 membered heteroaryl, 5 to 9 membered heteroaryl, or 5 to 6 membered heteroaryl).

In embodiments, $R^{51}$ is $R^{52}$-substituted or unsubstituted alkyl (e.g., $C_1$-$C_8$ alkyl, $C_1$-$C_6$ alkyl, or $C_1$-$C_4$ alkyl). In embodiments, $R^{51}$ is $R^{52}$-substituted alkyl (e.g., $C_1$-$C_8$ alkyl, $C_1$-$C_6$ alkyl, or $C_1$-$C_4$ alkyl). In embodiments, $R^{51}$ is an unsubstituted alkyl (e.g., $C_1$-$C_8$ alkyl, $C_1$-$C_6$ alkyl, or $C_1$-$C_4$ alkyl).

In embodiments, $R^{51}$ is $R^{52}$-substituted or unsubstituted heteroalkyl (e.g., 2 to 8 membered heteroalkyl, 2 to 6 membered heteroalkyl, or 2 to 4 membered heteroalkyl). In embodiments, $R^{51}$ is $R^{52}$-substituted heteroalkyl (e.g., 2 to 8 membered heteroalkyl, 2 to 6 membered heteroalkyl, or 2 to 4 membered heteroalkyl). In embodiments, $R^{51}$ is an unsubstituted heteroalkyl (e.g., 2 to 8 membered heteroalkyl, 2 to 6 membered heteroalkyl, or 2 to 4 membered heteroalkyl).

In embodiments, $R^{51}$ is $R^{52}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{51}$ is $R^{52}$-substituted cycloalkyl (e.g., $C_3$-$C_8$ cycloalkyl, $C_3$-$C_6$ cycloalkyl, or $C_5$-$C_6$ cycloalkyl). In embodiments, $R^{51}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{51}$ is $R^{52}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{51}$ is $R^{52}$-substituted heterocycloalkyl (e.g., 3 to 8 membered heterocycloalkyl, 3 to 6 membered heterocycloalkyl, or 5 to 6 membered heterocycloalkyl). In embodiments, $R^{51}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{51}$ is $R^{52}$-substituted or unsubstituted aryl (e.g., $C_6$-$C_{10}$ aryl, $C_{10}$ aryl, or phenyl). In embodiments, $R^{51}$ is $R^{52}$-substituted aryl (e.g., $C_6$-$C_{10}$ aryl, $C_{10}$ aryl, or phenyl). In embodiments, $R^{51}$ is an unsubstituted aryl (e.g., $C_6$-$C_{10}$ aryl, $C_{10}$ aryl, or phenyl).

In embodiments, $R^{51}$ is $R^{52}$-substituted or unsubstituted heteroaryl (e.g., 5 to 10 membered heteroaryl, 5 to 9 membered heteroaryl, or 5 to 6 membered heteroaryl). In embodiments, $R^{51}$ is $R^{52}$-substituted heteroaryl (e.g., 5 to 10 membered heteroaryl, 5 to 9 membered heteroaryl, or 5 to 6 membered heteroaryl). In embodiments, $R^{51}$ is an unsubstituted heteroaryl (e.g., 5 to 10 membered heteroaryl, 5 to 9 membered heteroaryl, or 5 to 6 membered heteroaryl).

$R^{53}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{54}$-substituted or unsubstituted alkyl (e.g., $C_1$-$C_8$ alkyl, $C_1$-$C_6$ alkyl, or $C_1$-$C_4$ alkyl), $R^{54}$-substituted or unsubstituted heteroalkyl (e.g., 2 to 8 membered heteroalkyl, 2 to 6 membered heteroalkyl, or 2 to 4 membered heteroalkyl), $R^{54}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{54}$-substituted or unsubstituted heterocycloalkyl (e.g., 3 to 8 membered heterocycloalkyl, 3 to 6 membered heterocycloalkyl, or 5 to 6 membered heterocycloalkyl), $R^{54}$-substituted or unsubstituted aryl (e.g., $C_6$-$C_{10}$ aryl, $C_{10}$ aryl, or phenyl), or $R^{54}$-substituted or unsubstituted heteroaryl (e.g., 5 to 10 membered heteroaryl, 5 to 9 membered heteroaryl, or 5 to 6 membered heteroaryl).

In embodiments, $R^{53}$ is $R^{54}$-substituted or unsubstituted alkyl (e.g., $C_1$-$C_8$ alkyl, $C_1$-$C_6$ alkyl, or $C_1$-$C_4$ alkyl). In embodiments, $R^{53}$ is $R^{54}$-substituted alkyl (e.g., $C_1$-$C_8$ alkyl, $C_1$-$C_6$ alkyl, or $C_1$-$C_4$ alkyl). In embodiments, $R^{53}$ is an unsubstituted alkyl (e.g., $C_1$-$C_8$ alkyl, $C_1$-$C_6$ alkyl, or $C_1$-$C_4$ alkyl).

In embodiments, $R^{53}$ is $R^{54}$-substituted or unsubstituted heteroalkyl (e.g., 2 to 8 membered heteroalkyl, 2 to 6 membered heteroalkyl, or 2 to 4 membered heteroalkyl). In embodiments, $R^{53}$ is $R^{54}$-substituted heteroalkyl (e.g., 2 to 8 membered heteroalkyl, 2 to 6 membered heteroalkyl, or 2 to 4 membered heteroalkyl). In embodiments, $R^{53}$ is an unsubstituted heteroalkyl (e.g., 2 to 8 membered heteroalkyl, 2 to 6 membered heteroalkyl, or 2 to 4 membered heteroalkyl).

In embodiments, $R^{53}$ is $R^{54}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{53}$ is $R^{54}$-substituted cycloalkyl (e.g., $C_3$-$C_8$ cycloalkyl, $C_3$-$C_6$ cycloalkyl, or $C_5$-$C_6$ cycloalkyl). In embodiments, $R^{53}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{53}$ is $R^{54}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{53}$ is $R^{54}$-substituted heterocycloalkyl (e.g., 3 to 8 membered heterocycloalkyl, 3 to 6 membered heterocycloalkyl, or 5 to 6 membered heterocycloalkyl). In embodiments, $R^{53}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{53}$ is $R^{54}$-substituted or unsubstituted aryl (e.g., $C_6$-$C_{10}$ aryl, $C_{10}$ aryl, or phenyl). In embodiments, $R^{53}$ is $R^{54}$-substituted aryl (e.g., $C_6$-$C_{10}$ aryl, $C_{10}$ aryl, or phenyl). In embodiments, $R^{53}$ is an unsubstituted aryl (e.g., $C_6$-$C_{10}$ aryl, $C_{10}$ aryl, or phenyl).

In embodiments, $R^{53}$ is $R^{54}$-substituted or unsubstituted heteroaryl (e.g., 5 to 10 membered heteroaryl, 5 to 9 membered heteroaryl, or 5 to 6 membered heteroaryl). In embodiments, $R^{53}$ is $R^{54}$-substituted heteroaryl (e.g., 5 to 10 membered heteroaryl, 5 to 9 membered heteroaryl, or 5 to 6 membered heteroaryl). In embodiments, $R^{53}$ is an unsubstituted heteroaryl (e.g., 5 to 10 membered heteroaryl, 5 to 9 membered heteroaryl, or 5 to 6 membered heteroaryl).

$R^{54}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, $R^{55}$-substituted or unsubstituted alkyl (e.g., C$_1$-C$_8$ alkyl, C$_1$-C$_6$ alkyl, or C$_1$-C$_4$ alkyl), $R^{55}$-substituted or unsubstituted heteroalkyl (e.g., 2 to 8 membered heteroalkyl, 2 to 6 membered heteroalkyl, or 2 to 4 membered heteroalkyl), $R^{55}$-substituted or unsubstituted cycloalkyl (e.g., C$_3$-C$_8$ cycloalkyl, C$_3$-C$_6$ cycloalkyl, or C$_5$-C$_6$ cycloalkyl), $R^{55}$-substituted or unsubstituted heterocycloalkyl (e.g., 3 to 8 membered heterocycloalkyl, 3 to 6 membered heterocycloalkyl, or 5 to 6 membered heterocycloalkyl), $R^{55}$-substituted or unsubstituted aryl (e.g., C$_6$-C$_{10}$ aryl, C$_{10}$ aryl, or phenyl), or $R^{55}$-substituted or unsubstituted heteroaryl (e.g., 5 to 10 membered heteroaryl, 5 to 9 membered heteroaryl, or 5 to 6 membered heteroaryl).

In embodiments, $R^{54}$ is $R^{55}$-substituted or unsubstituted alkyl (e.g., C$_1$-C$_8$ alkyl, C$_1$-C$_6$ alkyl, or C$_1$-C$_4$ alkyl). In embodiments, $R^{54}$ is $R^{55}$-substituted alkyl (e.g., C$_1$-C$_8$ alkyl, C$_1$-C$_6$ alkyl, or C$_1$-C$_4$ alkyl). In embodiments, $R^{54}$ is an unsubstituted alkyl (e.g., C$_1$-C$_8$ alkyl, C$_1$-C$_6$ alkyl, or C$_1$-C$_4$ alkyl).

In embodiments, $R^{54}$ is $R^{55}$-substituted or unsubstituted heteroalkyl (e.g., 2 to 8 membered heteroalkyl, 2 to 6 membered heteroalkyl, or 2 to 4 membered heteroalkyl). In embodiments, $R^{54}$ is $R^{55}$-substituted heteroalkyl (e.g., 2 to 8 membered heteroalkyl, 2 to 6 membered heteroalkyl, or 2 to 4 membered heteroalkyl). In embodiments, $R^{54}$ is an unsubstituted heteroalkyl (e.g., 2 to 8 membered heteroalkyl, 2 to 6 membered heteroalkyl, or 2 to 4 membered heteroalkyl).

In embodiments, $R^{54}$ is $R^{55}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, $R^{54}$ is $R^{55}$-substituted cycloalkyl (e.g., C$_3$-C$_8$ cycloalkyl, C$_3$-C$_6$ cycloalkyl, or C$_5$-C$_6$ cycloalkyl). In embodiments, $R^{54}$ is an unsubstituted cycloalkyl (e.g., C$_3$-C$_8$ cycloalkyl, C$_3$-C$_6$ cycloalkyl, or C$_5$-C$_6$ cycloalkyl).

In embodiments, $R^{54}$ is $R^{55}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{54}$ is $R^{55}$-substituted heterocycloalkyl (e.g., 3 to 8 membered heterocycloalkyl, 3 to 6 membered heterocycloalkyl, or 5 to 6 membered heterocycloalkyl). In embodiments, $R^{54}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{54}$ is $R^{55}$-substituted or unsubstituted aryl (e.g., C$_6$-C$_{10}$ aryl, C$_{10}$ aryl, or phenyl). In embodiments, $R^{54}$ is $R^{55}$-substituted aryl (e.g., C$_6$-C$_{10}$ aryl, C$_{10}$ aryl, or phenyl). In embodiments, $R^{54}$ is an unsubstituted aryl (e.g., C$_6$-C$_{10}$ aryl, C$_{10}$ aryl, or phenyl).

In embodiments, $R^{54}$ is $R^{55}$-substituted or unsubstituted heteroaryl (e.g., 5 to 10 membered heteroaryl, 5 to 9 membered heteroaryl, or 5 to 6 membered heteroaryl). In embodiments, $R^{54}$ is $R^{55}$-substituted heteroaryl (e.g., 5 to 10 membered heteroaryl, 5 to 9 membered heteroaryl, or 5 to 6 membered heteroaryl). In embodiments, $R^{54}$ is an unsubstituted heteroaryl (e.g., 5 to 10 membered heteroaryl, 5 to 9 membered heteroaryl, or 5 to 6 membered heteroaryl).

$R^{56}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, $R^{57}$-substituted or unsubstituted alkyl (e.g., C$_1$-C$_8$ alkyl, C$_1$-C$_6$ alkyl, or C$_1$-C$_4$ alkyl), $R^{57}$-substituted or unsubstituted heteroalkyl (e.g., 2 to 8 membered heteroalkyl, 2 to 6 membered heteroalkyl, or 2 to 4 membered heteroalkyl), $R^{57}$-substituted or unsubstituted cycloalkyl (e.g., C$_3$-C$_8$ cycloalkyl, C$_3$-C$_6$ cycloalkyl, or C$_5$-C$_6$ cycloalkyl), $R^{57}$-substituted or unsubstituted heterocycloalkyl (e.g., 3 to 8 membered heterocycloalkyl, 3 to 6 membered heterocycloalkyl, or 5 to 6 membered heterocycloalkyl), $R^{57}$-substituted or unsubstituted aryl (e.g., C$_6$-C$_{10}$ aryl, C$_{10}$ aryl, or phenyl), or $R^{57}$-substituted or unsubstituted heteroaryl (e.g., 5 to 10 membered heteroaryl, 5 to 9 membered heteroaryl, or 5 to 6 membered heteroaryl).

In embodiments, $R^{56}$ is $R^{57}$-substituted or unsubstituted alkyl (e.g., C$_1$-C$_8$ alkyl, C$_1$-C$_6$ alkyl, or C$_1$-C$_4$ alkyl). In embodiments, $R^{56}$ is $R^{57}$-substituted alkyl (e.g., C$_1$-C$_8$ alkyl, C$_1$-C$_6$ alkyl, or C$_1$-C$_4$ alkyl). In embodiments, $R^{56}$ is an unsubstituted alkyl (e.g., C$_1$-C$_8$ alkyl, C$_1$-C$_6$ alkyl, or C$_1$-C$_4$ alkyl).

In embodiments, $R^{56}$ is $R^{57}$-substituted or unsubstituted heteroalkyl (e.g., 2 to 8 membered heteroalkyl, 2 to 6 membered heteroalkyl, or 2 to 4 membered heteroalkyl). In embodiments, $R^{56}$ is $R^{57}$-substituted heteroalkyl (e.g., 2 to 8 membered heteroalkyl, 2 to 6 membered heteroalkyl, or 2 to 4 membered heteroalkyl). In embodiments, $R^{56}$ is an unsubstituted heteroalkyl (e.g., 2 to 8 membered heteroalkyl, 2 to 6 membered heteroalkyl, or 2 to 4 membered heteroalkyl).

In embodiments, $R^{56}$ is $R^{57}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, $R^{56}$ is $R^{57}$-substituted cycloalkyl (e.g., C$_3$-C$_8$ cycloalkyl, C$_3$-C$_6$ cycloalkyl, or C$_5$-C$_6$ cycloalkyl). In embodiments, $R^{56}$ is an unsubstituted cycloalkyl (e.g., C$_3$-C$_8$ cycloalkyl, C$_3$-C$_6$ cycloalkyl, or C$_5$-C$_6$ cycloalkyl).

In embodiments, $R^{56}$ is $R^{57}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{56}$ is $R^{57}$-substituted heterocycloalkyl (e.g., 3 to 8 membered heterocycloalkyl, 3 to 6 membered heterocycloalkyl, or 5 to 6 membered heterocycloalkyl). In embodiments, $R^{56}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{56}$ is $R^{57}$-substituted or unsubstituted aryl (e.g., C$_6$-C$_{10}$ aryl, C$_{10}$ aryl, or phenyl). In embodiments, $R^{56}$ is $R^{57}$-substituted aryl (e.g., C$_6$-C$_{10}$ aryl, C$_{10}$ aryl, or phenyl). In embodiments, $R^{56}$ is an unsubstituted aryl (e.g., C$_6$-C$_{10}$ aryl, C$_{10}$ aryl, or phenyl).

In embodiments, $R^{56}$ is $R^{57}$-substituted or unsubstituted heteroaryl (e.g., 5 to 10 membered heteroaryl, 5 to 9 membered heteroaryl, or 5 to 6 membered heteroaryl). In embodiments, $R^{56}$ is $R^{57}$-substituted heteroaryl (e.g., 5 to 10 membered heteroaryl, 5 to 9 membered heteroaryl, or 5 to 6 membered heteroaryl). In embodiments, $R^{56}$ is an unsubstituted heteroaryl (e.g., 5 to 10 membered heteroaryl, 5 to 9 membered heteroaryl, or 5 to 6 membered heteroaryl).

$R^{57}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, R$^{58}$-substituted or unsubstituted alkyl (e.g., C$_1$-C$_8$ alkyl, C$_1$-C$_6$ alkyl, or C$_1$-C$_4$ alkyl), R$^{58}$-substituted or unsubstituted heteroalkyl (e.g., 2 to 8 membered heteroalkyl, 2 to 6 membered heteroalkyl, or 2 to 4 membered heteroalkyl), R$^{58}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{58}$-substituted or unsubstituted heterocycloalkyl (e.g., 3 to 8 membered heterocycloalkyl, 3 to 6 membered heterocycloalkyl, or 5 to 6 membered heterocycloalkyl), R$^{58}$-substituted or unsubstituted aryl (e.g., C$_6$-C$_{10}$ aryl, C$_{10}$ aryl, or phenyl), or R$^{58}$-substituted or unsubstituted heteroaryl (e.g., 5 to 10 membered heteroaryl, 5 to 9 membered heteroaryl, or 5 to 6 membered heteroaryl).

In embodiments, R$^{57}$ is R$^{58}$-substituted or unsubstituted alkyl (e.g., C$_1$-C$_8$ alkyl, C$_1$-C$_6$ alkyl, or C$_1$-C$_4$ alkyl). In embodiments, R$^{57}$ is R$^{58}$-substituted alkyl (e.g., C$_1$-C$_8$ alkyl, C$_1$-C$_6$ alkyl, or C$_1$-C$_4$ alkyl). In embodiments, R$^{57}$ is an unsubstituted alkyl (e.g., C$_1$-C$_8$ alkyl, C$_1$-C$_6$ alkyl, or C$_1$-C$_4$ alkyl).

In embodiments, R$^{57}$ is R$^{58}$-substituted or unsubstituted heteroalkyl (e.g., 2 to 8 membered heteroalkyl, 2 to 6 membered heteroalkyl, or 2 to 4 membered heteroalkyl). In embodiments, R$^{57}$ is R$^{58}$-substituted heteroalkyl (e.g., 2 to 8 membered heteroalkyl, 2 to 6 membered heteroalkyl, or 2 to 4 membered heteroalkyl). In embodiments, R$^{57}$ is an unsubstituted heteroalkyl (e.g., 2 to 8 membered heteroalkyl, 2 to 6 membered heteroalkyl, or 2 to 4 membered heteroalkyl).

In embodiments, R$^{57}$ is R$^{58}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, R$^{57}$ is R$^{58}$-substituted cycloalkyl (e.g., C$_3$-C$_8$ cycloalkyl, C$_3$-C$_6$ cycloalkyl, or C$_5$-C$_6$ cycloalkyl). In embodiments, R$^{57}$ is an unsubstituted cycloalkyl (e.g., C$_3$-C$_8$ cycloalkyl, C$_3$-C$_6$ cycloalkyl, or C$_5$-C$_6$ cycloalkyl).

In embodiments, R$^{57}$ is R$^{58}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, R$^{57}$ is R$^{58}$-substituted heterocycloalkyl (e.g., 3 to 8 membered heterocycloalkyl, 3 to 6 membered heterocycloalkyl, or 5 to 6 membered heterocycloalkyl). In embodiments, R$^{57}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, R$^{57}$ is R$^{58}$-substituted or unsubstituted aryl (e.g., C$_6$-C$_{10}$ aryl, C$_{10}$ aryl, or phenyl). In embodiments, R$^{57}$ is R$^{58}$-substituted aryl (e.g., C$_6$-C$_{10}$ aryl, C$_{10}$ aryl, or phenyl). In embodiments, R$^{57}$ is an unsubstituted aryl (e.g., C$_6$-C$_{10}$ aryl, C$_{10}$ aryl, or phenyl).

In embodiments, R$^{57}$ is R$^{58}$-substituted or unsubstituted heteroaryl (e.g., 5 to 10 membered heteroaryl, 5 to 9 membered heteroaryl, or 5 to 6 membered heteroaryl). In embodiments, R$^{57}$ is R$^{58}$-substituted heteroaryl (e.g., 5 to 10 membered heteroaryl, 5 to 9 membered heteroaryl, or 5 to 6 membered heteroaryl). In embodiments, R$^{57}$ is an unsubstituted heteroaryl (e.g., 5 to 10 membered heteroaryl, 5 to 9 membered heteroaryl, or 5 to 6 membered heteroaryl).

R$^{38L}$, R$^{40A}$, R$^{40B}$, R$^{40C}$, R$^{40D}$, R$^{41}$, R$^{44}$, R$^{46}$, R$^{47A}$, R$^{47B}$, R$^{47C}$, R$^{47D}$, R$^{49}$, R$^{50A}$, R$^{50B}$, R$^{50C}$, R$^{50D}$, R$^{52}$, R$^{53A}$, R$^{53B}$, R$^{53C}$, R$^{53D}$, R$^{55}$, R$^{56A}$, R$^{56B}$, R$^{56C}$, R$^{56D}$ and R$^{58}$ are independently hydrogen, oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, W is =O. In embodiments, z1 is 1. In embodiments, z1 is 2. In embodiments, R$^{19}$ is hydrogen. In embodiments, R$^{20}$ is hydrogen. In embodiments, R$^{21}$ is hydrogen. In embodiments, R$^{22}$ is hydrogen. In embodiments, R$^{23}$ is hydrogen. In embodiments, R$^{24}$ is hydrogen. In embodiments, the compound of formula (V) has a structure of

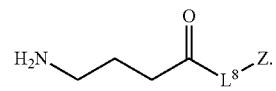

In embodiments, L$^8$ is a bond. In embodiments, Z is —O$^-$. In embodiments, L$^8$ is —CH$_2$—. In embodiments, Z is —C(O)O$^-$.

In embodiments, the compound of formula (V) is

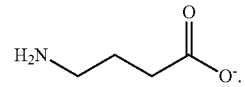

In embodiments, the salt composition of formula (II) is

DY316

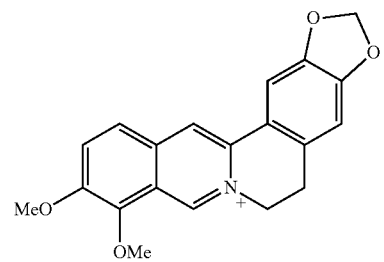

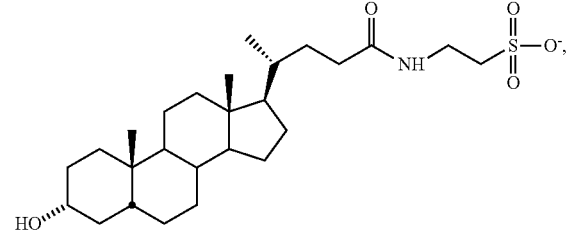

DY317

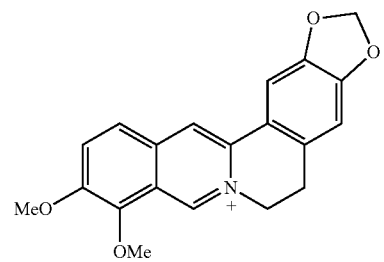

-continued

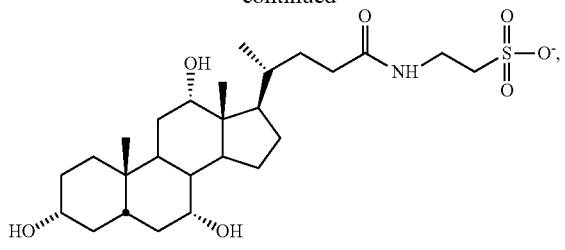
DY315

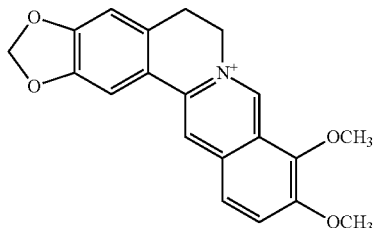

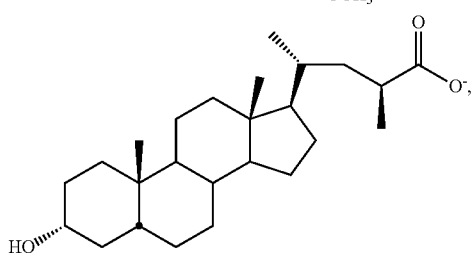
DY321

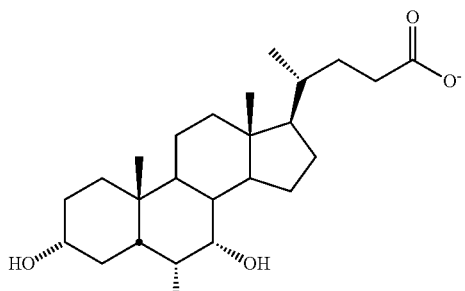

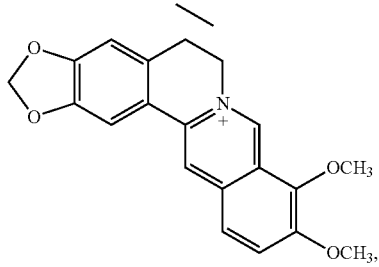
DY433

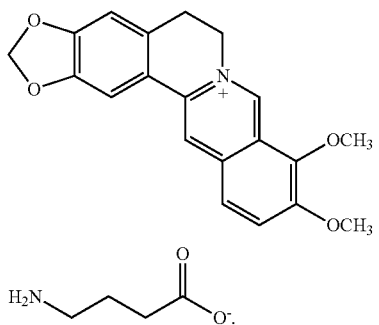

In another aspect, there is provided a compound having the formula:

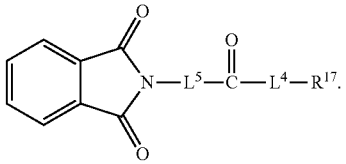

(VI)

$L^4$ is a bond, $-NR^{4L}-$, $-NR^{4L}C(O)-$, $-NR^{4L}C(O)-S(O)_2-O-$, $-NR^{4L}C(O)-S(O)_2-O-CH_2-$, $-NR^{4L}-S(O)_2-O-CH_2-$, $-S(O)_2-$, $-O-$ $-NR^{4L}C(O)NH-$, $-NHC(O)NR^{4L}-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $L^5$ is substituted or unsubstituted alkylene. $R^{17}$ is $-OH$, substituted or unsubstituted cycloalkyl, substituted or unsubstituted heterocycloalkyl, substituted or unsubstituted aryl or substituted or unsubstituted heteroaryl. $R^{4L}$ is hydrogen, $-CX^{4L}_3$, $-CN$, $-COOH$, $-CONH_2$, $-CHX^{4L}_2$, $-CH_2X^{4L}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $X^{4L}$ is halogen.

In embodiments, $X^{4L}$ is F. In embodiments, $X^{4L}$ is Cl. In embodiments, $X^{4L}$ is Br. In embodiments, $X^{4L}$ is I.

In embodiments, $L^4$ is a bond, $-NR^{4L}-$, $-NR^{4L}C(O)-$, $-NR^{4L}C(O)-S(O)_2-O-$, $-NR^{4L}C(O)-S(O)_2-O-CH_2-$, $-NR^{4L}-S(O)_2-O-CH_2-$, $-S(O)_2-$, $-O-$ $-NR^{4L}C(O)NH-$, $-NHC(O)NR^{4L}-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^4$ is $R^{59}$-substituted or unsubstituted alkylene (e.g., $C_1$-$C_8$ alkylene, $C_1$-$C_6$ alkylene, or $C_1$-$C_4$ alkylene). In embodiments, $L^4$ is $R^{59}$-substituted alkylene (e.g., $C_1$-$C_8$ alkylene, $C_1$-$C_6$ alkylene, or $C_1$-$C_4$ alkylene). In embodiments, $L^4$ is an unsubstituted alkylene (e.g., $C_1$-$C_8$ alkylene, $C_1$-$C_6$ alkylene, or $C_1$-$C_4$ alkylene).

In embodiments, $L^4$ is $R^{59}$-substituted or unsubstituted heteroalkylene (e.g., 2 to 8 membered heteroalkylene, 2 to 6 membered heteroalkylene, or 2 to 4 membered heteroalkylene). In embodiments, $L^4$ is $R^{59}$-substituted heteroalkylene (e.g., 2 to 8 membered heteroalkylene, 2 to 6 membered heteroalkylene, or 2 to 4 membered heteroalkylene). In embodiments, $L^4$ is an unsubstituted heteroalkylene (e.g., 2 to 8 membered heteroalkylene, 2 to 6 membered heteroalkylene, or 2 to 4 membered heteroalkylene).

In embodiments, $L^4$ is $R^{59}$-substituted or unsubstituted cycloalkylene (e.g., $C_3$-$C_8$ cycloalkylene, $C_3$-$C_6$ cycloalkylene, or $C_5$-$C_6$ cycloalkylene). In embodiments, $L^4$ is $R^{59}$-substituted cycloalkylene (e.g., $C_3$-$C_8$ cycloalkylene, $C_3$-$C_6$ cycloalkylene, or $C_5$-$C_6$ cycloalkylene). In embodiments, $L^4$ is an unsubstituted cycloalkylene (e.g., $C_3$-$C_8$ cycloalkylene, $C_3$-$C_6$ cycloalkylene, or $C_5$-$C_6$ cycloalkylene).

In embodiments, $L^4$ is $R^{59}$-substituted or unsubstituted heterocycloalkylene (e.g., 3 to 8 membered heterocycloalkylene, 3 to 6 membered heterocycloalkylene, or 5 to 6 membered heterocycloalkylene). In embodiments, $L^4$ is $R^{59}$-substituted heterocycloalkylene (e.g., 3 to 8 membered heterocycloalkylene, 3 to 6 membered heterocycloalkylene, or 5 to 6 membered heterocycloalkylene). In embodiments, $L^4$ is an unsubstituted heterocycloalkylene (e.g., 3 to 8 membered heterocycloalkylene, 3 to 6 membered heterocyloalkylene, or 5 to 6 membered heterocycloalkylene).

In embodiments, $L^4$ is $R^{59}$-substituted or unsubstituted arylene (e.g., $C_6$-$C_{10}$ arylene, $C_{10}$ arylene, or phenyl). In embodiments, $L^4$ is $R^{59}$-substituted arylene (e.g., $C_6$-$C_{10}$ arylene, $C_{10}$ arylene, or phenyl). In embodiments, $L^4$ is an unsubstituted arylene (e.g., $C_6$-$C_{10}$ arylene, $C_{10}$ arylene, or phenyl).

In embodiments, $L^4$ is $R^{59}$-substituted or unsubstituted heteroarylene (e.g., 5 to 10 membered heteroarylene, 5 to 9 membered heteroarylene, or 5 to 6 membered heteroarylene). In embodiments, $L^4$ is $R^{59}$-substituted heteroarylene (e.g., 5 to 10 membered heteroarylene, 5 to 9 membered heteroarylene, or 5 to 6 membered heteroarylene). In embodiments, $L^4$ is an unsubstituted heteroarylene (e.g., 5 to 10 membered heteroarylene, 5 to 9 membered heteroarylene, or 5 to 6 membered heteroarylene).

In embodiments, $L^5$ is $R^{61}$-substituted or unsubstituted alkylene (e.g., $C_1$-$C_{12}$ alkylene, $C1$-$C_6$ alkylene, or $C_1$-$C_4$ alkylene). In embodiments, $L^5$ is $R^{61}$-substituted alkylene (e.g., $C_1$-$C_{12}$ alkylene, $C_1$-$C_6$ alkylene, or $C_1$-$C_4$ alkylene). In embodiments, $L^5$ is an unsubstituted alkylene (e.g., $C_1$-$C_{12}$ alkylene, $C_1$-$C_6$ alkylene, or $C_1$-$C_4$ alkylene).

In embodiments, $R^{17}$ is —OH, substituted or unsubstituted cycloalkyl, substituted or unsubstituted heterocycloalkyl, substituted or unsubstituted aryl or substituted or unsubstituted heteroaryl.

In embodiments, $R^{17}$ is $R^{63}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{17}$ is $R^{63}$-substituted cycloalkyl (e.g., $C_3$-$C_8$ cycloalkyl, $C_3$-$C_6$ cycloalkyl, or $C_5$-$C_6$ cycloalkyl). In embodiments, $R^{17}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{17}$ is $R^{63}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{17}$ is $R^{63}$-substituted heterocycloalkyl (e.g., 3 to 8 membered heterocycloalkyl, 3 to 6 membered heterocycloalkyl, or 5 to 6 membered heterocycloalkyl). In embodiments, $R^{17}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{17}$ is $R^{63}$-substituted or unsubstituted aryl (e.g., $C_6$-$C_{10}$ aryl, $C_{10}$ aryl, or phenyl). In embodiments, $R^{17}$ is $R^{63}$-substituted aryl (e.g., $C_6$-$C_{10}$ aryl, $C_{10}$ aryl, or phenyl). In embodiments, $R^{17}$ is an unsubstituted aryl (e.g., $C_6$-$C_{10}$ aryl, $C_{10}$ aryl, or phenyl).

In embodiments, $R^{17}$ is $R^{63}$-substituted or unsubstituted heteroaryl (e.g., 5 to 10 membered heteroaryl, 5 to 9 membered heteroaryl, or 5 to 6 membered heteroaryl). In embodiments, $R^{17}$ is $R^{63}$-substituted heteroaryl (e.g., 5 to 10 membered heteroaryl, 5 to 9 membered heteroaryl, or 5 to 6 membered heteroaryl). In embodiments, $R^{17}$ is an unsubstituted heteroaryl (e.g., 5 to 10 membered heteroaryl, 5 to 9 membered heteroaryl, or 5 to 6 membered heteroaryl).

In embodiments, $R^{4L}$ is hydrogen, —$CX^{4L}{}_3$, —CN, —COOH, —$CONH_2$, —$CHX^{4L}{}_2$, —$CH_2X^{4L}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{4L}$ is $R^{59L}$-substituted or unsubstituted alkyl (e.g., $C_1$-$C_8$ alkyl, $C_1$-$C_6$ alkyl, or $C_1$-$C_4$ alkyl). In embodiments, $R^{4L}$ is $R^{59L}$-substituted alkyl (e.g., $C_1$-$C_8$ alkyl, $C_1$-$C_6$ alkyl, or $C_1$-$C_4$ alkyl). In embodiments, $R^{4L}$ is an unsubstituted alkyl (e.g., $C_1$-$C_8$ alkyl, $C_1$-$C_6$ alkyl, or $C_1$-$C_4$ alkyl).

In embodiments, $R^{4L}$ is $R^{59L}$-substituted or unsubstituted heteroalkyl (e.g., 2 to 8 membered heteroalkyl, 2 to 6 membered heteroalkyl, or 2 to 4 membered heteroalkyl). In embodiments, $R^{4L}$ is $R^{59L}$-substituted heteroalkyl (e.g., 2 to 8 membered heteroalkyl, 2 to 6 membered heteroalkyl, or 2 to 4 membered heteroalkyl). In embodiments, $R^{4L}$ is an unsubstituted heteroalkyl (e.g., 2 to 8 membered heteroalkyl, 2 to 6 membered heteroalkyl, or 2 to 4 membered heteroalkyl).

In embodiments, $R^{4L}$ is $R^{59L}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{4L}$ is $R^{59L}$-substituted cycloalkyl (e.g., $C_3$-$C_8$ cycloalkyl, $C_3$-$C_6$ cycloalkyl, or $C_5$-$C_6$ cycloalkyl). In embodiments, $R^{4L}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{4L}$ is $R^{59L}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{4L}$ is $R^{59L}$-substituted heterocycloalkyl (e.g., 3 to 8 membered heterocycloalkyl, 3 to 6 membered heterocycloalkyl, or 5 to 6 membered heterocycloalkyl). In embodiments, $R^{4L}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{4L}$ is $R^{59L}$-substituted or unsubstituted aryl (e.g., $C_6$-$C_{10}$ aryl, $C_{10}$ aryl, or phenyl). In embodiments, $R^{4L}$ is $R^{59L}$-substituted aryl (e.g., $C_6$-$C_{10}$ aryl, $C_{10}$ aryl, or phenyl). In embodiments, $R^{4L}$ is an unsubstituted aryl (e.g., $C_6$-$C_{10}$ aryl, $C_{10}$ aryl, or phenyl).

In embodiments, $R^{4L}$ is $R^{59L}$-substituted or unsubstituted heteroaryl (e.g., 5 to 10 membered heteroaryl, 5 to 9 membered heteroaryl, or 5 to 6 membered heteroaryl). In embodiments, $R^{4L}$ is $R^{59L}$-substituted heteroaryl (e.g., 5 to 10 membered heteroaryl, 5 to 9 membered heteroaryl, or 5 to 6 membered heteroaryl). In embodiments, $R^{4L}$ is an unsubstituted heteroaryl (e.g., 5 to 10 membered heteroaryl, 5 to 9 membered heteroaryl, or 5 to 6 membered heteroaryl).

$R^{59L}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{60L}$-substituted or unsubstituted alkyl (e.g., $C_1$-$C_8$ alkyl, $C_1$-$C_6$ alkyl, or $C_1$-$C_4$ alkyl), $R^{60L}$-substituted or unsubstituted heteroalkyl (e.g., 2 to 8 membered heteroalkyl, 2 to 6 membered heteroalkyl, or 2 to 4 membered heteroalkyl), $R^{60L}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{60L}$-substituted or unsubstituted heterocycloalkyl (e.g., 3 to 8 membered heterocycloalkyl, 3 to 6 membered heterocycloalkyl, or 5 to 6 membered heterocycloalkyl), $R^{60L}$-substituted or unsubstituted aryl (e.g., $C_6$-$C_{10}$ aryl, $C_{10}$ aryl, or phenyl), or $R^{60L}$-substituted or unsubstituted heteroaryl (e.g., 5 to 10 membered heteroaryl, 5 to 9 membered heteroaryl, or 5 to 6 membered heteroaryl).

In embodiments, $R^{59L}$ is $R^{60L}$-substituted or unsubstituted alkyl (e.g., $C_1$-$C_8$ alkyl, $C_1$-$C_6$ alkyl, or $C_1$-$C_4$ alkyl). In embodiments, $R^{59L}$ is $R^{60L}$-substituted alkyl (e.g., $C_1$-$C_8$ alkyl, $C_1$-$C_6$ alkyl, or $C_1$-$C_4$ alkyl). In embodiments, $R^{59L}$ is an unsubstituted alkyl (e.g., $C_1$-$C_8$ alkyl, $C_1$-$C_6$ alkyl, or $C_1$-$C_4$ alkyl).

In embodiments, $R^{59L}$ is $R^{60L}$-substituted or unsubstituted heteroalkyl (e.g., 2 to 8 membered heteroalkyl, 2 to 6 membered heteroalkyl, or 2 to 4 membered heteroalkyl). In embodiments, $R^{59L}$ is $R^{60L}$-substituted heteroalkyl (e.g., 2 to 8 membered heteroalkyl, 2 to 6 membered heteroalkyl, or 2 to 4 membered heteroalkyl). In embodiments, $R^{59L}$ is an unsubstituted heteroalkyl (e.g., 2 to 8 membered heteroalkyl, 2 to 6 membered heteroalkyl, or 2 to 4 membered heteroalkyl).

In embodiments, $R^{59L}$ is $R^{60L}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{59L}$ is $R^{60L}$-substituted cycloalkyl (e.g., $C_3$-$C_8$ cycloalkyl, $C_3$-$C_6$ cycloalkyl, or $C_5$-$C_6$ cycloalkyl). In embodiments, $R^{59L}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{59L}$ is $R^{60L}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{59L}$ is $R^{60L}$-substituted heterocycloalkyl (e.g., 3 to 8 membered heterocycloalkyl, 3 to 6 membered heterocycloalkyl, or 5 to 6 membered heterocycloalkyl). In embodiments, $R^{59L}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{59L}$ is $R^{60L}$-substituted or unsubstituted aryl (e.g., $C_6$-$C_{10}$ aryl, $C_{10}$ aryl, or phenyl). In embodiments, $R^{59L}$ is $R^{6L}$-substituted aryl (e.g., $C_6$-$C_{10}$ aryl, $C_{10}$ aryl, or phenyl). In embodiments, $R^{59L}$ is an unsubstituted aryl (e.g., $C_6$-$C_{10}$ aryl, $C_{10}$ aryl, or phenyl).

In embodiments, $R^{59L}$ is $R^{60L}$-substituted or unsubstituted heteroaryl (e.g., 5 to 10 membered heteroaryl, 5 to 9 membered heteroaryl, or 5 to 6 membered heteroaryl). In embodiments, $R^{59L}$ is $R^{6L}$-substituted heteroaryl (e.g., 5 to 10 membered heteroaryl, 5 to 9 membered heteroaryl, or 5 to 6 membered heteroaryl). In embodiments, $R^{59L}$ is an unsubstituted heteroaryl (e.g., 5 to 10 membered heteroaryl, 5 to 9 membered heteroaryl, or 5 to 6 membered heteroaryl).

$R^{59}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{60}$-substituted or unsubstituted alkyl (e.g., $C_1$-$C_8$ alkyl, $C_1$-$C_6$ alkyl, or $C_1$-$C_4$ alkyl), $R^{60}$-substituted or unsubstituted heteroalkyl (e.g., 2 to 8 membered heteroalkyl, 2 to 6 membered heteroalkyl, or 2 to 4 membered heteroalkyl), $R^{60}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{60}$-substituted or unsubstituted heterocycloalkyl (e.g., 3 to 8 membered heterocycloalkyl, 3 to 6 membered heterocycloalkyl, or 5 to 6 membered heterocycloalkyl), $R^{60}$-substituted or unsubstituted aryl (e.g., $C_6$-$C_{10}$ aryl, $C_{10}$ aryl, or phenyl), or $R^{60}$-substituted or unsubstituted heteroaryl (e.g., 5 to 10 membered heteroaryl, 5 to 9 membered heteroaryl, or 5 to 6 membered heteroaryl).

In embodiments, $R^{59}$ is $R^{60}$-substituted or unsubstituted alkyl (e.g., $C_1$-$C_8$ alkyl, $C_1$-$C_6$ alkyl, or $C_1$-$C_4$ alkyl). In embodiments, $R^{59}$ is $R^{60}$-substituted alkyl (e.g., $C_1$-$C_8$ alkyl, $C_1$-$C_6$ alkyl, or $C_1$-$C_4$ alkyl). In embodiments, $R^{59}$ is an unsubstituted alkyl (e.g., $C_1$-$C_8$ alkyl, $C_1$-$C_6$ alkyl, or $C_1$-$C_4$ alkyl).

In embodiments, $R^{59}$ is $R^{60}$-substituted or unsubstituted heteroalkyl (e.g., 2 to 8 membered heteroalkyl, 2 to 6 membered heteroalkyl, or 2 to 4 membered heteroalkyl). In embodiments, $R^{59}$ is $R^{60}$-substituted heteroalkyl (e.g., 2 to 8 membered heteroalkyl, 2 to 6 membered heteroalkyl, or 2 to 4 membered heteroalkyl). In embodiments, $R^{59}$ is an unsubstituted heteroalkyl (e.g., 2 to 8 membered heteroalkyl, 2 to 6 membered heteroalkyl, or 2 to 4 membered heteroalkyl).

In embodiments, $R^{59}$ is $R^{60}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{59}$ is $R^{60}$-substituted cycloalkyl (e.g., $C_3$-$C_8$ cycloalkyl, $C_3$-$C_6$ cycloalkyl, or $C_5$-$C_6$ cycloalkyl). In embodiments, $R^{59}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{59}$ is $R^{60}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{59}$ is $R^{60}$-substituted heterocycloalkyl (e.g., 3 to 8 membered heterocycloalkyl, 3 to 6 membered heterocycloalkyl, or 5 to 6 membered heterocycloalkyl). In embodiments, $R^{59}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{59}$ is $R^{60}$-substituted or unsubstituted aryl (e.g., $C_6$-$C_{10}$ aryl, $C_{10}$ aryl, or phenyl). In embodiments, $R^{59}$ is $R^{60}$-substituted aryl (e.g., $C_6$-$C_{10}$ aryl, $C_{10}$ aryl, or phenyl). In embodiments, $R^{59}$ is an unsubstituted aryl (e.g., $C_6$-$C_{10}$ aryl, $C_{10}$ aryl, or phenyl).

In embodiments, $R^{59}$ is $R^{60}$-substituted or unsubstituted heteroaryl (e.g., 5 to 10 membered heteroaryl, 5 to 9 membered heteroaryl, or 5 to 6 membered heteroaryl). In embodiments, $R^{59}$ is $R^{60}$-substituted heteroaryl (e.g., 5 to 10 membered heteroaryl, 5 to 9 membered heteroaryl, or 5 to 6 membered heteroaryl). In embodiments, $R^{59}$ is an unsubstituted heteroaryl (e.g., 5 to 10 membered heteroaryl, 5 to 9 membered heteroaryl, or 5 to 6 membered heteroaryl).

$R^{63}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{64}$-substituted or unsubstituted alkyl (e.g., $C_1$-$C_8$ alkyl, $C_1$-$C_6$ alkyl, or $C_1$-$C_4$ alkyl), $R^{64}$-substituted or unsubstituted heteroalkyl (e.g., 2 to 8 membered heteroalkyl, 2 to 6 membered heteroalkyl, or 2 to 4 membered heteroalkyl), $R^{64}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{64}$-substituted or unsubstituted heterocycloalkyl (e.g., 3 to 8 membered heterocycloalkyl, 3 to 6 membered heterocycloalkyl, or 5 to 6 membered heterocycloalkyl), $R^{64}$-substituted or unsubstituted aryl (e.g., $C_6$-$C_{10}$ aryl, $C_{10}$ aryl, or phenyl), or $R^{64}$-substituted or unsubstituted heteroaryl (e.g., 5 to 10 membered heteroaryl, 5 to 9 membered heteroaryl, or 5 to 6 membered heteroaryl).

In embodiments, $R^{63}$ is $R^{64}$-substituted or unsubstituted alkyl (e.g., $C_1$-$C_8$ alkyl, $C_1$-$C_6$ alkyl, or $C_1$-$C_4$ alkyl). In embodiments, $R^{63}$ is $R^{64}$-substituted alkyl (e.g., $C_1$-$C_8$ alkyl, $C_1$-$C_6$ alkyl, or $C_1$-$C_4$ alkyl). In embodiments, $R^{63}$ is an unsubstituted alkyl (e.g., $C_1$-$C_8$ alkyl, $C_1$-$C_6$ alkyl, or $C_1$-$C_4$ alkyl).

In embodiments, $R^{63}$ is $R^{64}$-substituted or unsubstituted heteroalkyl (e.g., 2 to 8 membered heteroalkyl, 2 to 6 membered heteroalkyl, or 2 to 4 membered heteroalkyl). In embodiments, $R^{63}$ is $R^{64}$-substituted heteroalkyl (e.g., 2 to 8 membered heteroalkyl, 2 to 6 membered heteroalkyl, or 2 to 4 membered heteroalkyl). In embodiments, $R^{63}$ is an unsubstituted heteroalkyl (e.g., 2 to 8 membered heteroalkyl, 2 to 6 membered heteroalkyl, or 2 to 4 membered heteroalkyl).

In embodiments, $R^{63}$ is $R^{64}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{63}$ is $R^{64}$-substituted cycloalkyl (e.g., $C_3$-$C_8$ cycloalkyl, $C_3$-$C_6$ cycloalkyl, or $C_5$-$C_6$ cycloalkyl). In embodiments, $R^{63}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{63}$ is $R^{64}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{63}$ is $R^{64}$-substituted heterocycloalkyl (e.g., 3 to 8 membered heterocycloalkyl, 3 to 6 membered heterocycloalkyl, or 5 to 6 membered heterocycloalkyl). In embodiments, $R^{63}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{63}$ is $R^{64}$-substituted or unsubstituted aryl (e.g., $C_6$-$C_{10}$ aryl, $C_{10}$ aryl, or phenyl). In embodiments, $R^{63}$ is $R^{64}$-substituted aryl (e.g., $C_6$-$C_{10}$ aryl, $C_{10}$ aryl, or phenyl). In embodiments, $R^{63}$ is an unsubstituted aryl (e.g., $C_6$-$C_{10}$ aryl, $C_{10}$ aryl, or phenyl).

In embodiments, $R^{63}$ is $R^{64}$-substituted or unsubstituted heteroaryl (e.g., 5 to 10 membered heteroaryl, 5 to 9 membered heteroaryl, or 5 to 6 membered heteroaryl). In embodiments, $R^{63}$ is $R^{64}$-substituted heteroaryl (e.g., 5 to 10 membered heteroaryl, 5 to 9 membered heteroaryl, or 5 to 6 membered heteroaryl). In embodiments, $R^{63}$ is an unsubstituted heteroaryl (e.g., 5 to 10 membered heteroaryl, 5 to 9 membered heteroaryl, or 5 to 6 membered heteroaryl).

$R^{64}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{65}$-substituted or unsubstituted alkyl (e.g., $C_1$-$C_8$ alkyl, $C_1$-$C_6$ alkyl, or $C_1$-$C_4$ alkyl), $R^{65}$-substituted or unsubstituted heteroalkyl (e.g., 2 to 8 membered heteroalkyl, 2 to 6 membered heteroalkyl, or 2 to 4 membered heteroalkyl), $R^{65}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{65}$-substituted or unsubstituted heterocycloalkyl (e.g., 3 to 8 membered heterocycloalkyl, 3 to 6 membered heterocycloalkyl, or 5 to 6 membered heterocycloalkyl), $R^{65}$-substituted or unsubstituted aryl (e.g., $C_6$-$C_{10}$ aryl, $C_{10}$ aryl, or phenyl), or $R^{65}$-substituted or unsubstituted heteroaryl (e.g., 5 to 10 membered heteroaryl, 5 to 9 membered heteroaryl, or 5 to 6 membered heteroaryl).

In embodiments, $R^{64}$ is $R^{65}$-substituted or unsubstituted alkyl (e.g., $C_1$-$C_8$ alkyl, $C_1$-$C_6$ alkyl, or $C_1$-$C_4$ alkyl). In embodiments, $R^{64}$ is $R^{65}$-substituted alkyl (e.g., $C_1$-$C_8$ alkyl, $C_1$-$C_6$ alkyl, or $C_1$-$C_4$ alkyl). In embodiments, $R^6$ is an unsubstituted alkyl (e.g., $C_1$-$C_8$ alkyl, $C_1$-$C_6$ alkyl, or $C_1$-$C_4$ alkyl).

In embodiments, $R^{64}$ is $R^{65}$-substituted or unsubstituted heteroalkyl (e.g., 2 to 8 membered heteroalkyl, 2 to 6 membered heteroalkyl, or 2 to 4 membered heteroalkyl). In embodiments, $R^{64}$ is $R^{65}$-substituted heteroalkyl (e.g., 2 to 8 membered heteroalkyl, 2 to 6 membered heteroalkyl, or 2 to 4 membered heteroalkyl). In embodiments, $R^{64}$ is an unsubstituted heteroalkyl (e.g., 2 to 8 membered heteroalkyl, 2 to 6 membered heteroalkyl, or 2 to 4 membered heteroalkyl).

In embodiments, $R^{64}$ is $R^{65}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{64}$ is $R^{65}$-substituted cycloalkyl (e.g., $C_3$-$C_8$ cycloalkyl, $C_3$-$C_6$ cycloalkyl, or $C_5$-$C_6$ cycloalkyl). In embodiments, $R^6$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{64}$ is $R^{65}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{64}$ is $R^{65}$-substituted heterocycloalkyl (e.g., 3 to 8 membered heterocycloalkyl, 3 to 6 membered heterocycloalkyl, or 5 to 6 membered heterocycloalkyl). In embodiments, $R^6$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{64}$ is $R^{65}$-substituted or unsubstituted aryl (e.g., $C_6$-$C_{10}$ aryl, $C_{10}$ aryl, or phenyl). In embodiments, $R^{64}$ is $R^{65}$-substituted aryl (e.g., $C_6$-$C_{10}$ aryl, $C_{10}$ aryl, or phenyl). In embodiments, $R^{64}$ is an unsubstituted aryl (e.g., $C_6$-$C_{10}$ aryl, $C_{10}$ aryl, or phenyl).

In embodiments, $R^{64}$ is $R^{65}$-substituted or unsubstituted heteroaryl (e.g., 5 to 10 membered heteroaryl, 5 to 9 membered heteroaryl, or 5 to 6 membered heteroaryl). In embodiments, $R^{64}$ is $R^{65}$-substituted heteroaryl (e.g., 5 to 10 membered heteroaryl, 5 to 9 membered heteroaryl, or 5 to 6 membered heteroaryl). In embodiments, $R^{64}$ is an unsubstituted heteroaryl (e.g., 5 to 10 membered heteroaryl, 5 to 9 membered heteroaryl, or 5 to 6 membered heteroaryl).

$R^{60}$, $R^{60L}$, $R^{61}$, and $R^{65}$ are independently hydrogen, oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O) $NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

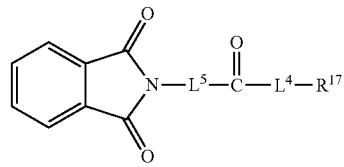

In embodiments, $L^5$ is unsubstituted $C_1$-$C_{12}$ alkylene. In embodiments, $L^5$ is unsubstituted $C_3$-$C_{12}$ alkylene. In embodiments, $L^5$ is unsubstituted propylene. In embodiments, $L^5$ is unsubstituted butylene.

In embodiments, $L^4$ is a bond. In embodiments, $L^4$ is —NH—$S(O)_2$—O—$CH_2$—. In embodiments, $L^4$ is —$S(O)_2$—. In embodiments, $L^4$ is —O—.

In embodiments, $R^{17}$ is —OH. In embodiments, $R^{17}$ is substituted heterocycloalkyl. In embodiments, $R^{17}$ is substituted 6 to 12 membered heterocycloalkyl.

In embodiments, $R^{17}$ is

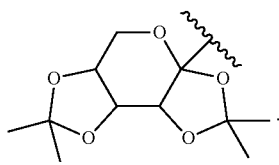

In embodiments, $R^{17}$ is

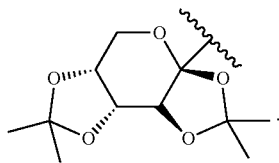

In embodiments, $R^{17}$ is

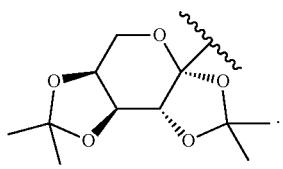

In embodiments, the compound of formula (VI) is

In another aspect, there is provided a compound of the formula:

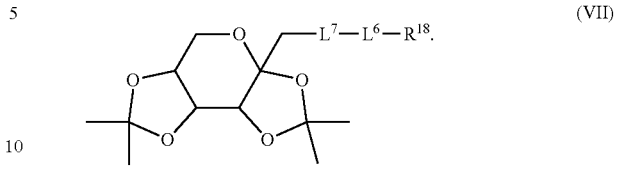
(VII)

$L^6$ is a substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $L^7$ is a bond, —C(O)—, —C(O)O—, —O—, —S—, —NR$^{7L}$—, —C(O)NR$^{7L}$—, —NR$^{7L}$C(O)—, —S(O)$_2$—, —O—S(O)$_2$NR$^{7L}$—, —O—S(O)$_2$NR$^{7L}$C(O)—, —NR$^{7L}$C(O)NH—, —NHC(O)NR$^{7L}$—. $R^{18}$ is —NH$_2$ or

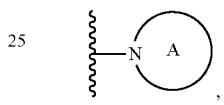

wherein ring A is a substituted or unsubstituted heteroaryl or substituted or unsubstituted heterocycloalkyl. $R^{7L}$ is hydrogen, —CX$^{7L}_3$, —CN, —COOH, —CONH$_2$, —CHX$^{7L}_2$, —CH$_2$X$^{7L}$, substituted or unsubstituted alkyl, substituted or

DY419

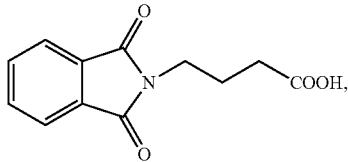

DY420

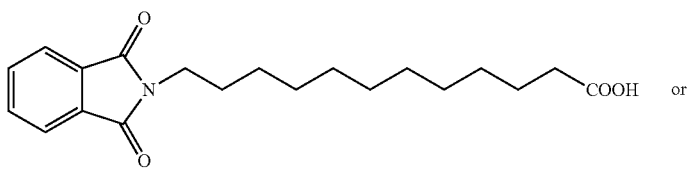
or

DY424

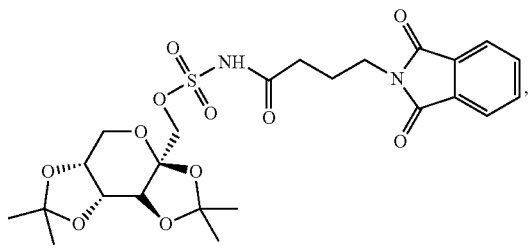

DY421

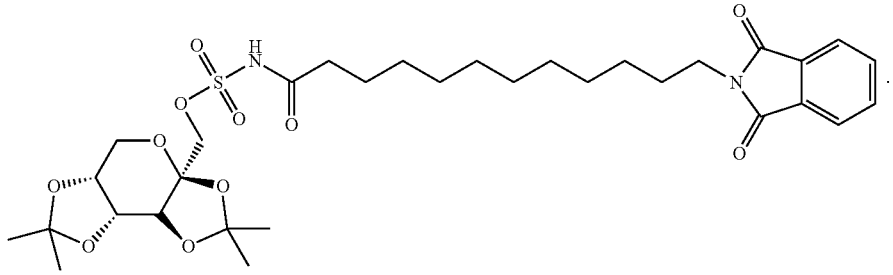

unsubstituted heteroalkyl, substituted or unsubstituted cycloalkyl, substituted or unsubstituted heterocycloalkyl, substituted or unsubstituted aryl, or substituted or unsubstituted heteroaryl, wherein $X^{7L}$ is halogen.

In embodiments, $X^{7L}$ is F. In embodiments, $X^{7L}$ is Cl. In embodiments, $X^{7L}$ is Br. In embodiments, $X^{7L}$ is I.

In embodiments, $L^6$ is a substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^6$ is $R^{66}$-substituted or unsubstituted alkylene (e.g., $C_1$-$C_{12}$ alkylene, $C_1$-$C_6$ alkylene, or $C_1$-$C_4$ alkylene). In embodiments, $L^6$ is $R^{66}$-substituted alkylene (e.g., $C_1$-$C_{12}$ alkylene, $C_1$-$C_6$ alkylene, or $C_1$-$C_4$ alkylene). In embodiments, $L^6$ is an unsubstituted alkylene (e.g., $C_1$-$C_{12}$ alkylene, $C_1$-$C_6$ alkylene, or $C_1$-$C_4$ alkylene).

In embodiments, $L^6$ is $R^{66}$-substituted or unsubstituted heteroalkylene (e.g., 2 to 8 membered heteroalkylene, 2 to 6 membered heteroalkylene, or 2 to 4 membered heteroalkylene). In embodiments, $L^6$ is $R^{66}$-substituted heteroalkylene (e.g., 2 to 8 membered heteroalkylene, 2 to 6 membered heteroalkylene, or 2 to 4 membered heteroalkylene). In embodiments, $L^6$ is an unsubstituted heteroalkylene (e.g., 2 to 8 membered heteroalkylene, 2 to 6 membered heteroalkylene, or 2 to 4 membered heteroalkylene).

In embodiments, $L^6$ is $R^{66}$-substituted or unsubstituted cycloalkylene (e.g., $C_3$-$C_8$ cycloalkylene, $C_3$-$C_6$ cycloalkylene, or $C_5$-$C_6$ cycloalkylene). In embodiments, $L^6$ is $R^{66}$-substituted cycloalkylene (e.g., $C_3$-$C_8$ cycloalkylene, $C_3$-$C_6$ cycloalkylene, or $C_5$-$C_6$ cycloalkylene). In embodiments, $L^6$ is an unsubstituted cycloalkylene (e.g., $C_3$-$C_8$ cycloalkylene, $C_3$-$C_6$ cycloalkylene, or $C_5$-$C_6$ cycloalkylene).

In embodiments, $L^6$ is $R^{66}$-substituted or unsubstituted heterocycloalkylene (e.g., 3 to 8 membered heterocycloalkylene, 3 to 6 membered heterocycloalkylene, or 5 to 6 membered heterocycloalkylene). In embodiments, $L^6$ is $R^{66}$-substituted heterocycloalkylene (e.g., 3 to 8 membered heterocycloalkylene, 3 to 6 membered heterocycloalkylene, or 5 to 6 membered heterocycloalkylene). In embodiments, $L^6$ is an unsubstituted heterocycloalkylene (e.g., 3 to 8 membered heterocycloalkylene, 3 to 6 membered heterocycloalkylene, or 5 to 6 membered heterocycloalkylene).

In embodiments, $L^6$ is $R^{66}$-substituted or unsubstituted arylene (e.g., $C_6$-$C_{10}$ arylene, $C_{10}$ arylene, or phenyl). In embodiments, $L^6$ is $R^{66}$-substituted arylene (e.g., $C_6$-$C_{10}$ arylene, $C_{10}$ arylene, or phenyl). In embodiments, $L^6$ is an unsubstituted arylene (e.g., $C_6$-$C_{10}$ arylene, $C_{10}$ arylene, or phenyl).

In embodiments, $L^6$ is $R^{66}$-substituted or unsubstituted heteroarylene (e.g., 5 to 10 membered heteroarylene, 5 to 9 membered heteroarylene, or 5 to 6 membered heteroarylene). In embodiments, $L^6$ is $R^{66}$-substituted heteroarylene (e.g., 5 to 10 membered heteroarylene, 5 to 9 membered heteroarylene, or 5 to 6 membered heteroarylene). In embodiments, $L^6$ is an unsubstituted heteroarylene (e.g., 5 to 10 membered heteroarylene, 5 to 9 membered heteroarylene, or 5 to 6 membered heteroarylene).

In embodiments, $L^7$ is a bond, —C(O)—, —C(O)O—, —O—, —S—, —$NR^{7L}$—, —C(O)$NR^{7L}$—, —$NR^{7L}$C(O)—, —S(O)$_2$—, —O—S(O)$_2NR^{7L}$—, —O—S(O)$_2NR^{7L}$C(O)—, —$NR^{7L}$C(O)NH—, —NHC(O)$NR^{7L}$—.

In embodiments, $R^{7L}$ is hydrogen, —$CX^{7L}_3$, —CN, —COOH, —CONH$_2$, —$CHX^{7L}_2$, —$CH_2X^{7L}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $X^{7L}$ is halogen.

In embodiments, $R^{7L}$ is $R^{68L}$-substituted or unsubstituted alkyl (e.g., $C_1$-$C_8$ alkyl, $C_1$-$C_6$ alkyl, or $C_1$-$C_4$ alkyl). In embodiments, $R^{7L}$ is $R^{68L}$-substituted alkyl (e.g., $C_1$-$C_8$ alkyl, $C_1$-$C_6$ alkyl, or $C_1$-$C_4$ alkyl). In embodiments, $R^{7L}$ is an unsubstituted alkyl (e.g., $C_1$-$C_8$ alkyl, $C_1$-$C_6$ alkyl, or $C_1$-$C_4$ alkyl).

In embodiments, $R^{7L}$ is $R^{68L}$-substituted or unsubstituted heteroalkyl (e.g., 2 to 8 membered heteroalkyl, 2 to 6 membered heteroalkyl, or 2 to 4 membered heteroalkyl). In embodiments, $R^{7L}$ is $R^{68L}$-substituted heteroalkyl (e.g., 2 to 8 membered heteroalkyl, 2 to 6 membered heteroalkyl, or 2 to 4 membered heteroalkyl). In embodiments, $R^{7L}$ is an unsubstituted heteroalkyl (e.g., 2 to 8 membered heteroalkyl, 2 to 6 membered heteroalkyl, or 2 to 4 membered heteroalkyl).

In embodiments, $R^{7L}$ is $R^{68L}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{7L}$ is $R^{68L}$-substituted cycloalkyl (e.g., $C_3$-$C_8$ cycloalkyl, $C_3$-$C_6$ cycloalkyl, or $C_5$-$C_6$ cycloalkyl). In embodiments, $R^{7L}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{7L}$ is $R^{68L}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{7L}$ is $R^{68L}$-substituted heterocycloalkyl (e.g., 3 to 8 membered heterocycloalkyl, 3 to 6 membered heterocycloalkyl, or 5 to 6 membered heterocycloalkyl). In embodiments, $R^{7L}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{7L}$ is $R^{68L}$-substituted or unsubstituted aryl (e.g., $C_6$-$C_{10}$ aryl, $C_{10}$ aryl, or phenyl). In embodiments, $R^{7L}$ is $R^{68L}$-substituted aryl (e.g., $C_6$-$C_{10}$ aryl, $C_{10}$ aryl, or phenyl). In embodiments, $R^{7L}$ is an unsubstituted aryl (e.g., $C_6$-$C_{10}$ aryl, $C_{10}$ aryl, or phenyl).

In embodiments, $R^{7L}$ is $R^{68L}$-substituted or unsubstituted heteroaryl (e.g., 5 to 10 membered heteroaryl, 5 to 9 membered heteroaryl, or 5 to 6 membered heteroaryl). In embodiments, $R^{7L}$ is $R^{68L}$-substituted heteroaryl (e.g., 5 to 10 membered heteroaryl, 5 to 9 membered heteroaryl, or 5 to 6 membered heteroaryl). In embodiments, $R^{7L}$ is an unsubstituted heteroaryl (e.g., 5 to 10 membered heteroaryl, 5 to 9 membered heteroaryl, or 5 to 6 membered heteroaryl).

In embodiments, $R^{18}$ is —NH$_2$ or

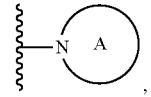

, wherein ring A is a substituted or unsubstituted heteroaryl or substituted or unsubstituted heterocycloalkyl.

In embodiments, A is $R^{70}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, A is $R^{70}$-substituted heterocycloalkyl (e.g., 3 to 8 membered heterocycloalkyl, 3 to 6 membered heterocycloalkyl, or 5 to 6 membered heterocycloalkyl). In embodiments, A is an unsubstituted heterocycloalkyl (e.g., 3 to 8 membered heterocycloalkyl, 3 to 6 membered heterocycloalkyl, or 5 to 6 membered heterocycloalkyl).

In embodiments, A is $R^{70}$-substituted or unsubstituted heteroaryl (e.g., 5 to 10 membered heteroaryl, 5 to 9 membered heteroaryl, or 5 to 6 membered heteroaryl). In embodiments, A is $R^{70}$-substituted heteroaryl (e.g., 5 to 10 membered heteroaryl, 5 to 9 membered heteroaryl, or 5 to 6 membered heteroaryl). In embodiments, A is an unsubstituted heteroaryl (e.g., 5 to 10 membered heteroaryl, 5 to 9 membered heteroaryl, or 5 to 6 membered heteroaryl).

$R^{66}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{67}$-substituted or unsubstituted alkyl (e.g., $C_1$-$C_8$ alkyl, $C_1$-$C_6$ alkyl, or $C_1$-$C_4$ alkyl), $R^{67}$-substituted or unsubstituted heteroalkyl (e.g., 2 to 8 membered heteroalkyl, 2 to 6 membered heteroalkyl, or 2 to 4 membered heteroalkyl), $R^{67}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{67}$-substituted or unsubstituted heterocycloalkyl (e.g., 3 to 8 membered heterocycloalkyl, 3 to 6 membered heterocycloalkyl, or 5 to 6 membered heterocycloalkyl), $R^{67}$-substituted or unsubstituted aryl (e.g., $C_6$-$C_{10}$ aryl, $C_{10}$ aryl, or phenyl), or $R^{67}$-substituted or unsubstituted heteroaryl (e.g., 5 to 10 membered heteroaryl, 5 to 9 membered heteroaryl, or 5 to 6 membered heteroaryl).

In embodiments, $R^{66}$ is $R^{67}$-substituted or unsubstituted alkyl (e.g., $C_1$-$C_8$ alkyl, $C_1$-$C_6$ alkyl, or $C_1$-$C_4$ alkyl). In embodiments, $R^{66}$ is $R^{67}$-substituted alkyl (e.g., $C_1$-$C_8$ alkyl, $C_1$-$C_6$ alkyl, or $C_1$-$C_4$ alkyl). In embodiments, $R^{66}$ is an unsubstituted alkyl (e.g., $C_1$-$C_8$ alkyl, $C_1$-$C_6$ alkyl, or $C_1$-$C_4$ alkyl).

In embodiments, $R^{66}$ is $R^{67}$-substituted or unsubstituted heteroalkyl (e.g., 2 to 8 membered heteroalkyl, 2 to 6 membered heteroalkyl, or 2 to 4 membered heteroalkyl). In embodiments, $R^{66}$ is $R^{67}$-substituted heteroalkyl (e.g., 2 to 8 membered heteroalkyl, 2 to 6 membered heteroalkyl, or 2 to 4 membered heteroalkyl). In embodiments, $R^{66}$ is an unsubstituted heteroalkyl (e.g., 2 to 8 membered heteroalkyl, 2 to 6 membered heteroalkyl, or 2 to 4 membered heteroalkyl).

In embodiments, $R^{66}$ is $R^{67}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{66}$ is $R^{67}$-substituted cycloalkyl (e.g., $C_3$-$C_8$ cycloalkyl, $C_3$-$C_6$ cycloalkyl, or $C_5$-$C_6$ cycloalkyl). In embodiments, $R^{66}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{66}$ is $R^{67}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{66}$ is $R^{67}$-substituted heterocycloalkyl (e.g., 3 to 8 membered heterocycloalkyl, 3 to 6 membered heterocycloalkyl, or 5 to 6 membered heterocycloalkyl). In embodiments, $R^{66}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{66}$ is $R^{67}$-substituted or unsubstituted aryl (e.g., $C_6$-$C_{10}$ aryl, $C_{10}$ aryl, or phenyl). In embodiments, $R^{66}$ is $R^{67}$-substituted aryl (e.g., $C_6$-$C_{10}$ aryl, $C_{10}$ aryl, or phenyl). In embodiments, $R^{66}$ is an unsubstituted aryl (e.g., $C_6$-$C_{10}$ aryl, $C_{10}$ aryl, or phenyl).

In embodiments, $R^{66}$ is $R^{67}$-substituted or unsubstituted heteroaryl (e.g., 5 to 10 membered heteroaryl, 5 to 9 membered heteroaryl, or 5 to 6 membered heteroaryl). In embodiments, $R^{66}$ is $R^{67}$-substituted heteroaryl (e.g., 5 to 10 membered heteroaryl, 5 to 9 membered heteroaryl, or 5 to 6 membered heteroaryl). In embodiments, $R^{66}$ is an unsubstituted heteroaryl (e.g., 5 to 10 membered heteroaryl, 5 to 9 membered heteroaryl, or 5 to 6 membered heteroaryl).

$R^{68L}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{69L}$-substituted or unsubstituted alkyl (e.g., $C_1$-$C_8$ alkyl, $C_1$-$C_6$ alkyl, or $C_1$-$C_4$ alkyl), $R^{69L}$-substituted or unsubstituted heteroalkyl (e.g., 2 to 8 membered heteroalkyl, 2 to 6 membered heteroalkyl, or 2 to 4 membered heteroalkyl), $R^{69L}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{69L}$-substituted or unsubstituted heterocycloalkyl (e.g., 3 to 8 membered heterocycloalkyl, 3 to 6 membered heterocycloalkyl, or 5 to 6 membered heterocycloalkyl), $R^{69L}$-substituted or unsubstituted aryl (e.g., $C_6$-$C_{10}$ aryl, $C_{10}$ aryl, or phenyl), or $R^{69L}$-substituted or unsubstituted heteroaryl (e.g., 5 to 10 membered heteroaryl, 5 to 9 membered heteroaryl, or 5 to 6 membered heteroaryl).

In embodiments, $R^{68L}$ is $R^{69L}$-substituted or unsubstituted alkyl (e.g., $C_1$-$C_8$ alkyl, $C_1$-$C_6$ alkyl, or $C_1$-$C_4$ alkyl). In embodiments, $R^{68L}$ is $R^{69L}$-substituted alkyl (e.g., $C_1$-$C_8$ alkyl, $C_1$-$C_6$ alkyl, or $C_1$-$C_4$ alkyl). In embodiments, $R^{68L}$ is an unsubstituted alkyl (e.g., $C_1$-$C_8$ alkyl, $C_1$-$C_6$ alkyl, or $C_1$-$C_4$ alkyl).

In embodiments, $R^{68L}$ is $R^{69L}$-substituted or unsubstituted heteroalkyl (e.g., 2 to 8 membered heteroalkyl, 2 to 6 membered heteroalkyl, or 2 to 4 membered heteroalkyl). In embodiments, $R^{68L}$ is $R^{69L}$-substituted heteroalkyl (e.g., 2 to 8 membered heteroalkyl, 2 to 6 membered heteroalkyl, or 2 to 4 membered heteroalkyl). In embodiments, $R^{68L}$ is an unsubstituted heteroalkyl (e.g., 2 to 8 membered heteroalkyl, 2 to 6 membered heteroalkyl, or 2 to 4 membered heteroalkyl).

In embodiments, $R^{68L}$ is $R^{69L}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{68L}$ is $R^{69L}$-substituted cycloalkyl (e.g., $C_3$-$C_8$ cycloalkyl, $C_3$-$C_6$ cycloalkyl, or $C_5$-$C_6$ cycloalkyl). In embodiments, $R^{68L}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{68L}$ is $R^{69L}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{68L}$ is $R^{69L}$-substituted heterocycloalkyl (e.g., 3 to 8 membered heterocycloalkyl, 3 to 6 membered heterocycloalkyl, or 5 to 6 membered heterocycloalkyl). In embodiments, $R^{68L}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{68L}$ is $R^{69L}$-substituted or unsubstituted aryl (e.g., $C_6$-$C_{10}$ aryl, $C_{10}$ aryl, or phenyl). In embodiments, $R^{68L}$ is $R^{69L}$-substituted aryl (e.g., $C_6$-$C_{10}$ aryl, $C_{10}$ aryl, or phenyl). In embodiments, $R^{68L}$ is an unsubstituted aryl (e.g., $C_6$-$C_{10}$ aryl, $C_{10}$ aryl, or phenyl).

In embodiments, $R^{68L}$ is $R^{69L}$-substituted or unsubstituted heteroaryl (e.g., 5 to 10 membered heteroaryl, 5 to 9 membered heteroaryl, or 5 to 6 membered heteroaryl). In embodiments, $R^{68L}$ is $R^{69L}$-substituted heteroaryl (e.g., 5 to 10 membered heteroaryl, 5 to 9 membered heteroaryl, or 5 to 6 membered heteroaryl). In embodiments, $R^{68L}$ is an unsubstituted heteroaryl (e.g., 5 to 10 membered heteroaryl, 5 to 9 membered heteroaryl, or 5 to 6 membered heteroaryl).

$R^{70}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, $R^{71}$-substituted or unsubstituted alkyl (e.g., C$_1$-C$_8$ alkyl, C$_1$-C$_6$ alkyl, or C$_1$-C$_4$ alkyl), $R^{71}$-substituted or unsubstituted heteroalkyl (e.g., 2 to 8 membered heteroalkyl, 2 to 6 membered heteroalkyl, or 2 to 4 membered heteroalkyl), $R^{71}$-substituted or unsubstituted cycloalkyl (e.g., C$_3$-C$_8$ cycloalkyl, C$_3$-C$_6$ cycloalkyl, or C$_5$-C$_6$ cycloalkyl), $R^{71}$-substituted or unsubstituted heterocycloalkyl (e.g., 3 to 8 membered heterocycloalkyl, 3 to 6 membered heterocycloalkyl, or 5 to 6 membered heterocycloalkyl), $R^{71}$-substituted or unsubstituted aryl (e.g., C$_6$-C$_{10}$ aryl, C$_{10}$ aryl, or phenyl), or $R^{71}$-substituted or unsubstituted heteroaryl (e.g., 5 to 10 membered heteroaryl, 5 to 9 membered heteroaryl, or 5 to 6 membered heteroaryl).

In embodiments, $R^{70}$ is $R^{71}$-substituted or unsubstituted alkyl (e.g., C$_1$-C$_8$ alkyl, C$_1$-C$_6$ alkyl, or C$_1$-C$_4$ alkyl). In embodiments, $R^{70}$ is $R^{71}$-substituted alkyl (e.g., C$_1$-C$_8$ alkyl, C$_1$-C$_6$ alkyl, or C$_1$-C$_4$ alkyl). In embodiments, $R^{70}$ is an unsubstituted alkyl (e.g., C$_1$-C$_8$ alkyl, C$_1$-C$_6$ alkyl, or C$_1$-C$_4$ alkyl).

In embodiments, $R^{70}$ is $R^{71}$-substituted or unsubstituted heteroalkyl (e.g., 2 to 8 membered heteroalkyl, 2 to 6 membered heteroalkyl, or 2 to 4 membered heteroalkyl). In embodiments, $R^{70}$ is $R^{71}$-substituted heteroalkyl (e.g., 2 to 8 membered heteroalkyl, 2 to 6 membered heteroalkyl, or 2 to 4 membered heteroalkyl). In embodiments, $R^{70}$ is an unsubstituted heteroalkyl (e.g., 2 to 8 membered heteroalkyl, 2 to 6 membered heteroalkyl, or 2 to 4 membered heteroalkyl).

In embodiments, $R^{70}$ is $R^{71}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, $R^{70}$ is $R^{71}$-substituted cycloalkyl (e.g., C$_3$-C$_8$ cycloalkyl, C$_3$-C$_6$ cycloalkyl, or C$_5$-C$_6$ cycloalkyl). In embodiments, $R^{70}$ is an unsubstituted cycloalkyl (e.g., C$_3$-C$_8$ cycloalkyl, C$_3$-C$_6$ cycloalkyl, or C$_5$-C$_6$ cycloalkyl).

In embodiments, $R^{70}$ is $R^{71}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{70}$ is $R^{71}$-substituted heterocycloalkyl (e.g., 3 to 8 membered heterocycloalkyl, 3 to 6 membered heterocycloalkyl, or 5 to 6 membered heterocycloalkyl). In embodiments, $R^{70}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{70}$ is $R^{71}$-substituted or unsubstituted aryl (e.g., C$_6$-C$_{10}$ aryl, C$_{10}$ aryl, or phenyl). In embodiments, $R^{70}$ is $R^{71}$-substituted aryl (e.g., C$_6$-C$_{10}$ aryl, C$_{10}$ aryl, or phenyl). In embodiments, $R^{70}$ is an unsubstituted aryl (e.g., C$_6$-C$_{10}$ aryl, C$_{10}$ aryl, or phenyl).

In embodiments, $R^{70}$ is $R^{71}$-substituted or unsubstituted heteroaryl (e.g., 5 to 10 membered heteroaryl, 5 to 9 membered heteroaryl, or 5 to 6 membered heteroaryl). In embodiments, $R^{70}$ is $R^{71}$-substituted heteroaryl (e.g., 5 to 10 membered heteroaryl, 5 to 9 membered heteroaryl, or 5 to 6 membered heteroaryl). In embodiments, $R^{70}$ is an unsubstituted heteroaryl (e.g., 5 to 10 membered heteroaryl, 5 to 9 membered heteroaryl, or 5 to 6 membered heteroaryl).

$R^{71}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, $R^{72}$-substituted or unsubstituted alkyl (e.g., C$_1$-C$_8$ alkyl, C$_1$-C$_6$ alkyl, or C$_1$-C$_4$ alkyl), $R^{72}$-substituted or unsubstituted heteroalkyl (e.g., 2 to 8 membered heteroalkyl, 2 to 6 membered heteroalkyl, or 2 to 4 membered heteroalkyl), $R^{72}$-substituted or unsubstituted cycloalkyl (e.g., C$_3$-C$_8$ cycloalkyl, C$_3$-C$_6$ cycloalkyl, or C$_5$-C$_6$ cycloalkyl), $R^{72}$-substituted or unsubstituted heterocycloalkyl (e.g., 3 to 8 membered heterocycloalkyl, 3 to 6 membered heterocycloalkyl, or 5 to 6 membered heterocycloalkyl), $R^{72}$-substituted or unsubstituted aryl (e.g., C$_6$-C$_{10}$ aryl, C$_{10}$ aryl, or phenyl), or $R^{72}$-substituted or unsubstituted heteroaryl (e.g., 5 to 10 membered heteroaryl, 5 to 9 membered heteroaryl, or 5 to 6 membered heteroaryl).

In embodiments, $R^{71}$ is $R^{72}$-substituted or unsubstituted alkyl (e.g., C$_1$-C$_8$ alkyl, C$_1$-C$_6$ alkyl, or C$_1$-C$_4$ alkyl). In embodiments, $R^{71}$ is $R^{72}$-substituted alkyl (e.g., C$_1$-C$_8$ alkyl, C$_1$-C$_6$ alkyl, or C$_1$-C$_4$ alkyl). In embodiments, $R^{71}$ is an unsubstituted alkyl (e.g., C$_1$-C$_8$ alkyl, C$_1$-C$_6$ alkyl, or C$_1$-C$_4$ alkyl).

In embodiments, $R^{71}$ is $R^{72}$-substituted or unsubstituted heteroalkyl (e.g., 2 to 8 membered heteroalkyl, 2 to 6 membered heteroalkyl, or 2 to 4 membered heteroalkyl). In embodiments, $R^{71}$ is $R^{72}$-substituted heteroalkyl (e.g., 2 to 8 membered heteroalkyl, 2 to 6 membered heteroalkyl, or 2 to 4 membered heteroalkyl). In embodiments, $R^{71}$ is an unsubstituted heteroalkyl (e.g., 2 to 8 membered heteroalkyl, 2 to 6 membered heteroalkyl, or 2 to 4 membered heteroalkyl).

In embodiments, $R^{71}$ is $R^{72}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, $R^{71}$ is $R^{72}$-substituted cycloalkyl (e.g., C$_3$-C$_8$ cycloalkyl, C$_3$-C$_6$ cycloalkyl, or C$_5$-C$_6$ cycloalkyl). In embodiments, $R^{71}$ is an unsubstituted cycloalkyl (e.g., C$_3$-C$_8$ cycloalkyl, C$_3$-C$_6$ cycloalkyl, or C$_5$-C$_6$ cycloalkyl).

In embodiments, $R^{71}$ is $R^{72}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{71}$ is $R^{72}$-substituted heterocycloalkyl (e.g., 3 to 8 membered heterocycloalkyl, 3 to 6 membered heterocycloalkyl, or 5 to 6 membered heterocycloalkyl). In embodiments, $R^{71}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{71}$ is $R^{72}$-substituted or unsubstituted aryl (e.g., C$_6$-C$_{10}$ aryl, C$_{10}$ aryl, or phenyl). In embodiments, $R^{71}$ is $R^{72}$-substituted aryl (e.g., C$_6$-C$_{10}$ aryl, C$_{10}$ aryl, or phenyl). In embodiments, $R^{71}$ is an unsubstituted aryl (e.g., C$_6$-C$_{10}$ aryl, C$_{10}$ aryl, or phenyl).

In embodiments, $R^{71}$ is $R^{72}$-substituted or unsubstituted heteroaryl (e.g., 5 to 10 membered heteroaryl, 5 to 9 membered heteroaryl, or 5 to 6 membered heteroaryl). In embodiments, $R^{71}$ is $R^{72}$-substituted heteroaryl (e.g., 5 to 10 membered heteroaryl, 5 to 9 membered heteroaryl, or 5 to 6 membered heteroaryl). In embodiments, $R^{71}$ is an unsubstituted heteroaryl (e.g., 5 to 10 membered heteroaryl, 5 to 9 membered heteroaryl, or 5 to 6 membered heteroaryl).

$R^{67}$, $R^{69L}$ and $R^{72}$ are independently hydrogen, oxo, halogen, —CCl$_3$, —CBr$_3$, —CF$_3$, —CI$_3$, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $L^7$ is —O—S(O)₂NHC(O)—. In embodiments, $L^6$ is unsubstituted $C_1$-$C_{12}$ alkylene. In embodiments, $L^6$ is unsubstituted $C_3$-$C_{12}$ alkylene. In embodiments, $L^6$ is unsubstituted propylene. In embodiments, $L^6$ is unsubstituted $C_{11}$ alkylene.

In embodiments, $R^{18}$ is —NH₂. In embodiments, $R^{18}$ is

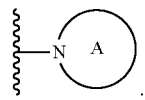

In embodiments, $R^{18}$ is

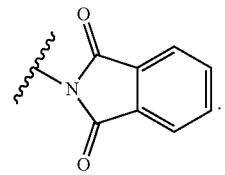 [SMILES: *N1C(=O)c2ccccc2C1=O]

In embodiments, the compound of formula (VII) is

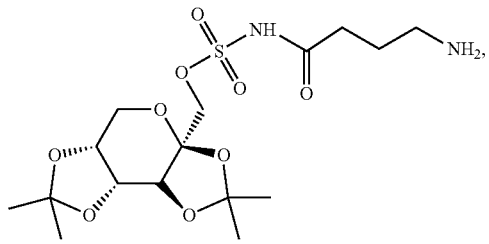

DY425

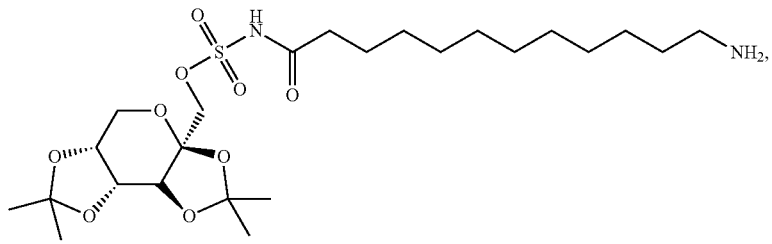

DY422

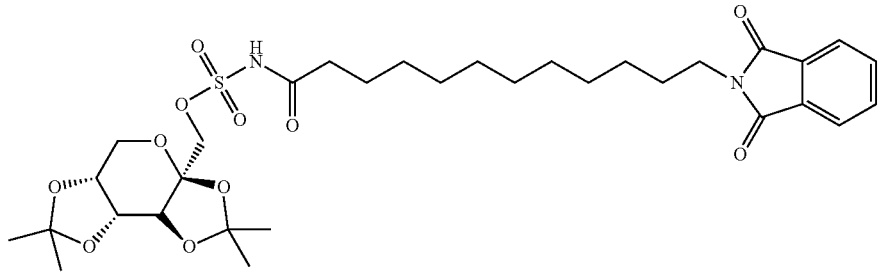

DY421 or

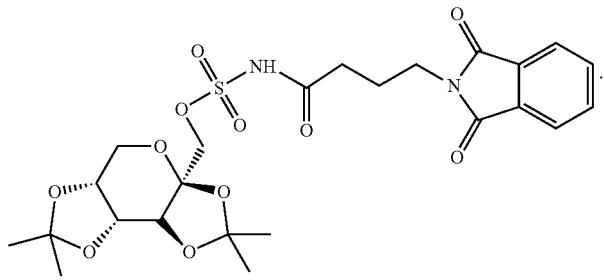

DY424

Methods of Use

In another aspect, there is provided a method of activating TGR5 in a cell. The method includes contacting TGR5 with a compound or a composition disclosed herein. In embodiments, the amount of the compound is an effective amount to activate the TGR5.

In embodiments, the cell is an intestinal cell.

In another aspect, there is provided a method of inhibiting FXR in a cell. The method includes contacting FXR with a compound or a composition disclosed herein. In embodiments, the amount of the compound is an effective amount to activate the TGR5.

In embodiments, the cell is an intestinal cell.

In another aspect, there is provided a method of treating or preventing a TGR5-mediated disease or disorder. The method includes administering to a subject in need thereof a therapeutically effective amount of a compound or a composition disclosed herein.

In another aspect, there is provided a method of treating or preventing an FXR-mediated disease or disorder. The method includes administering to a subject in need thereof a therapeutically effective amount of a compound or a composition disclosed herein.

Further to any aspect directed to a method of treating or preventing a TGR5-mediated disease or disorder or an FXR-mediated disease or disorder, and embodiments thereof, in embodiments the disease or disorder is a metabolic disease or disorder.

In embodiments, the metabolic disease or disorder is diabetes, obesity, insulin resistance, metabolic syndrome, atheroscleosis or liver disease. In embodiments, the liver disease is non-alcoholic fatty liver disease.

Further to any aspect directed to a method of treating or preventing a TGR5-mediated disease or disorder or an FXR-mediated disease or disorder, and embodiments thereof, in embodiments the disease or disorder is cancer.

Further to any aspect directed to a method of treating or preventing a TGR5-mediated disease or disorder or an FXR-mediated disease or disorder, and embodiments thereof, in embodiments the administration is enteral. In embodiments, the administration is oral.

It is understood that the examples and embodiments described herein are for illustrative purposes only and that various modifications or changes in light thereof will be suggested to persons skilled in the art and are to be included within the spirit and purview of this application and scope of the appended claims. All publications, patents and patent applications cited herein are hereby incorporated by reference in their entirety for all purposes.

EMBODIMENTS

In another aspect, there is provided a method of activating TGR5 in a cell. The method includes contacting TGR5 with a compound or a composition disclosed herein.

In embodiments, the cell is an intestinal cell.

In another aspect, there is provided a method of inhibiting FXR in a cell. The method includes contacting FXR with a compound or a composition disclosed herein.

In embodiments, the cell is an intestinal cell.

In another aspect, there is provided a method of treating or preventing a TGR5-mediated disease or disorder. The method includes administering to a subject in need thereof a therapeutically effective amount of a compound or a composition disclosed herein.

In another aspect, there is provided a method of treating or preventing an FXR-mediated disease or disorder. The method includes administering to a subject in need thereof a therapeutically effective amount of a compound or a composition disclosed herein.

Further to any aspect directed to a method of treating or preventing a TGR5-mediated disease or disorder or an FXR-mediated disease or disorder, and embodiments thereof, in embodiments the disease or disorder is a metabolic disease or disorder.

In embodiments, the metabolic disease or disorder is diabetes, obesity, insulin resistance, metabolic syndrome, atheroscleosis or liver disease. In embodiments, the liver disease is non-alcoholic fatty liver disease.

Further to any aspect directed to a method of treating or preventing a TGR5-mediated disease or disorder or an FXR-mediated disease or disorder, and embodiments thereof, in embodiments the disease or disorder is cancer.

Further to any aspect directed to a method of treating or preventing a TGR5-mediated disease or disorder or an FXR-mediated disease or disorder, and embodiments thereof, in embodiments the administration is enteral. In embodiments, the administration is oral.

It is understood that the examples and embodiments described herein are for illustrative purposes only and that various modifications or changes in light thereof will be suggested to persons skilled in the art and are to be included within the spirit and purview of this application and scope of the appended claims. All publications, patents and patent applications cited herein are hereby incorporated by reference in their entirety for all purposes.

EMBODIMENTS

Embodiment 1

A compound having the formula:

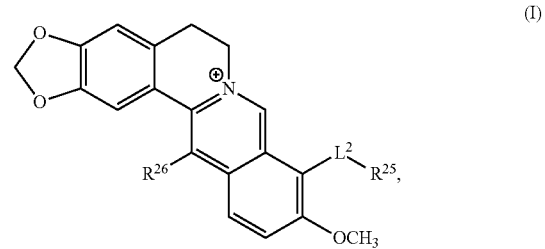

wherein $L^1$, $R^{25}$ and $R^{26}$ are described herein.

Embodiment 2

The compound of Embodiment 1 ionically bound to $Y^1$, wherein $Y^1$ is an anionic counterion selected from the groups consisting of a halogen anion, an inorganic anion, an organic anion or an anionic bile acid receptor modulator.

Embodiment 3

The compound of Embodiment 2, wherein the halogen anion is $F^-$, $Cl^-$, $Br^-$ or $I^-$.

Embodiment 4

The compound of Embodiment 2, wherein the anionic counterion is selected from the group consisting of carbonate, bicarbonate, chlorate, chromate, cyanide, dichromate, dihydrogen phosphate, hydrogen carbonate, hydrogen bicarbonate, hydrogen phosphate, hydrogen sulfate, hydrogen bisulfate, hydroxide, nitrate, nitride, nitrite, oxide, permanganate, peroxide, phosphate, sulfate, sulfide, sulfite and thiocyanate.

Embodiment 5

The compound of Embodiment 2, wherein the anionic counterion is selected from the group consisting of a bile acid, carboxylate, phosphate, mesylate, tosylate and triflate.

Embodiment 6

The compound of Embodiment 2, wherein the anionic bile acid receptor modulator is an anionic farnesoid X receptor (FXR) modulator or an anionic Takeda G-protein-coupled Receptor 5 (TGR5) modulator.

Embodiment 7

The compound of Embodiment 6, wherein the anionic bile acid receptor modulator is an anionic TGR5 agonist.

Embodiment 8

The compound of Embodiment 7, wherein the anionic TGR5 agonist is a berberine derivative, a berberine salt, a bile acid derivative or a bile acid salt.

Embodiment 9

The compound of Embodiment 6, wherein the anionic bile acid receptor modulator is an anionic FXR antagonist.

Embodiment 10

The compound of Embodiment 9, wherein the anionic FXR antagonist is a berberine derivative, a berberine salt, a bile acid derivative, a bile acid salt or a γ-aminobutyric acid (GABA) derivative.

Embodiment 11

The compound of Embodiment 1, wherein the compound is:

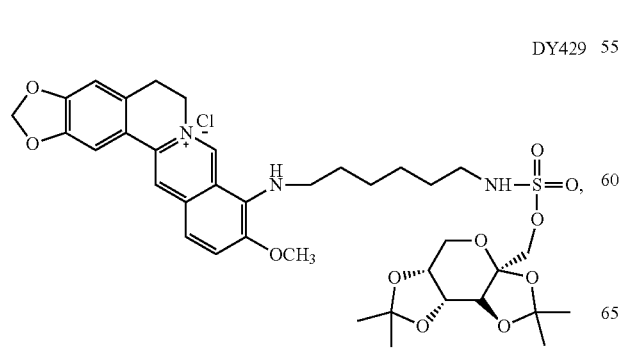

DY429

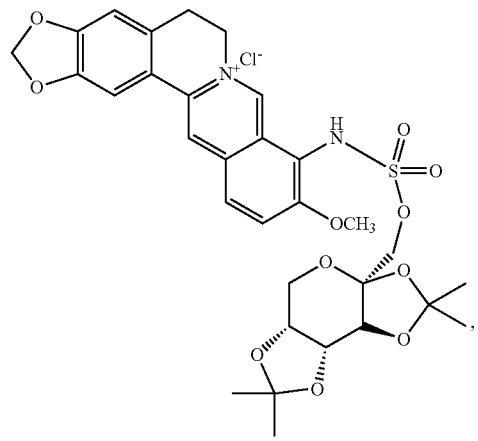

DY319

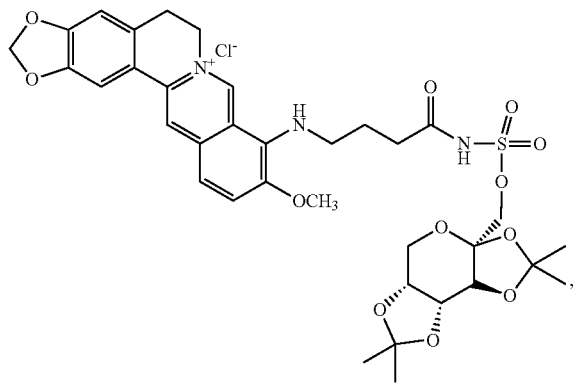

DY324

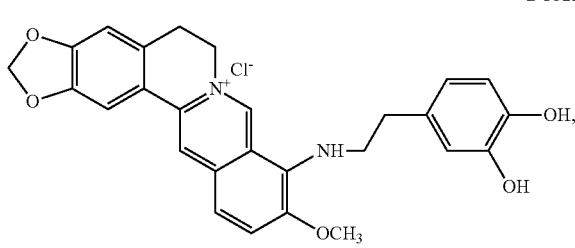

DY322

DY328 or

113

-continued

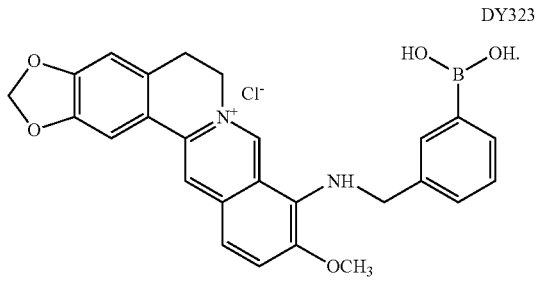

DY323

Embodiment 12

A composition comprising a bile acid receptor modulator and compound of the formula:

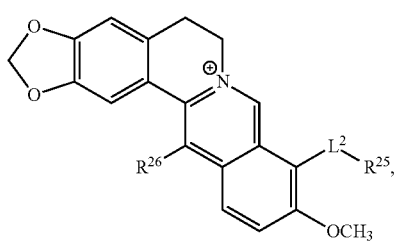

(I)

wherein $L^1$, $R^{25}$ and $R^{26}$ are described herein.

Embodiment 13

The composition of Embodiment 14, wherein the compound of Formula (I) and the bile acid receptor modulator are ionically bound together to form a salt composition having the formula:

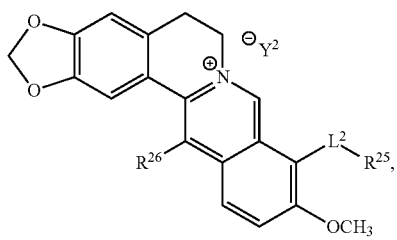

(II)

wherein $Y^2$ is the bile acid receptor modulator.

114

Embodiment 14

The composition of Embodiment 13, wherein $Y^2$ is

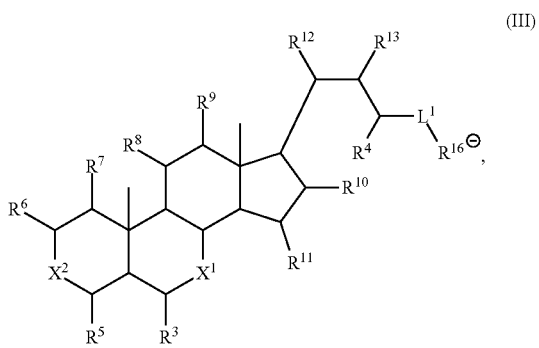

(III)

wherein $L^1$, $X^1$, $X^2$, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ are disclosed herein.

Embodiment 15

The composition of Embodiment 14, wherein $Y^2$ is:

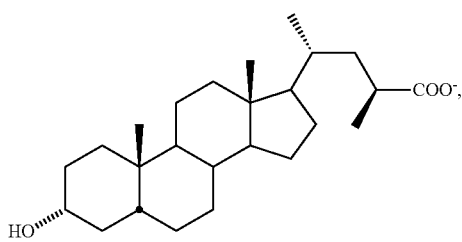

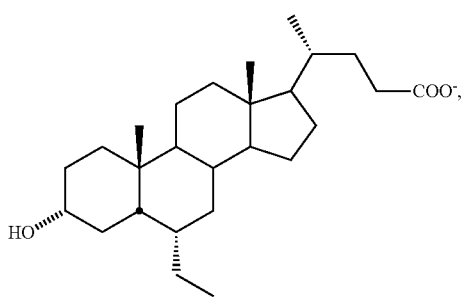

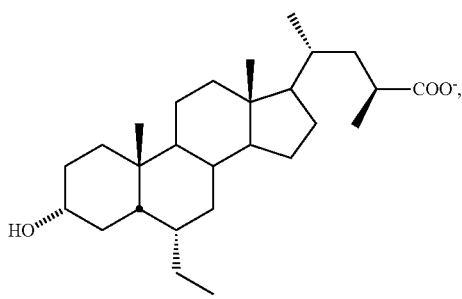

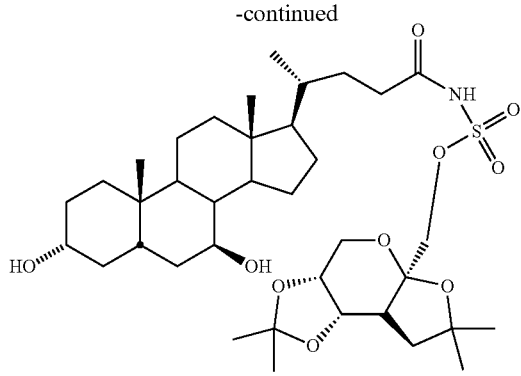

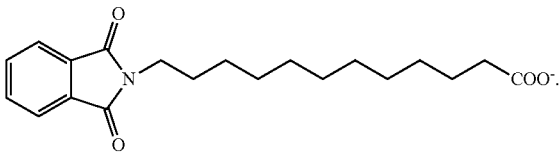

or

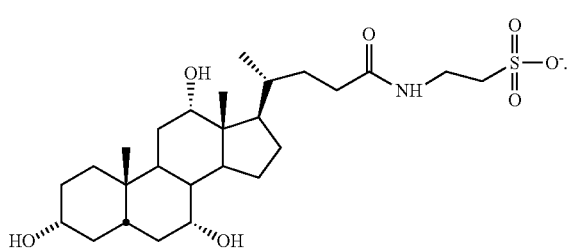

Embodiment 16

The composition of Embodiment 13, wherein $Y^2$ is:

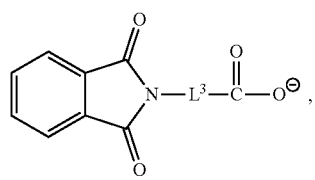 (IV)

wherein $L^3$ is substituted or unsubstituted alkylene.

Embodiment 17

The composition of Embodiment 16, wherein $Y^2$ is

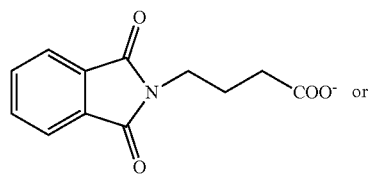 DY419 or

Embodiment 18

The composition of Embodiment 13, wherein $Y^2$ is γ-aminobutyric acid or biologically active derivative thereof.

Embodiment 19

The composition of Embodiment 13, wherein $Y^2$ is:

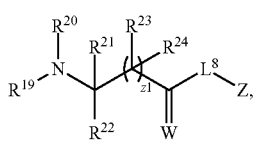 (V)

wherein W, Z, $L^8$, $R^{19}$, $R^{20}$, $R^{21}$, $R^{22}$, $R^{23}$, and $R^{24}$ are described herein.

Embodiment 20

The composition of Embodiment 19, wherein $Y^2$ is

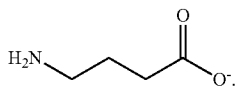

Embodiment 21

The composition of Embodiment 13, wherein the salt composition is:

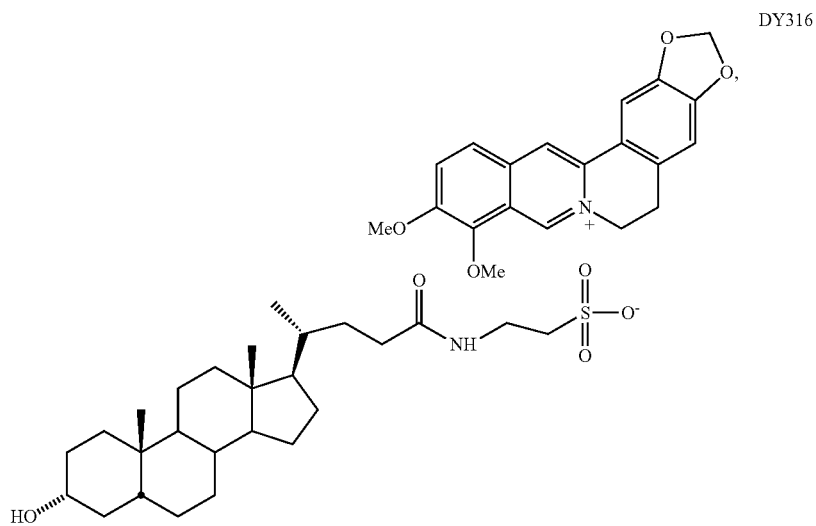
DY316
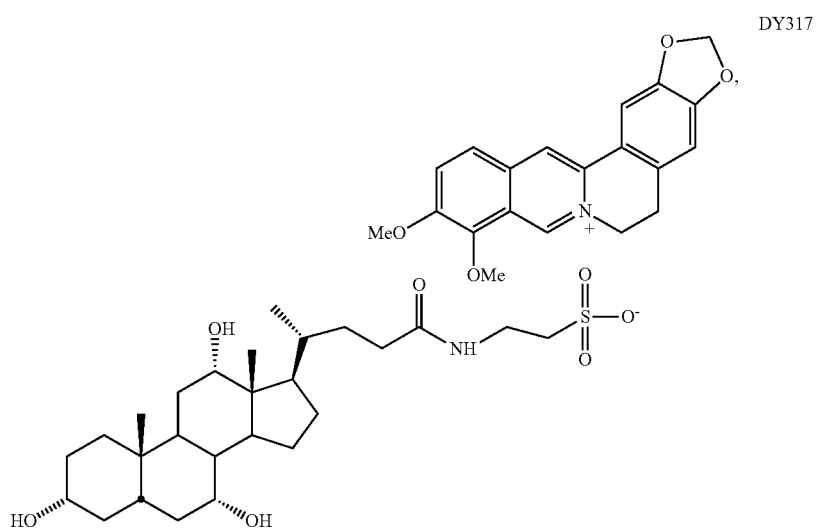
DY317
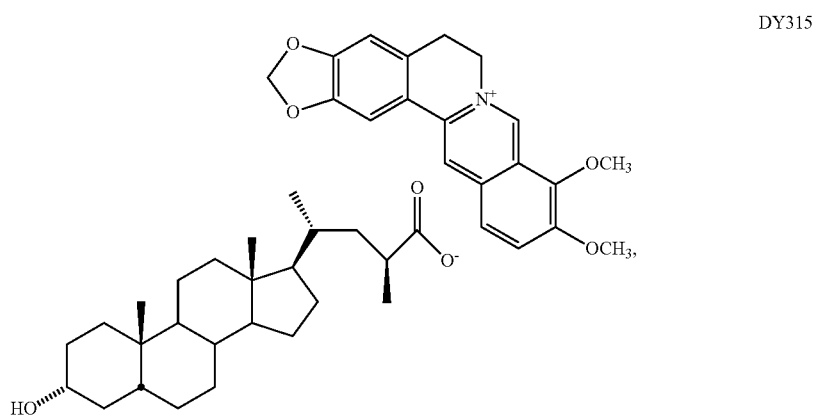
DY315

-continued
DY321
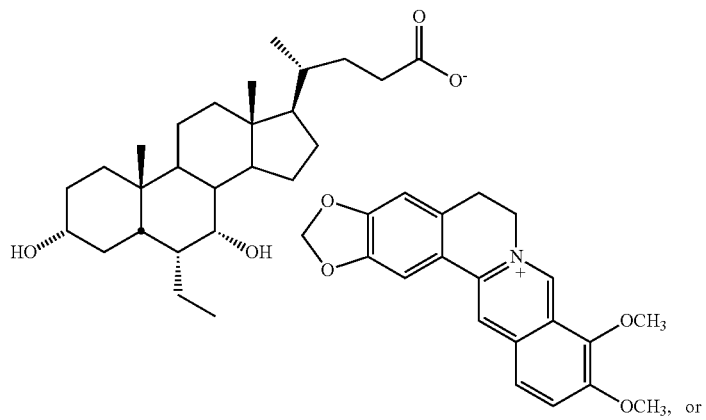
DY433
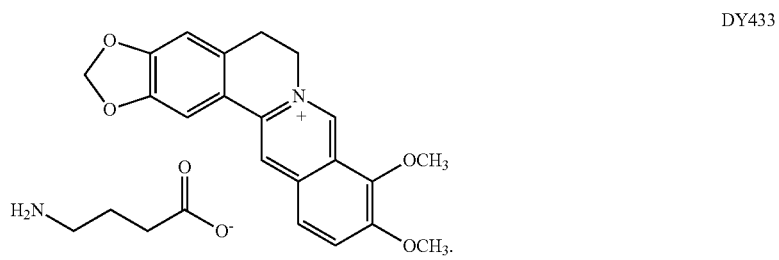
Embodiment 22
A compound having the formula:
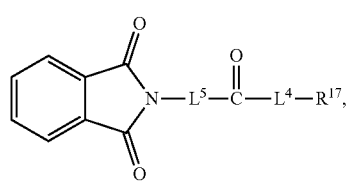  (VI)
wherein $L^4$, $L^5$, and $R^{17}$ are described herein.
Embodiment 23
The compound of Embodiment 22, wherein the compound is
DY419
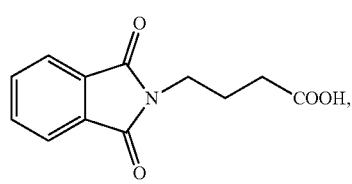

-continued
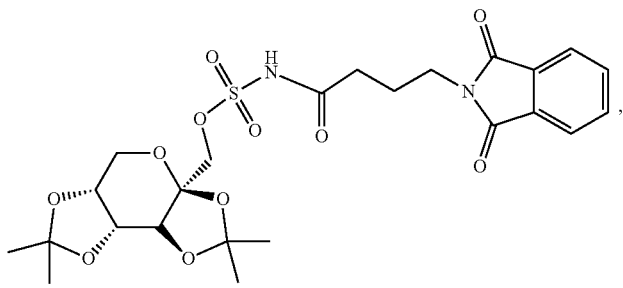
DY424
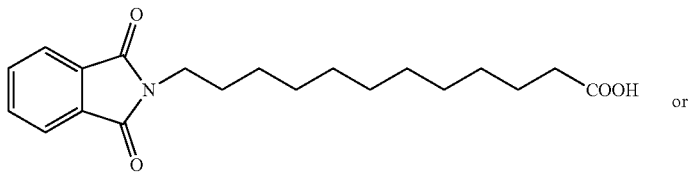
DY420
or
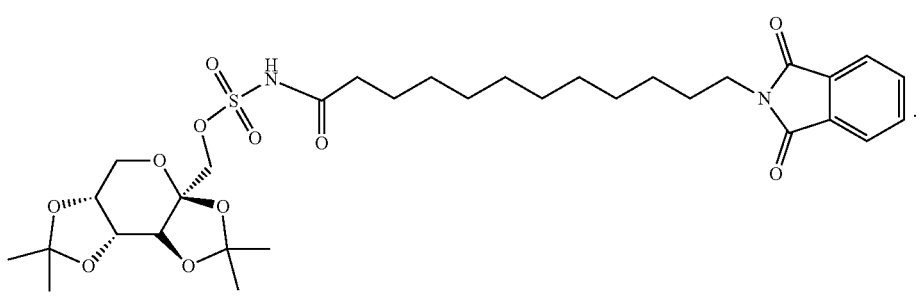
DY421
Embodiment 24
A compound of the formula:
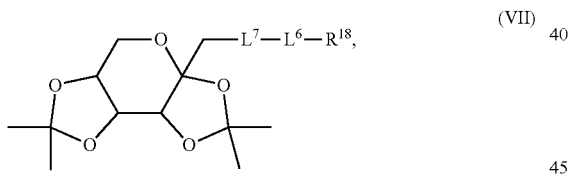
(VII)
wherein $L^6$, $L^7$ and $R^{18}$ are descried herein.
Embodiment 25
The compound of Embodiment 24, wherein the compound is
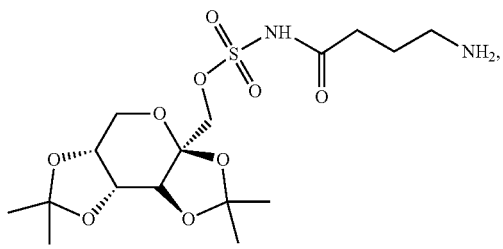
DY425

-continued

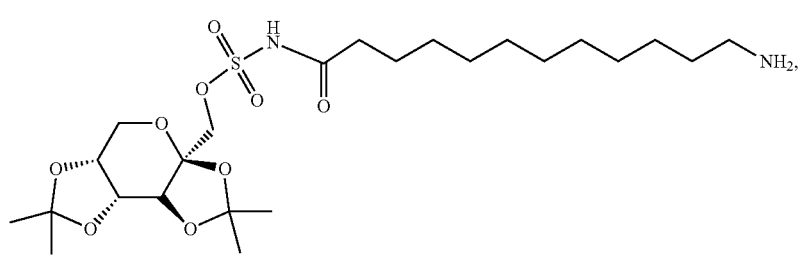

DY422

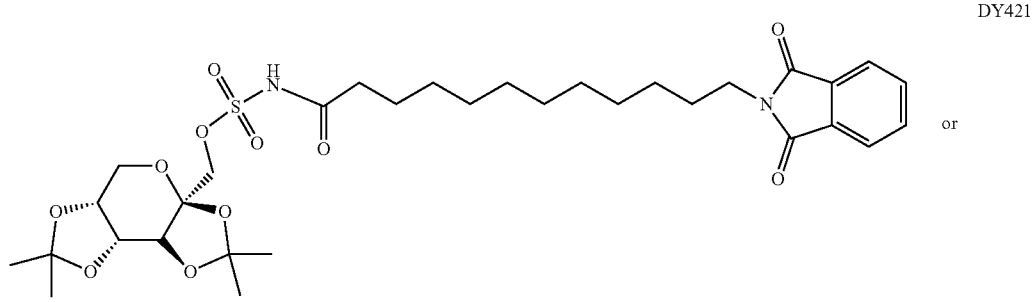

DY421 or

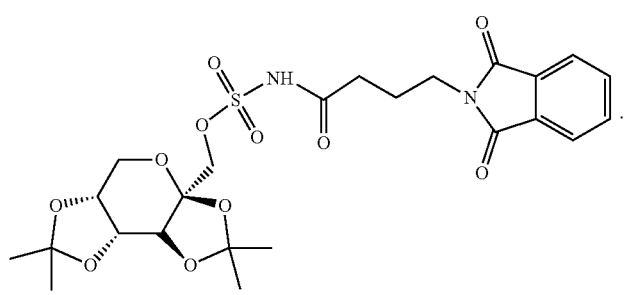

DY424

Embodiment 26

A method of activating TGR5 in a cell, comprising contacting TGR5 with a compound of any one of Embodiments 1-11 or 22-25 or a composition of any one of Embodiments 12-21.

Embodiment 27

The method of Embodiment 26, wherein the cell is an intestinal cell.

Embodiment 28

A method of inhibiting FXR in a cell, comprising contacting FXR with a compound of any one of Embodiments 1-11 or 22-25 or a composition of any one of Embodiments 12-21.

Embodiment 29

The method of Embodiment 28, wherein the cell is an intestinal cell.

Embodiment 30

A method of treating or preventing a TGR5-mediated disease or disorder, comprising administering to a subject a therapeutically effective amount of the compound of any one of Embodiments 1-11 or 22-25 or a composition of any one of Embodiments 12-21.

Embodiment 31

A method of treating or preventing an FXR-mediated disease or disorder, comprising administering to a subject a therapeutically effective amount of the compound of any one of Embodiments 1-11 or 22-25 or a composition of any one of Embodiments 12-21.

Embodiment 32

The method of Embodiments 30 or 31, wherein the disease or disorder is a metabolic disease or disorder.

Embodiment 33

The method of Embodiment 32, wherein the metabolic disease or disorder is diabetes, obesity, insulin resistance, metabolic syndrome, atherosclerosis or liver disease.

Embodiment 34

The method of Embodiment 33, wherein the liver disease is non-alcoholic fatty liver disease.

Embodiment 35

The method of Embodiments 30 or 31, wherein the disease or disorder is cancer.

Embodiment 36

The method of Embodiment 35, wherein the cancer is liver cancer.

Embodiment 37

The method of any one of Embodiments 30-36, wherein the administration is enteral.

Embodiment 38

The method of Embodiment 37, wherein the administration is oral.

EXAMPLES

Type 2 diabetes in particular has become much more common, along with the obesity epidemic. Diabetes is a worldwide health concern, with a rapidly increasing diabetic population predicted to reach 366 million by 2030.[1] Type 2 diabetes mellitus (T2DM) is a metabolic dysfunction characterized by increased insulin resistance and impaired insulin secretion, resulting in higher blood glucose levels. Almost 80 percent of people living with type 2 diabetes are overweight or have obesity, making it harder for them to control their blood sugar levels as they are unable to properly break down carbohydrates, either because their bodies do not produce enough insulin or they have become resistant to the hormone, which controls blood sugar levels. These patients are at higher risk for heart attacks, kidney problems, blindness and other serious complications. Pharmacologic agents, such as insulin secretagogues, sulfonylureas and glinides, are commonly used to increase insulin levels in diabetic patients.[2] However, these drugs promote insulin secretion independent of blood glucose levels, thereby leading to the risk of hypoglycemia.

Type 2 diabetes in particular has become much more common, along with the obesity epidemic. Obesity has been linked to a number of health problems, some of which are major causes of morbidity and mortality in the United States, for example, cardiovascular diseases, diabetes and cancer, as well as orthopedic problems, and, of course, social stigma. Currently, bariatric surgery, such as Roux-en-Y gastric bypass and vertical sleeve gastrectomy, are among the most effective surgical treatments for obesity. However, bariatric surgery is invasive and can cause surgical complications and not all patients with obesity are candidates for surgery.

Furthermore, the incidence of metabolic diseases, such as obesity, is rapidly rising in the United States.[3] Obesity induces chronic inflammation, which is an important component of the etiology of insulin resistance, itself a key component of diabetes. Therapies for obesity range from slimming clubs, low-calorie diets, and behavioral modification to appetite suppressants but are in general ineffective, leaving bariatric surgery as the only effective, yet invasive, treatment for obesity. Conservative estimates for the obesity drug market in the United States include $15 billion by 2015.

The growing incidence of metabolic disease has led to an intense interest in identifying new molecular targets and pharmacologic agents to treat and/or prevent these disorders. In the quest for improved therapies targeting a variety of pathways involved in the diabetes and obesity, bile acid-activated receptors have emerged as attractive and novel targets for the treatment of metabolic disorder. Two bile acid activated receptors have been identified for drug discovery efforts, a member of the "metabolic" subfamily of nuclear receptors, FXR[4] and, more recently, the G-protein coupled receptor TGR5.[5]

Clearly different from that of bile acid-activating FXR, which mediates downstream activation via a genomic pathway, TGR5 mediates several non-genomic functional responses induced by the binding of bile acids.[6] TGR5 agonism induces the secretion of clinically relevant glucagon-like peptide 1 (GLP-1), and peptide YY (PYY) raising expectations of an alternative therapeutic mechanism for the treatment of obesity.[7] However, activation by ligands of TGR5 stimulates its exposure to other tissues such as heart and gall bladder resulted in unwanted side effects.[8] Thus, a significant step in understanding the physiologic activity of TGR5 is to identify selective modulators that are selective for receptor recognition, selective for target gene modulation, and selective for the tissue specificity. As such, a TGR5 modulator being developed for diabetes should maximize exposure in the gastrointestinal tract (GI) tract, where TGR5 stimulate GLP-1 release (secreted from colonic L cells)[9] and minimize significant systemic exposure to the bloodstream.

TGR5 is a G protein-coupled receptor (GPCR), the activation of which promotes secretion of glucagon-like peptide-1 (GLP-1) and modulates insulin secretion. Novel mechanisms would be expected to induce secretion of GLP-1 and other peptides (PYY) from the distal gastrointestinal tract that could provide a means to elicit an antidiabetic effect. Specifically, TGR5 promotes secretion of GLP-1 to release insulin, reduce plasma glucose levels, delay gastric emptying and other beneficial effects. Notably, absorption of active GLP-1 occurs in the intestine, which is secreted by intestinal L cells.[22] Thus, an important advance in the elucidation of TGR5 receptor biology and stimulation of GLP-1 is the identification of intestine-restricted modulators that can be used to modulate TGR5 activities and induce GLP-1 in cells and in vivo.[23] However, activation by ligands of TGR5 stimulates its exposures to other tissues such as heart and gall bladder resulted resulting in unwanted side effects.

In this study, the designed selective TGR5 modulators were effective at increasing secretion of endogenous GLP-1 in the gut, which resulted in decreased glucose levels, inhibition of appetite and gastric emptying, and regulation of weight-loss properties. The selective TGR5 modulators should be poorly be absorbed into the circulation, which could limit significant systemic exposure to other internal organs and result in intestinally restricted TGR5 modulation thereby reducing side effects. Such modulation can be achieved through selective activation of TGR5 by a new class of orally bioavailable berberine derivatives, bile acid derivatives, or their pharmaceutically acceptable salts.

Farnesoid X receptor (FXR, NRIH4), a member of the bile acid nuclear hormone receptor superfamily, is a ligand-dependent transcription factor that regulates gene networks involved in regulating lipid and cholesterol homeostasis. FXR is expressed primarily in tissues exposed to high concentrations of bile acids, such as the intestine, kidney, adrenal gland, and liver.

Consistent with the role of FXR, bile acids are the primary activating endogenous ligands of FXR. As the bile acid sensor, FXR regulates the expression of transporters and biosynthetic enzymes crucial for the physiological maintenance of bile acid homeostasis. Interestingly, recent studies suggest that FXR antagonism can lead to a new line of therapeutics to treat obesity and diabetes. Thus, inhibition of FXR may represent an attractive target for the treatment of obesity or type II diabetes.

Berberine is a potent natural oral hypoglycemic agent and a ligand of TGR5. It is safe and the cost of treatment is very low. A series of berberine derivatives were prepared that may serve as new appetite-suppressant drug candidates for the prevention and treatment of obesity and type 2 diabetes. Berberine derivatives and pharmaceutically acceptable salts thereof were found to suppress food intake and body weight in high-diet induced mouse models. A dose-dependent increase in glucose uptake by C2C12 cells exposed to berberine derivatives was observed. Additionally, berberine derivatives and pharmaceutically acceptable salts thereof were shown to induce insulin secretion from pancreatic beta cells of wild type mice, but not in TGR5 knock-out mice, suggesting a novel role of TGR5 in maintaining glucose homeostasis. Taken together, these results suggest that berberine derivatives have great potential for the treatment of obesity and type II diabetes. The mechanisms of TGR5 signaling and the evaluation of new derivatives of berberine in activating TGR5 in pancreatic beta cells to stimulate beta cell mass increase, insulin production and secretion, will be further investigated.

In this study the berberine, bile acid, and γ-aminobutyric acid scaffolds were optimized with the aim of developing novel dual TGR5/FXR modulatory compounds. We identified several berberine derivatives and bile acid derivatives as novel dual TGR5 agonism/FXR antagonism modulators. Interestingly, these compounds displayed TGR5 agonistic activity with considerable FXR antagonistic potency in a single molecule, demonstrating the existence of a dual TGR5 agonist/FXR antagonist. These results demonstrate a proof of concept for the linkage of berberine, bile acids, γ-aminobutyric acid derivatives and their pharmaceutically acceptable salts or other agents and/or medical interventions in a single molecule while retaining or possibly enhancing the activity of the parent compounds.

Since inhibitors of FXR[20] are useful in treating or preventing obesity, type 2 diabetes/insulin resistance and non alcoholic fatty liver disease, dual TGR5 agonism/FXR antagonism modulators might be a potential target for anti-obesity drugs. A combination of a TGR5 agonist followed by FXR antagonist for treating obesity could be optimal. To address fixed-ratio combinations of the individual drugs, provided herein are potential combinations of drug ratios that may be more effective in some respects than a single drug. Specifically, two drugs that are linked (i.e., dual TGR5 agonism/FXR antagonism modulators) may offer a simpler and possibly more effective way to deliver these agents.

Disclosed herein are novel compositions and methods for the preparation thereof. In embodiments, the compositions disclosed herein are quaternary ammonium-containing alkaloids, such as berberine derivatives that activate TGR5, a G-protein-coupled receptor (GPCR), and inhibit FXR (Farnesoid X receptor), a nuclear receptor, thereby mediating cellular responses to bile acids (BAs). Disclosed herein is a series of novel berberine derivatives that are TGR5 modulators, or FXR modulators. In some embodiments, the compounds disclosed herein are dual TGR5 agonism/FXR antagonism modulators that display TGR5 agonistic activity with considerable FXR antagonistic activity in a single molecule. The compounds described herein would be systemically unavailable or less systemically available and or/and possess poor systemic exposure to avoid the unwanted side effects. The compounds are useful for treatment of any number of TGR5 or FXR mediated diseases or conditions, such as type II diabetes, obesity, hyperglycemia, hyperlipidemia, gluconeogenesis, metabolic syndrome, insulin resistance, and other serious diseases such as cancer.

Also provided are methods for the use of the compounds disclosed herein which in particular, possesses appetite-suppressant properties to regulate food intake and body weight for treating diabetes and obesity. The invention also, relates to a pharmaceutical composition containing novel berberine derivatives, bile acid derivatives, or a pharmaceutically acceptable salts thereof or other agents and/or medical interventions.

Disclosed herein are novel derivatives of a natural product γ-aminobutyric acid (GABA) and methods for the preparation thereof. The derivatives of γ-aminobutyric acid (GABA) disclosed herein were identified as FXR antagonists, or partial antagonists. Recent studies performed in rodents, including in vivo studies of xenotransplanted human islets, reveal that γ-aminobutyric acid exerts β-cell regenerative effects. γ-aminobutyric acid appears to be beneficial to T2D. Studies demonstrated that oral treatment with GABA improves glucose tolerance and insulin sensitivity in high fat diet-fed mice. However, a molecular link between γ-aminobutyric acid and T2D remain unclear. Surprisingly, we found that γ-aminobutyric acid and its derivatives displayed antagonistic action for the nuclear farnesoid-X receptor.

FXR is a member of the "metabolic" subfamily of nuclear receptors, which has emerged as an attractive target for the treatment of metabolic disorders. Our preliminary data suggest that inhibiting FXR in the intestine might be a potential target for anti-obesity drugs. Disclosed herein are γ-aminobutyric acid derivatives and pharmaceutically acceptable salts thereof. Also disclosed herein are compositions containing a combination of γ-aminobutyric acid derivatives or their pharmaceutically acceptable salts or other agents and/ or medical interventions, combined to a γ-aminobutyric acid derivative, such as a TGR5 agonist, such as a berberine derivative, or a bile acid derivative, as an active medicinal combination to treat obesity and diabetes.

Also disclosed herein are protected derivatives of compounds of this invention that may not possess pharmacological activity until they are metabolized in the blood to form pharmacologically active compounds. Such derivatives may therefore be described as "prodrug." All prodrugs of compounds of this invention are included within the scope of the invention.

We recently identified the natural product berberine as a novel TGR5 agonist ($EC_{50}$=0.46 μM, unpublished data). Thus, berberine may be beneficial for the treatment of type 2 diabetes with simultaneous management of obesity. Interestingly, berberine is a gut-restricted compound and keeps low concentration in plasma. Most interestingly, berberine failed to activate FXR, and, modulated GLP-1 release, suggesting that berberine has an excellent biological profile that makes it of particular interest as a starting point for optimization.

To potentially identify selective TGR5 modulators via a novel strategy, we synthesized and screened a focused chemical compounds library to search for derivatives that have higher affinity and/or higher selectivity to effectively modulate TGR5 activity in vivo. A focused small chemical compound library was evaluated in in vitro TGR5 assays to search for berberine-derived agonists that have higher affinity, potency, and/or higher selectivity for TGR5. The receptor binding assay was performed by measuring the level of cyclic AMP (cAMP) using TR-FRET (time-resolved fluorescence resonance energy transfer) assay. The level of intracellular cAMP was determined with Lance kit (PerkinElmer). Lithocholic acid was used as control ligand. Z' factor was used to validate assays. Non-linear regression curves, without constraints, was performed by using four parameter equation and GraphPad Prism Software (GraphPad Inc.) to obtain the $EC_{50}$ values. All drugs tested positive with TR-FRET for TGR5 binding affinities were evaluated in cell-based assays, using HEK293 cells stably over expressing human TGR5 transfected with the cAMP-sensitive reporter plasmid pCRE-Luc. Compounds were initially tested at doses of 10 M and the relative fold activation on TGR5 was determined. Compounds with promising activity in this initial screen were re-tested and control experiments were performed to confirm that the effect is TGR5-mediated. Dose-response experiments were performed on the most promising compounds that were tested to confirm that they do no activate other receptor pathways.

A series of FXR modulators from a small chemical library were also identified. FXR antagonist is a ligand that either represses or fails to activate the receptor upon binding. An antagonist can function by recruiting coprocessor or by failing to recruit coactivator. In the latter case, the antagonist is an inactive competitor that competes for binding with an agonist.

A better understanding of how FXR is involved in lipid and cholesterol metabolism and new methods for modifying the effects of FXR on this metabolism would be of great use in providing methods to modify lipid use in the body, including de novo cholesterol synthesis, cholesterol catabolism, lipogenesis, lipid storage and other metabolic pathways connected to common metabolic disorders such as obesity and the metabolic syndrome, as well as related syndromes, including atheroscleosis and type 2 diabetes. Methods of modifying lipid metabolism would be of great benefit to patients suffering from conditions involving or caused by increased lipogenesis or lipid storage and high serum cholesterol.

Interestingly, several berberine derivatives were identified as FXR antagonists by cell-based FXR transactivation assay, exemplified with DY322 and DY323. Novel dual TGR5 agonism/FXR antagonism modulators were also identified. Recent studies indicated that obese as well as older FXR knockout mice showed an improvement in glucose control and protection from excessive bodyweight gain. The therapeutic value of FXR antagonism remains unknown since robust in vivo data is lacking. In light of the entangled activity of both bile acid receptors, berberine derivatives would be very interesting agents with unique dual activity of FXR antagonism and TGR5 agonism. We reason that an effective TGR5 agonist endowed with antagonistic activity toward FXR in a single molecule may represent a highly efficacious targeted therapy for obesity.

Our preliminary data suggest that inhibiting FXR and activating TGR5 in the intestine might be a potential target for anti-obesity drugs.

In addition to identification of berberine derivatives and bile acid derivatives as TGR5 and FXR modulators, γ-aminobutyric acid and derivatives thereof that activate FXR and displayed antagonistic action were also identified. We now provide the first evidence that γ-aminobutyric acid derivatives can activate the bile acid receptor FXR. γ-Aminobutyric acid (GABA), the major inhibitory transmitter in the central nervous system, has long been known to be present at significant concentrations in the endocrine pancreas. Oral treatment with GABA improves glucose tolerance and insulin sensitivity in high-fat diet-fed mice. Importantly, orally administered GABA is safe for humans, since it does not cross the blood-brain barrier. Thus, GABA and its derivatives represent promising new therapeutic agents for diabetes. However, the mechanisms of γ-aminobutyric acid related obesity and diabetes have not been fully elucidated. Our findings may shed light on the molecular mechanisms involving FXR in obesity, i.e., a link between obesity and glucose homeostasis.

Identification of Berberine as a TGR5 Agonist

We identified berberine as a novel TGR5 agonist ($EC_{50}$=0.46 μM, unpublished data). Interestingly, berberine is a gut-restricted compound in the intestine and keeps low concentration in plasma. Most interestingly, berberine failed to activate FXR (FIG. 1, unpublished data). This selective activity establishes berberine as a novel pharmacologic tool to study the biological activities of TGR5 with a promising future for the treatment of type II diabetes and obesity.

Berberine is a natural isoquinoline alkaloid derived from a plant used traditionally in Chinese and Ayurvedic medicine with good safety.[10] In a previous human trial, oral administration of berberine at such a dose of 1.0 g/day/person for 3 months is effective and safe in the treatment of type 2 diabetes and dyslipidemia.[11] Berberine hydrochloride is the most common form. Its log P value was determined to be −1.5. It has recently been reported to exhibit insulin sensitizing as well as weight- and lipid-lowering properties in db/db mice. Although berberine has been reported to have antidiabetic effects and dyslipidemia in humans, the molecular targets have not been revealed and the exact underlying mechanisms are unclear. Its beneficial effects are possibly related in part to activated AMPK.[12] However, its mechanism of action in AMPK remains controversial. The lack of mechanistic data for its molecular actions has precluded its widespread use. We now provide the first evidence that berberine can activate the bile acid receptor TGR5 and initiate increases in intracellular cAMP (FIG. 1, unpublished data). Moreover, these effects are specific to TGR5 as the effects of berberine are lost in cells lacking TGR5.

Figure 2A:
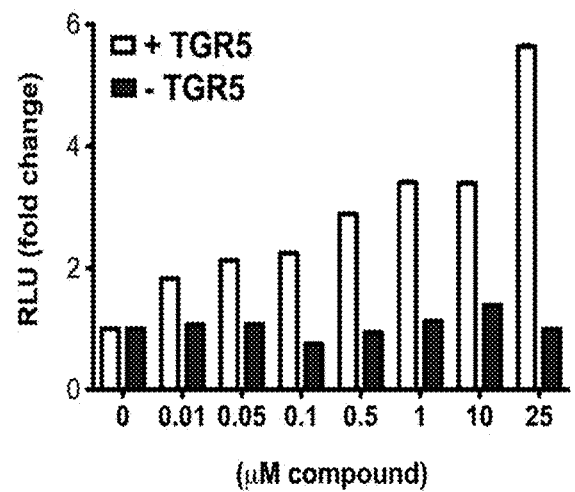
FIG. 2(A) HEK293 cells lacking or overexpressing TGR5 were treated with increasing doses of berberine for 16 hours and TGR5-reporting activity was evaluated using luciferase assays.
Figure 2B:
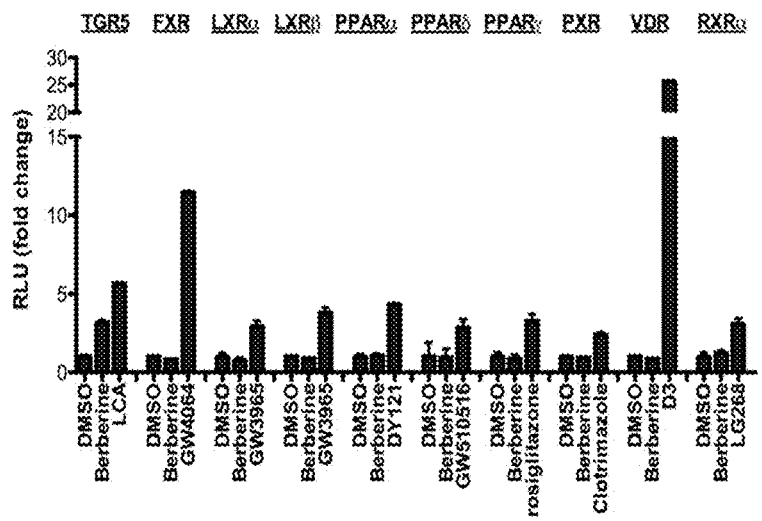
FIG. 2(B) Ability of berberine to activate metabolic nuclear receptors was evaluated in comparison to native ligands. All ligands were used at a 10 µM concentration.

Thus far, our studies also indicate that berberine does not activate other metabolic nuclear receptors (FIG. 2, unpublished data). We are currently engaged in efforts using time-resolved FRET analysis to prove bona fide ligand binding of berberine to TGR5. Our current efforts are also aimed at extending these studies in vivo to murine type II diabetic models (using high fat diet feeding) with and without the TGR5 receptor. Confirmation of the berberine effect was evaluated using q-RT-PCR to assess activated TGR5 target genes including inflammatory gene expression and deiodinase-2.

Berberine has been used to treat gastrointestinal problems traditionally particularly bacterial diarrhea. Berberine is substantially active in the intestinal tract and may induce TGR5-mediated signaling causing an increase in the secretion of GLP-1. This suggests that berberine showed antidiabetic effect partly via promotion of GLP-1 secretion.[13] In vitro, berberine concentration-dependently stimulated GLP-1 release in NCI-H716 cells.[14] Berberine also promoted both prohormone convertase 3 and proglucagon mRNA expression. This demonstrates that berberine showed its modulation on GLP-1 via promoting GLP-1 secretion and GLP-1 biosynthesis. Berberine concentrates in intestine and induces GLP-1 secretion in the intestinal tract and is poorly absorbed into the bloodstream from the gut. However, the mechanism through which berberine promotes GLP-1 secretion and reduces blood glucose is not entirely clear at present.

Berberine suppresses food intake, which may partly due to enhancement of GLP-1 release. However, a high dose of berberine is required to show significant efficacy in patients with diabetes or obesity, which is possibly due to the poor physicochemical properties of berberine.

With berberine in hand, aiming to improve its physicochemical properties, overcome its limitations, and enhance its therapeutic efficacy, we set out to develop a series of more effective berberine derivatives that activate and selectively target the TGR5 to promote secretion of GLP-1 in the intestine without significant systemic exposure. These derivatives are substantially active in the gastrointestinal (GI) tract to induce TGR5-mediated signaling, with such interaction causing an increase in the secretion of GLP-1. The derivatives are designed to be substantially non-permeable or substantially non-bioavailable in the blood stream and limit their exposure to other internal organs such as gall bladder and heart.

Figure 19:
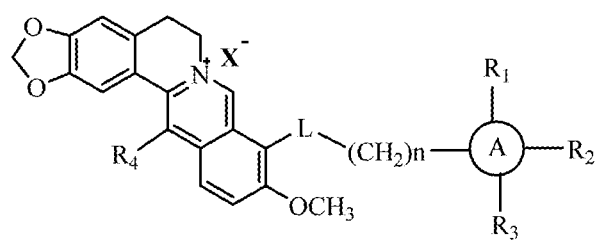
FIG. 19: Berberine derivatives and pharmaceutically acceptable salts (compounds contain berberine moiety and/or fragments conjugated with N- or O-substituted chemical entities).
Figure 20:
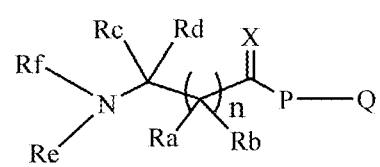
FIG. 20: γ-Aminobutyric acid (GABA) derivatives, including pharmaceutically acceptable salts.
Figure 21:
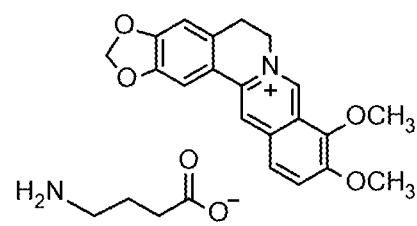
FIG. 21: A chemical structure of the berberine-GABA salt.
Figure 22:
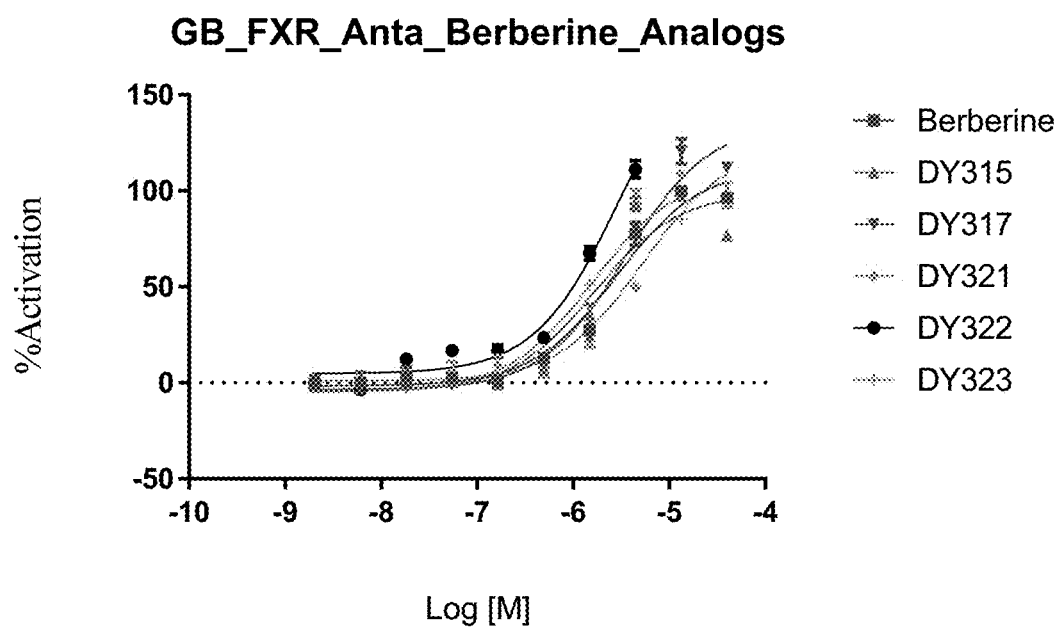
FIG. 22: GeneBlazer FXR cell-based assay.
Figure 23:
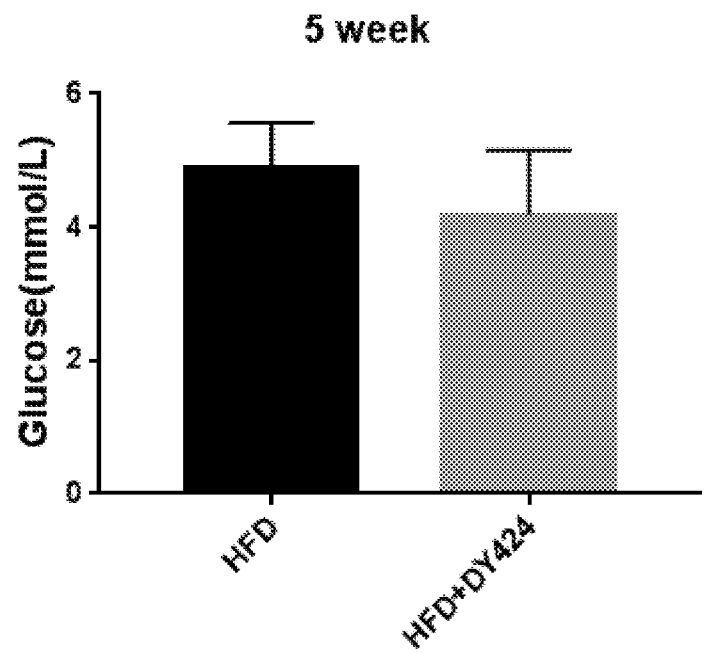
FIG. 23: Improvement of glycemic control in HFD obese mice by DY424. Plasma levels of non-fasting glucose were measured at the end of the 5-week treatment period.

Design & Synthesis of TGR5 and FXR Modulators by a Focused Diverse Library that would Provide Structure-Activity Relationships (SAR) in Primary Screens for Biological Activity of the N- or O-Substituted Berberine Derivatives The first strategy involved the synthesis of berberine-hybrid molecules. We reasoned that berberine-hybrid molecules the combination of different pharmacophores may lead to compounds with interesting antidiabetes and antiobesity profiles. We prepared a series of covalently linked berberine-hybrids in which the desired hybrids were prepared by a nucleophilic aromatic displacement reaction of berberine.[15] The chemical structures of library will be characterized by $^1$H and $^{13}$C NMR and element analysis. We reasoned that a linker, perhaps with hydrogen bond acceptors such as nitrogen or oxygen, that fits suitably in the TGR5 or FXR binding pocket and thus could provide conformational flexibility and positional adaptability. N- or O-substituted berberine derivatives that are hybrid compounds, which would have tissue-selective effects, specifically, the gut-restricted TGR5 agonists or FXR antagonists and other benefits. Moreover, further substitution on the 9 extended-position (FIG. 19) may also provide an opportunity for potential hydrogen bonds or π-π interactions.

Berberine hybrid compounds show potential diabetes treatment and appetite suppressant activity. These compounds are interesting since they increase the design potential of non-systemic related compounds and hence represent a novel and unexplored strategy for therapeutic drug discovery. The berberine hybrid compounds described herein may provide a promising treatment for diabetes and obesity by virtue of their properties as excellent diet pills and appetite suppressants to exert their therapeutic effects locally in the GI tract.

Figure 15:
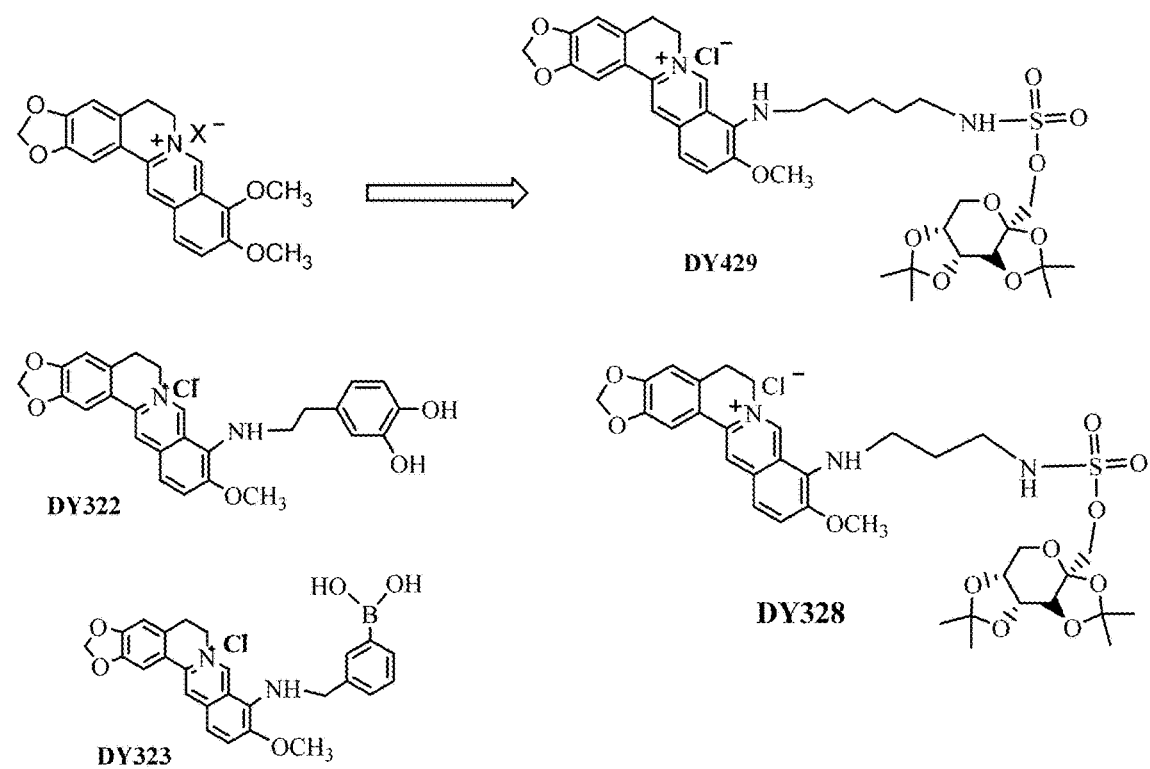
FIG. 15: Representative examples of berberine derivatives.
Figure 16:
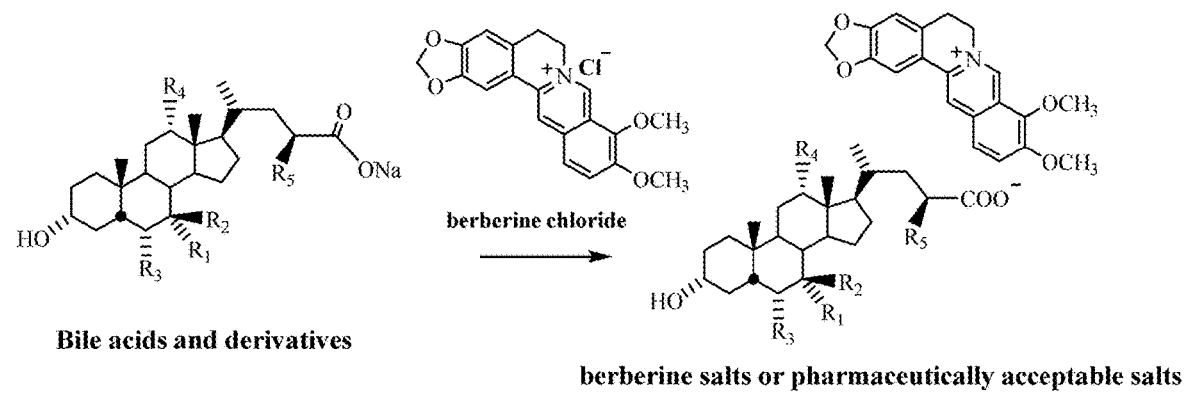
FIG. 16: General scheme for preparation and characterization of berberine-bile acid organic ion pairs or pharmaceutically acceptable salts.

To improve efficacy and safety, the 9-position of the berberine moiety has been incorporated into a series of bioactive agents or medical interventions. These frameworks are connected together to form hybrid molecules which would be even better than berberine itself. Exemplified with DY319 (FIG. 24) and DY429 (FIG. 15), which are berberine hybrids with topiramate (topi), which is a sugar sulfamate anticonvulsant drug that is marketed worldwide for the treatment of epilepsy and migraine. In late 2012, topiramate was approved by FDA in combination with phentermine named Qsymia for treating obesity.[16] Recent preclinical and clinical observations have suggested that topiramate possesses antimetabolic dysfunction activity, which could be useful for treating obesity which is known to increase satiety (satisfaction) and alter taste. However, the precise mechanism of topiramate's effect on weight is unclear. To our knowledge, this is the first example of berberine-topi hybrid.

Preparation and Characterization of the Berberine Bile-Acid Salts

A focused stereochemically diverse library of compounds according to FIG. 1 provided structure-activity relationships (SAR) for the TGR5 agonism and FXR antagonism modulators. In addition to berberine-hybrid molecules, we also identified berberine pharmaceutically acceptable salts, berberine-bile acid salts, berberine-bile acid derivative salts, including berberine-tauro-, berberine-glyco, bile acid salts, berberine-bile tauro, glyco-derivative salts, berberine-acid salts, and other pharmaceutically acceptable salts. These compounds contain a berberine moiety and/or fragments thereof, which are conjugated to bile acids or bile acid derivatives and which demonstrate bioactivity similar to or greater than berberine while maintaining the tissue-selective effect. The designed berberine-bile acid salts and pharmaceutically acceptable salts are poorly absorbed into the blood and lead to gut-restricted TGR5 activation, or lead to the gut-restricted FXR inhibition, (i.e., devoid of FXR agonism in the intestine). These berberine-bile salts and pharmaceutically acceptable salts could be non-absorbed synthetic TGR5 modulators, or intestinal FXR antagonists, or a dual FXR/TGR5 axis modulation since bile acids cover the same chemical space of the endogenous activators, they are intrinsically promiscuous toward FXR and TGR5. Our invention represents a rational strategy to circumvent obesity and side effects thereof.

Using berberine and bile acid scaffolds as templates, we designed, synthesized, and screened a chemical library to search for ligands that have higher affinity and/or specificity for TGR5, FXR, and dual modulators. The salts formed between the aromatic berberine cation and a carboxylate anion of bile acids and their derivatives were synthesized and used to evaluate their biological activity. To obtain hydrophilic salts, the bile acids and their derivatives were transformed to the corresponding sodium salts. An aliquot of the sodium salts of bile acid and their derivatives previously dissolved in a small volume of water followed by treatment of the berberine chloride with a series of sodium salts in stoichiometric proportions resulted in the production of berberine salts as a 1:1 (berberine:bile acid formation of the salts) as bright yellow precipitates that were collected by crystallization with ethyl acetate and dried at 60° C. under vacuum. The characterization was made by $^1$H NMR and $^{13}$C spectroscopy, and combustion analysis. The organic anions of bile acid derivatives and the berberine cation were in stoichiometric proportion as confirmed by NMR analysis.

Physiologically, bile salts exist in the intestine via enterohepatic circulation, therefore, bile salts may affect intestinal absorption of berberine if ion-pair complexes are formed between berberine and the bile salts or bile acid derivative salts. We reasoned that the formation of organic ion pairs (salts) between berberine with bile acids or bile acid derivatives, or other agents may be a contributing factor for the remaining of derivatives in the intestines. Berberine salts are absorbed in the intestine slowly because they precipitate in the fluids of the stomach and intestine, their rate of dissolution may become the factor limiting the rate of absorption. The positive charge of berberine would be masked by the negative charges of bile acids, which are absorbed slowly in the intestine. Specifically, as compared with berberine, the anti-diabetic efficacy of berberine salts might be significantly improved by activation of TGR5 to stimulate intestinal GLP-1 (glucagon-like peptide-1), and peptide YY (PYY) release. Thus, the idea was to make low-absorbed TGR5 agonists to associate berberine (isoquinolinium cation) with an aliphatic moiety (bile acid anion) to form an organic ion pair (salt). Note that the berberine cation associated with various organic and inorganic anions has been reported to investigate the effect of ion pairing on the fluorescence of berberine.[17] However, berberine-bile acid salts for obesity and as an anti-diabetic has not been investigated.

Notably, berberine has a quaternary ammonium ion moiety which is believed to have non-systemic effects compared to the same compounds without quaternary ammonium ion moiety.[18] Completely ionized drugs, e.g., quaternary ammonium compounds such as berberine derivatives, are absorbed with great difficulty. Neutral substances (i.e., non-ionic) with very low lipid solubilities like sulphaguanidine are absorbed slowly. This may be explained based on the assumption that the barrier between the gastrointestinal tract and the bloodstream behaves towards foreign compounds as a lipoid membrane.

Novel berberine-bile acid salts could be new diet pills, which don't dissolve into the blood, but remain in the intestines as a contributing factor for selectively activating intestinal TGR5 and increase secretion of GLP-1. Molecular size and physico-chemical properties could be the more important characteristics to make predictions concerning the gastrointestinal absorption of drugs. Berberine cations complexed with the carboxylate anion of a bile acid, or other compounds that have a carboxylate anion that would result in bulky salts could be poorly absorbed from the intestine based on Lipinski's rule.[19] Specifically, by taking advantage of the berberine tissue-selective effect, berberine-acid complexes may be non-absorbed TGR5 agonists, i.e., salts that would improve the efficacy of berberine in non-systemic exposure.

Discovery of Berberine Derivatives with Dual TGR5 Agonistic and Farnesoid X Receptor (FXR) Modulatory Activity A series of dual TGR5 agonism/FXR (farnesoid X receptor) antagonism modulators have also been synthesized and identified. These compounds possess dual TGR5 agonistic and FXR modulatory activity. Interestingly, these compounds displayed TGR5 agonistic activity with considerable FXR antagonistic potency in a single molecule. The discovery of highly selective dual TGR5 agonism/FXR antagonism modulators could maximize exposure in the gastrointestinal tract (GI) tract to stimulate GLP-1 and PYY release, devoid of FXR agonism in the intestine and liver, effectively reducing intrahepatic bile duct pressure, and avoid TGR5 agonist-induced gallbladder filling, represents a rational strategy to circumvent the obesity and side effects.

This work addresses an important issue in the early-stage development of therapeutically useful dual TGR5/FXR modulators which represent a novel and unexplored strategy.

TGR5 mediates several non-genomic functional responses induced by the binding of bile acids. TGR5 agonism induces the secretion of clinically relevant glucagon-like peptide 1 (GLP-1) and peptide YY (PYY) raising expectations of an alternative therapeutic mechanism for the treatment of obesity. However, activation by ligands of TGR5 stimulates its exposures to other tissues such as heart and gallbladder resulted in unwanted side effects, implying the benefits and potential risks of using TGR5 agonists for obesity treating. This formidable challenge may require a FXR/TGR5 axis modulation since recent studies suggest that there are indications that FXR plays a role in human obesity and diabetes, inhibiting FXR in the intestine might be a potential target for anti-obesity drugs.

Figure 18:
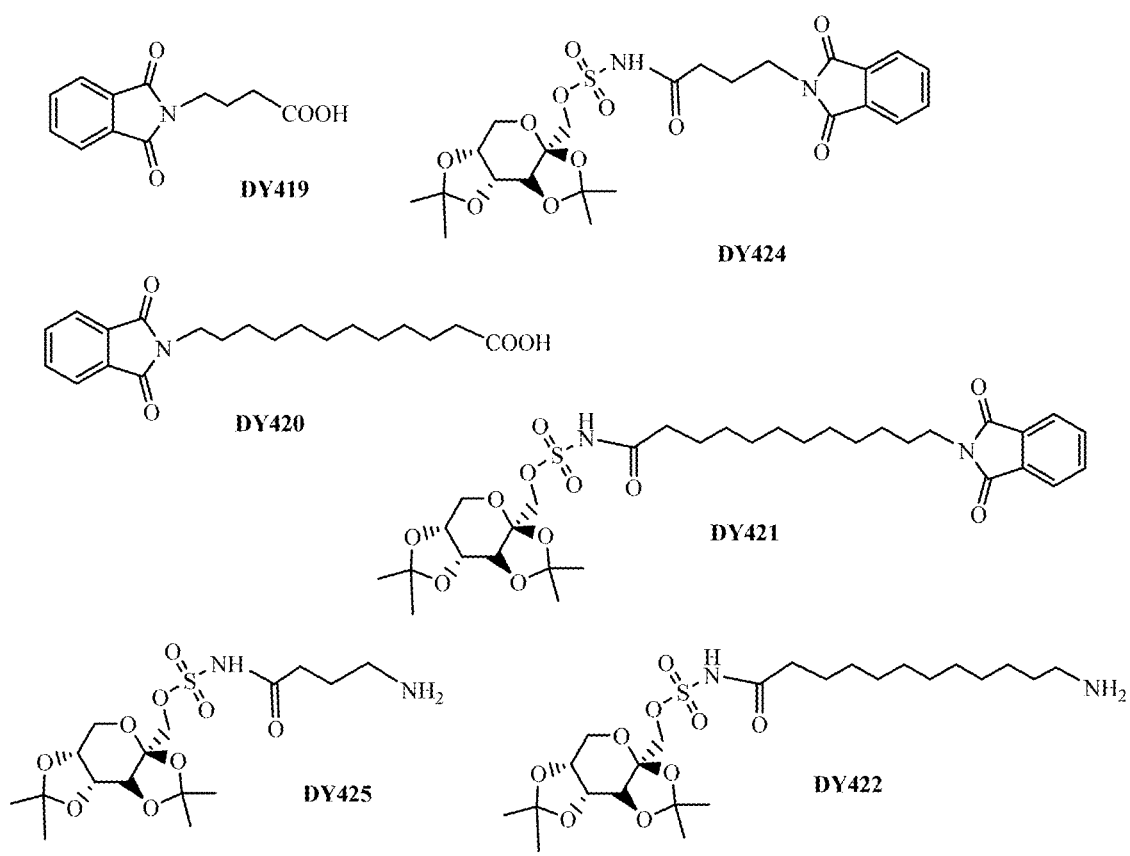
FIG. 18: Representative examples of γ-aminobutyric acid derivatives.

Discovery of γ-Aminobutyric Acid Derivatives with Farnesoid X Receptor (FXR) Modulatory Activity Following our earlier work in an endeavor to further improve lead selectivity against the FXR, a series of FXR modulators were designed, synthesized, and their TGR5 and FXR synergistic activity was evaluated in vitro. We have recently identified γ-aminobutyric acid derivatives from a small chemical library as novel FXR antagonists. Interestingly, the in vitro data showed that γ-aminobutyric acid did not exert FXR inhibition. However, γ-aminobutyric acid derivatives, exemplified with DY419 (FIG. 18), activated FXR receptor to exert FXR antagonistic biological function, implying that the γ-aminobutyric acid derivatives could be further developed to improve their potency and binding affinity for the FXR.

γ-Aminobutyric acid amides were synthesized by coupling γ-aminobutyric acid with a series of amines or their pharmaceutically acceptable salts or other agents and/or medical interventions using coupling reagent and characterized by $^1$H, $^{13}$C NMR and combustion analysis. As we expected, most of them exhibited FXR antagonistic activity. γ-Aminobutyric acid (GABA) is the major principal inhibitory neurotransmitter in the mammalian central nervous system. Recently study suggested that GABA appears to be beneficial to T2D. As FXR ligands and the diabetes linkage were first identified here, these studies could eventually lead to novel anti-obesity agents.

Based on these experiments, we reasoned that derivatives of γ-aminobutyric acid (a naturally occurring substance), have the potential to reduce the inflammation and protect the pancreatic beta cells from autoimmune destruction. γ-Aminobutyric acid derivatives as FXR antagonists may contribute to the food intake or body weight, or may improve glycemic control and long-term complications in diabetes, and may be useful with TGR5 agonists in the combination clinical trials. Importantly, γ-aminobutyric acid has already been used in humans, and its side-effects are well documented and understood. The identification of γ-aminobutyric acid derivatives here improved their biological activity on FXR, raising the possibility of a rapid translation of these γ-aminobutyric acid derivatives to clinical use in the treatment of obesity and diabetes.

Significance of Combination of TGR5 Agonist and FXR Antagonist

TGR5 Agonist and FXR Antagonist Combination Therapy

It is hypothesized that hybridizing two compounds that target TGR5 and FXR with anti-obesity activity might yield a potent and selective molecule with minimal side effects. Inhibitors of FXR[20] are useful in treating or preventing obesity, type 2 diabetes/insulin resistance and non-alcoholic fatty liver disease, therefore, a combination of a TGR5 agonist and an FXR antagonist might be a valuable pharmacological tool for treating obesity, in addition to combinations of TGR5 agonists and FXR antagonists with other drugs.

It is proposed that a TGR5 agonist combined with an FXR antagonist that is orally administered and retained in the intestine and that inhibits intestinal FXR and has no effect on FXR expressed in liver would have utility in the treatment of patients with obesity, insulin resistance and related diseases. A combination, such as a combined preparation or pharmaceutical composition comprising, at least one TGR5 agonist selected from berberine derivatives, or bile acid derivatives, or natural TGR5 agonists, and FXR antagonist chosen from berberine derivatives, or natural FXR antagonists, or bile acid derivatives, or γ-aminobutyric acid derivatives, or other agents and/or medical interventions is a novel strategy to exert synergistic activities. The ratios of the respective amounts of TGR5 agonist and of FXR antagonist thus vary in consequence. Preferably, the weight ratio of TGR5 agonist or its pharmaceutical acceptable salt to FXR antagonist from 1:1 to 5:1, preferably from 2:1 to 5:1. It is to be understood that this combination is not limited to the particular methodology, protocols, reagents and ratio described herein as these may vary.

Major advantages of combination therapy include, but are not limited to:
 More than one cause of action can be targeted (TGR5 and FXR) and complimentary actions can be achieved;
 A combination treatment could increases the number of mechanisms potentially capable of reducing unwanted side effects due to synergistic effects and low individual dose; and
 Could reduce the possibilities of complications of diabetes.

Results

In the present study, a series of novel berberine derivatives, bile acid derivatives, and γ-aminobutyric acid derivatives or pharmaceutically acceptable salts were designed and synthesized to develop long-acting drug candidates for treating obesity and related metabolic disorders. These compounds demonstrated a suppression of food intake and body weight in high-diet induced mouse models. Dose-dependent increase in glucose uptake by C2C12 cells exposed to berberine derivatives, bile acid derivatives, and pharmaceutically acceptable salts at the indicated concentrations for 2 h were evaluated. Notably, berberine derivatives and bile acid derivatives, or their pharmaceutically acceptable salts can also induce insulin secretion from pancreatic beta cells of wild type mice but not in TGR5 knock-out mice, suggesting a novel role of TGR5 in maintaining glucose homeostasis. Taken together, these results suggested that berberine derivatives and bile acid derivatives, or their pharmaceutically acceptable salts may have a potential benefit in preventing obesity and diabetes.

Effects of Berberine Derivatives on Body Weight

Interestingly, berberine derivatives and their pharmaceutically acceptable salts induced diminution of food intake and body weight in a mouse model of obesity probably due to expression levels of satiety hormones such as GLP-1 and PYY.

Since bile salts exist in the intestine via enterohepatic circulation and the systemic expression of the TGR5 in the intestinal tract has led to promising therapies. In contrast to systemic therapy, localized stimulation of TGR5 by its ligands within the colon to initiate GLP-1, PYY release should be possible, because the colon has been identified as a major source of GLP-1 secretion after non-systemic drugs treatment.

It is conceivable that berberine derivatives and their pharmaceutically acceptable salts exerted anti-obesity effects in our experiments. The mechanism may go through the TGR5-GLP-1 pathway. Studies have also indicated that agonism of TGR5 is a promising therapeutic target for the treatment of diabetes and obesity.[21] In animal studies, they show significantly decreased food intake and body weights compared to normal mice. Therefore, a TGR5 agonist such as a systemic agonist is novel and unique, which have important functions in the body by lowering glucose levels. However, a systemic TGR5 agonist has unwanted side effects. As such, the non-systemic agonism of TGR5 is an alternative to overcome current limitations in treating diabetes and obesity to target the intestine. Unlike systemic agonism of TGR5, berberine derivatives and their pharmaceutically acceptable salts stimulate the TGR5-mediated release of GLP-1 in the intestine but are substantially non-systemic thereby limiting their exposure to other internal organs (e.g., gall bladder, heart, brain, etc.). In some embodiments, the derivatives are designed to be substantially non-permeable or substantially non-bioavailable in the blood stream. Since anti-obesity drugs should always be considered as a chronic treatment excluding side effects in a long-term perspective. Therefore, using berberine derivatives and their pharmaceutically acceptable salts as non-bioavailable in the blood stream for obesity is currently considered as a strategy of choice.

Figure 3:
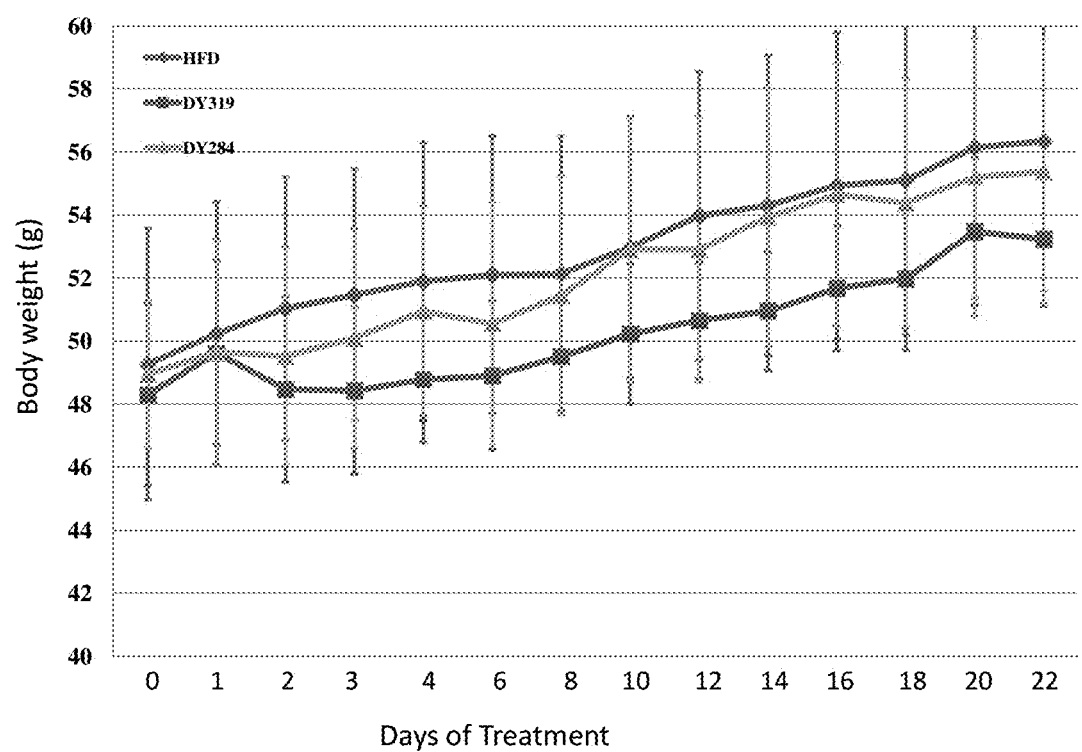
FIG. 3: Effects of berberine derivatives on high fat diet (HFD)-induced obese mice. HFD mice were treated with berberine derivatives or vehicle control (0.5% sodium carboxymethyl cellulose double distilled water) via oral gavage (30 mg/kg BW) for 22 days. Four groups of HFD mice (n=6) fasted for 4 h received daily gavage for 5 consecutive weeks of control solution, 30 mg/kg berberine derivatives suspended in a total volume of 2 mL of control solution at the beginning of the feeding cycle (lights off).
Figure 4:
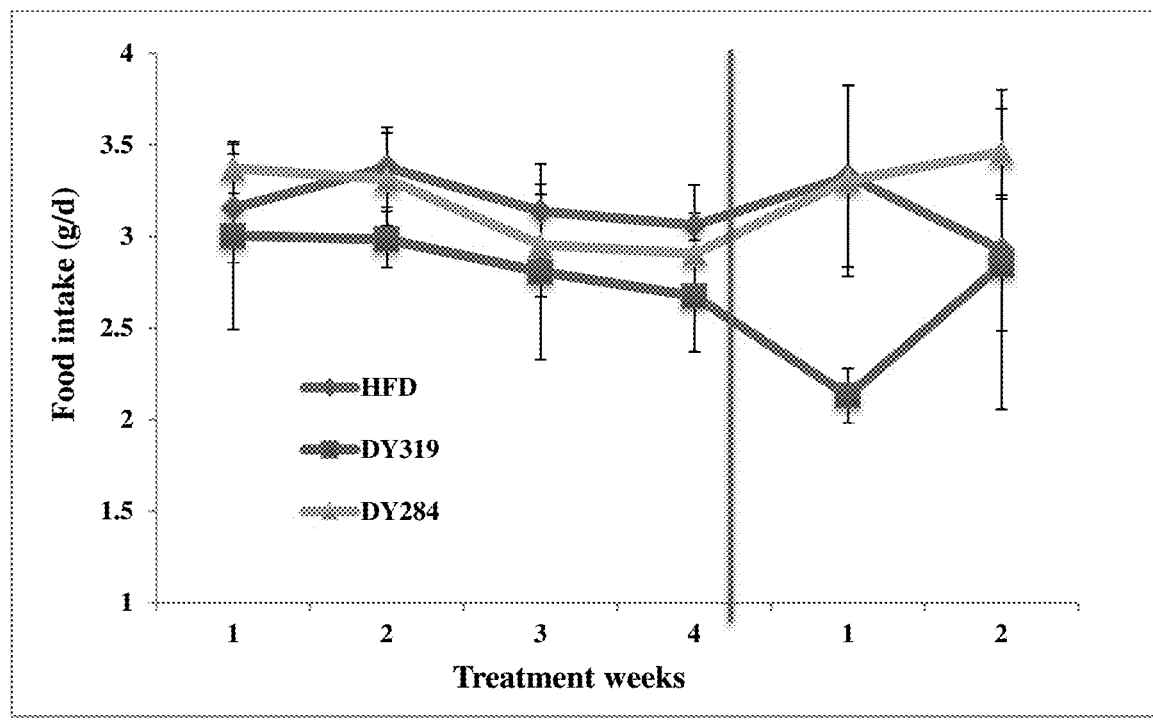
FIG. 4: Effects of berberine derivatives on food intake in DIO (diet induced obese) mice. Daily food intake of male C57BL/6J mice (n=6) orally administered with vehicle (HFD) or 30 mg/kg/day of berberine derivatives during five dosing weeks and one recovery week. DY319 reduced body weight partly because mice appetite was lowered during the food intake in the first week. 12 days after treated high dosage of compounds, DY319 reduced mice food intake. Daily food intake of male mice (n=6) orally administered with vehicle (HFD, a high-fat diet) and berberine derivatives during 4 weeks of 30 mg/kg/day and 1 week of 50 mg/kg/day. Food intake was measured daily for the duration of the experiment and corrected for spillage. All animals were sacrificed on week 5 of the treatment with the exception of the control (n=3) and 30 mg/kg groups (n=3) that were sacrificed on the week 5 of the experiment following completion of the recovery phase.
Figure 5:
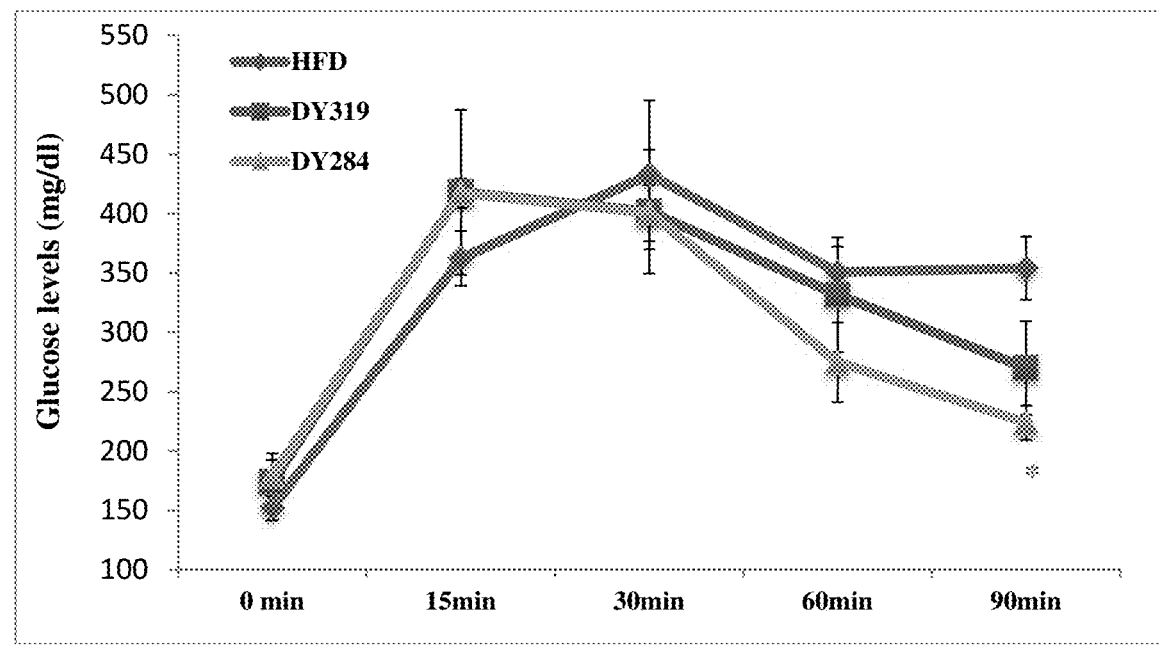
FIG. 5: Effects of berberine derivative and bile acid derivative on glucose tolerance tests, DY319 and DY284 lowered fasting glucose levels and improved glucose tolerance.
Figure 6:
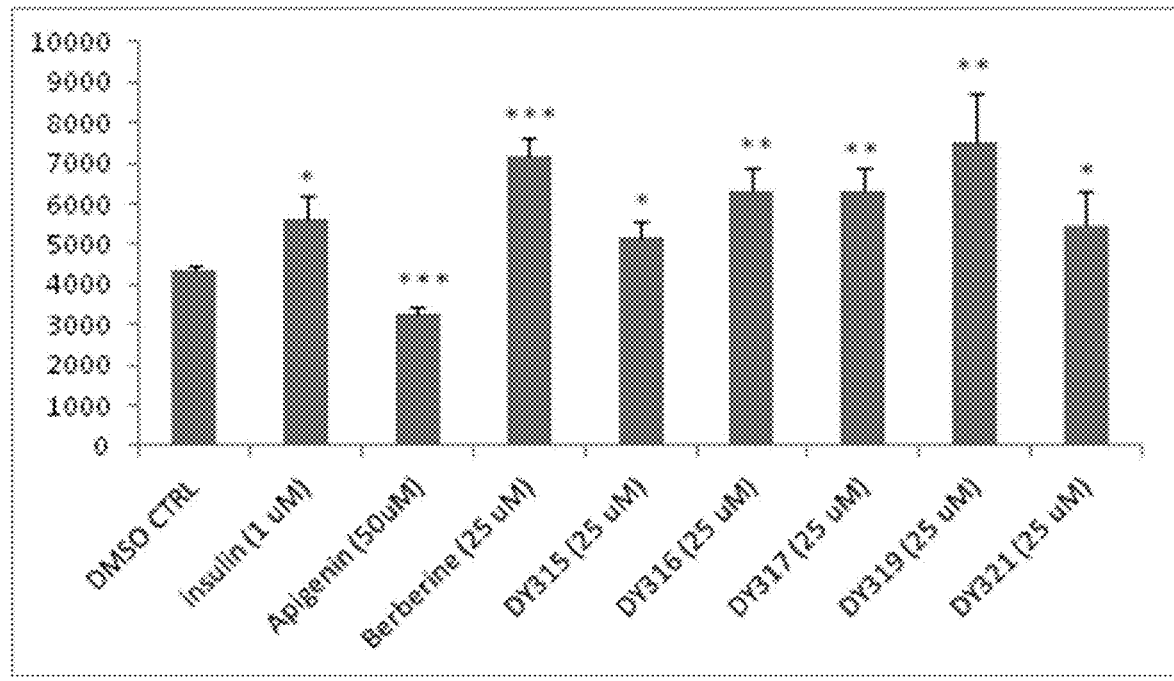
FIG. 6: Effects of glucose uptake on berberine and bile acid derivatives, dose-dependent increase in glucose uptake by C2C12 cells at the indicated concentrations for 2 h. Results are expressed as mean±SEM, n=3, independent experiments. **p<0.01 vs control.
Figure 7:
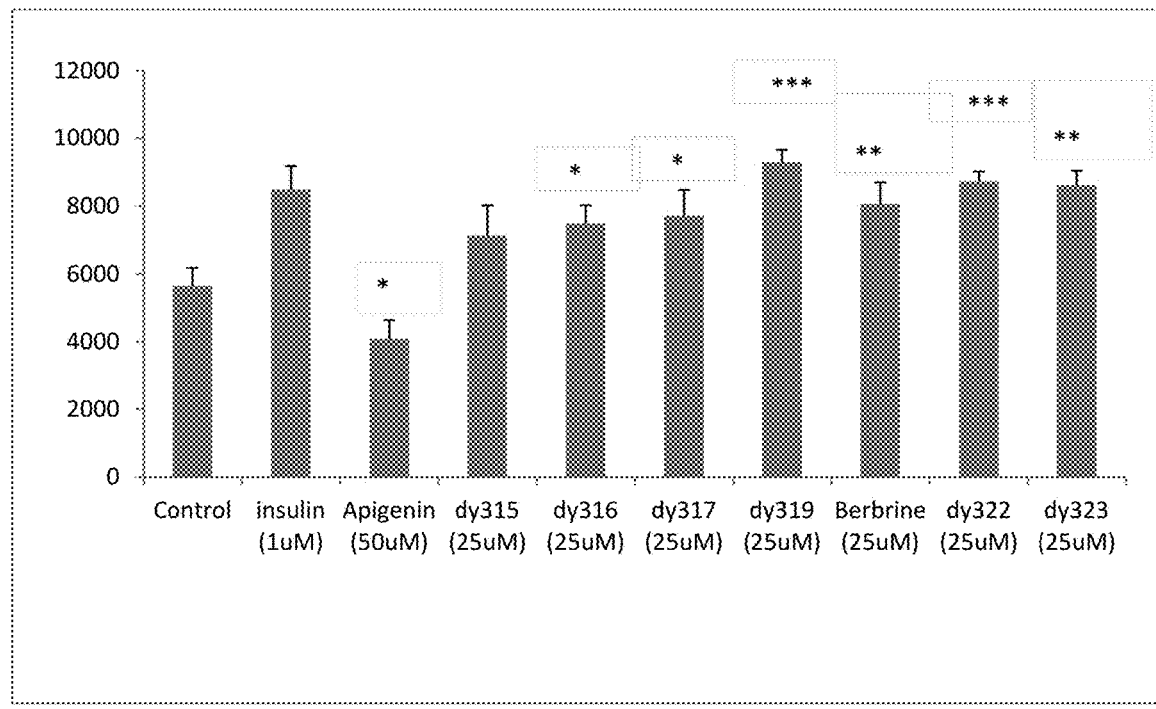
FIG. 7: Effects of glucose uptake on berberine and bile acid derivatives, dose-dependent increase in glucose uptake by C2C12 cells at the indicated concentrations for 2 h. Results are expressed as mean±SEM, n=3, independent experiments. **p<0.01 vs control.

The berberine derivatives and their pharmaceutically acceptable salts were evaluated in a study where they were administered daily for 5 weeks acute study measuring the effect on body weight in male DIO mice. The selected derivatives, especially compound DY319 at 30 mg/kg caused dose dependent reductions in food intake and body weight. The results of which are displayed in FIG. 3.

Beneficial effects of berberine derivatives and their pharmaceutically acceptable salts were observed in diet-induced obesity (DIO) mice. As can be seen from the plots in FIG. 3, there is a dose dependent decrease in body weight gain out to be administered daily for 5 weeks, between each dose group and vehicle control throughout the remainder of the administered daily for 5 weeks experiment. Although the decrease in body weight gain appears to last for administered daily for 5 weeks, the effect on body weight was maintained throughout the dosing period (data not shown). DY319 seems effective in body weight loss; however, since the dose used is extremely low as compared with 500 mg of berberine necessary for the treatment, it is assumed that the effective dose for berberine derivatives could increase to 50-75 mg/kg. The failure of appetite control is a major reason for weight gain. The mechanism of weight loss for DY319 could be due to increased satiety.

To assess the appetite-suppressing properties of berberine derivatives, we orally administered different doses to evaluate their ability to suppress food intake in DIO (diet-induced-obese) mice. A significant reduction in food intake was seen in animals receiving 30 mg/kg per day of DY319. The results for the period show that DY319 is potent in the suppression of food intake, as can be seen, the inhibition was greater at a dose of 50 mg/kg, suggesting that DY319 affects food intake in part by increasing GLP-1 release which appears to be an excellent drug target for appetite control and the treatment of obesity.

The food intake of HFD-fed rats was reduced by DY319, particularly in the last 5 weeks. Note that DY319 possesses two unique structural properties, which contain a berberine moiety and topiramate attached at the C-9 position of berberine, so it is not surprising that DY319 could have biological activity as in the case of suppressing food intake. Since endocrine L cells of the small and large intestines secrete GLP-1 and GLP-1 could inhibit appetite or gastric emptying, GLP-1 may be a factor for the appetite-suppressing properties of berberine derivatives. However, the exact mechanism of how DY319 affect appetite remains to be further investigated.

Glucose tolerance tests performed on each mouse on the last week of treatment. For the glucose tolerance test (GTT), after an overnight fast, mice were injected intraperitoneally with glucose (2 g/kg body weight). Blood was sampled from the tail vein before and 0, 15, 30, 60, and 90 min after the injection, and plasma glucose concentrations will be determined by a glucometer. Mice were euthanized by $CO_2$ asphyxiation.

Figure 24:
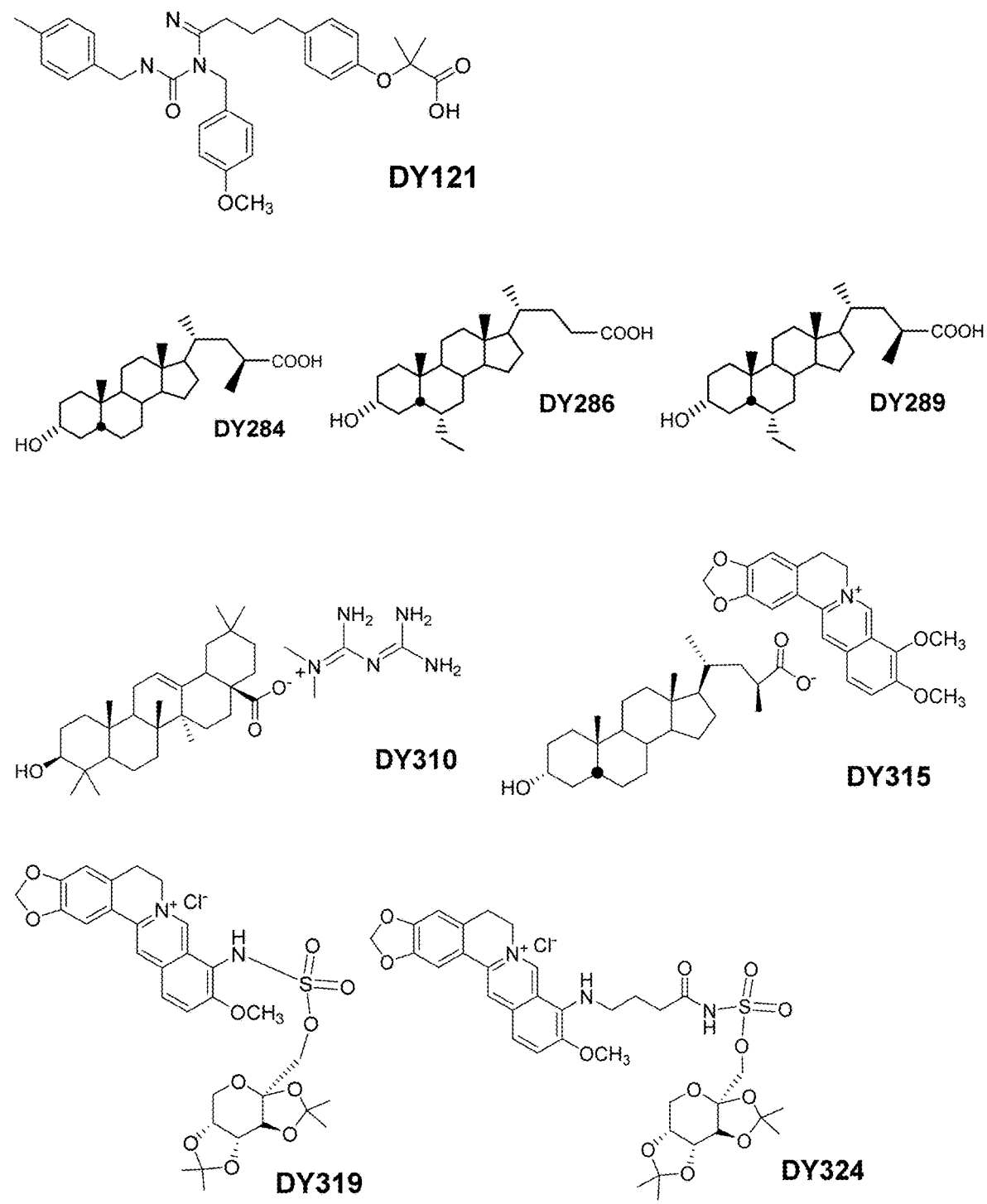
FIG. 24: Chemical structures of the tested compounds.

In vivo studies were conducted with DY284 (FIG. 24, a dual TGR5 agonism/FXR antagonism modulator). It has no significant effect on SHP, IBABP or FGF15 expression, however it suppressed cyp7a 5-fold in liver (p=0.08, n=6) which may be consistent with TGR5 activity (data not shown). It had no effect on inflammatory markers but the mice were not treated with LPS or the equivalent. The drug also suppressed FOXM1b 20-fold (p=0.03). It is therefore a candidate to inhibit hepatocellular carcinoma.

Effect of Berberine Derivatives on Glucose Uptake

The results of a preliminary study of the dose-dependent increase in glucose uptake in C2C12 cells show that berberine derivatives and bile acid derivatives display similar enhancement properties.

Effects of Berberine and Bile Acid Derivatives on Insulin Secretion

Figure 8:
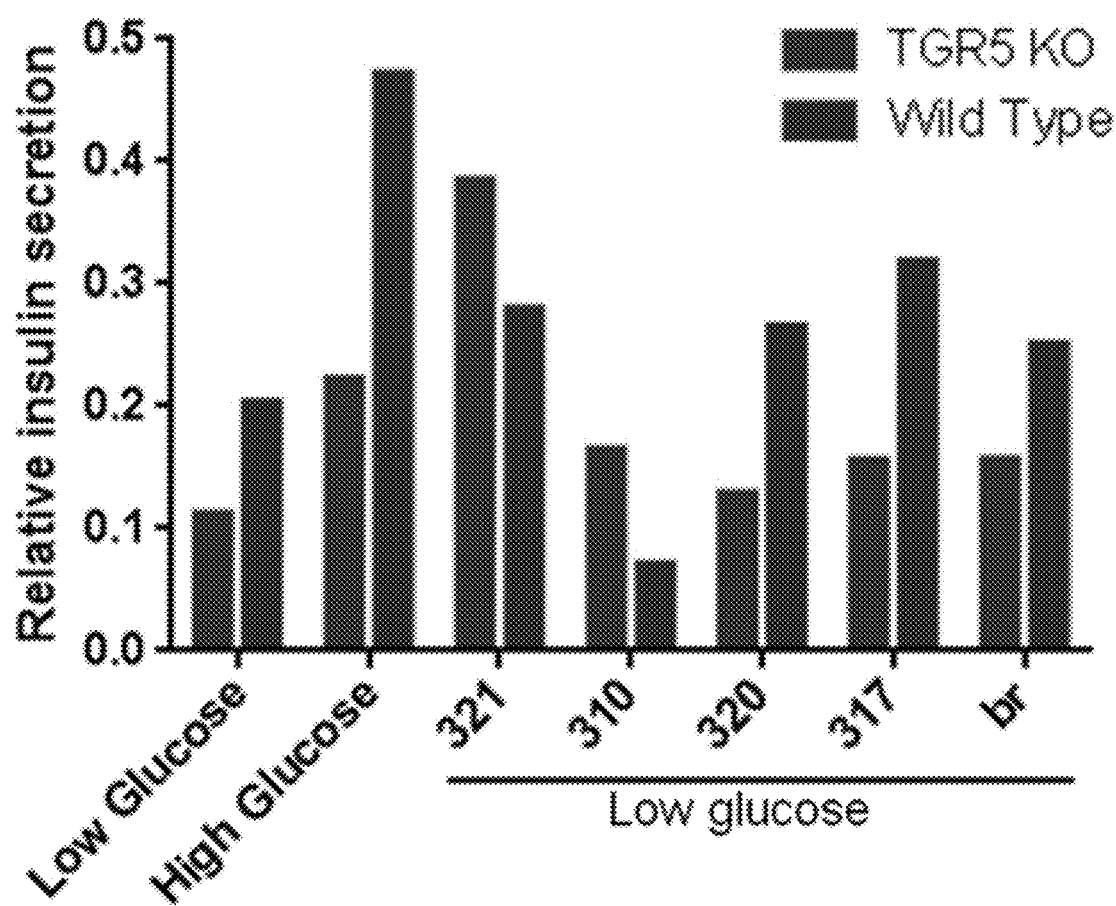
FIG. 8: Effects of berberine derivatives on insulin secretion.
Figure 9A:
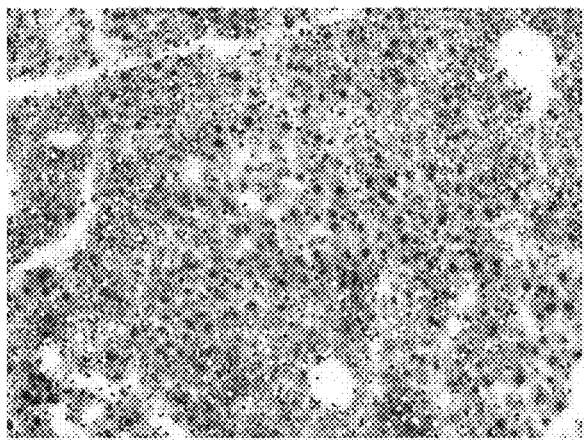
FIG. 9(A). lean mice.
Figure 9B:
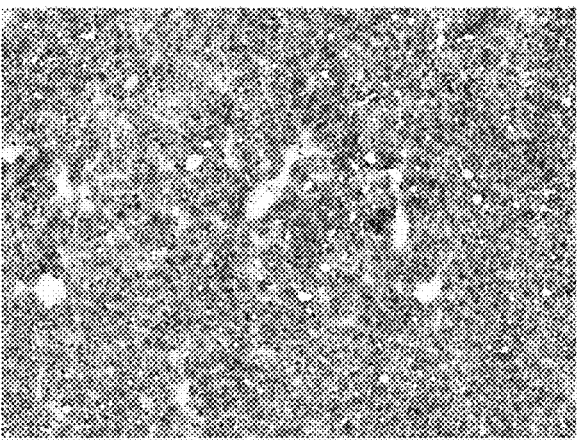
FIG. 9(B). DIO mice, FIG. 9(C). berberine, and FIG. 9(D). DY319. Intracellular lipids were stained with Oil Red O and visualized by phase-contrast microscopy (×200 magnification).
Figure 9C:
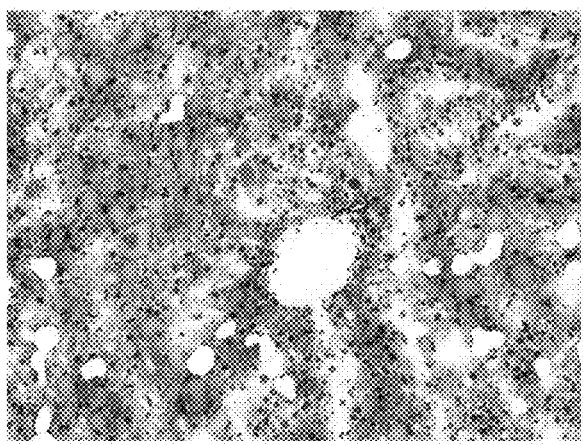
FIG. 9(A-D): DY319 and berberine prevent hepatic lipid accumulation.
Figure 9D:
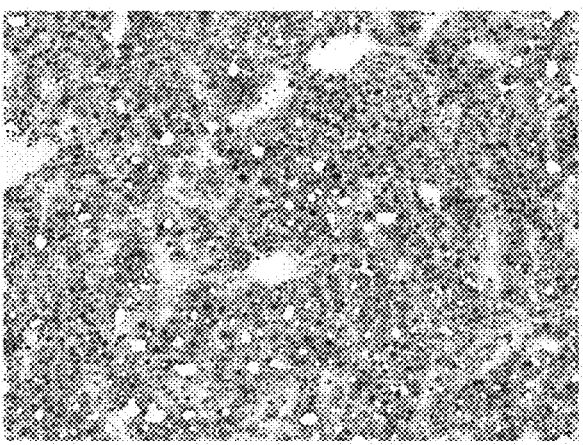

Our recent studies indicates that TGR5 agonists, specifically berberine and bile acid derivatives, can induce insulin secretion from pancreatic beta cells of wild type mice but not in TGR5 knock-out mice, suggesting a novel role of TGR5 in maintaining glucose homeostasis, (FIG. 8). We reasoned that the expression and activity of TGR5 in pancreatic beta cells that plays a critical role in increasing pancreatic beta cell mass, insulin synthesis and secretion. The objective of this study was to investigate the mechanisms of TGR5 signaling and evaluate new derivatives of berberine and bile acid in activating TGR5 in pancreatic beta cells to stimulate beta cell mass increase, insulin production and secretion.

Effect of Berberine and Bile Acid Derivatives on FXR Activity was Initially Assessed Using Transient Transfections with a Synthetic FXR Responsive Reporter Plasmid.

Figure 10:
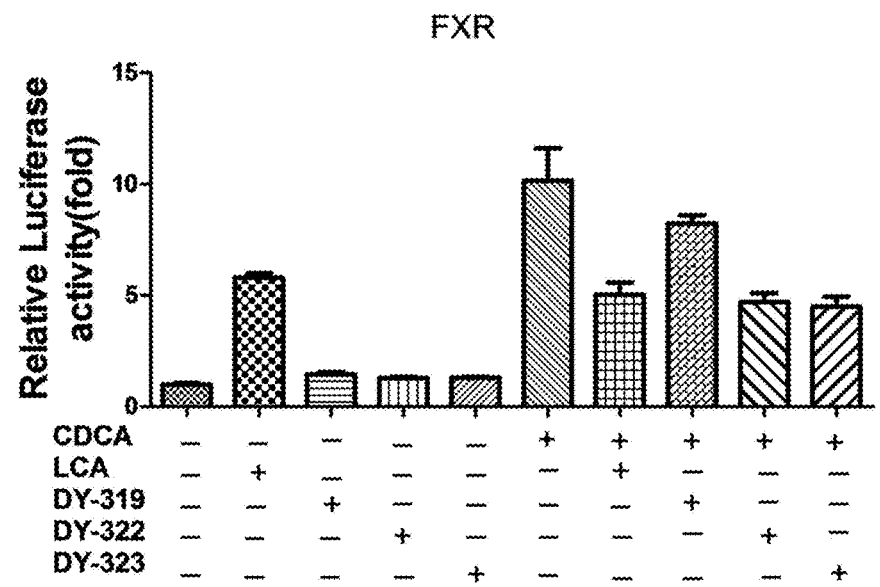
FIG. 10: Berberine derivatives inhibit FXR transactivation. HEK 293 cells were cotransfected with a luciferase reporter plasmid containing five copies of the Gal4 binding site and an expression vector for a Gal4 DNA binding domain FXR ligand-binding domain fusion protein, along with a CMX-β-gal internal control. CDCA: 100 µM, Compounds: 10 µM
Figure 11:
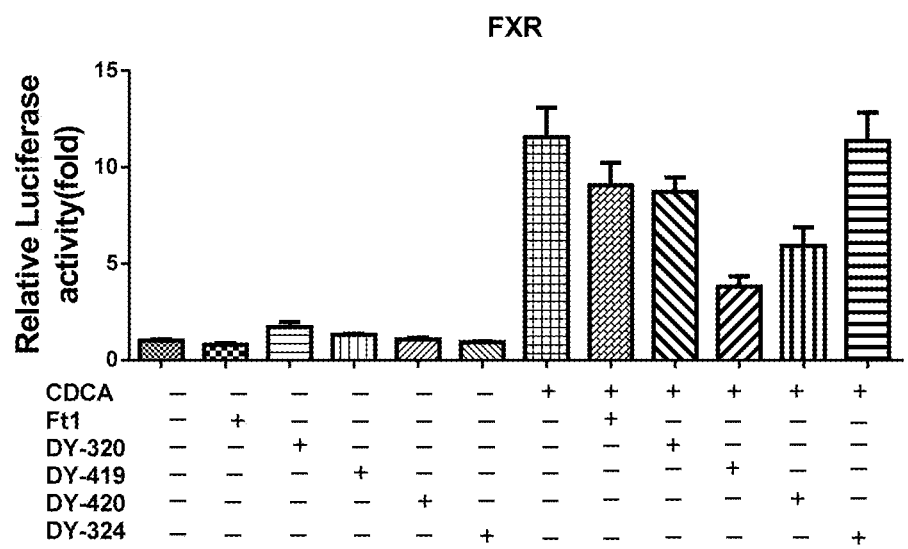
FIG. 11: FXR antagonists identified in the initial in vitro using a standard FXR-reporter assay, exemplified with DY419, an γ-aminobutyric acid derivative. DY419 alone had no effect on FXR activity, but it strongly inhibited FXR activation by chenodeoxycholic acid (CDCA), the most potent of the bile acid agonist ligands.

Berberine alone had no effect on FXR activity (FIG. 1), but its selected derivatives inhibited FXR activation by chenodeoxycholic acid (CDCA), the most potent of the bile acid agonist ligand for the FXR. In the presence of 100 µM CDCA, a concentration approximately threefold above that required for half-maximal activation of FXR, 10 µM selected berberine derivatives decreased FXR transactivation by nearly 50%. Berberine and its derivatives did not affect specific DNA binding by FXR-RXR heterodimers in vitro (data not shown) but did inhibit transactivation by a chimera consisting of the DNA binding domain of GAL4 and the ligand-binding domain of FXR (FIG. 10).

Berberine Derivatives and γ-Aminobutyric Acid Derivatives Inhibit FXR Transactivation.

Effect of berberine derivatives and γ-aminobutyric acid derivative on FXR inhibition was initially assessed using transient transfections with a synthetic FXR responsive reporter plasmid. HEK 293 Cells were treated with vehicle alone or 100 µM CDCA with or without compounds, as indicated. Results are luciferase expression normalized using the β-gal internal control.

Identification of Dual TGR5 Agonism/FXR Antagonism Modulators.

Several dual TGR5 agonism/FXR antagonism modulators have been synthesized and identified, exemplified with DY284, DY286, and DY289 (FIG. 24).

Figure 12:
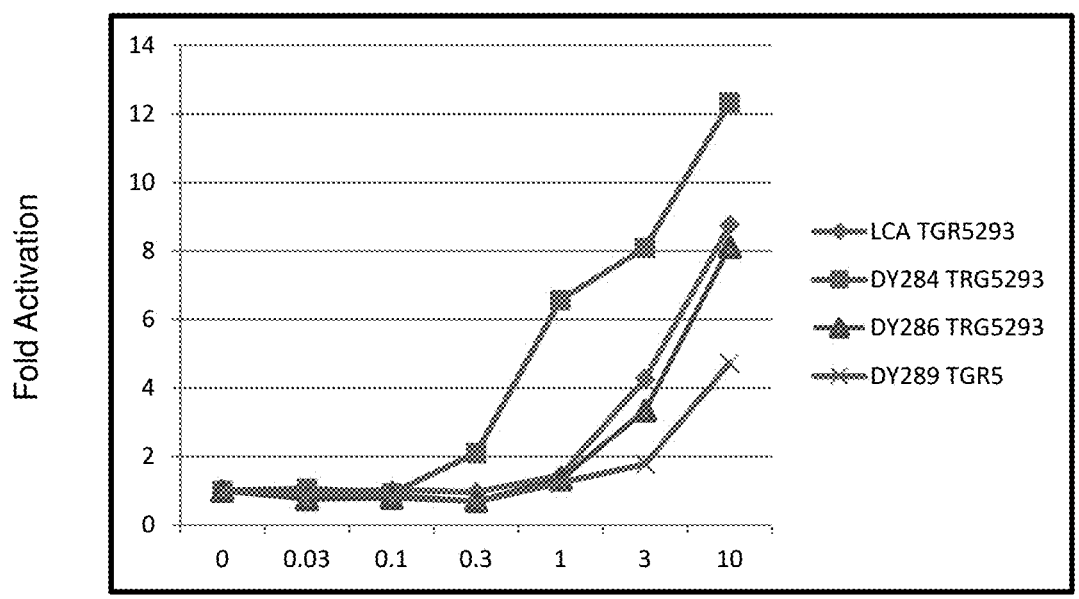
FIG. 12: Effects on TGR5 activity of DY284, DY286, and DY289: luciferase reporter activities of dual TGR5 agonism/FXR antagonism modulators.
Figure 13:
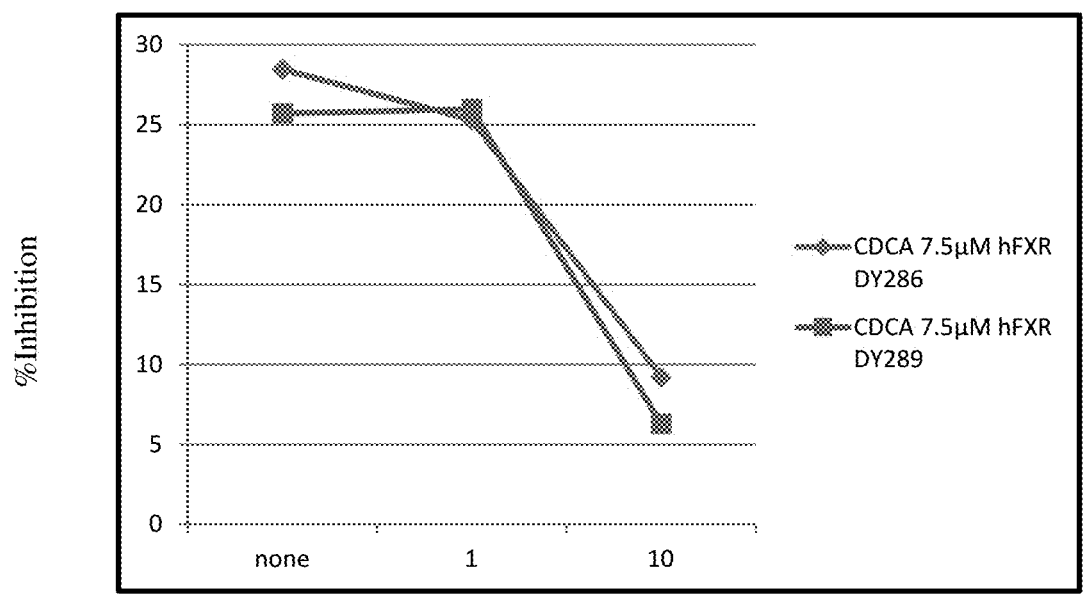
FIG. 13: Effect of dual TGR5/FXR agonism/FXR antagonism modulators on FXR activity were initially assessed using transient transfections with a synthetic FXR responsive reporter plasmid. DY286 and DY289 have been identified as dual TGR5 agonism/FXR antagonism modulators.
Figure 14:
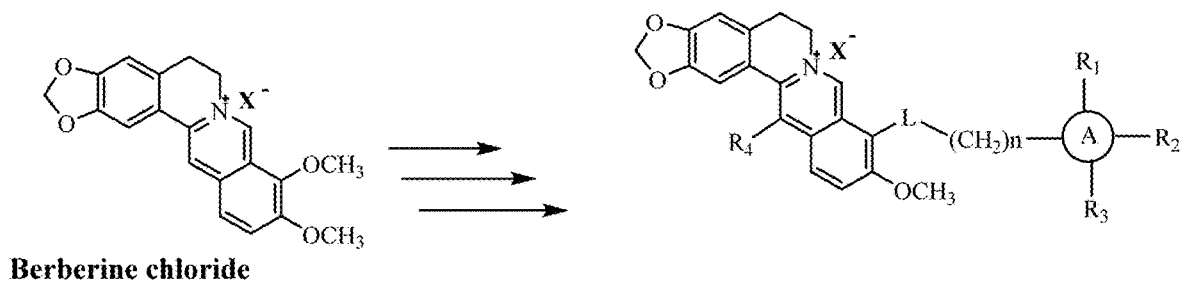
FIG. 14: General synthetic scheme for preparation and characterization in the 9-position (N- or O-substituted berberine derivatives) and 13-position substituted berberine derivatives.

Dual TGR5 agonism/FXR antagonism modulators increased their potency for TGR5, but also have inhibited effect on FXR, in vitro (FIGS. 12-13). HEK293 cells overexpressed TGR5 were treated with increasing doses of dual TGR5 agonism/FXR antagonism modulators. TGR5-reporting activity was evaluated by luciferase assay. Treatments were performed in quadruplicate and normalized with β-galactosidase. HEK293 cells were transfected with FXR and RXRα, and FXRE-containing luciferase construct. Cells were treated with 10 µM of indicated compounds; luciferase was measured and normalized with β-galactosidase.

Experimental Section

Chemistry General Procedure.

Organic reagents were purchased from commercial suppliers unless otherwise noted and were used without further purification. All solvents were analytical or reagent grade. All reactions were carried out in flame-dried glassware under argon or nitrogen. Melting points were determined and reported automatically by an optoelectronic sensor in open capillary tubes and were uncorrected. $^1H$ NMR and $^{13}C$ NMR spectra were measured at 500 MHz and 125 MHz respectively, using $CDCl_3$ or $CD_3OD$ as the solvents and tetramethylsilane ($Me_4Si$) as the internal standard. Flash column chromatography was performed using Sigma-Aldrich silica gel 60 (200-400 mesh), carried out under moderate pressure by using columns of an appropriate size packed and eluted with appropriate eluents. Silica gel chromatography was performed on a Biotage flash column gradient pump system using 15 cm long columns. All reactions were monitored by TLC on precoated plates (silica gel HLF). TLC spots were visualized either by exposure to iodine vapors or by irradiation with UV light. Organic solvents were removed in vacuum by rotary evaporator. Elemental analyses were performed by Columbia Analytical Services Inc, Tucson, Ariz.

General Procedure for the Preparation of Berberine-Bile Acids or Bile Acid Derivatives Salts.

Berberine chloride (0.45 g, 1.21 mmol) was dissolved in 400 mL of water by gentle heating under stirring at 40° C. The corresponding carboxyl sodium bile acids or bile acid derivatives (1.21 mmol) was dissolved in 40 mL of water at 60° C., the two hot solutions were mixing together. The resulting mixture was stirred at 50-60° C. for 1-2 h (monitored by TLC). The reaction mixture was cooled down under stirring to precipitate completely. The resulting filtrated was then purified by crystallization in EtoAc and then dried under vacuum at 60-70° C. overnight, to give a desired salts as bright yellow powders.

Example 1

DY315 (Berberine-DY284 Salt).

Using the general procedure to give DY315 (FIG. 24) as a bright yellow powder (0.74 mg, 84%), mp: 233.2° C. $^1H$ NMR (600 MHz, $CD_3OD+CDCl_3$): (selected data) δ 9.64 (s, 1H), 8.47 (s, 1H), 7.90 (d, 1H), 7.86 (d, 1H), 7.45 (s, 1H), 6.81 (s, 1H), 6.00 (s, 2H), 4.10 (s, 3H), 4.00 (s, 3H), 3.45 (t, 2H), 3.14 (s, 1H), 3.12 (s, 2H), 2.83 (t, 2H), 2.15 (m, 1H), 1.95 (m, 1H), 1.11 (d, 1H), 1.18 (d, 3H), 0.82 (d, 3H), 0.78 (s, 3H), 0.53 (s, 3H). $^{13}C$ NMR (125 MHz, $CD_3OD+CDCl_3$) δ 177.4, 156.3, 155.9, 152.9, 143.7, 146.1, 136.7, 133.1, 128.9, 125.3, 121.7, 118.8, 106.7, 103.6, 100.7, 69.9, 55.1, 54.2, 48.5, 40.5, 38.8, 38.5, 34.2, 33.6, 26.4, 25.5, 24.7, 24.7, 22.4, 19.1, 16.1, 9.8.

Example 2

DY317 (Berberine-Tauro-CA).

Using the general procedure to give DY317 (FIG. 24) as a bright yellow powder (0.75 mg, 73%), mp: 263.2° C. $^1H$ NMR (600 MHz, $CDCl_3+CD_3OD$): (selected data) δ 9.64 (s, 1H), 8.50 (s, 1H), 7.97 (d, 1H), 7.87 (d, 1H), 7.53 (s, 1H), 6.83 (s, 1H), 6.00 (s, 2H), 4.11 (s, 3H), 3.99 (s, 3H), 3.83 (s, 1H), 3.69 (s, 1H), 3.44 (t, 2H), 3.25 (brs, 1H), 3.16 (s, 1H), 3.14 (t, 2H), 2.83 (t, 2H), 2.15 (m, 1H), 1.95 (m, 1H), 1.11 (d, 1H), 0.83 (d, 3H), 0.77 (s, 3H), 0.58 (s, 3H). $^{13}$C NMR (125 MHz, CD$_3$OD+CDCl$_3$) δ 178.0, 156.3, 155.9, 152.9, 147.4, 146.1, 133.0, 133.1, 129.7, 126.1, 123.1, 111.1, 108.0, 105.1, 75.7, 73.9, 71.1, 49.2, 44.3, 42.1, 38.2, 37.9, 37.8, 37.1, 35.7, 34.3, 32.4, 30.7, 30.0, 29.8, 29.1, 25.7, 24.8, 19.4, 14.7. Anal. Calcd for C$_{46}$H$_{62}$N$_2$O$_{11}$S.1$_{1/2}$H$_2$O: C, 62.92; H, 7.71; N, 3.19. Found: C, 62.95; H, 7.81; N, 3.19.

Example 3

DY321 (Berberine-6ECDCA).

Figure 17:
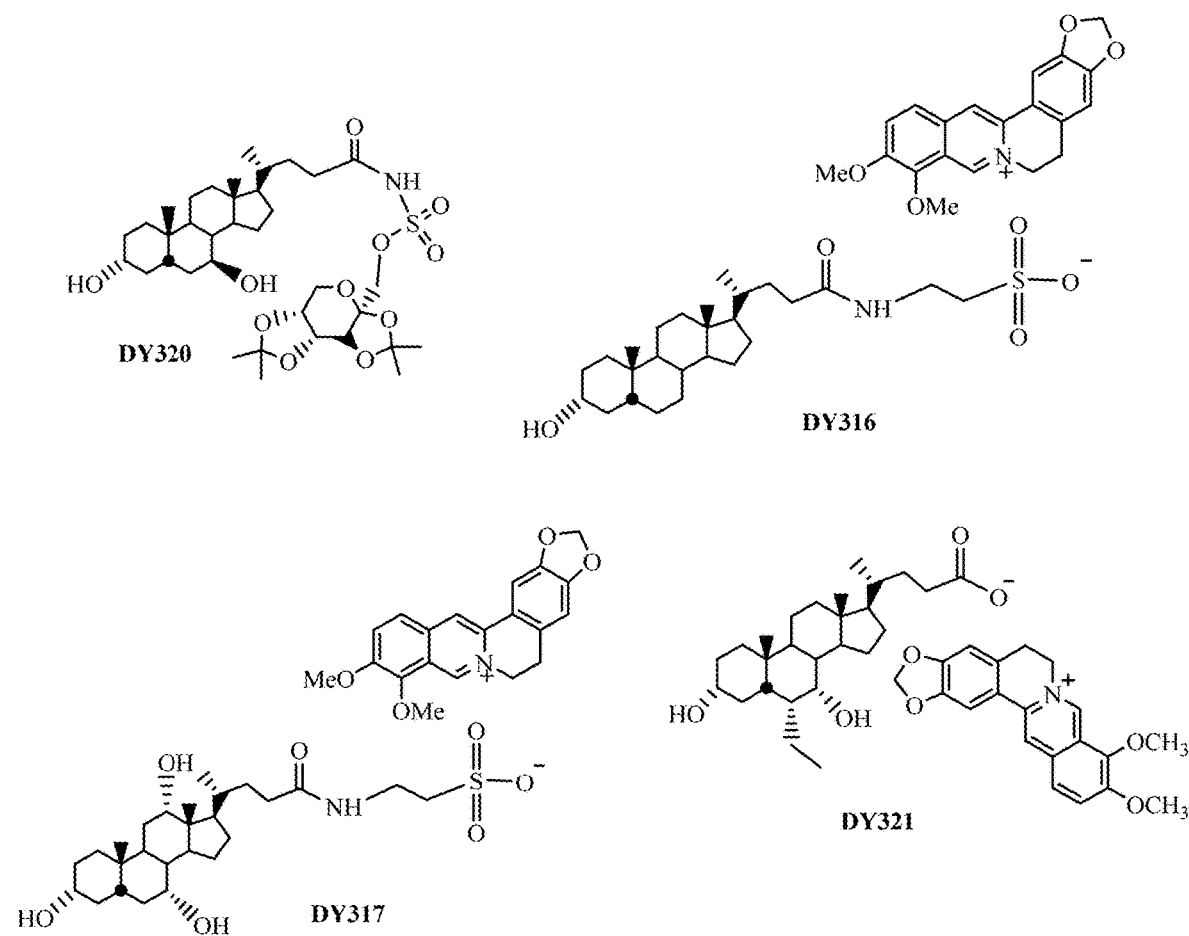
FIG. 17: Representative examples of berberine derivatives.

Using the general procedure to give DY315 to give a desired product DY321 (FIG. 17) as a bright yellow powder (0.073 mg, 70%), mp: 194.8° C. $^1$H NMR (600 MHz, CD$_3$OD): (selected data) δ 9.75 (s, 1H), 8.70 (s, 1H), 8.11 (d, 1H), 8.01 (d, 1H), 7.66 (s, 1H), 6.97 (s, 1H), 6.11 (s, 2H), 4.21 (s, 3H), 4.11 (s, 3H), 3.63 (s, 1H), 3.31 (t, 2H), 3.24 (s, 1H), 2.20 (brs, 1H), 0.96 (d, 3H), 0.91 (s, 3H), 0.89 (d, 3H), 0.68 (s, 3H). $^{13}$C NMR (125 MHz, CD$_3$OD) δ 177.4.0, 150.3, 149.6, 147.5, 145.3, 143.5, 136.9, 136.8, 136.7, 134.7, 131.2, 130.5, 124.5, 119.9, 116.7, 112.9, 109.3, 108.1, 106.6, 106.3, 94.2, 91.3, 88.5, 73.0, 71.1, 58.1, 56.0, 47.4, 42.5, 42.4, 42.0, 36.4, 34.2, 31.8, 28.5, 28.0, 25.8, 22.1, 19.3, 14.1. Anal. Calcd for C$_{46}$H$_{61}$NO$_8$.H$_2$O: C, 71.36; H, 7.94, N, 1.81. Found: C, 71.07; H, 7.83, N, 1.47.

General Procedures for the Preparation of 9-N-Substituted Berberine Derivatives

To a solution of berberine (0.45 g, 1.21 mmol) in anhydrous ethanol, the substituted amines (4-10 mmol) were added. The mixture was stirred and refluxed for 12-24 hours. After the reaction completed (monitored by TLC), the mixture was concentrated in vacuo and solidified by EtOAc to remove un-reacted berberine. The residual oil was purified by flash column chromatography (CHCl$_3$/MeOH 8:2) to give the desired products as red-yellow solids.

Example 4

DY319 (Berberine-Topi Derivative).

To a warm solution of berberine chloride (0.45 g, 1.21 mmol) in anhydrous ethanol (20 mL), topiramate (4.11 g, 12.1 mmol) was added and the mixture was refluxed 16 h. After cooling down, the reaction mixture was filtrated to remove unreacted berberine. The solvent was concentrated in vacuo to get crude dark brown oil which was solidified by EtOAc, filtrated on a Buchner apparatus, extensively rinsed with EtOAc, CHCl$_3$, and then dried under vacuum at 60° C. overnight to give a desired product DY319 as a red-yellow powder (0.17 mg, 20%), mp: 211.1° C. $^1$H NMR (600 MHz, CD$_3$OD): δ 10.22 (s, 1H), 8.15 (s, 1H), 7.97 (s, 1H), 7.51 (d, 1H), 7.42 (d, 1H), 6.96 (s, 2H), 6.05 (s, 2H), 5.08 (t, 2H), 4.59 (d, 1H), 4.35 (s, 2H), 4.10 (t, 2H), 4.05 (d, 1H), 3.92 (s, 3H), 3.89 (d, 3H), 3.75 (d, 1H), 3.26 (t, 2H), 1.42 (s, 3H), 1.36 (s, 3H), 1.35 (s, 3H), 1.34 (s, 3H). $^{13}$C NMR (125 MHz, CD$_3$OD) δ 154.1, 151.1, 147.5, 140.2, 139.4, 136.6, 133.2, 129.1, 126.3, 124.8, 123.2, 111.1, 108.1, 105.2, 73.4, 72.9, 72.1, 63.7, 59.4, 58.8, 29.8, 28.4, 27.8, 27.2, 25.9. Anal. Calcd for C$_{32}$H$_{39}$N$_2$O$_{12}$ClS: C, 54.04; H, 5.53; N, 3.94. Found: C, 53.80; H, 5.72; N, 3.59.

Example 5

DY322 (Berberine-Dopamine Hybrid).

To a solution of dopamine hydrochloride (0.92 g, 4.85 mmol) in 5 ml of methanol, 0.5 mL of triethyl amine (Et$_3$N) was added to the stirred solution. The reaction mixture was refluxed for 2 h to provide dopamine free base, and then the reaction mixture was cooled to room temperature. To a stirred solution of dopamine free base was added a solution of berberine chloride (0.45 g, 1.21 mmol) in warm ethanol (50 mL) and the reaction mixture was refluxed overnight. After cooling down, the reaction mixture was concentrated in vacuo. Solidified by EtOAc, filtrated on a Buchner apparatus, extensively rinsed with EtOAc, and ethanol and then dried under vacuum at 40° C. overnight, to give a desired product DY322 (FIG. 15) as a gray yellow powder (0.39 mg, 66%), mp: 198.4° C. $^1$H NMR (600 MHz, CD$_3$OD): δ 9.79 (s, 1H), 8.72 (s, 1H), 8.14 (d, 1H), 8.03 (d, 1H), 7.68 (s, 1H), 6.98 (s, 1H), 6.76 (d, 1H), 6.71 (d, 1H), 6.61 (d, 1H), 6.12 (s, 2H), 4.99 (d, 2H), 4.22 (s, 3H), 4.12 (s, 3H), 3.13 (t, 2H), 2.83 (t, 2H). $^{13}$C NMR (125 MHz, CD$_3$OD) δ 150.9, 149.7, 147.6, 145.2, 145.0, 144.3, 138.6, 137.7, 134.1, 133.2, 130.8, 127.7, 126.7, 123.1, 120.1, 119.6, 115.3, 107.9, 105.2, 102.3, 56.3, 55.8, 40.8, 32.6, 26.6. Anal. Calcd for C$_{27}$H$_{25}$N$_2$O$_5$$^+$.H$_2$O: C, 63.46; H, 4.93; N, 5.48. Found: C, 63.81; H, 5.27; N, 5.03.

Example 6

DY323 (Berberine-Phenylboronic Hybrid).

To a solution of (3-aminomethylphenyl) boronic acid hydrochloride (0.25 g, 1.33 mmol) in 5 ml of methanol, 0.2 mL of triethyl amine (Et$_3$N) was added to the stirred solution. The reaction mixture was refluxed for 2 h to provide 3-aminoboronic acid free base, and then the reaction mixture was cooled to room temperature. To a stirred solution of phenylboronic free base was added a solution of berberine chloride (0.74 g, 2.1 mmol) in warm ethanol (50 mL) and the reaction mixture was refluxed 4 hours. After cooling down, the reaction mixture was concentrated in vacuo. Solidified by EtOAc, filtrated on a Buchner apparatus, extensively rinsed with EtOAc, and ethanol and then dried under vacuum at 50° C. overnight, to give a desired product DY323 (FIG. 15) as a red solid (0.39 mg, 61%), mp: 228.7° C. $^1$H NMR (600 MHz, CD$_3$OD): δ 9.80 (s, 1H), 8.79 (s, 1H), 8.13 (d, 1H), 8.01 (d, 1H), 7.85 (d, 2H), 7.99 (brs, 1H), 7.81 (s, 1H), 7.45 (m, 3H), 6.92 (s, 1H), 6.12 (s, 2H), 4.90 (t, 2H), 4.19 (t, 2H), 4.20 (s, 2H), 3.96 (s, 3H), 3.37 (t, 2H). $^{13}$C NMR (125 MHz, CD$_3$OD) δ 150.6, 148.4, 145.0, 138.2, 133.9, 133.7, 130.4, 129.9, 128.2, 127.8, 126.6, 123.1, 121.9, 120.4, 120.1, 119.2, 115.6, 115.3, 107.9, 105.1, 102.2, 61.8, 55.8, 43.4, 26.8. Anal. Calcd for C$_{26}$H$_{24}$BClN$_2$O$_5$.4H$_2$O: C, 55.48; H, 4.29; N, 4.97. Found: C, 55.30; H, 4.72, N, 4.49.

General Procedures for the Amination of Berberine Derivatives

Example 7

DY320 (UDCA-Topi Hybrid).

To a solution of UDCA (0.5 g, 1.27 mmol) in 5 mL of dry DMF was added EDCI (0.29 g, 1.52 mmol), DMAP (0.19 g, 1.52 mmol), and topi (0.52 g, 1.52 mmol). The reaction mixture was stirred at room temperature for 6 h. The reaction mixture was diluted in CH$_2$Cl$_2$, washed twice with 10% HCl. The organic solvent was dried over Na$_2$SO$_4$ and evaporated under a vacuum. The resulting oil was purified by flash column chromatography (MeOH/CHCl$_3$ 9:1) to afford DY320 (FIG. 17) as a white solid (0.54 g, 60% yield), mp 124.1° C. $^1$H NMR (600 MHz, CDCl$_3$): (selected data) 4.62 (d, 1H), 4.42 (d, 1H), 4.32 (s, 1H), 4.29 (d, 1H), 3.89 (d, 1H), 3.77 (d, 1H), 3.58 brs, 2H), 2.45 (m, 1H), 2.35 (m, 1H), 1.54 (s, 3H), 1.49 (s, 3H), 1.42 (s, 3H), 1.33 (s, 3H), 0.92 (s, 3H), 0.91 (d, 3H), 0.66 (s, 3H). $^{13}$C NMR (125 MHz, CDCl3): 178.3, 109.6, 109.5, 100.2, 72.1, 71.5, 71.4, 70.6, 70.3, 69.8, 61.3, 55.8, 54.8, 43.7, 42.4, 40.2, 39.2, 37.3, 36.9, 35.1, 34.9, 32.8, 30.3, 28.6, 26.9, 25.8, 25.1, 24.0, 23.3, 21.2, 18.5, 12.2. Anal. Calcd for $C_{36}H_{59}NO_{11}S \cdot H_2O$: C, 59.07; H, 8.13; N, 1.91. Found: C, 58.92; H, 8.87, N, 1.94.

General Procedures for the γ-Aminobutyric Acid Derivatives

Example 8

DY419.

γ-Aminobutyric acid (1.0 g, 9.69 mmol) and phthalic anhydride (1.72 g, 11.6 mmol) in 30 mL of acetic acid were stirred and refluxed at 120° C. for 6 h. The reaction mixture was poured into water after cooling to room temperature and extracted with ethyl acetate (3×20 mL). The organic layers were combined, washed with brine (2×30 mL), dried over anhydrous $Na_2SO_4$, and evaporated under reduced pressure to give the crude product. Solidified by Hexanes to afford DY419 (FIG. 18) as a white solid (1.85 g, 82% yield), mp 115.0° C. The solid was used for the next step without further purifications. $^1$H NMR (600 MHz, CDCl$_3$): δ 7.85 (d, 2H), 7.75 (t, 2H), 3.78 (t, 2H), 2.44 (t, 2H), 2.02 (t, 2H). $^{13}$C NMR (125 MHz, CDCl$_3$): δ 177.9, 168.4, 134.0, 132.0, 131.7, 37.0, 31.2, 23.7. Anal. Calcd for $Cl_2H_{11}NO_4$: C, 61.80; H, 4.75; N, 6.01. Found: C, 61.90; H, 4.96, N, 6.02.

Example 9

DY421.

DY420 (0.5 g, 1.45 mmol), topi (0.5 g, 1.45 mmol), and TBTU (4.21 g, 2.17 mmol) were dissolved in a 1:1 DMF/pyridine solution (10 mL). The reaction was stirred overnight under nitrogen, and the solvent was removed in vacuo. The reaction was dissolved in ethyl acetate and extracted with 30% citric acid and brine. The organic layer was dried with $Na_2SO_4$ and evaporated in vacuo to afford DY421 (FIG. 18) as a crude oil. The residue was used for the next step without further purifications. $^1$H NMR (600 MHz, CD$_3$OD): $^1$H NMR (600 MHz, CDCl$_3$): δ 7.84 (t, 2H), 7.71 (t, 2H), 4.61 (d, 1H), 4.35 (s, 2H), 4.10 (t, 2H), 4.05 (d, 1H), 3.67 (t, 2H), 2.32 (t, 2H), 1.65 (m, 4H), 1.50 (s, 3H), 1.49 (s, 3H), 1.35 (s, 3H), 1.34 (s, 3H), 1.25 (t, 4H), 1.20 (t, 6H). $^{13}$C NMR (125 MHz, CDCl$_3$) δ 176.9, 168.4, 162.7, 149.2, 136.4, 133.8, 132.1, 123.9, 109.2, 100.9, 77.2, 77.1, 76.8, 61.2, 38.1, 36.5, 29.4, 29.3, 29.2, 28.5, 26.8, 25.7, 25.1, 24.9, 23.9.

Example 10

DY422.

An solution of DY421 (1.2 mmol) and hydrazine hydrate (80%) (2 mL, 31 mmol) in ethanol (10 mL) was refluxed for 4 h, and then cooled to room temperature. The mixture was filtered and the solid was washed with 95% EtOH. The whole filtrate was concentrated and the crude oil was dissolved in CHCl$_3$, and dried over $Na_2SO_4$, filtered, and concentrated to give the crude product DY422 (FIG. 18), which was used in the next step without further purification. $^1$H NMR (600 MHz, CD$_3$OD): $^1$H NMR (600 MHz, CDCl$_3$): δ 4.60 (d, 1H), 4.35 (s, 2H), 4.10 (t, 2H), 4.05 (d, 1H), 3.65 (t, 2H), 3.05 (brs, 2H), 2.32 (t, 2H), 1.75 (m, 4H), 1.54 (s, 3H), 1.47 (s, 3H), 1.34 (s, 3H), 1.33 (s, 3H), 1.25 (t, 4H), 1.23 (t, 2H). $^{13}$C NMR (125 MHz, CDCl$_3$) δ 175.1, 123.2, 111.1, 109.4, 70.5, 70.4, 69.8, 61.2, 42.0, 41.0, 32.5, 26.4, 25.7, 25.1, 23.9, 24.9.

Example 11

DY424.

To a solution of DY419 (0.5 g, 2.14 mmol) in 10 mL of dry $CH_2Cl_2$ was added EDCI (0.62 g, 3.25 mmol), DMAP (0.41 g, 3.25 mmol), and topiramate (0.72 g, 2.14 mmol). The reaction mixture was stirred at room temperature for overnight. The reaction mixture was diluted in $CH_2Cl_2$, washed twice with 10% HCl and brine. The organic solvent was dried over $Na_2SO_4$ and evaporated under a vacuum. Solidified by hexanes to afford compound DY424 (FIG. 18) as a white solid (1.03 g, 88% yield), mp 74.1° C. $^1$H NMR (600 MHz, CDCl$_3$): δ 9.69 (brs, 1H), 7.88 (d, 2H), 7.78 (t, 2H), 4.62 (d, 1H), 4.45 (d, 1H), 4.35 (t, 2H), 4.23 (d, 1H), 3.93 (d, 1H), 3.78 (t, 2H), 3.76 (d, 1H), 2.86 (t, 2H), 2.46 (t, 2H), 1.88 (t, 2H), 1.57 (s, 3H), 1.51 (s, 3H), 1.44 (s, 3H), 1.37 (s, 3H). $^{13}$C NMR (125 MHz, CDCl$_3$): δ 175.0, 168.7, 134.3, 131.8, 123.6, 123.5, 109.5, 72.2, 70.6, 70.2, 69.9, 61.4, 36.8, 33.4, 26.5, 25.8, 24.4, 23.9. Anal. Calcd for $C_{24}H_{30}N_2O_{11}S$: C, 51.98; H, 5.45; N, 5.05. Found: C, 51.64; H, 6.02, N, 5.09.

Biology

Cell Culture

HEK293 and HEK293-GP-TGR5 overexpressing cells were cultured in high glucose Dulbecco's modified Eagle's medium (DMEM, Cellgro, Manassas, Va.) with L-glutamine supplemented with 10% (vol/vol) heat-inactivated fetal bovine serum (Gemini Bio-Products, West Sacramento, Calif.). GP-TGR5-overexpressing HEK293 cells were maintained in G418-containing media until plating. Cells were plated in 24-well plates (5×10$^5$ cells/well) 24 h before transfection. Prior to transfection, cells were rinsed with PBS, and media was replaced with DMEM without phenol red supplemented with 10% super-stripped FBS.

TGR5 and FXR Luciferase Assay

To evaluate TGR5 activity of compounds, cells were transfected 100 ng pCRE-luc reporter along with pCMV-galactosidase (10 ng) as an internal control for normalization of transfection efficiency. Plasmids were complexed with 2 mL of Fugene 6 reagent (Promega, Madison, Wis.) in OptiMEM (Invitrogen, Carlsbad, Calif.) and cells were transfected for 18 h. The following day, cells were treated with vehicle and appropriate ligand as indicated. Luciferase and β-galactosidase activities were assayed 6 h later using Luciferase Assay System (Promega) and Galacto-Star (Applied Biosystems, Foster City, Calif.) reagents, respectively, and a MLX luminometer (Dynex Technologies, Chantilly, Va.). To evaluate the FXR activity of compounds, HEK293 cells were transfected with 25 ng of farnesoid X receptor expression plasmid (pCMX-hFXR), 25 ng of retinoid X receptor expression plasmid (pCMXhRXR), 100 ng of reporter plasmid (pEcREx6-TK-Luc), and 10 ng of pCMV-b-galactosidase as an internal control in each well, using Fugene 6 reagent. Approximately 18 h after transfection, cells were incubated for 12 h with different concentrations of each.

Cell-Based FXR Transactivation Assay

To investigate the cellular activities of the novel berberine derivatives, we used a GeneBLAzer FXR cell-based assay, which detects the levels of a β-lactamase reporter controlled by a promoter containing the binding site of the DNA binding domain (DBD) of the GAL4 transcription factor; the Gal4 DBD was fused to the LBD of FXR in this assay. In typical test for agonists, DMSO (vehicle and negative control), 10 μM GW4064 (positive control), and titrations of GW4064, LCA or the 24 newly synthesized novel berberien derivatives analogs were mixed with GeneBLAzer FXR- UAS-bla HEK 293T cells. Reporter assays were performed after a 16 h incubation. No agonistic activities were observed for any of the newly synthesized compounds (data not shown). For the experiments to evaluate the antagonistic activity, titrations of compounds were tested in the presence of 400 nM GW4064. Assay controls included: DMSO alone (100% inhibition), 400 nM GW4064 alone (0% inhibition), and titrations of LCA in the presence of 400 nM GW4064 (as an assay reference).

cAMP Assays

HEK293 overexpressing TGR5 were treated with vehicle and appropriate ligand for 30 min in induction buffer comprised of serum-free Krebs Ringer buffer supplemented with 100 mM Ro 20-1274 and 500 mM IBMX (Sigma, St. Louis, Mo.) and cAMP levels were determined in lysates using cAMP-Glo Assay Kit (Promega) according to the manufacturer's protocol. Data analysis to determine $EC_{50}$ values was performed with GraphPad Prism software using a cAMP standard curve and sigmoidal dose-response (variable slope) equation based on dose-response curves with tested compounds.

hTGR5 Reporter Gene Assay

Chinese Hamster Ovarian (CHO) K1 cells were plated in 24 well tissue culture plate at a density of 4×104 cells/well in a Nutrient Mixture F-12 HAM containing 10% Fetal Bovine Serum, cultured for 24 h at 37° C., 5% CO2, and then transfected with 50 ng of human (h) TGR5 expression plasmid (pCMV SPORT6-hTGR5), 300 ng of cAMP-responsive element (CRE)-driven luciferase reporter plasmid (pCRE-Luc) and 100 ng of β-galactosidase reporter vector in each well using Polyfect Transfection Reagent (QIAGEN, Cat. No.: 301107) according to the manufacturer's instructions. After 4 h of incubation, cells were washed once with phosphate-buffered saline (PBS) and medium was exchanged to Nutrient Mixture F-12 HAM containing 0.5% Fatty acid free bovine serum albumin (FAFBSA) and 1 mM Sodium Pyruvate Solution. After incubation for another 18 h, cells were treated for 5 h with different concentrations of each compound. After treatment, the cells were lysed with 100 μL of Glo Lysis buffer (Promega, Cat. No.: E2661) and subjected to Luciferase and β-Galactosidase assays.

GLP-1 Secretion Assay

Human NCI-H716 cells were seeded into 96-well culture plate pre-coated with Collagen type I. Twenty-four hours later, the supernatants were replaced by KRB containing 0.18% Glucose & 0.2% BSA and stimulated in presence & absence of compounds for 2 h at 37° C., 5% $CO_2$. GLP-1 was measured by EDITM Total GLP1 ELISA Kit (Epitope Diagnostic Inc.) and normalized to total protein content.

Glucose Uptake Assay

The glucose uptake measurement was carried out according to the method described previously by Figarola et al. with some modifications.15 Adipocytes were grown in 24-well plates and used 10-11 days after initiation of differentiation. Adipocytes were rinsed in sterile, fresh Krebs-Ringer-HEPES (KRH) buffer (HEPES pH=7.4, 1 mM CaCl2, 1.2 mM MgSO4, 1 mM KH2PO4, 1.4 mM KCl, and 20 and 130 mM NaCl), and then preincubated for 24 h in KRH buffer. Then, the buffer was removed, and adipocytes were incubated in KRH buffer containing glyceollins for specified time period. Ten microliters of [3H]-2-deoxy-D-glucose (Vitrax, Placentia, Calif.) diluted to 0.01 μCi/μL with D-glucose (100 mM) was added to each well and incubated for 10 min in a 37° C. water bath. The supernatant was removed, and plates were rinsed rapidly three times with ice cold KRH. The final rinse was aspirated, being careful to not remove the cellular monolayer, and 500 μL of ice cold RIPA buffer (Sigma Chemical Co.) was added to lyse the cells. The cellular content in each well was triturated with a 1 mL pipet several times to remove attached cells and cellular components from the bottom of the plate. A 450 μL aliquot was added to 5 mL of Ecolume scintillation fluid (MP Biomedical, Santa Ana, Calif.). The vials were mixed and counted for 10 min in an Applied Biosystems 1100 liquid scintillation counter using the factory preset window to detect tritium. Data are the average of three experiments that were normalized by calculating the percent cpm glucose uptake as compared to basal cpm glucose uptake.

Animal Treatments and Quantitative RT-PCR

Ten week old male C57BL/6J mice were injected intraperitoneally once per day with vehicle or selected compounds (30 mg/kg) for seven days. After seven days of treatment, animals were sacrificed and mouse ileums were dissected and frozen immediately in liquid nitrogen. Total RNA was extracted using Trizol and purified using the RNeasy Mini Kit (Qiagen). One microgram of RNA was reverse transcribed into cDNA using oligo(dT)18 primers and SuperScript II Reverse Transcriptase (Invitrogen, Carlsbad, Calif.) at 42° C. for 1 h according to the manufacturer's instructions. Quantitative real time PCR for mouse GLP-1 was performed using SYBR Green PCR Master Mix and an ABI Prism 7300 Sequence Detection System (Applied Biosystems, Foster City, Calif., USA). Expression levels were obtained by normalization with the value of the housekeeping gene encoding β-actin. Fold changes were determined using the delta-delta Ct method.

Evaluation of Pharmacological Efficacy of TGR5 Agonist Compounds

The high fat diet induced obesity (DIO) in mice exhibits various features of metabolic syndrome in humans. The metabolic syndrome is characterized by abdominal obesity, high triglycerides, impaired fasting glucose and hyperinsulinemia. In this DIO model, C57 mice of 4-6 week of age will be kept on high (60%) fat diet for 4-6 weeks, when they will become glucose intolerant, used for the single dose Oral Glucose Tolerance Test (OGTT) study for antidiabetic activity. On day 0 non fasting body weight of animals will be recorded, grouped based on non-fasting body weights and will be kept on fasting for overnight, on the day of experiment animals will be subjected for OGTT (oral glucose tolerance test). In OGTT, body weight of all animals will be recorded and mice will receive a single dose of vehicle administered per orally on the basis of body weight, 10 min post dosing single dose of vehicle/test compounds will be administered, 15 min post dosing blood collection will be done (0 min) and glucose load (2 g/kg/10 mL) will be administered per orally. Blood will then be collected at time points corresponding to 10, 30, 60, and 120 min after glucose load administration. At 10 min plasma will also be collected for insulin and GLP-1 level measurement. Serum will be separated for determination of glucose levels at all time points. Glucose AUC and glucose excursion was calculated using MS excel sheet and graph pad software.

Dose Range Study

Four groups of DIO mice DIO mice (n=6) fasted for 4 h received daily gavage for 5 consecutive weeks of control solution [5% dimethyl sulfoxide (DMSO) in water] or 30 and 100 mg/kg berberine derivatives suspended in a total volume of 2 mL of control solution at the beginning of the feeding cycle (lights off, 1400 h). This dose range was chosen based on the pharmacological activity of berberine in rats. Food intake was measured daily for the duration of the experiment and corrected for spillage. All animals were sacrificed on week 5 of the treatment with the exception of the control (n=3) and 30 mg/kg groups (n=3) that were sacrificed on the week 5 of the experiment following completion of the recovery phase.

Biological Assays

Screening of DY Berberine-Based Derivatives for Anti-Diabetic Activities

HepG2 Cells

C2C12 Cells

Set up cells at 20,000 cells/well (1×96 well plates total) with 1 ml complete DMEM media and cells were incubated for 24 hr at 37° C., 5% $CO_2$.

Experimental Plates:

1×96 well plates for MTS Assay 3 wells each treatment

Day 1

Media changed to fresh DMEM with or without test compounds (250 ul)* note: Cells were accidentally incubated in MDA-MB-231 media which contains higher glucose concentration than the normal DMEM for HepG2 cells.

(Test compounds added on separate 12 well plates where they were mixed with the culture media, then 250 ul of this mixture was added to each well). Total volume prepared: 2 ml DMEM+DMSO=add 2 ul DMSO to 3 ml media DMSO+Berberine=add 2 ul DMSO to 3 ml media DMSO+DY317 (25 uM)=add 2 ul 25 uM stock solution of Pen to 2 ml media DMSO+DY319 (25 uM)=add 2 ul 25 uM stock solution of Pen to 2 ml media DMSO+DY320 (25 uM)=add 2 ul 25 uM stock solution of Pen to 2 ml media DMSO+DY321 (25 uM)=add 2 ul 25 uM stock solution of Pen to 2 ml media All test compounds in DMSO stock solution Day 2

After 48 hr of drug treatment, MTS assay was performed.
1. Added 25 ul to MTS solution (Sigma 50 mg/5 ml PBS) added to each well, and incubated for 4 hrs.
2. After 4 hrs, 0.25 ml of isopropanol/0.04 N HCl solution was added to each well.
3. Let color develop for 10 minutes, then solubilized precipitates by mixing them by pipetting up and down several times.
4. When no more precipitates were visible, absorbance was taken at 595 nm (Tecan microplate reader).

Metabolic Stability

Test compound was incubated with 0.5 mg/mL protein of liver microsomes of mouse, rat, and human in phosphate buffer pH 7.4 in the presence of 1 mM NADPH at 37° C., 100 rpm in shaking water bath. After incubation, reactions were terminated by addition of acetonitrile-containing analytical internal standard at 0, 5, 10, 15 and 30 min. The 0 min samples were made in the absence of NADPH and used as control. The metabolic stability in incubated samples was assessed with respect to zero min control samples. Controls included an NADPH-free incubation at 30 min as negative control for chemical instability/non-NADPH dependent metabolism. All samples were centrifuged and analyzed by liquid chromatography tandem mass spectrometry method.

Oil Red O Staining

Cells on day 7 were washed twice with PBS, fixed with 10% neutral buffered formalin for 1 h at room temperature, washed with PBS and then dried completely. The fixed cells were stained with Oil Red O in an isopropanol/distilled water (6:4) solution for 30 min at room temperature and then washed twice with distilled water. The stained lipid droplets were observed, and microscopic images were obtained from randomly selected fields under a phase contrast microscope (AX70; Olympus, Tokyo, Japan) equipped with a digital camera and processed using ImagePro Plus software (Media Cybernetics, Silver Spring, Md., USA).

Example 12

Interestingly, several berberine derivatives were identified as FXR antagonists by the receptor binding assay using TR-FRET (time-resolved fluorescence resonance energy transfer) assay and cell-based FXR transactivation assay.

The FXR TR-FRET binding assay was performed as previously described[7, 20] with modifications. Briefly, in a black polypropylene 384-well plate, DMSO, 10 μM GW4064, and titrations of GW4064, chenodeoxycholic acid (CDCA) or the synthesized chemicals were mixed with 10 nM GST-hFXR-LBD, 1.5 nM Tb-anti-GST antibody, and 10 nM DY246 in a 20 UL/well of coregulator buffer G supplemented with 10 mM DTT. The final DMSO concentration was 0.4% for all wells. The plate was spun down after a brief shake and incubated at room temperature for 20 min. The TR-FRET emission signals at 520 nm and 490 nm for each well were determined using a PHERAstar plate reader (BMG LABTECH, Cary, N.C.) and an excitation wavelength of 337 nm, 100 μs delay time, and 200 μs integration time. The 10,000×520 nm/490 nm ratio from each well was then calculated. The DMSO group and 10 μM GW4064 group served as negative (0% inhibition) and positive (100% inhibition) controls, respectively. The % Inhibition of tested chemicals at given concentration was calculated based on negative and positive controls using Eq. 1.

$$\% \text{ Inhibition} = 100\% - 100\% \times \frac{Chemical_{520\,nm/490\,nm} - 10\ \mu M\ GW4064_{520\,nm/490\,nm}}{DMSO_{520\,nm/490\,nm} - 10\ \mu M\ GW4064_{520\,nm/490\,nm}} \quad \text{(Eq. 1)}$$

For those chemicals with a maximal % Inhibition>50% and activities that behaved in a dose-dependent manner, the inhibitory activities at different concentrations were fit into a one-site competitive binding equation with GraphPad PRISM 7.00 (GraphPad Software, Inc., La Jolla, Calif.) to derive $IC_{50}$ values.

Novel dual TGR5 agonism/FXR antagonism modulators were also identified. Recent studies indicated that obese as well as older FXR knockout mice showed an improvement in glucose control and protection from excessive body-weight gain. The therapeutic value of FXR antagonism remains unknown since robust in vivo data is lacking. In light of the entangled activity of both bile acid receptors, berberine derivatives would be very interesting agents with unique dual activity of FXR antagonism and TGR5 agonism. We reason that an effective TGR5 agonist endowed with antagonistic activity toward FXR in a single molecule may represent a highly efficacious targeted therapy for obesity.

Biological Assays

Materials: DMSO and charcoal/dextran-treated FBS were obtained from Fisher Scientific (Pittsburgh, Pa.). GW4064 and Tc-g 1005 were purchased from R&D Systems, Inc. (Minneapolis, Minn.); chenodeoxycholic acid, Ro 20-1274 and IBMX were purchased from Sigma-Aldrich (St. Louis, Mo.); Black 384-well plates and white 384-well tissue culture-treated plates were purchased from Corning Incorporated (Corning, N.Y.). GST-hFXR-LBD, Tb-anti-GST antibody, coregulator buffer G, 1 M DTT, GeneBLAzer FXR-UAS-bla HEK 293T cells, DPBS, DMEM, phenol red-free DMEM, OptiMEM medium, dialyzed FBS, non-essential amino acids, sodium pyruvate, HEPES, hygromycin B, zeocin, penicillin/streptomycin, G418 and CCF4-AM substrate were purchased from Invitrogen (Carlsbad, Calif.). TK-Renilla luciferase plasmid and Fugene 6 were purchase from Promega (Madison, Wis.). All chemicals were initially solubilized in DMSO as 10 mM stocks and then diluted in corresponding assay buffer or medium to indicated concentrations. All experiments were repeated in triplicate and representative results were reported.

FXR Cell-Based Transactivation Assay

FXR transactivation assay was performed using GeneBLAzer FXR-UAS-bla HEK 293T cells (Invitrogen) as previously described [2] with minor modifications. Cells were maintained according to the manufacturer's instructions. Briefly, cells were grown in DMEM supplemented with 10% dialyzed FBS, 0.1 mM non-essential amino acids, 25 mM HEPES, 100 µg/mL of hygromycin B, 100 µg/mL of zeocin, 100 units/mL penicillin and 100 µg/mL streptomycin in regular tissue culture flasks. Upon transactivation assay, DMSO, 200 nM GW4064, 10 µM GW4064, and titrations of GW4064, chenodeoxycholic acid (CDCA) or chemicals without 200 nM GW4064 (for FXR agonistic activity determination) or with 200 nM GW4064 (for FXR antagonistic activity determination) were mixed with cells (20,000 cells/well in a 30 µL) in assay medium (phenol red-free DMEM supplemented with 2% charcoal/dextran-treated FBS, 0.1 mM non-essential amino acids, 1 mM sodium pyruvate, 100 units/mL penicillin and 100 µg/mL streptomycin) in black 384-well tissue culture-treated clear bottom plates (Corning Incorporated, Corning, N.Y.). As a background control, the wells in column 24 of each plate were filled with 30 µL assay medium along with 0.5% DMSO. The final DMSO concentration was 0.5% in each assay well. Plates were incubated (16 h, cell culture incubator at 37° C.), after which 6 UL/well of loading solution with CCF4-AM substrate was added. Plates were then incubated in the dark for 90 min at room temperature before measuring the fluorescent emissions at 460 nm and 535 nm (using excitation at 400 nm) with an Envision plate reader with bottom read capacity. After background signal subtraction for individual emission channels, emission signals at 460 nm and 535 nm from each well were used to determine the ratio of 460 nm/535 nm. For agonist assays, the DMSO group and 10 µM GW4064 group served as negative (0% activation) and positive (100% activation) controls, respectively. The % Activation was calculated using Eq. 2.

$$\% \text{ Activation} = 100\% \times \frac{Chemical_{460nm/535nm} - DMSO_{460nm/535nm}}{10 \text{ µM } GW4064_{460nm/535nm} - DMSO_{460nm/53nm}} \quad \text{(Eq. 2)}$$

For antagonistic assays in which 200 nM GW4064 was included in the assay conditions, the DMSO group and 200 nM GW4064 group served as positive (100% inhibition) and negative (0% inhibition) controls, respectively. The % Inhibition was calculated using Eq. 3.

$$\% \text{ Inhibition} = 100\% - 100\% \times \frac{(Chemical + 200 \text{ nM } GW4064)_{460nm/535nm} - DMSO_{460nm/535nm}}{(200 \text{ nM } GW4064_{460nm/535nm} - DMSO_{460nm/535nm})} \quad \text{(Eq. 3)}$$

For those chemicals with a maximal % Activation or % Inhibition>50% and activities that behaved in a dose-dependent manner, the activation or inhibitory activities at different concentrations were fit into a sigmoidal dose-response equation with GraphPad PRISM 7.00 to derive $EC_{50}$ or $IC_{50}$ values.

Cell-Based Cytotoxicity Assay Against FXR-UAS-bla HEK 293T Cells

Cytotoxicity assay was performed side-by-side with the FXR agonistic assay using GeneBLAzer FXR-UAS-bla HEK 293T cells and the CellTiter-Glo® Luminescent Cell Viability Assay reagent (Promega, Madison, Wis.) as previously described.[7] Briefly, cells were maintained in DMEM supplemented with 10% dialyzed FBS, 0.1 mM non-essential amino acids, 25 mM HEPES, 100 µg/mL of hygromycin B, 100 µg/mL of zeocin, 100 units/mL penicillin and 100 µg/mL streptomycin in regular tissue culture flasks. For the cytotoxicity assay, DMSO, titrations of GW4064, chenodeoxycholic acid (CDCA) or chemicals were mixed with cells (20,000 cells/well in a 30 µL) in assay medium (phenol red-free DMEM supplemented with 2% charcoal/dextran-treated FBS, 0.1 mM non-essential amino acids, 1 mM sodium pyruvate, 100 units/mL penicillin and 100 µg/mL streptomycin) in black 384-well tissue culture-treated clear bottom plates. As a positive control, the wells in column 24 of each plate were filled with 30 µL assay medium along with 0.5% DMSO. The final DMSO concentration was 0.5% in each assay well. After a 16 h incubation in a cell culture incubator at 37° C., the cell plates were cooled at room temperature for 20 min and then CellTiter-Glo® reagent 20 UL/well was added followed by an incubation for 20 min in the dark to allow the development of optimal luminescence signal. The luminescence signal from each well was collected with an Envision plate reader equipped with Ultra-sensitive Luminescence detector. The DMSO group and no cell group served as negative (0% inhibition) and positive (100% inhibition) controls, respectively. The % Inhibition was calculated using Eq. 4.

$$\% \text{ Inhibition} = 100\% - 100\% \times \frac{Signal_{compound} - Signal_{No\,Cell}}{Signal_{DMSO} - Signal_{No\,Cell}} \quad \text{(Eq. 4)}$$

For those chemicals with a maximal % Inhibition>50% and activities that behaved in a dose-dependent manner, the inhibitory activities at different concentrations were fit into a one-site competitive binding equation with GraphPad PRISM 7.00 (GraphPad Software, Inc., La Jolla, Calif.) to derive $IC_{50}$ values.

cAMP Assay

HEK293 overexpressing TGR5 were treated with vehicle and appropriate ligand for 30 min in induction buffer comprised of serum-free Krebs Ringer buffer supplemented with 100 mM Ro 20-1274 and 500 mM IBMX (Sigma, St. Louis, Mo.) and cAMP levels were determined in lysates using cAMP-Glo Assay Kit (Promega) according to the manufacturer's protocol. Data analysis to determine $EC_{50}$ values was performed with GraphPad Prism software using a cAMP standard curve and sigmoidal dose-response (variable slope) equation based on dose-response curves with tested compounds.

cAMP assay with cAMP-Glo™ Assay hits (Promega, Madison, Wis.) was performed with HEK293 cells stably overexpressing TGR5 receptor (TGR5-HEK 293 cells) as previously described[23] with minor modifications. Briefly, cells were maintained in high glucose Dulbecco's modified Eagle's medium (DMEM) supplemented with L-glutamine, 10% fetal bovine serum and 250 µg/mL G418. Upon cAMP assays, cells were harvested and washed with in serum-free Krebs Ringer buffer (DPBS supplemented with 100 µM Ro 20-1274 and 500 µM IBMX). DMSO, 40 µM Tc-g 1005, and titrations of Tc-g 1005, or chemicals were then mixed with washed cells (7,500 cells/well in 8 µL) in white 384-well plates in serum-free Krebs Ringer buffer with a final DMSO concentration of 0.4% in each well at 8 µL volume. After brief spun down, the plates were incubated under 37° C. for 30 min. Each well was then subsequently received treatment of cAMP-glo lysis buffer (7.5 µL/well, 15 min room temperature incubation), cAMP detection solution (15 µL/well, 20 min room temperature incubation) and Kinase Glo reagent (30 µL/well, 10 min room temperature incubation) with a brief spin down incorporated after each reagent addition step. The luminescence signal from each well was then collected with an Envision plate reader equipped with Ultra-sensitive Luminescence detector. The DMSO group and 40 µM Tc-g 1005 group served as negative (0% activation) and positive (100% activation) controls, respectively. The % Activation was calculated using Eq. 5.

$$\% \text{ Activation} = 100\% \times \frac{Signal_{DMSO} - Signal_{Chemical}}{Signal_{DMSO} - Signal_{40\,\mu M\ Tc\text{-}g1005}} \quad \text{(Eq. 5)}$$

For those chemicals with a maximal % Activation>50% and activities that behaved in a dose-dependent manner, the activation activities at different concentrations were fit into a sigmoidal dose-response equation with GraphPad PRISM 7.00 to derive $EC_{50}$ values.

REFERENCES

1. Wild, S.; Roglic, G.; Green, A.; Sicree, R.; King, H. Global prevalence of diabetes: estimates for the year 2000 and projections for 2030. *Diabetes Care* 2004, 27, 1047-53.
2. Pentikainen P. J; Neuvonen P. J; Penttila A. Pharmacokinetics of metformin after intravenous and oral administration to man. Eur J Clin Pharmacol 1979, 16, 195-202.
3. Flegal, K. M., Carroll, M. D., Ogden, C. L., and Curtin, L. R. Prevalence and trends in obesity among US adults, 1999-2008. J. Am. Med. Assoc. 2010, 303, 235-241.
4. Forman, B. M.; Goode, E.; Chen, J.; Oro, A. E.; Bradley, D. J.; Perlmann, T.; Noonan, D. J.; Burka, L. T.; McMorris, T.; Lamph, W. W.; Evans, R. M.; Weinberger, C. Identification of a nuclear receptor that is activated by farnesol metabolites. *Cell* 1995, 81, 687-693.
5. Maruyama, T.; Miyamoto, Y.; Nakamura, T.; Tamai, Y.; Okada, H.; Sugiyama, E.; Nakamura, T.; Itadani, H.; Tanaka, K. Identification of membrane-type receptor for bile acids (M-BAR). *Biochem. Biophys. Res. Commun.* 2002, 298, 714-719.
6. Thomas, C.; Pellicciari, R.; Pruzanski, M.; Auwerx, J.; Schoonjans, K. Targeting bile-acid signalling for metabolic diseases. Nat. Rev. Drug Discovery 2008, 7, 678-693.
7. Donna Yu, Wenwei Lin, Barry M. Forman, and Taosheng, Chen. Identification of Trisubstituted-pyrazol Carboxamide Analogs as Novel and Potent Antagonists of Farnesoid X Receptor, *Bioorganic & Medicinal Chemistry*, 2014, 22, 2919-2938.
8. Li, T.; Holmstrom, S. R.; Kir, S.; Umetani, M.; Schmidt, D. R.; Kliewer, S. A.; Mangelsdorf, D. J. The G protein coupled bile acid receptor, TGR5, stimulates gallbladder filling. Mol. Endocrinol. 2011, 25, 1066-1071.
9. Kawamata Y, Fujii R, Hosoya M, Harada M, Yoshida H, Miwa M, et al. A G protein coupled receptor responsive to bile acids. *J Biol Chem* 2003, 11, 9435-40.
10. Ko, B. S, Choi, S. B, Park, S. K, Jang, J. S, Kim, Y. E, Park, S. Insulin sensitizing and insulin tropic action of berberine from *Cortidis rhizoma*. Biol Pharm Bull, 2005, 28, 1431-1437.
11. Lu S. S; Yu Y. L; Zhu H. J; Liu X. D; Liu L; Liu Y. W; et al. Berberine promotes glucagonlike peptide 1 (7-36) amide secretion in streptozotocin-induced diabetic rats. *J Endocrinol* 2009, 200, 159-65.
12. Brusq J. M; Ancellin N; Grondin P; Guillard R; Martin S; Saintillan Y; Issandou M. Inhibition of lipid synthesis through activation of AMP kinase: an additional mechanism for the hypolipidemic effects of berberine. *J Lipid Res* 2006, 47, 1281-1288.
13. Yu Y, Liu L, Wang X, Liu X, Xie L, Wang G. Modulation of glucagon-like peptide-1 release by berberine: in vivo and in vitro studies. *Biochem Pharmacol* 2009, 79, 1000-6.
14. Kalantzi, L., Goumas, K., Kalioras, V., Abrahamsson, B., Dressman, J. B., and Reppas, C., Characterization of the human upper gastrointestinal contents under conditions simulating bioavailability/bioequivalence studies. *Pharm. Res.*, 2006, 23, 165-176.
15. S. Naruto, H. Mizuta, H. Nishimura, Tetrahedron Lett. 1976, 17, 1597-1600.
16. Mercer, S. L. ACS Chemical Neuroscience Molecule Spotlight on Qnexa, *ACS Chem. Neurosci.* 2011, 2, 183-184.
17. Megyesi, M.; Biczok, L. Effect of ion pairing on the fluorescence of berberine, a natural isoquinoline alkaloid. *Chem. Phys. Lett.* 2007, 447, 247-251.
18. Brenton, F.; Raju, M. TGR5 agonists having an imidazole or triazole core with substituent having a quaternary nitrogen. WO2014100025A1, 2013.
19. Lipinski, C. A.; Lombardo, F.; Dominy, B. W.; Feeney, P. J. Experimental and computational approaches to estimate solubility and permeability in drug discovery and development settings. *Adv. Drug Delivery Rev.* 2001, 46, 3-26
20. Donna Yu, Wenwei Lin, Barry M. Forman, and Taosheng, Chen. Identification of Trisubstituted-pyrazol Carboxamide Analogs as Novel and Potent Antagonists of Farnesoid X Receptor, *Bioorganic & Medicinal Chemistry*, 2014, 22, 2919-2938.
21. Zhong, M. TGR5 as a therapeutic target for treating obesity. *Curr. Top. Med. Chem.* 2010, 10, 386-396.
22. Barrera, J. G., D. A. Sandoval, D. A. D'Alessio, and R. J. Seeley. GLP-1 and energy balance: An integrated model of short term and long-term control. Nat. Rev. Endocrinol. 2011, 7, 507-516.
23. Donna Yu, Barry Forman, Wendong Huang, et al. Stereoselective Synthesis, Biological Evaluation, and Modeling of Novel Bile Acid-Derived G-Protein Coupled Bile Acid Receptor 1 (GP-BAR1, TGR5) Agonists. Bioorganic & Medicinal Chemistry 2015, 23, 1613-1628.

24. Zhang Y, Li X, Zou D, Liu W, Yang J, et al. Treatment of type 2 diabetes and dyslipidemia with the natural plant alkaloid berberine. *J Clin Endocrinol Metab* 2008, 93, 2559-2565.

What is claimed is:

1. A salt composition having the formula:

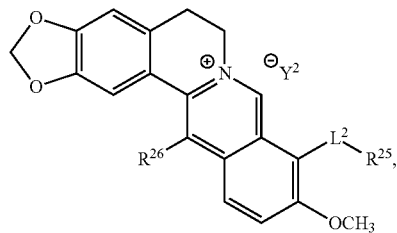

(II)

wherein
- $L^2$ is a bond, —C(O)—, —C(O)O—, —O—, —S—, —NR$^{2L}$—, —C(O)NR$^{2L}$—, —NR$^{2L}$C(O)—, —S(O)$_2$—, —S(O)NR$^{2L}$—, —NR$^{2L}$C(O)NH—, —NHC(O)NR$^{2L}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
- $R^{25}$ is —OCH$_3$, substituted or unsubstituted cycloalkyl, substituted or unsubstituted heterocycloalkyl, substituted or unsubstituted aryl or substituted or unsubstituted heteroaryl;
- $R^{26}$ is hydrogen, halogen, —CX$^{26}_3$, —CHX$^{26}_2$, —CH$_2$X$^{26}$, —OCX$^{26}_3$, —OCH$_2$X$^{26}$, —OCHX$^{26}_2$, —CN, —SO$_{n26}$R$^{26C}$, —SO$_{v26}$NR$^{26A}$R$^{26B}$, —NHC(O)NR$^{26A}$R$^{26B}$, —(O)$_{m26}$, —NR$^{26A}$R$^{26B}$, —C(O)R$^{26C}$, —C(O)—OR$^{26C}$, —C(O)NR$^{26A}$R$^{26B}$, —OR$^{26C}$, —NR$^{26A}$SO$_2$R$^{26C}$, —NR$^{26A}$C(O)R$^{26C}$, —NR$^{26A}$C(O)OR$^{26C}$, —NR$^{26A}$OR$^{26C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
- $R^{2L}$, $R^{26A}$, $R^{26B}$ and $R^{26C}$ are independently hydrogen, —CX$^{26A}_3$, —CN, —COOH, —CONH$_2$, —CHX$^{26A}_2$, —CH$_2$X$^{26A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
- $X^{26}$ and $X^{26A}$ are independently halogen;
- n26 is an integer from 0 to 4;
- m26 and v26 are independently 1 or 2; and
- $Y^2$ is an anionic bile acid receptor modulator the formula:

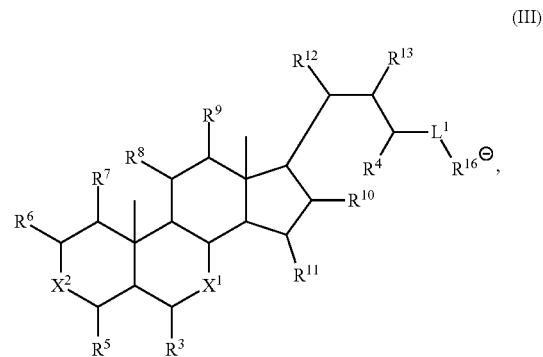

(III)

wherein:
- $L^1$ is a bond, —C(O)—, —C(O)O—, —C(O)NH—, or —CH$_2$—;
- $X^1$ is —CH$_2$—;
- $X^2$ is —C(R$^{14}$)(R$^{15}$)—;
- $R^3$ is hydrogen, or unsubstituted alkyl;
- $R^4$ is hydrogen or unsubstituted alkyl;
- $R^5$ is hydrogen, unsubstituted alkyl, or —OR$^{5A}$;
- $R^6$ is hydrogen, unsubstituted alkyl, or —OR$^{6A}$;
- $R^7$ is hydrogen, unsubstituted alkyl, or —OR$^{7A}$;
- $R^8$ is hydrogen, unsubstituted alkyl, or —OR$^{8A}$;
- $R^9$ is hydrogen, or unsubstituted alkyl;
- $R^{10}$ is hydrogen, unsubstituted alkyl, or —OR$^{10A}$;
- $R^{11}$ is hydrogen, unsubstituted alkyl, or —OR$^{11A}$;
- $R^{12}$ is hydrogen, unsubstituted alkyl, or —OR$^{12A}$;
- $R^{13}$ is hydrogen, unsubstituted alkyl, or —OR$^{13A}$;
- $R^{14}$ is hydrogen, unsubstituted alkyl, or —OR$^{14A}$;
- $R^{15}$ is hydrogen, unsubstituted alkyl, or —OR$^{15A}$;
- $R^{16}$ is —COO$^-$, —S(O)$_3^-$, —SO$_4^-$ or —NHS(O)$_3^-$,
- $R^{1A}$, $R^{2A}$, $R^{5A}$, $R^{6A}$, $R^{7A}$, $R^{8A}$, $R^{10A}$, $R^{11A}$, $R^{12A}$, $R^{13A}$, $R^{14A}$, and $R^{15A}$ are independently hydrogen, unsubstituted alkyl, or an alcohol protecting group.

2. The salt composition of claim 1, wherein $Y^2$ is:

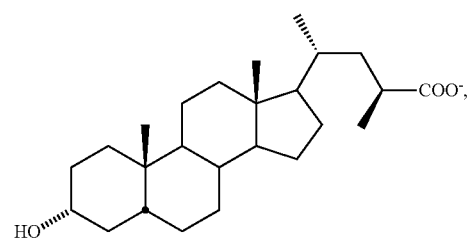

-continued

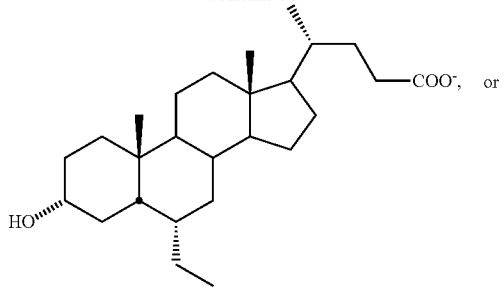

, or

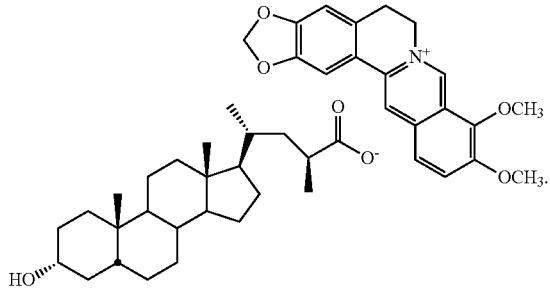

4. A method of treating a TGR5-mediated and/or FXR-mediated disease or disorder, selected from the group consisting of cancer and a metabolic disease or disorder, comprising administering to a subject a therapeutically effective amount of a compound of claim 1.

5. The method of claim above 4, wherein the metabolic disease or disorder is selected from the group consisting of diabetes, obesity, insulin resistance, metabolic syndrome, atherosclerosis and liver disease.

6. The method of claim 5, wherein the liver disease is non-alcoholic fatty liver disease.

7. The method of claim 4, wherein the disease or disorder is cancer.

8. The method of claim 7, wherein the cancer is liver cancer.

9. The method of claim 4, wherein the administration is enteral or oral.

10. The salt composition of claim 1, wherein $R^{14}$ is —OH, or —OCH$_3$.

11. The salt composition of claim 1, wherein $R^{15}$ is —OH, or —OCH$_3$.

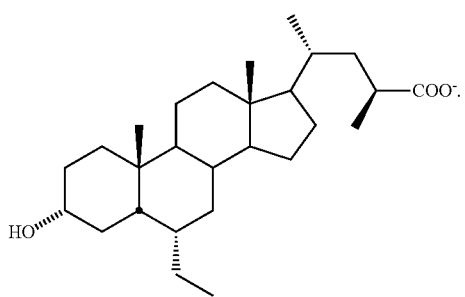

3. The salt composition of claim 1, wherein the salt composition is:

* * * * *